US012708649B2

(12) United States Patent
Brucker et al.

(10) Patent No.: US 12,708,649 B2
(45) Date of Patent: Aug. 18, 2026

(54) COMPOSITIONS AND METHODS FOR IMPROVING SKIN HEALTH AND FOR THE TREATMENT AND PREVENTION OF DISEASES, DISORDERS AND CONDITIONS ASSOCIATED WITH FUNGI AND OTHER PATHOGENIC MICROBES

(71) Applicant: DermBiont, Inc., Boston, MA (US)

(72) Inventors: Robert Brucker, Boston, MA (US); Yanjun Huang, Boston, MA (US); Nikola Jovanovic, Boston, MA (US); Bhanu Prakash Chowdary Sakhamuri, Boston, MA (US); Ida Lister, Boston, MA (US); Xuecheng Zhang, Boston, MA (US); Sanjay Jain, Shrewsbury, MA (US); Emma Jean Mildred Taylor, San Francisco, CA (US)

(73) Assignee: DermBiont, Inc., Boston, MA (US)

( * ) Notice: Subject to any disclaimer, the term of this patent is extended or adjusted under 35 U.S.C. 154(b) by 542 days.

(21) Appl. No.: 18/031,723

(22) PCT Filed: Oct. 13, 2021

(86) PCT No.: PCT/US2021/054856
§ 371 (c)(1),
(2) Date: Apr. 13, 2023

(87) PCT Pub. No.: WO2022/081762
PCT Pub. Date: Apr. 21, 2022

(65) Prior Publication Data

US 2024/0269198 A1 Aug. 15, 2024

Related U.S. Application Data

(60) Provisional application No. 63/091,783, filed on Oct. 14, 2020.

(51) Int. Cl.

| | |
|---|---|
| ***A61K 35/742*** | (2015.01) |
| ***A61K 9/00*** | (2006.01) |
| ***A61K 9/19*** | (2006.01) |
| ***A61K 47/26*** | (2006.01) |
| ***A61P 31/04*** | (2006.01) |
| ***A61P 31/10*** | (2006.01) |
| *A61K 35/00* | (2006.01) |

(52) U.S. Cl.
CPC .......... *A61K 35/742* (2013.01); *A61K 9/0014* (2013.01); *A61K 9/19* (2013.01); *A61K 47/26* (2013.01); *A61P 31/04* (2018.01); *A61P 31/10* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 3,261,761 | A | 7/1966 | Anderson |
| 4,205,132 | A | 5/1980 | Sandine et al. |
| 4,900,348 | A | 2/1990 | Hoitink |
| 5,081,225 | A | 1/1992 | O'Sullivan et al. |
| 5,428,175 | A | 6/1995 | Hoshino et al. |
| 6,224,863 | B1 | 5/2001 | Bacic et al. |
| 6,244,346 | B1 | 6/2001 | Perriello |
| 6,245,235 | B1 | 6/2001 | Perriello |
| 6,461,607 | B1 | 10/2002 | Farmer |
| 6,531,126 | B2 | 3/2003 | Farmer |
| 6,645,506 | B1 | 11/2003 | Farmer |
| 6,716,435 | B1 | 4/2004 | Farmer et al. |
| 6,723,326 | B1 | 4/2004 | Farmer |
| 6,733,751 | B2 | 5/2004 | Farmer |
| 6,811,786 | B1 | 11/2004 | Farmer et al. |
| 6,849,256 | B1 | 2/2005 | Farmer |
| 6,905,692 | B2 | 6/2005 | Farmer |
| 6,926,831 | B2 | 8/2005 | Matsumura et al. |
| 6,962,697 | B2 | 11/2005 | Cavaliere et al. |
| 7,048,950 | B2 | 5/2006 | Farmer |
| 7,052,688 | B2 | 5/2006 | De Simone |

(Continued)

FOREIGN PATENT DOCUMENTS

| | | |
|---|---|---|
| CN | 110982734 A | 4/2020 |
| CN | 111514172 A | 8/2020 |

(Continued)

OTHER PUBLICATIONS

Xing et al., "Study of cryoprotective agents during freeze-drying *Lactobacillus casei* subsp. *rhamnosus* 719", Rupin Gongye, vol. 37, pp. 15-17 (Year: 2009).*

(Continued)

*Primary Examiner* — Michelle F. Paguio Frising

(74) *Attorney, Agent, or Firm* — Wilson Sonsini Goodrich & Rosati

(57) ABSTRACT

Among other things, disclosed herein are compositions and methods for using human-isolated or synthetic *Alcaligenes faecalis, Bacillus altitudinis, Bacillus pumilus, Bacillus subtilis*, or *Janthinobacterium lividum*. Compositions may improve skin health. Methods may include applying human-isolated or synthetic *Alcaligenes faecalis, Bacillus altitudinis, Bacillus pumilus, Bacillus subtilis*, or *Janthinobacterium lividum* over a host or host area, such as skin or mucosa to minimize the presence of one or more pathogenic microbes, maximize therapeutic effects of one or more additional therapeutics, and/or improve health of a host or host area.

17 Claims, 33 Drawing Sheets

Specification includes a Sequence Listing.

(56) References Cited

U.S. PATENT DOCUMENTS

| | | | | |
|---|---|---|---|---|
| 7,060,465 | B2 | 6/2006 | Xu et al. | |
| 7,232,571 | B2 | 6/2007 | Farmer et al. | |
| 7,244,607 | B2 | 7/2007 | Martin et al. | |
| 7,371,407 | B2 | 5/2008 | Farmer | |
| 7,374,753 | B1 | 5/2008 | Farmer et al. | |
| 7,507,402 | B1 | 3/2009 | Farmer et al. | |
| 7,541,042 | B2 | 6/2009 | Farmer | |
| 7,544,363 | B2 | 6/2009 | Farmer | |
| 7,651,680 | B2 | 1/2010 | Breton et al. | |
| 7,700,093 | B2 | 4/2010 | Farmer et al. | |
| 7,708,988 | B2 | 5/2010 | Farmer | |
| 7,713,726 | B2 | 5/2010 | Farmer | |
| 7,807,185 | B2 | 10/2010 | Farmer | |
| 8,097,247 | B2 | 1/2012 | Farmer | |
| 8,506,952 | B2 | 8/2013 | Minbiole et al. | |
| 11,040,077 | B2 | 6/2021 | Brucker et al. | |
| 12,064,459 | B2 | 8/2024 | Brucker et al. | |
| 2003/0072829 | A1 | 4/2003 | Austin, Jr. | |
| 2004/0243076 | A1 | 12/2004 | Husmark et al. | |
| 2005/0201996 | A1 | 9/2005 | Conway et al. | |
| 2005/0271758 | A1 | 12/2005 | Farmer | |
| 2009/0186057 | A1 | 7/2009 | Farmer et al. | |
| 2011/0002891 | A1 | 1/2011 | Minbiole et al. | |
| 2015/0203897 | A1 | 7/2015 | Robins et al. | |
| 2017/0065647 | A1* | 3/2017 | Kim | A61K 35/747 |
| 2017/0151291 | A1 | 6/2017 | Henn et al. | |
| 2021/0145899 | A1* | 5/2021 | Deaton | A61P 31/10 |
| 2021/0361725 | A1 | 11/2021 | Brucker et al. | |
| 2021/0386802 | A1 | 12/2021 | Brucker et al. | |
| 2022/0160617 | A1 | 5/2022 | Brucker et al. | |
| 2025/0295713 | A1 | 9/2025 | Brucker et al. | |

FOREIGN PATENT DOCUMENTS

| | | | | |
|---|---|---|---|---|
| EP | 0045718 | A2 | 2/1982 | |
| JP | H05194141 | A | 8/1993 | |
| JP | 2001139612 | A | 5/2001 | |
| JP | 2005126375 | A | 5/2005 | |
| JP | 2006253864 | A | 9/2006 | |
| JP | 2006341069 | A | 12/2006 | |
| JP | 2007227290 | A | 9/2007 | |
| JP | 2010113169 | A | 5/2010 | |
| JP | 2011152687 | A | 8/2011 | |
| KR | 20070088150 | A | 8/2007 | |
| WO | WO-2011003062 | A2 | 1/2011 | |
| WO | WO-2012098358 | A1 | 7/2012 | |
| WO | WO-2013032328 | A1 * | 3/2013 | A61P 3/06 |
| WO | WO-2014029578 | A1 | 2/2014 | |
| WO | WO-2014145958 | A2 | 9/2014 | |
| WO | WO-2015000972 | A1 | 1/2015 | |
| WO | WO-2019118984 | A2 | 6/2019 | |
| WO | WO-2020127637 | A1 * | 6/2020 | A61K 8/11 |
| WO | WO-2020139316 | A1 | 7/2020 | |
| WO | WO-2020179999 | A1 | 9/2020 | |
| WO | WO-2020210553 | A1 | 10/2020 | |

OTHER PUBLICATIONS

Mare et al., "Antibiotics of Alcaligenes faecalis", Nature, vol. 203, pp. 430-431 (Year: 1964).*

Altschul et al.: Basic Local Alignment Search Tool. J. Mol. Biol. 215: 403-410 (1990).

Becker et al.: The bacterially-produced metabolite violacein is associated with survival in amphibians . . . Applied Environmental Microbiology. 6635-6638 (2009).

Borneman et al.: PCR Primers That Amplify Fungal rRNA Genes from Environmental Samples. Applied and Environmental Microbiology. 4356-4360 (2000).

Brucker et al.: Amphibian chemical defense: antifungal metabolites of the microsymbiont *Janthinobacterium lividum* on the salamander *Plethodon cinereus*. J. Chem. Ecol. 34(11):1422-1429 (2008).

Chandrakar et al.: Antibiotic Potential of Endophytic Actinomycetes of Medicinal Herbs Against Human Pathogenic Bacteria. Proc. Natl. Acad. Sci. India. Sect. B Biol. Sci. 87:905-915 (2017) https://doi.org/10.1007/s40011-015-0668-9.

Cherif et al.: Pseudomonas isolates have in vitro antagonistic activity against the dermatophytes *Trichophyton rubrum, Trichophyton mentagrophytes* var *interdigitale* and *Microsporum canis*. Journal de Mycologie Medicale. 19:178-184 (2009).

DermBiont: Dermbiont Begins Phase 2 Clinical Trial for Athlete's Foot with a Live Bacterial Tropical Probiotic. Retrieved from the Internet: (2019) www.dermbiont/com/in-the-news/2019/3/13/dermbiont-begins-phase-2-clinical-trial-for-athletes-foot-with-a-live-bacterial-topical-probiotic.

Doneanu et al.: UPLC-MS Monitoring of Water-Soluble Vitamin Bs in Cell Culture Media in Minutes. Waters. 14 pages (2011).

Eckelmann et al.: Spatial-temporal profiling of prodiginines and serratamolides produced by endophytic Serratia marcescens harbored in maytenus serrata. Sci Rep 8. 5283 (2018) https://doi.org/10.1038/s41598-018-23538-5.

Effendy et al.: Epidemiology and clinical classification of onychomycosis. J Eur Acad Dermatol Venereol. 19:8-12 (2005).

Ellis. Diagnosis of onychomycosis made simple. J Am Acad Dermatol. 40:S3-8 (1999).

Fostel et al.: Emerging novel antifungal agents. Drug Discov Tod. 5:25-32 (2000).

GenBank Accession No. DQ473538.1. created May 1, 2007.

Gill et al.: A review of epidemiology of tinea unguium in the community. Austral J Dermatol. 40:6-13 (1999).

Goris et al.: DNA-DNA hybridization values and their relationship to whole-genome sequence similarities. Int J Syst Evol Microbiol. 57(Pt 1):81-91 (2007) doi:10.1099/ijs.0.64483-0. PMID: 17220447.

Grice et al.: A diversity profile of the human skin microbiota. Genome Research. 18:1043-1050 (2008).

Grice et al.: Topographical and Temporal Diversity of the Human Skin Microbiome. Science. 324(5931):1190-1192 (2009).

Gueniche et al.: Bifidobacterium longum Lysate, a New Ingredient for Reactive Skin. Experimental Dermatology. 19(8):e1-38 (2010).

Gupta et al.: ARG-ANNOT, a new bioinformatic tool to discover antibiotic resistance genes in bacterial genomes. Antimicrob Agents Chemother. 58(1):212-220 (2014).

Han et al.: Antagonistic Activities of *Bacillus* spp. Strains Isolated from Tidal Flat Sediment Towards Anthracnose Pathogens Colletotrichum acutatum and C. gloeosporioides in South Korea. Plant Pathol J. 31(2):165-175 (2015) DOI:10.5423/ppj.oa.03.2015.0036.

Harris et al.: Skin microbes on frogs prevent morbidity and mortality caused by a lethal skin fungus. The ISME J. 37(7):818-827 Epub 2009.

Isolaurie et al.: Probiotics in the Management of Atopic Eczema. Clinical and Experimental Allergy. 30:1604-1610 (2000).

Koburger et al.: Isolation of *Chromobacterium* spp. From Foods, Soil, and Water. Applied and Environmental Microbiology. 1463-1465 (1982).

Roller et al.: *Janthinobacterium* sp. 1-2014MBL-MicDiv, complete genome. NCBI. (2016) Retrieved from Internet: www.ncbi.nlm.nih.gov/nuccore/CP011319.1.

Krutmann. Pre- and probiotics for human skin. Journal of Dermatological Science. 54:1-5 (2009).

Lauer et al.: Common Cutaneous Bacteria from the Eastern Red-Backed Salamander Can Inhibit Pathogenic Fungi. Copeia. 3:630-640 (2007).

Lauer et al.: (Diversity of cutaneous bacteria with antifungal activity isolated from female four-toed salamanders. The ISME Journal. Published online 2007.

Madiha et al.: Diazotrophic Bacteria as Biological Control Agent for Lasiodiplodia theobromaeIsolated From Kenaf Seeds. ARPN Journal of Agricultural and Biological Science. 7(12):1076-1082 (2012).

Nakamura et al.: Production of antibacterial violet pigment by Psychotropic bacterial RT012 strain. Biotech and processes Eng. 8:37-40 (2003).

Needleman et al.: A General Method Applicable to the Search for Similarities in the Amino Acid Sequence of Two Proteins. J. Mol. Biol. 48:443-453 (1970).

Ouwehand et al.: Probiotics of the skin: a new area of potential application? Lett Appl Microbiol 36:327-331 (2003).

(56) References Cited

OTHER PUBLICATIONS

Pantanella et al.: Violacein and biofilm production in Janthinobacterium lividum. Journal of Applied Microbiology. 1364-5072 (2009).
PCT/US2010/040898 International Search Report and Written Opinion dated Mar. 23, 2011.
PCT/US2020/027556 International Search Report and Written Opinion of the International Searching Authority mailed Aug. 4, 2020.
PCT/US2021/054856 International Invitation to Pay Additional Fees, Partial International Search Report and Provisional Written Opinion dated Feb. 4, 2022.
PCT/US2021/054856 International Preliminary Report on Patentability dated Apr. 27, 2023.
Pearson et al., Improved tools for biological sequence comparison. Proc Natl Acad Sci U S A. Apr. 1988;85(8):2444-8. doi: 10.1073/pnas.85.8.2444. PMID: 3162770; PMCID: PMC280013.
Ramsey et al.: The Cutaneous Bacterium *Janthinobacterium lividum* Inhibits the Growth of Trichophyton Rubrum in Vitro. International Journal of Dermatology. 54(2):156-159 (2015).
Jorgensen et al.: Antimicrobial Susceptibility Testing: A Review of General Principles and Contemporary Practices. Clinical Infectious Diseases. 49(11):1749-1755 (2009).
Rodriguez et al.: The enveomincs collection: a toolbox for specialized analyses of microbial genomes and metagenomes. Peer J Preprints 4:e1900v1 16 pages (2016) https://doi.org/10.7287/peerj.preprints.1900v1https://protect-us.mimecast.com/s/kjWsC829XAhkmWP2u1jYjJ?domain=doi.org.
Sanders. Probiotics: Considerations for Human Health. Nutrition Reviews. 91-99 (2003).
Shirata et al.: Isolation of bacteria producing bluish-purple pigment and use for dyeing. JARQ. 34:131-140 (2000).
Skowronek et al.: Bacteria from the Midgut of Common Cockchafer (*Melolontha melolontha* L) Larvae Exhibiting Antagonistic Activity Against Bacterial Symbionts of Entomopathogenic Nematodes: Isolation and Molecular Identification. Int. J. Mol. Sci. 21:580 18 pages (2020).
Smith et al.: Identification of common molecular subsequences. Adv. Appl. Math. 2(4):482-489 (1981).
Stamatakis: RAxML version 8: a tool for phylogenetic analysis and post-analysis of large phylogenies. Bioinformatics. 39(9):1312-1313 (2014).
Tong et al.: Characterization of a fungal competition faxtor: Production of a conidial cell-wall associated antifungal peptide. PLOS Pathogens. 16(4):1-29 e1008518 (2020) https://doi.org/10.1371/journal.ppat.1008518.
U.S. Appl. No. 12/829,520 Office Action dated Aug. 27, 2012.
U.S. Appl. No. 12/829,520 Office Action dated Feb. 8, 2012.
U.S. Appl. No. 16/885,152 Office Action dated Nov. 4, 2020.
U.S. Appl. No. 16/885,152 Office Action dated Sep. 14, 2020.
U.S. Appl. No. 17/243,509 Restriction Requirement dated Oct. 12, 2022.
U.S. Appl. No. 17/384,598 Restriction Requirement dated Dec. 23, 2022.
Xu et al., Bioactive constituents from the bacterium *Alcaligenes faecalis* YMF 3.175. Applied Biochemistry and Microbiology 51(1):52-57 (2015).
Co-pending U.S. Appl. No. 18/762,414, inventors Brucker; Robert M et al., filed Jul. 2, 2024.
Janda, J.M., et al.: 16S rRNA Gene Sequencing for Bacterial Identification in the Diagnostic Laboratory: Pluses, Perils, and Pitfalls. Journal of Clinical Microbiology. 45(9):2761-2764 (2007).
Moissl et al.: Molecular bacterial community analysis of clean rooms where a spacecraft are assembled. FEMS Microbiol Ecol. 61:509-521 (2007).
Schloss, Patrick D et al. Psychrotophic Strain of Janthinobacterium Lividum from a Cold Alaskan Soil Produces Prodigiosin. DNA Cell Biology vol. 29,9: pp. 533-541 (2010).
Shivaji, S. et al. GenBank Accession No. JF313003. Version No. JF313003.1. *Janthinobacterium* sp. HC5-1 16S ribosomal RNA gene, partial sequence: pp. 1-2. Record created Mar. 10, 2012. Retrieved Oct. 7, 2025. Retrieved from: https://www.ncbi.nlm.nih.gov/nucleotide/JF313003.1?report=genbank&log$=nuclalign&blast_rank=21&RID=54B97P.
Watanabe. A personality and commensal factors of human microbiome. Doctoral dissertation. Department of Bioscience and Biotechnology. School of Bioscience and Biotechnology. Tokyo Institute of Technology. Report No. A No. 11072. 1-14 (2019).
Watanabe: A personality and commensal factors of human microbiome. Tokyo Institute of Technology, School of Life Science and Technology, Department of Life Science and Technology, Course of Life Science and Technology, Doctoral Dissertation. Mar. 2019, p. 1-45, https://dl.ndl.go.jp/pid/11671843/1/1.

* cited by examiner

*Bacillus altitudinis*
DB10033

*Bacillus pumilus*
DB03376

*Bacillus subtilis*
DB02475

*Alcaligenes faecalis*
DB05646

Pivot Field Names

| F1 | Achromobacter xyl.. | Db05646 | Gca 0009 67305.2 | Gca 0016 41975.2 | Gca 0022 42175.1 | Gca 0024 43155.1 | Gca 0037 16855.1 | Gca 0038 13085.1 | Gca 0043 19585.1 | Gca 0100 92625.1 | Gca 0161 28035.1 |
|---|---|---|---|---|---|---|---|---|---|---|---|
| Achromobacter_x.. | 100.00 | 74.00 | 74.00 | 74.00 | 73.00 | 74.00 | 73.00 | 74.00 | 73.00 | 73.00 | 74.00 |
| DB05646 | 74.00 | 100.00 | 98.00 | 98.00 | 91.00 | 98.00 | 90.00 | 98.00 | 87.00 | 98.00 | 98.00 |
| GCA_000967305.2 | 74.00 | 98.00 | 100.00 | 98.00 | 91.00 | 98.00 | 90.00 | 98.00 | 87.00 | 98.00 | 98.00 |
| GCA_001641975.2 | 74.00 | 98.00 | 98.00 | 100.00 | 91.00 | 98.00 | 90.00 | 98.00 | 87.00 | 98.00 | 98.00 |
| GCA_002242175.1 | 73.00 | 91.00 | 91.00 | 91.00 | 100.00 | 91.00 | 96.00 | 91.00 | 86.00 | 91.00 | 91.00 |
| GCA_002443155.1 | 74.00 | 98.00 | 98.00 | 98.00 | 91.00 | 100.00 | 90.00 | 100.00 | 87.00 | 98.00 | 100.00 |
| GCA_003716855.1 | 73.00 | 90.00 | 90.00 | 90.00 | 96.00 | 90.00 | 100.00 | 90.00 | 86.00 | 90.00 | 90.00 |
| GCA_003813085.1 | 73.00 | 98.00 | 98.00 | 98.00 | 91.00 | 100.00 | 90.00 | 100.00 | 87.00 | 98.00 | 100.00 |
| GCA_004319585.1 | 73.00 | 87.00 | 87.00 | 87.00 | 86.00 | 87.00 | 86.00 | 87.00 | 100.00 | 87.00 | 87.00 |
| GCA_010092625.1 | 74.00 | 98.00 | 98.00 | 98.00 | 91.00 | 98.00 | 90.00 | 98.00 | 87.00 | 100.00 | 98.00 |
| GCA_016128035.1 | 74.00 | 98.00 | 98.00 | 98.00 | 91.00 | 100.00 | 90.00 | 100.00 | 87.00 | 98.00 | 100.00 |
| GCA_016446305.1 | 74.00 | 98.00 | 98.00 | 98.00 | 91.00 | 98.00 | 90.00 | 98.00 | 87.00 | 98.00 | 98.00 |
| GCA_016807785.1 | 73.00 | 92.00 | 92.00 | 92.00 | 90.00 | 92.00 | 89.00 | 92.00 | 87.00 | 92.00 | 92.00 |
| GCF_000967305.2 | 74.00 | 98.00 | 100.00 | 98.00 | 91.00 | 98.00 | 98.00 | 98.00 | 87.00 | 98.00 | 98.00 |
| GCF_001641975.2 | 74.00 | 98.00 | 98.00 | 100.00 | 91.00 | 98.00 | 90.00 | 98.00 | 87.00 | 98.00 | 98.00 |
| GCF_002242175.1 | 73.00 | 91.00 | 91.00 | 91.00 | 100.00 | 91.00 | 96.00 | 91.00 | 86.00 | 91.00 | 91.00 |
| GCF_002443155.1 | 74.00 | 98.00 | 98.00 | 98.00 | 91.00 | 100.00 | 90.00 | 100.00 | 87.00 | 98.00 | 100.00 |
| GCF_003716855.1 | 73.00 | 90.00 | 90.00 | 90.00 | 96.00 | 90.00 | 100.00 | 90.00 | 86.00 | 90.00 | 90.00 |
| GCF_003813085.1 | 73.00 | 98.00 | 98.00 | 98.00 | 91.00 | 100.00 | 90.00 | 100.00 | 87.00 | 98.00 | 100.00 |
| GCF_004319585.1 | 73.00 | 87.00 | 87.00 | 87.00 | 86.00 | 87.00 | 86.00 | 86.00 | 100.00 | 87.00 | 87.00 |
| GCF_010092625.1 | 74.00 | 98.00 | 98.00 | 98.00 | 91.00 | 98.00 | 90.00 | 98.00 | 87.00 | 100.00 | 98.00 |
| GCF_016128035.1 | 74.00 | 98.00 | 98.00 | 98.00 | 91.00 | 100.00 | 90.00 | 100.00 | 87.00 | 98.00 | 100.00 |
| GCF_016446305.1 | 74.00 | 98.00 | 98.00 | 98.00 | 91.00 | 98.00 | 90.00 | 98.00 | 87.00 | 98.00 | 98.00 |
| GCF_016807785.1 | 73.00 | 92.00 | 92.00 | 92.00 | 90.00 | 92.00 | 89.00 | 92.00 | 87.00 | 92.00 | 92.00 |

| Gca 0164 46305.1 | Gca 0168 07785.1 | Gcf 00096 7305.2 | Gcf 00164 1975.2 | Gcf 00224 2175.1 | Gcf 00244 3155.1 | Gcf 00371 6855.1 | Gcf 00381 3085.1 | Gcf 00431 9585.1 | Gcf 01009 2625.1 | Gcf 01612 8035.1 | Gcf 01644 6305.1 | Gcf 01680 7785.1 |
|---|---|---|---|---|---|---|---|---|---|---|---|---|
| 74.00 | 73.00 | 74.00 | 74.00 | 73.00 | 74.00 | 73.00 | 74.00 | 73.00 | 73.00 | 74.00 | 74.00 | 73.00 |
| 98.00 | 92.00 | 98.00 | 98.00 | 91.00 | 98.00 | 90.00 | 98.00 | 87.00 | 98.00 | 98.00 | 98.00 | 92.00 |
| 98.00 | 92.00 | 100.00 | 98.00 | 91.00 | 98.00 | 90.00 | 98.00 | 87.00 | 98.00 | 98.00 | 98.00 | 92.00 |
| 98.00 | 92.00 | 98.00 | 100.00 | 91.00 | 98.00 | 90.00 | 98.00 | 87.00 | 98.00 | 98.00 | 98.00 | 92.00 |
| 91.00 | 90.00 | 91.00 | 91.00 | 100.00 | 91.00 | 96.00 | 91.00 | 86.00 | 91.00 | 91.00 | 91.00 | 90.00 |
| 98.00 | 92.00 | 98.00 | 98.00 | 91.00 | 100.00 | 90.00 | 100.00 | 87.00 | 98.00 | 100.00 | 100.00 | 92.00 |
| 90.00 | 89.00 | 90.00 | 90.00 | 96.00 | 90.00 | 100.00 | 98.00 | 86.00 | 90.00 | 90.00 | 90.00 | 89.00 |
| 98.00 | 92.00 | 98.00 | 98.00 | 91.00 | 100.00 | 90.00 | 100.00 | 87.00 | 98.00 | 98.00 | 98.00 | 92.00 |
| 87.00 | 87.00 | 87.00 | 87.00 | 86.00 | 87.00 | 86.00 | 87.00 | 100.00 | 87.00 | 87.00 | 87.00 | 87.00 |
| 98.00 | 92.00 | 98.00 | 98.00 | 91.00 | 98.00 | 90.00 | 98.00 | 87.00 | 100.00 | 98.00 | 98.00 | 92.00 |
| 98.00 | 92.00 | 98.00 | 98.00 | 91.00 | 100.00 | 90.00 | 100.00 | 87.00 | 98.00 | 100.00 | 98.00 | 92.00 |
| 100.00 | 92.00 | 98.00 | 98.00 | 91.00 | 98.00 | 90.00 | 98.00 | 87.00 | 98.00 | 98.00 | 100.00 | 92.00 |
| 92.00 | 100.00 | 92.00 | 92.00 | 90.00 | 92.00 | 89.00 | 92.00 | 87.00 | 92.00 | 92.00 | 92.00 | 100.00 |
| 98.00 | 92.00 | 100.00 | 98.00 | 91.00 | 98.00 | 90.00 | 98.00 | 87.00 | 98.00 | 98.00 | 98.00 | 92.00 |
| 98.00 | 92.00 | 98.00 | 100.00 | 91.00 | 98.00 | 90.00 | 98.00 | 87.00 | 98.00 | 98.00 | 98.00 | 92.00 |
| 91.00 | 90.00 | 91.00 | 91.00 | 100.00 | 91.00 | 96.00 | 91.00 | 86.00 | 91.00 | 91.00 | 91.00 | 90.00 |
| 98.00 | 92.00 | 98.00 | 98.00 | 91.00 | 100.00 | 90.00 | 100.00 | 87.00 | 98.00 | 100.00 | 98.00 | 92.00 |
| 90.00 | 89.00 | 90.00 | 90.00 | 96.00 | 90.00 | 100.00 | 90.00 | 86.00 | 90.00 | 90.00 | 90.00 | 89.00 |
| 98.00 | 92.00 | 98.00 | 98.00 | 91.00 | 100.00 | 90.00 | 100.00 | 87.00 | 98.00 | 100.00 | 98.00 | 92.00 |
| 87.00 | 87.00 | 87.00 | 87.00 | 86.00 | 87.00 | 86.00 | 87.00 | 100.00 | 87.00 | 87.00 | 87.00 | 87.00 |
| 98.00 | 92.00 | 98.00 | 98.00 | 91.00 | 98.00 | 90.00 | 98.00 | 87.00 | 100.00 | 98.00 | 98.00 | 92.00 |
| 98.00 | 92.00 | 98.00 | 98.00 | 91.00 | 100.00 | 90.00 | 100.00 | 87.00 | 98.00 | 100.00 | 98.00 | 92.00 |
| 100.00 | 92.00 | 98.00 | 98.00 | 91.00 | 98.00 | 90.00 | 98.00 | 87.00 | 98.00 | 98.00 | 100.00 | 92.00 |
| 92.00 | 100.00 | 92.00 | 92.00 | 90.00 | 92.00 | 89.00 | 92.00 | 87.00 | 92.00 | 92.00 | 92.00 | 100.00 |

SEQUENCE LISTING

<160> NUMBER OF SEQ ID NOS: 40

<210> SEQ ID NO 1
<211> LENGTH: 1413
<212> TYPE: DNA
<213> ORGANISM: Alcaligenes faecalis

<400> SEQUENCE: 1

```
gaacggcagc gcgagagagc ttgctctctt ggcggcgagt ggcggacggg tgagtaatat     60
atcggaacgt gcccagtagc gggggataac tactcgaaag agtggctaat accgcatacg    120
ccctacgggg gaaagggggg gatcgcaaga cctctcacta ttggagcggc cgatatcgga    180
ttagctagtt ggtggggtaa aggctcacca aggcaacgat ccgtagctgg tttgagagga    240
cgaccagcca cactgggact gagacacggc ccagactcct acgggaggca gcagtgggga    300
attttggaca atgggggaaa ccctgatcca gccatcccgc gtgtatgatg aaggccttcg    360
ggttgtaaag tacttttggc agagaagaaa aggtacctcc taatacgagg tactgctgac    420
ggtatctgca gaataagcac cggctaacta cgtgccagca gccgcggtaa tacgtagggt    480
gcaagcgtta atcggaatta ctgggcgtaa agcgtgtgta ggcggttcgg aaagaaagat    540
gtgaaatccc agggctcaac cttggaactg catttttaac tgccgagcta gagtatgtca    600
gaggggggta gaattccacg tgtagcagtg aaatgcgtag atatgtggag gaataccgat    660
ggcgaaggca gccccctggg ataatactga cgctcagaca cgaaagcgtg gggagcaaac    720
aggattagat accctggtag tccacgccct aaacgatgtc aactagctgt tggggccgtt    780
aggccttagt agcgcagcta acgcgtgaag ttgaccgcct ggggagtacg gtcgcaagat    840
taaaactcaa aggaattgac ggggacccgc acaagcggtg gatgatgtgg attaattcga    900
tgcaacgcga aaaaccttac ctacccttga catgtctgga aagccgaaga gatttggccg    960
tgctcgcaag agaaccggaa cacaggtgct gcatggctgt cgtcagctcg tgtcgtgaga   1020
tgttgggtta agtcccgcaa cgagcgcaac ccttgtcatt agttgctacg caagagcact   1080
ctaatgagac tgccggtgac aaaccggagg aaggtgggga tgacgtcaag tcctcatggc   1140
ccttatgggt agggcttcac acgtcataca atggtcggga cagagggtcg ccaacccgcg   1200
agggggagcc aatctcagaa acccgatcgt agtccggatc gcagtctgca actcgactgc   1260
gtgaagtcgg aatcgctagt aatcgcggat cagaatgtcg cggtgaatac gttcccgggt   1320
cttgtacaca ccgcccgtca caccatggga gtgggtttca ccagaagtag gtagcctaac   1380
cgtaaggagg gcgcttacca cggtgggatt cat                                1413
```

<210> SEQ ID NO 2
<211> LENGTH: 1482
<212> TYPE: DNA
<213> ORGANISM: Bacillus altitudinis

<400> SEQUENCE: 2

```
gacttcaccc caatcatctg ccccaccttc ggcggctggc tccataaagg ttacctcacc     60
gacttcgggt gttgcaaact ctcgtggtgt gacgggcggt gtgtacaagg cccgggaacg    120
tattcaccgc ggcatgctga tccgcgatta ctagcgattc cagcttcacg cagtcgagtt    180
gcagactgcg atccgaactg agaacagatt tgtgggattg gctaaacctt gcggtctcgc    240
agccctttgt tctgtccatt gtagcacgtg tgtagcccag gtcataaggg gcatgatgat    300
ttgacgtcat ccccaccttc ctccggtttg tcaccggcag tcaccttaga gtgcccaact    360
gaatgctggc aactaagatc aagggttgcg ctcgttgcgg gacttaaccc aacatctcac    420
gacacgagct gacgacaacc atgcaccacc tgtcactctg tccccgaagg gaaagcccta    480
tctctagggt tgtcagagga tgtcaagacc tggtaaggtt cttcgcgttg cttcgaatta    540
aaccacatgc tccaccgctt gtgcgggccc ccgtcaattc ctttgagttt cagtcttgcg    600
accgtactcc ccaggcggag tgcttaatgc gttagctgca gcactaaggg gcggaaaccc    660
```

```
cctaacactt agcactcatc gtttacggcg tggactacca gggtatctaa tcctgttcgc    720

tccccacgct ttcgctcctc agcgtcagtt acagaccaga gagtcgcctt cgccactggt    780

gttcctccac atctctacgc atttcaccgc tacacgtgga attccactct cctcttctgc    840

actcaagttt cccagtttcc aatgaccctc cccggttgag ccgggggctt tcacatcaga    900

cttaagaaac cgcctgcgag ccctttacgc ccaataattc cggacaacgc ttgccaccta    960

cgtattaccg cggctgctgg cacgtagtta gccgtggctt tctggttagg taccgtcaag   1020

gtgcaagcag ttactcttgc acttgttctt ccctaacaac agagctttac gatccgaaaa   1080

ccttcatcac tcacgcggcg ttgctccgtc agactttcgt ccattgcgga agattcccta   1140

ctgctgcctc ccgtaggagt ctgggccgtg tctcagtccc agtgtggccg atcaccctct   1200

caggtcggct acgcatcgtc gccttggtga gccgttacct caccaactag ctaatgcgcc   1260

gcgggtccat ctgtaagtga cagccgaaac cgtctttcat ccttgaacca tgcggttcaa   1320

ggaactatcc ggtattagct ccggtttccc ggagttatcc cagtcttaca ggcaggttac   1380

ccacgtgtta ctcacccgtc cgccgctaac atccgggagc aagctccctt ctgtccgctc   1440

gacttgcatg tattaggcac gccgccagcg ttcgtcctga gc                      1482
```

```
<210> SEQ ID NO 3
<211> LENGTH: 1435
<212> TYPE: DNA
<213> ORGANISM: Bacillus pumilus

<400> SEQUENCE: 3

tcatctgtcc caccttcggc ggctggctcc ataaaggtta cctcaccgac ttcgggtgtt     60

acaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg ggggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260
```

-continued taagtgacag ccgaaaccgt ctttcatcct tgaaccatgc ggttcaagga actatccggt 1320
attagctccg gtttcccgga gttatcccag tcttacaggc aggttaccca cgtgttactc 1380
acccgtccgc cgctaacatc cgggagcaag ctcccttctg tccgctcgac ttgca 1435

<210> SEQ ID NO 4
<211> LENGTH: 1550
<212> TYPE: DNA
<213> ORGANISM: Bacillus subtilis

<400> SEQUENCE: 4
ttatcggaga gtttgatcct ggctcaggac gaacgctggc ggcgtgccta atacatgcaa 60
gtcgagcgga cagatgggag cttgctccct gatgttagcg gcggacgggt gagtaacacg 120
tgggtaacct gcctgtaaga ctgggataac tccgggaaac cggggctaat accggatgct 180
tgtttgaacc gcatggttca aacataaaag gtggcttcgg ctaccactta cagatggacc 240
cgcggcgcat tagctagttg gtgaggtaac ggctcaccaa ggcaacgatg cgtagccgac 300
ctgagagggt gatcggccac actgggactg agacacggcc cagactccta cgggaggcag 360
cagtagggaa tcttccgcaa tggacgaaag tctgacggag caacgccgcg tgagtgatga 420
aggttttcgg atcgtaaagc tctgttgtta gggaagaaca agtaccgttc gaatagggcg 480
gtaccttgac ggtacctaac cagaaagcca cggctaacta cgtgccagca gccgcggtaa 540
tacgtaggtg gcaagcgttg tccggaatta ttgggcgtaa agggctcgca ggcggtttct 600
taagtctgat gtgaaagccc ccggctcaac cggggagggt cattggaaac tggggaactt 660
gagtgcagaa gaggagagtg gaattccacg tgtagcggtg aaatgcgtag agatgtggag 720
gaacaccagt ggcgaaggcg actctctggt ctgtaactga cgctgaggag cgaaagcgtg 780
gggagcgaac aggattagat accctggtag tccacgccgt aaacgatgag tgctaagtgt 840
tagggggttt ccgcccctta gtgctgcagc taacgcatta agcactccgc ctggggagta 900
cggtcgcaag actgaaactc aaaggaattg acgggggccc gcacaagcgg tggagcatgt 960
ggtttaattc gaagcaacgc gaagaacctt accaggtctt gacatcctct gacaatccta 1020
gagataggac gtccccttcg ggggcagagt gacaggtggt gcatggttgt cgtcagctcg 1080
tgtcgtgaga tgttgggtta agtcccgcaa cgagcgcaac ccttgatctt agttgccagc 1140
attcagttgg gcactctaag gtgactgccg gtgacaaacc ggaggaaggt ggggatgacg 1200
tcaaatcatc atgcccctta tgacctgggc tacacacgtg ctacaatgga cagaacaaag 1260
ggcagcgaaa ccgcgaggtt aagccaatcc cacaaatctg ttctcagttc ggatcgcagt 1320
ctgcaactcg actgcgtgaa gctggaatcg ctagtaatcg cggatcagca tgccgcggtg 1380
aatacgttcc cgggccttgt acacaccgcc cgtcacacca cgagagtttg taacacccga 1440
agtcggtgag gtaacctttt aggagccagc cgccgaaggt gggacagatg attggggtga 1500
agtcgtaaca aggtagccgt atcggaaggt gcggctggat cacctccttt 1550

<210> SEQ ID NO 5
<211> LENGTH: 1523
<212> TYPE: DNA
<213> ORGANISM: Janthinobacterium lividum

<400> SEQUENCE: 5
aaggaggtga tccagccgca ccttccgata cggctacctt gttacgactt caccccagtc 60
acgaatccta ccgtggtaag cgccctcctt acggttaagc tacctacttc tggtaaaacc 120
cgctcccatg gtgtgacggg cggtgtgtac aagacccggg aacgtattca ccgcgacatg 180

```
ctgatccgcg attactagcg attccaactt catgcagtcg agttgcagac tacaatccgg    240

actacgatac actttctgcg attagctccc cctcgcgggt tggcggcgct ctgtatgtac    300

cattgtatga cgtgtgaagc cctacccata agggccatga ggacttgacg tcatccccac    360

cttcctccgg tttgtcaccg gcagtctcat tagagtgccc tttcgtagca actaatgaca    420

agggttgcgc tcgttgcggg acttaaccca acatctcacg acacgagctg acgacagcca    480

tgcagcacct gtgtactggt tctctttcga gcactcccca atctctcgag gattccagcc    540

atgtcaaggg taggtaaggt tttcgcgtt gcatcgaatt aatccacatc atccaccgct    600

tgtgcgggtc cccgtcaatt cctttgagtt ttaatcttgc gaccgtactc cccaggcggt    660

ctacttcacg cgttagctgc gttaccaagt caattaagac ccgacaacta gtagacatcg    720

tttagggcgt ggactaccag ggtatctaat cctgtttgct ccccacgctt tcgtgcatga    780

gcgtcaatct tgacccaggg ggctgccttc gccatcggtg ttcctccaca tatctacgca    840

tttcactgct acacgtggaa ttctaccccc ctctgccaga ttctagcctt gcagtctcca    900

atgcaattcc caggttgagc ccggggattt cacatcagac ttacaaaacc gcctgcgcac    960

gctttacgcc cagtaattcc gattaacgct tgcaccctac gtattaccgc ggctgctggc   1020

acgtagttag ccggtgctta ttcttcaggt accgtcatta gcaagagata ttagctctca   1080

ccgtttcttc cctgacaaaa gagctttaca acccgaaggc cttcttcact cacgcggcat   1140

tgctggatca ggctttcgcc cattgtccaa aattccccac tgctgcctcc cgtaggagtc   1200

tggaccgtgt ctcagttcca gtgtggctgg tcgtcctctc agaccagcta ctgatcgatg   1260

ccttggtagg cttttaccct accaactagc taatcagata tcggccgctc cacgagcatg   1320

aggtcttgcg atcccccact ttcatcctta gatcgtatgc ggtattagcg taactttcgc   1380

tacgttatcc cccactctag ggtacgttcc gatatattac tcacccgttc gccactcgcc   1440

accagagcaa gctccgtgct gccgttcgac ttgcatgtgt aaggcatgcc gccagcgttc   1500

aatctgagcc aggatcaaac tct                                           1523
```

<210> SEQ ID NO 6
<211> LENGTH: 780
<212> TYPE: DNA
<213> ORGANISM: Unknown
<220> FEATURE:
<221> NAME/KEY: source
<223> OTHER INFORMATION: /note="Description of Unknown: HDLJNHPI_02397 ycgJ putative methyltransferase sequence"

<400> SEQUENCE: 6

```
atggctatca attttcatga tcaaaagaat cgcaaaacct acgccactcg tgaggcggac     60

ggctcctggg tgcaagctat cgaaaccctg atcaacctgt tcggtttgcg tgtggccgat    120

ataggttgcg gcggcgggat ttattcctcg gcctttctgg atcagggcgc aagcagcgtg    180

gtgggcgtgg atttttctca ggccatgatt tctggcgctc aagaacgcaa tgcgggccgg    240

gaggggattg agttccgtca gggggacgcg acggcgaccg gcttgccctc tgagagtgtg    300

gacctggttt ttcagcgcgc cttgattcat cacctgacag actatgaggc ctgctttacc    360

gaagccaagc gtttgctggt tccgggtggc gctttgctgg tgcaggaccg gacggcggtg    420

gatgtgcagc agcctgcttc agcctctcat ttgcggggct acttctttga atgtttcccc    480

cgcctgttgg aggtggagct gaaacgccgc cccgatacgt ccaaggtaca ggcagcactg    540

caggccgtcg gttttgtgga tctgcaatcc agcaccgtgt gggaagaccg gcgctactac    600
```

```
aacagctttg aggactatgc tcaggagctg gtccagcgta ccgggcgctc tatcttgcat    660

gagctaagtg acgccgagct gcaagagctg atcgactata ttcgcgcccg agttcctgcg    720

aatcagtcct ttgtggagcg tgattgctgg accttgtggt taggcaagcg gggcagataa    780


<210> SEQ ID NO 7
<211> LENGTH: 1482
<212> TYPE: DNA
<213> ORGANISM: Bacillus altidudinis

<400> SEQUENCE: 7

gacttcaccc caatcatctg ccccaccttc ggcggctggc tccataaagg ttacctcacc     60

gacttcgggt gttgcaaact ctcgtggtgt gacgggcggt gtgtacaagg cccgggaacg    120

tattcaccgc ggcatgctga tccgcgatta ctagcgattc cagcttcacg cagtcgagtt    180

gcagactgcg atccgaactg agaacagatt tgtgggattg gctaaacctt gcggtctcgc    240

agccctttgt tctgtccatt gtagcacgtg tgtagcccag gtcataaggg gcatgatgat    300

ttgacgtcat ccccaccttc ctccggtttg tcaccggcag tcaccttaga gtgcccaact    360

aaatgctggc aactaagatc aagggttgcg ctcgttgcgg gacttaaccc aacatctcac    420

gacacgagct gacgacaacc atgcaccacc tgtcactctg tccccgaagg gaaagcccta    480

tctctagggt tgtcagagga tgtcaagacc tggtaaggtt cttcgcgttg cttcgaatta    540

aaccacatgc tccaccgctt gtgcgggccc ccgtcaattc ctttgagttt cagtcttgcg    600

accgtactcc ccaggcggag tgcttaatgc gttagctgca gcactaaggg gcggaaaccc    660

cctaacactt agcactcatc gtttacggcg tggactacca gggtatctaa tcctgttcgc    720

tccccacgct ttcgctcctc agcgtcagtt acagaccaga gagtcgcctt cgccactggt    780

gttcctccac atctctacgc atttcaccgc tacacgtgga attccactct cctcttctgc    840

actcaagttt cccagtttcc aatgaccctc cccggttgag ccgggggctt tcacatcaga    900

cttaagaaac cgcctgcgag ccctttacgc ccaataattc cggacaacgc ttgccaccta    960

cgtattaccg cggctgctgg cacgtagtta gccgtggctt tctggttagg taccgtcaag   1020

gtgcaagcag ttactcttgc acttgttctt ccctaacaac agagctttac gatccgaaaa   1080

ccttcatcac tcacgcggcg ttgctccgtc agactttcgt ccattgcgga agattcccta   1140

ctgctgcctc ccgtaggagt ctgggccgtg tctcagtccc agtgtggccg atcaccctct   1200

caggtcggct acgcatcgtc gccttggtga gccgttacct caccaactag ctaatgcgcc   1260

gcgggtccat ctgtaagtga cagccgaaac cgtctttcat ccttgaacca tgcggttcaa   1320

ggaactatcc ggtattagct ccggtttccc ggagttatcc cagtcttaca ggcaggttac   1380

ccacgtgtta ctcacccgtc cgccgctaac atccgggagc aagctccctt ctgtccgctc   1440

gacttgcatg tattaggcac gccgccagcg ttcgtcctga gc                      1482


<210> SEQ ID NO 8
<211> LENGTH: 1482
<212> TYPE: DNA
<213> ORGANISM: Bacillus altidudinis

<400> SEQUENCE: 8

gacttcaccc caatcatctg ccccaccttc ggcggctggc tccataaagg ttacctcacc     60

gacttcgggt gttgcaaact ctcgtggtgt gacgggcggt gtgtacaagg cccgggaacg    120

tattcaccgc ggcatgctga tccgcgatta ctagcgattc cagcttcacg cagtcgagtt    180

gcagactgcg atccgaactg agaacagatt tgtgggattg gctaaacctt gcggtctcgc    240
```

```
agccctttgt tctgtccatt gtagcacgtg tgtagcccag gtcataaggg gcatgatgat    300
ttgacgtcat ccccaccttc ctccggtttg tcaccggcag tcaccttaga gtgcccaact    360
gaatgctggc aactaagatc aagggttgcg ctcgttgcgg gacttaaccc aacatctcac    420
gacacgagct gacgacaacc atgcaccacc tgtcactctg tccccgaagg gaaagcccta    480
tctctagggt tgtcagagga tgtcaagacc tggtaaggtt cttcgcgttg cttcgaatta    540
aaccacatgc tccaccgctt gtgcgggccc ccgtcaattc ctttgagttt cagtcttgcg    600
accgtactcc ccaggcggag tgcttaatgc gttagctgca gcactaaggg gcggaaaccc    660
cctaacactt agcactcatc gtttacggcg tggactacca gggtatctaa tcctgttcgc    720
tccccacgct ttcgctcctc agcgtcagtt acagaccaga gagtcgcctt cgccactggt    780
gttcctccac atctctacgc atttcaccgc tacacgtgga attccactct cctcttctgc    840
actcaagttt cccagtttcc aatgaccctc cccggttgag ccgggggctt tcacatcaga    900
cttaagaaac cgcctgcgag ccctttacgc ccaataattc cggacaacgc ttgccaccta    960
cgtattaccg cggctgctgg cacgtagtta gccgtggctt tctggttagg taccgtcaag   1020
gtgcaagcag ttactcttgc acttgttctt ccctaacaac agagctttac gatccgaaaa   1080
ccttcatcac tcacgcggcg ttgctccgtc agactttcgt ccattgcgga agattcccta   1140
ctgctgcctc ccgtaggagt ctgggccgtg tctcagtccc agtgtggccg atcaccctct   1200
caggtcggct acgcatcgtc gccttggtga gccgttacct caccaactag ctaatgcgcc   1260
gcgggtccat ctgtaagtga cagccgaaac cgtctttcat ccttgaacca tgcggttcaa   1320
ggaactatcc ggtattagct ccggtttccc ggagttatcc cagtcttaca ggcaggttac   1380
ccacgtgtta ctcacccgtc cgccgctaac atccgggagc aagctccctt ctgtccgctc   1440
gacttgcatg tattaggcac gccgccagcg ttcgtcctga gc                      1482
```

<210> SEQ ID NO 9
<211> LENGTH: 1482
<212> TYPE: DNA
<213> ORGANISM: Bacillus altidudinis

<400> SEQUENCE: 9

```
gacttcaccc caatcatctg ccccaccttc ggcggctggc tccataaagg ttacctcacc     60
gacttcgggt gttgcaaact ctcgtggtgt gacgggcggt gtgtacaagg cccgggaacg    120
tattcaccgc ggcatgctga tccgcgatta ctagcgattc cagcttcacg cagtcgagtt    180
gcagactgcg atccgaactg agaacagatt tgtgggattg gctaaacctt gcggtctcgc    240
agccctttgt tctgtccatt gtagcacgtg tgtagcccag gtcataaggg gcatgatgat    300
ttgacgtcat ccccaccttc ctccggtttg tcaccggcag tcaccttaga gtgcccaact    360
gaatgctggc aactaagatc aagggttgcg ctcgttgcgg gacttaaccc aacatctcac    420
gacacgagct gacgacaacc atgcaccacc tgtcactctg tccccgaagg gaaagcccta    480
tctctagggt tgtcagagga tgtcaagacc tggtaaggtt cttcgcgttg cttcgaatta    540
aaccacatgc tccaccgctt gtgcgggccc ccgtcaattc ctttgagttt cagtcttgcg    600
accgtactcc ccaggcggag tgcttaatgc gttagctgca gcactaaggg gcggaaaccc    660
cctaacactt agcactcatc gtttacggcg tggactacca gggtatctaa tcctgttcgc    720
tccccacgct ttcgctcctc agcgtcagtt acagaccaga gagtcgcctt cgccactggt    780
gttcctccac atctctacgc atttcaccgc tacacgtgga attccactct cctcttctgc    840
```

```
actcaagttt cccagtttcc aatgaccctc cccggttgag ccgggggctt tcacatcaga    900
cttaagaaac cgcctgcgag ccctttacgc ccaataattc cggacaacgc ttgccaccta    960
cgtattaccg cggctgctgg cacgtagtta gccgtggctt tctggttagg taccgtcaag   1020
gtgcaagcag ttactcttgc acttgttctt ccctaacaac agagctttac gatccgaaaa   1080
ccttcatcac tcacgcggcg ttgctccgtc agactttcgt ccattgcgga agattcccta   1140
ctgctgcctc ccgtaggagt ctgggccgtg tctcagtccc agtgtggccg atcaccctct   1200
caggtcggct acgcatcgtc gccttggtga gccgttacct caccaactag ctaatgcgcc   1260
gcgggtccat ctgtaagtga cagccgaaac cgtctttcat ccttgaacca tgcggttcaa   1320
ggaactatcc ggtattagct ccggtttccc ggagttatcc cagtcttaca ggcaggttac   1380
ccacgtgtta ctcacccgtc cgccgctaac atccgggagc aagctccctt ctgtccgctc   1440
gacttgcatg tattaggcac gccgccagcg ttcgtcctga gc                      1482
```

```
<210> SEQ ID NO 10
<211> LENGTH: 1482
<212> TYPE: DNA
<213> ORGANISM: Bacillus altidudinis

<400> SEQUENCE: 10
```

```
gacttcaccc caatcatctg ccccaccttc ggcggctggc tccataaagg ttacctcacc     60
gacttcgggt gttgcaaact ctcgtggtgt gacgggcggt gtgtacaagg cccgggaacg    120
tattcaccgc ggcatgctga tccgcgatta ctagcgattc cagcttcacg cagtcgagtt    180
gcagactgcg atccgaactg agaacagatt tgtgggattg gctaaacctt gcggtctcgc    240
agccctttgt tctgtccatt gtagcacgtg tgtagcccag gtcataaggg gcatgatgat    300
ttgacgtcat ccccaccttc ctccggtttg tcaccggcag tcaccttaga gtgcccaact    360
gaatgctggc aactaagatc aagggttgcg ctcgttgcgg gacttaaccc aacatctcac    420
gacacgagct gacgacaacc atgcaccacc tgtcactctg tccccgaagg gaaagcccta    480
tctctagggt tgtcagagga tgtcaagacc tggtaaggtt cttcgcgttg cttcgaatta    540
aaccacatgc tccaccgctt gtgcgggccc ccgtcaattc ctttgagttt cagtcttgcg    600
accgtactcc ccaggcggag tgcttaatgc gttagctgca gcactaaggg gcggaaaccc    660
cctaacactt agcactcatc gtttacggcg tggactacca gggtatctaa tcctgttcgc    720
tccccacgct ttcgctcctc agcgtcagtt acagaccaga gagtcgcctt cgccactggt    780
gttcctccac atctctacgc atttcaccgc tacacgtgga attccactct cctcttctgc    840
actcaagttt cccagtttcc aatgaccctc cccggttgag ccgggggctt tcacatcaga    900
cttaagaaac cgcctgcgag ccctttacgc ccaataattc cggacaacgc ttgccaccta    960
cgtattaccg cggctgctgg cacgtagtta gccgtggctt tctggttagg taccgtcaag   1020
gtgcaagcag ttactcttgc acttgttctt ccctaacaac agagctttac gatccgaaaa   1080
ccttcatcac tcacgcggcg ttgctccgtc agactttcgt ccattgcgga agattcccta   1140
ctgctgcctc ccgtaggagt ctgggccgtg tctcagtccc agtgtggccg atcaccctct   1200
caggtcggct acgcatcgtc gccttggtga gccgttacct caccaactag ctaatgcgcc   1260
gcgggtccat ctgtaagtga cagccgaaac cgtctttcat ccttgaacca tgcggttcaa   1320
ggaactatcc ggtattagct ccggtttccc ggagttatcc cagtcttaca ggcaggttac   1380
ccacgtgtta ctcacccgtc cgccgctaac atccgggagc aagctccctt ctgtccgctc   1440
gacttgcatg tattaggcac gccgccagcg ttcgtcctga gc                      1482
```

<210> SEQ ID NO 11
<211> LENGTH: 1482
<212> TYPE: DNA
<213> ORGANISM: Bacillus altidudinis

<400> SEQUENCE: 11
gctcaggacg aacgctggcg gcgtgcctaa tacatgcaag tcgagcggac agaagggagc 60
ttgctcccgg atgttagcgg cggacgggtg agtaacacgt gggtaacctg cctgtaagac 120
tgggataact ccgggaaacc ggagctaata ccggatagtt ccttgaaccg catggttcaa 180
ggatgaaaga cggtttcggc tgtcacttac agatggaccc gcggcgcatt agctagttgg 240
tgaggtaacg gctcaccaag gcgacgatgc gtagccgacc tgagagggtg atcggccaca 300
ctgggactga gacacggccc agactcctac gggaggcagc agtagggaat cttccgcaat 360
ggacgaaagt ctgacggagc aacgccgcgt gagtgatgaa ggttttcgga tcgtaaagct 420
ctgttgttag ggaagaacaa gtgcaagagt aactgcttgc accttgacgg tacctaacca 480
gaaagccacg gctaactacg tgccagcagc cgcggtaata cgtaggtggc aagcgttgtc 540
cggaattatt gggcgtaaag ggctcgcagg cggtttctta agtctgatgt gaaagccccc 600
ggctcaaccg gggagggtca ttggaaactg ggaaacttga gtgcagaaga ggagagtgga 660
attccacgtg tagcggtgaa atgcgtagag atgtggagga acaccagtgg cgaaggcgac 720
tctctggtct gtaactgacg ctgaggagcg aaagcgtggg gagcgaacag gattagatac 780
cctggtagtc cacgccgtaa acgatgagtg ctaagtgtta gggggtttcc gccccttagt 840
gctgcagcta acgcattaag cactccgcct ggggagtacg gtcgcaagac tgaaactcaa 900
aggaattgac gggggcccgc acaagcggtg gagcatgtgg tttaattcga agcaacgcga 960
agaaccttac caggtcttga catcctctga caaccctaga gatagggctt tcccttcggg 1020
gacagagtga caggtggtgc atggttgtcg tcagctcgtg tcgtgagatg ttgggttaag 1080
tcccgcaacg agcgcaaccc ttgatcttag ttgccagcat ttagttgggc actctaaggt 1140
gactgccggt gacaaaccgg aggaaggtgg ggatgacgtc aaatcatcat gccccttatg 1200
acctgggcta cacacgtgct acaatggaca gaacaaaggg ctgcgagacc gcaaggttta 1260
gccaatccca caaatctgtt ctcagttcgg atcgcagtct gcaactcgac tgcgtgaagc 1320
tggaatcgct agtaatcgcg gatcagcatg ccgcggtgaa tacgttcccg ggccttgtac 1380
acaccgcccg tcacaccacg agagtttgca acacccgaag tcggtgaggt aacctttatg 1440
gagccagccg ccgaaggtgg ggcagatgat tggggtgaag tc 1482

<210> SEQ ID NO 12
<211> LENGTH: 1482
<212> TYPE: DNA
<213> ORGANISM: Bacillus altidudinis

<400> SEQUENCE: 12
gctcaggacg aacgctggcg gcgtgcctaa tacatgcaag tcgagcggac agaagggagc 60
ttgctcccgg atgttagcgg cggacgggtg agtaacacgt gggtaacctg cctgtaagac 120
tgggataact ccgggaaacc ggagctaata ccggatagtt ccttgaaccg catggttcaa 180
ggatgaaaga cggtttcggc tgtcacttac agatggaccc gcggcgcatt agctagttgg 240
tgaggtaacg gctcaccaag gcgacgatgc gtagccgacc tgagagggtg atcggccaca 300
ctgggactga gacacggcca agactcctac gggaggcagc agtagggaat cttccgcaat 360

```
ggacgaaagt ctgacggagc aacgccgcgt gagtgatgaa ggttttcgga tcgtaaagct    420

ctgttgttag ggaagaacaa gtgcaagagt aactgcttgc accttgacgg tacctaacca    480

gaaagccacg gctaactacg tgccagcagc cgcggtaata cgtaggtggc aagcgttgtc    540

cggaattatt gggcgtaaag ggctcgcagg cggtttctta agtctgatgt gaaagccccc    600

ggctcaaccg gggagggtca ttggaaactg ggaaacttga gtgcagaaga ggagagtgga    660

attccacgtg tagcggtgaa atgcgtagag atgtggagga acaccagtgg cgaaggcgac    720

tctctggtct gtaactgacg ctgaggagcg aaagcgtggg gagcgaacag gattagatac    780

cctggtagtc cacgccgtaa acgatgagtg ctaagtgtta gggggtttcc gccccttagt    840

gctgcagcta acgcattaag cactccgcct ggggagtacg gtcgcaagac tgaaactcaa    900

aggaattgac gggggcccgc acaagcggtg gagcatgtgg tttaattcga agcaacgcga    960

agaaccttac caggtcttga catcctctga caaccctaga gatagggctt tcccttcggg   1020

gacagagtga caggtggtgc atggttgtcg tcagctcgtg tcgtgagatg ttgggttaag   1080

tcccgcaacg agcgcaaccc ttgatcttag ttgccagcat ttagttgggc actctaaggt   1140

gactgccggt gacaaaccgg aggaaggtgg ggatgacgtc aaatcatcat gccccttatg   1200

acctgggcta cacacgtgct acaatggaca gaacaaaggg ctgcgagacc gcaaggttta   1260

gccaatccca caaatctgtt ctcagttcgg atcgcagtct gcaactcgac tgcgtgaagc   1320

tggaatcgct agtaatcgcg gatcagcatg ccgcggtgaa tacgttcccg ggccttgtac   1380

acaccgcccg tcacaccacg agagtttgca acacccgaag tcggtgaggt aacctttatg   1440

gagccagccg ccgaaggtgg ggcagatgat tggggtgaag tc                      1482
```

<210> SEQ ID NO 13
<211> LENGTH: 1421
<212> TYPE: DNA
<213> ORGANISM: Bacillus pumilus

<400> SEQUENCE: 13

```
tcatctgtcc caccttcggc ggctggctcc ataaaggtta cctcaccgac ttcgggtgtt     60

acaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaaccccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg gggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020
```

```
ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg t                        1421
```

<210> SEQ ID NO 14
<211> LENGTH: 1435
<212> TYPE: DNA
<213> ORGANISM: Bacillus pumilus

<400> SEQUENCE: 14

```
tcatctgccc caccttcggc ggctggctcc ataaaggtta cctcaccgac ttcgggtgtt     60

gcaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg gggggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca         1435
```

<210> SEQ ID NO 15
<211> LENGTH: 1435
<212> TYPE: DNA
<213> ORGANISM: Bacillus pumilus

<400> SEQUENCE: 15

```
tcatctgccc caccttcggc ggctggctcc ataaaggtta cctcaccgac ttcgggtgtt     60

gcaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccct aacacttagc     660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagttcccc    840

agtttccaat gaccctcccc ggttgagccg ggggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca         1435
```

<210> SEQ ID NO 16
<211> LENGTH: 1435
<212> TYPE: DNA
<213> ORGANISM: Bacillus pumilus

<400> SEQUENCE: 16

```
tcatctgtcc caccttcggc ggctggctcc ataaaggtta cctcaccgac ttcgggtgtt     60

acaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccct aacacttagc     660

actcatcgtt tacggcgtgg actaccaggg tatctaatcc tgttcgctcc ccacgctttc    720
```

gctcctcagc gtcagttaca gaccagagag tcgccttcgc cactggtgtt cctccacatc 780
tctacgcatt tcaccgctac acgtggaatt ccactctcct cttctgcact caagtttccc 840
agtttccaat gaccctcccc ggttgagccg gggctttca catcagactt aagaaaccgc 900
ctgcgagccc tttacgccca ataattccgg acaacgcttg ccacctacgt attaccgcgg 960
ctgctggcac gtagttagcc gtggctttct ggttaggtac cgtcaaggtg cgagcagtta 1020
ctctcgcact tgttcttccc taacaacaga gctttacgat ccgaaaacct tcatcactca 1080
cgcggcgttg ctccgtcaga ctttcgtcca ttgcggaaga ttccctactg ctgcctcccg 1140
taggagtctg ggccgtgtct cagtcccagt gtggccgatc accctctcag gtcggctacg 1200
catcgtcgcc ttggtgagcc attaccccac caactagcta atgcgccgcg ggtccatctg 1260
taagtgacag ccgaaaccgt ctttcatcct tgaaccatgc ggttcaagga actatccggt 1320
attagctccg gtttcccgga gttatcccag tcttacaggc aggttaccca cgtgttactc 1380
acccgtccgc cgctaacatc cgggagcaag ctcccttctg ttcgctcgac ttgca 1435

<210> SEQ ID NO 17
<211> LENGTH: 808
<212> TYPE: DNA
<213> ORGANISM: Bacillus pumilus

<400> SEQUENCE: 17
gcactaaggg gcggaaaccc cctaacactt agcactcatc gtttacggcg tggactacca 60
gggtatctaa tcctgttcgc tccccacgct ttcgctcctc agcgtcagtt acagaccaga 120
gagtcgcctt cgccactggt gttcctccac atctctacgc atttcaccgc tacacgtgga 180
attccactct cctcttctgc actcaagttt cccagtttcc aatgaccctc cccggttgag 240
ccgggggctt tcacatcaga cttaagaaac cgcctgcgag ccctttacgc ccaataattc 300
cggacaacgc ttgccaccta cgtattaccg cggctgctgg cacgtagtta gccgtggctt 360
tctggttagg taccgtcaag gtgcgagcag ttactctcgc acttgttctt ccctaacaac 420
agagctttac gatccgaaaa ccttcatcac tcacgcggcg ttgctccgtc agactttcgt 480
ccattgcgga agattcccta ctgctgcctc ccgtaggagt ctgggccgtg tctcagtccc 540
agtgtggccg atcaccctct caggtcggct acgcatcgtc gccttggtga gccattaccc 600
caccaactag ctaatgcgcc gcgggtccat ctgtaagtga cagccgaaac cgtctttcat 660
ccttgaacca tgcggttcaa ggaactatcc ggtattagct ccggtttccc ggagttatcc 720
cagtcttaca ggcaggttac ccacgtgtta ctcacccgtc cgccgctaac atccgggagc 780
aagctccctt ctgttcgctc gacttgca 808

<210> SEQ ID NO 18
<211> LENGTH: 1435
<212> TYPE: DNA
<213> ORGANISM: Bacillus pumilus

<400> SEQUENCE: 18
tcatctgccc caccttcggc ggctggctcc ataaaggtta cctcaccgac ttcgggtgtt 60
gcaaactctc gtggtgtgac gggcggtgtg tacaaggccc gggaacgtat tcaccgcggc 120
atgctgatcc gcgattacta gcgattccag cttcacgcag tcgagttgca gactgcgatc 180
cgaactgaga acagatttat gggattggct aaaccttgcg gtctcgcagc cctttgttct 240
gtccattgta gcacgtgtgt agcccaggtc ataaggggca tgatgatttg acgtcatccc 300

```
caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg gggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca        1435


<210> SEQ ID NO 19
<211> LENGTH: 1367
<212> TYPE: DNA
<213> ORGANISM: Bacillus pumilus

<400> SEQUENCE: 19

tcgtggtgtg acgggcggtg tgtacaaggc ccgggaacgt attcaccgcg gcatgctgat     60

ccgcgattac tagcgattcc agcttcacgc agtcgagttg cagactgcga tccgaactga    120

gaacagattt gtgggattgg ctaaaccttg cggtctcgca gccctttgtt ctgtccattg    180

tagcacgtgt gtagcccagg tcataagggg catgatgatt tgacgtcatc cccaccttcc    240

tccggtttgt caccggcagt caccttagag tgcccaactg aatgctggca actaagatca    300

agggttgcgc tcgttgcggg acttaaccca acatctcacg acacgagctg acgacaacca    360

tgcaccacct gtcactctgt ccccgaaggg aaagccctat ctctagggtt gtcagaggat    420

gtcaagacct ggtaaggttc ttcgcgttgc ttcgaattaa accacatgct ccaccgcttg    480

tgcgggcccc cgtcaattcc tttgagtttc agtcttgcga ccgtactccc caggcggagt    540

gcttaatgcg ttagctgcag cactaagggg cggaaacccc ctaacactta gcactcatcg    600

tttacggcgt ggactaccag ggtatctaat cctgttcgct ccccacgctt tcgctcctca    660

gcgtcagtta cagaccagag agtcgccttc gccactggtg ttcctccaca tctctacgca    720

tttcaccgct acacgtggaa ttccactctc ctcttctgca ctcaagtttc ccagtttcca    780

atgaccctcc ccggttgagc cgggggcttt cacatcagac ttaagaaacc gcctgcgagc    840

cctttacgcc caataattcc ggacaacgct tgccacctac gtattaccgc ggctgctggc    900

acgtagttag ccgtggcttt ctggttaggt accgtcaagg tgcaagcagt tactcttgca    960

cttgttcttc cctaacaaca gagctttacg atccgaaaac cttcatcact cacgcggcgt   1020
```

```
tgctccgtca gactttcgtc cattgcggaa gattccctac tgctgcctcc cgtaggagtc   1080

tgggccgtgt ctcagtccca gtgtggccga tcaccctctc aggtcggcta cgcatcgtcg   1140

ccttggtgag ccgttacctc accaactagc taatgcgccg cgggtccatc tgtaagtgac   1200

agccgaaacc gtctttcatc cttgaaccat gcggttcaag gaactatccg gtattagctc   1260

cggtttcccg gagttatccc agtcttacag gcaggttacc cacgtgttac tcacccgtcc   1320

gccgctaaca tccgggagca agctcccttc tgtccgctcg acttgca                 1367


<210> SEQ ID NO 20
<211> LENGTH: 1421
<212> TYPE: DNA
<213> ORGANISM: Bacillus pumilus

<400> SEQUENCE: 20

tcatctgccc caccttcggc ggctggctcc ataaaggtta cctcaccgac ttcgggtgtt     60

gcaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg gggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg t                       1421


<210> SEQ ID NO 21
<211> LENGTH: 1117
<212> TYPE: DNA
<213> ORGANISM: Bacillus pumilus

<400> SEQUENCE: 21

caccggcagt caccttagag tgcccaacta aatgctggca actaagatca agggttgcgc     60
```

-continued

```
tcgttgcggg acttaaccca acatctcacg acacgagctg acgacaacca tgcaccacct    120
gtcactctgt ccccgaaggg aaagccctat ctctagggtt gtcagaggat gtcaagacct    180
ggtaaggttc ttcgcgttgc ttcgaattaa accacatgct ccaccgcttg tgcgggcccc    240
cgtcaattcc tttgagtttc agtcttgcga ccgtactccc caggcggagt gcttaatgcg    300
ttagctgcag cactaagggg cggaaacccc ctaacactta gcactcatcg tttacggcgt    360
ggactaccag ggtatctaat cctgttcgct ccccacgctt tcgctcctca gcgtcagtta    420
cagaccagag agtcgccttc gccactggtg ttcctccaca tctctacgca tttcaccgct    480
acacgtggaa ttccactctc ctcttctgca ctcaagtttc ccagtttcca atgaccctcc    540
ccggttgagc cgggggcttt cacatcagac ttaagaaacc gcctgcgagc cctttacgcc    600
caataattcc ggacaacgct tgccacctac gtattaccgc ggctgctggc acgtagttag    660
ccgtggcttt ctggttaggt accgtcaagg tgcgagcagt tactctcgca cttgttcttc    720
cctaacaaca gagctttacg atccgaaaac cttcatcact cacgcggcgt tgctccgtca    780
gactttcgtc cattgcggaa gattccctac tgctgcctcc cgtaggagtc tgggccgtgt    840
ctcagtccca gtgtggccga tcaccctctc aggtcggcta cgcatcgtcg ccttggtgag    900
ccattacccc accaactagc taatgcgccg cgggtccatc tgtaagtgac agccgaaacc    960
gtctttcatc cttgaaccat gcggttcaag gaactatccg gtattagctc cggtttcccg   1020
gagttatccc agtcttacag gcaggttacc cacgtgttac tcacccgtcc gccgctaaca   1080
tccgggagca agctcccttc tgtccgctcg acttgca                            1117
```

<210> SEQ ID NO 22
<211> LENGTH: 1435
<212> TYPE: DNA
<213> ORGANISM: Bacillus pumilus

<400> SEQUENCE: 22

```
tcatctgtcc caccttcggc ggctggctcc ataaaggtta cctcaccgac ttcgggtgtt     60
acaaactctc gtggtgtgac gggcggtgtg tacaaggccc gggaacgtat tcaccgcggc    120
atgctgatcc gcgattacta gcgattccag cttcacgcag tcgagttgca gactgcgatc    180
cgaactgaga acagatttat gggattggct aaaccttgcg gtctcgcagc cctttgttct    240
gtccattgta gcacgtgtgt agcccaggtc ataaggggca tgatgatttg acgtcatccc    300
caccttcctc cggtttgtca ccggcagtca ccttagagtg cccaactaaa tgctggcaac    360
taagatcaag ggttgcgctc gttgcgggac ttaacccaac atctcacgac acgagctgac    420
gacaaccatg caccacctgt cactctgtcc ccgaagggaa agccctatct ctagggttgt    480
cagaggatgt caagacctgg taaggttctt cgcgttgctt cgaattaaac cacatgctcc    540
accgcttgtg cgggcccccg tcaattcctt tgagtttcag tcttgcgacc gtactcccca    600
ggcggagtgc ttaatgcgtt agctgcagca ctaaggggcg gaaaccccct aacacttagc    660
actcatcgtt tacggcgtgg actaccaggg tatctaatcc tgttcgctcc ccacgctttc    720
gctcctcagc gtcagttaca gaccagagag tcgccttcgc cactggtgtt cctccacatc    780
tctacgcatt tcaccgctac acgtggaatt ccactctcct cttctgcact caagtttccc    840
agtttccaat gaccctcccc ggttgagccg ggggctttca catcagactt aagaaaccgc    900
ctgcgagccc tttacgccca ataattccgg acaacgcttg ccacctacgt attaccgcgg    960
ctgctggcac gtagttagcc gtggctttct ggttaggtac cgtcaaggtg cgagcagtta   1020
ctctcgcact tgttcttccc taacaacaga gctttacgat ccgaaaacct tcatcactca   1080
```

```
cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca        1435


<210> SEQ ID NO 23
<211> LENGTH: 1435
<212> TYPE: DNA
<213> ORGANISM: Bacillus pumilus

<400> SEQUENCE: 23

tcatctgtcc caccttcggc ggctggctcc ataaaggtta cctcaccgac ttcgggtgtt     60

acaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccccc aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg ggggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca        1435


<210> SEQ ID NO 24
<211> LENGTH: 1435
<212> TYPE: DNA
<213> ORGANISM: Bacillus pumilus

<400> SEQUENCE: 24

tcatctgccc caccttcggc ggctggctcc ataaaggtta cctcaccgac ttcgggtgtt     60
```

```
gcaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg gggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca        1435


<210> SEQ ID NO 25
<211> LENGTH: 1435
<212> TYPE: DNA
<213> ORGANISM: Bacillus pumilus

<400> SEQUENCE: 25

tcatctgccc caccttcggc ggctggctcc ataaaggtta cctcaccgac ttcgggtgtt     60

gcaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780
```

```
tctacgcatt tcaccgctac acgtggaatt ccactctcct cttctgcact caagtttccc    840

agtttccaat gaccctcccc ggttgagccg gggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca         1435
```

<210> SEQ ID NO 26
<211> LENGTH: 1435
<212> TYPE: DNA
<213> ORGANISM: Bacillus pumilus

<400> SEQUENCE: 26

```
tcatctgccc caccttcggc ggctggctcc ataaaggtta cctcaccgac ttcgggtgtt     60

gcaaactctc gtggtgtgac gggcggtgtg tacaaggccc gggaacgtat tcaccgcggc    120

atgctgatcc gcgattacta gcgattccag cttcacgcag tcgagttgca gactgcgatc    180

cgaactgaga acagatttat gggattggct aaaccttgcg gtctcgcagc cctttgttct    240

gtccattgta gcacgtgtgt agcccaggtc ataaggggca tgatgatttg acgtcatccc    300

caccttcctc cggtttgtca ccggcagtca ccttagagtg cccaactaaa tgctggcaac    360

taagatcaag ggttgcgctc gttgcgggac ttaacccaac atctcacgac acgagctgac    420

gacaaccatg caccacctgt cactctgtcc ccgaagggaa agccctatct ctagggttgt    480

cagaggatgt caagacctgg taaggttctt cgcgttgctt cgaattaaac cacatgctcc    540

accgcttgtg cgggcccccg tcaattcctt tgagtttcag tcttgcgacc gtactcccca    600

ggcggagtgc ttaatgcgtt agctgcagca ctaaggggcg gaaacccccct aacacttagc    660

actcatcgtt tacggcgtgg actaccaggg tatctaatcc tgttcgctcc ccacgctttc    720

gctcctcagc gtcagttaca gaccagagag tcgccttcgc cactggtgtt cctccacatc    780

tctacgcatt tcaccgctac acgtggaatt ccactctcct cttctgcact caagtttccc    840

agtttccaat gaccctcccc ggttgagccg gggctttca catcagactt aagaaaccgc    900

ctgcgagccc tttacgccca ataattccgg acaacgcttg ccacctacgt attaccgcgg    960

ctgctggcac gtagttagcc gtggctttct ggttaggtac cgtcaaggtg cgagcagtta   1020

ctctcgcact tgttcttccc taacaacaga gctttacgat ccgaaaacct tcatcactca   1080

cgcggcgttg ctccgtcaga ctttcgtcca ttgcggaaga ttccctactg ctgcctcccg   1140

taggagtctg ggccgtgtct cagtcccagt gtggccgatc accctctcag gtcggctacg   1200

catcgtcgcc ttggtgagcc attaccccac caactagcta atgcgccgcg ggtccatctg   1260

taagtgacag ccgaaaccgt ctttcatcct tgaaccatgc ggttcaagga actatccggt   1320

attagctccg gtttcccgga gttatcccag tcttacaggc aggttaccca cgtgttactc   1380

acccgtccgc cgctaacatc cgggagcaag ctcccttctg ttcgctcgac ttgca         1435
```

<210> SEQ ID NO 27
<211> LENGTH: 2009
<212> TYPE: DNA
<213> ORGANISM: Bacillus subtilis

<400> SEQUENCE: 27

```
agtcatcatg ggaatccctg cgtacggcta tgactgggat gtaaaagacg gaagtaccag     60
cacaataagg gaatggaatg agctcaaatc cctcatcaaa aaacaaaaag caaagccggc    120
attcaacaaa aaatcaggct cgatgacatt ttcttatgtt gacaaaaaga agcataaaca    180
tgtcgtgtgg tatgaaaacg aaaaaaccgt tcaaacgaaa agccatctgg caaagcaata    240
taaaatagca ggtgtttcag tttacgcatt aggaaacgag tcagaatcct tttggaaagc    300
cattcgaaaa gggacaaaat aacagtttct tttttctctg aagttattga cagttaaaag    360
agaagcacgt atattatgtt aatatattca gatcataaaa tttgagtttt tcagaaaact    420
aaaacacata gattgggagc agtaaaagaa agtgatcaga acagagagct gcggggtggt    480
gcgacgcagc ctgattcttc tttgaactcg cccgggagtg gtaagacgga acggaataga    540
ttgaatattc cctatgtttt aacggctaac cttcgttaca ggtcaaaagc aggattcttc    600
atgaagaatc aacaagagtg gtaccgcggt cagccgaagg ctcgtcgtct ctttatctat    660
tagattaggt aggagacggc gggctttttt gtttttgaaa acgagaatga gaggtagaag    720
aggatgaaaa acgacaatca aacgttaaaa cgcacgatga cgtcccgcca tattatgatg    780
atggcgctgg gcggagcaat cggcgcaggt ttatttaagg ggagcagctc agcgatcgat    840
gtggcagggc catctgtcat tatcgcatac ctgctcggcg ggattatttt gctgtttatt    900
atgcaggggc tggcggaaat ggctgttcga aaccgtaacg ccagaacctt ccgtgatctt    960
gtccagcagg tattgggaaa ttacgctgct tactttttgg actggatcta ctggaaaatg   1020
tgggtgctta acattgcggc tgaagctgtt gtagctgcga ttttcattca atattggctg   1080
ccgggctgcc cgatctgggt gttggcatta ggaatttctc ttatcgtcac gattgtaaac   1140
ttgctttctg ttaaaatctt cgccgaaact gaatattggc tggcaatgat caagattacc   1200
gttattatta tctttattat tctgggattg ctgctcttat ttgtatcatt cggtgatcat   1260
acagcatccg gattttccaa cctgacagac cacggcggat tttcccgca cggcggcaca   1320
gggctgatca cggcgatgct tgtcgtcatc tactcttacg gcggtacaga aattatcggt   1380
gtaacgcttg cagagacaaa aaatccggaa aaggttgtcc cgaaagctgt ccgcagcaca   1440
ctgacacgga ttgtcgcgtt ttacctgctg ccgtttttca tcatcgtcag cctgattcca   1500
tggaaccaag tcaattcggt tccggaaagt cctttcgtga tggtctttaa aatggtaggc   1560
attccgggcg cggatcatat catgaatgca gtcatcctgc tggcgatcat ttcttctatg   1620
aattcaggtt tatacggatc atcacgcatt ttgtatacac aggcaagtga cggaaggctt   1680
ccaaaaatct tctcgaagct ttcatcgaaa aacgtaccga tgtttgcgat tctgatgtgc   1740
acttcttctc tctatattgg cgtattgatt tctctgttcg caggaagcca aacatttaat   1800
tatttaatgg gatcattggg atataccgtt ttattcattt ggctgatcat cggattcgct   1860
catttaaaat cgagaaaaca gcaaacggaa acaccggcct attatgtaaa atggttcccg   1920
tacacgacat ggtttgcgat tgtggcatta ctcgccattc tgatcggggt catcatgaca   1980
acatcaattg tcattaccgg cattactgc                                      2009
```

<210> SEQ ID NO 28
<211> LENGTH: 2009

<212> TYPE: DNA
<213> ORGANISM: Bacillus subtilis

<400> SEQUENCE: 28
gcagtaatgc cggtaatgac aattgatgtt gtcatgatga ccccgatcag aatggcgagt 60
aatgccacaa tcgcaaacca tgtcgtgtac gggaaccatt ttacataata ggccggtgtt 120
tccgtttgct gttttctcga ttttaaatga gcgaatccga tgatcagcca aatgaataaa 180
acggtatatc ccaatgatcc cattaaataa ttaaatgttt ggcttcctgc gaacagagaa 240
atcaatacgc caatatagag agaagaagtg cacatcagaa tcgcaaacat cggtacgttt 300
ttcgatgaaa gcttcgagaa gacctttgga agccttccgt cacttgcctg tgtatacaaa 360
atgcgtgatg atccgtataa acctgaattc atagaagaaa tgatcgccag caggatgact 420
gcattcatga tatgatccgc gcccggaatg cctaccattt taaagaccat cacgaaagga 480
ctttccggga cggaattgac ttggttccat ggaatcaggc tgacgatgat gaaaaacggc 540
agcaggtaaa acgcgacaat ccgtgtcagt gtgctgcgga cagctttcgg gacaaccttt 600
tccggatttt ttgtctctgc aagcgttaca ccgataattt ctgtaccgcc gtaagagtag 660
atgacgacaa gcatcgccgt gatcagccct gtgccgccgt gcgggaaaaa tccgccgtgg 720
tctgtcagat ttgaaaatcc ggatgctgta tgatcaccga atgatacaaa taagagcagc 780
aatcccagaa taataaagat aataataacg gtaatcttga tcattgccag ccaatattcg 840
gtttcggcga agattttaac agaaagcaag tttacaatcg tgacgataag agaaattcct 900
aatgccaaca cccagatcgg gcagcccggc agccaatatt gaatgaaaat cgcagctaca 960
acagcttcag ccgcaatgtt aagcacccac attttccagt agatccagtc caaaaagtaa 1020
gcggcgtaat ttcccaatac ctgctggaca agatcacgga aggttctggc gttacggttt 1080
cgaacagcca tttccgccag cccctgcata ataaacagca aaataatccc gccgagcaga 1140
tatgcgagaa ttacagatgg ccctgccaca tcgatcgctg agctgctccc cttaaataaa 1200
cctgcgccga ttgcgccgcc cagcgccatc atcataaatat ggcgggacgt catcgtgcgt 1260
tttaacgttt gattgtcgtt tttcatcctc ttctacctct ccttctcgtt ttcaaaaaca 1320
aaaaagcccg ccgtctccta cctaatctaa tagataaaga gacgacgagc cttcggctga 1380
ccgcggtacc actcttgttg attcttcatg aagaatcctg cttttgacct gtaacgaagg 1440
ttagccgtta aaacataggg aatattcaat ctattccgtt ccgtcttacc actcccgggc 1500
gagttcaaag aagaatcagg ctgcgtcgca ccaccccgca gttctctgtt ctgatcactt 1560
tcttttactg ctcccaatct atgtgtttta gttttctgaa aaactcaaat tttatgatct 1620
gaatatatta acataatata cgtgcttctc ttttaactgt caataacttc agagaaaaaa 1680
gaaactgtta ttttgtccct tttcgaatgg ctttccaaaa ggattctgac tcgtttccta 1740
atgcgtaaac tgaaacacct gctattttat attgctttgc cagatggctt ttcgtttgaa 1800 cggtttttttc gttttcatac cacacgacat gtttatgctt ctttttgtca acataagaaa 1860
acgtcatcga gcctgatttt ttgttgaatg ccggctttgc tttttgtttt ttgatgaggg 1920
atttgagctc attccattcc cttattgtgc tggtacttcc gtcttttaca tcccagtcat 1980
agccgtacgc agggattccc atgatgact 2009

<210> SEQ ID NO 29
<211> LENGTH: 2009
<212> TYPE: DNA
<213> ORGANISM: Bacillus subtilis

<400> SEQUENCE: 29

```
gcagtaatgc cggtaatgac aattgatgtt gtcatgatga ccccgatcag aatggcgagt     60
aatgccacaa tcgcaaacca tgtcgtgtac gggaaccatt ttacataata ggccggtgtt    120
tccgtttgct gttttctcga ttttaaatga gcgaatccga tgatcagcca aatgaataaa    180
acggtatatc ccaatgatcc cattaaataa ttaaatgttt ggcttcctgc gaacagagaa    240
atcaatacgc caatatagag agaagaagtg cacatcagaa tcgcaaacat cggtacgttt    300
ttcgatgaaa gcttcgagaa gatttttgga agccttccgt cacttgcctg tgtatacaaa    360
atgcgtgatg atccgtataa acctgaattc atagaagaaa tgatcgccag caggatgact    420
gcattcatga tatgatccgc gcccggaatg cctaccattt taaagaccat cacgaaagga    480
ctttccggaa ccgaattgac ttggttccat ggaatcaggc tgacgatgat gaaaaacggc    540
agcaggtaaa acgcgacaat ccgtgtcagt gtgctgcgga cagctttcgg gacaaccttt    600
tccggatttt ttgtctctgc aagcgttaca ccgataattt ctgtaccgcc gtaagagtag    660
atgacgacaa gcatcgccgt gatcagccct gtgccgccgt gcgggaaaaa tccgccgtgg    720
tctgtcaggt tggaaaatcc ggatgctgta tgatcaccga atgatacaaa taagagcagc    780
aatcccagaa taataaagat aataataacg gtaatcttga tcattgccag ccaatattca    840
gtttcggcga agattttaac agaaagcaag tttacaatcg tgacgataag agaaattcct    900
aatgccaaca cccagatcgg gcagcccggc agccaatatt gaatgaaaat cgcagctaca    960
acagcttcag ccgcaatgtt aagcacccac attttccagt agatccagtc caaaaagtaa   1020
gcagcgtaat ttcccaatac ctgctggaca agatcacgga aggttctggc gttacggttt   1080
cgaacagcca tttccgccag cccctgcata ataaacagca aaataatccc gccgagcagg   1140
tatgcgataa tgacagatgg ccctgccaca tcgatcgctg agctgctccc cttaaataaa   1200
cctgcgccga ttgctccgcc cagcgccatc atcataaatat ggcgggacgt catcgtgcgt   1260
tttaacgttt gattgtcgtt tttcatcctc ttctacctct cattctcgtt ttcaaaaaca   1320
aaaaagcccg ccgtctccta cctaatctaa tagataaaga gacgacgagc cttcggctga   1380
ccgcggtacc actcttgttg attcttcatg aagaatcctg cttttgacct gtaacgaagg   1440
ttagccgtta aaacataggg aatattcaat ctattccgtt ccgtcttacc actcccgggc   1500
gagttcaaag aagaatcagg ctgcgtcgca ccacccgca gctctctgtt ctgatcactt    1560
tcttttactg ctcccaatct atgtgtttta gttttctgaa aaactcaaat tttatgatct   1620
gaatatatta acataatata cgtgcttctc ttttaactgt caataacttc agagaaaaaa   1680
gaaactgtta ttttgtccct tttcgaatgg ctttccaaaa ggattctgac tcgtttccta   1740
atgcgtaaac tgaaacacct gctattttat attgctttgc cagatggctt ttcgtttgaa   1800
cggttttttc gttttcatac cacacgacat gtttatgctt ctttttgtca acataagaaa   1860
atgtcatcga gcctgatttt ttgttgaatg ccggctttgc tttttgtttt ttgatgaggg   1920
atttgagctc attccattcc cttattgtgc tggtacttcc gtcttttaca tcccagtcat   1980
agccgtacgc agggattccc atgatgact                                     2009
```

<210> SEQ ID NO 30
<211> LENGTH: 2009
<212> TYPE: DNA
<213> ORGANISM: Bacillus subtilis

<400> SEQUENCE: 30

```
gcagtaatgc cggtaatgac aattgatgtt gtcatgatga ccccgatcag aatggcgagt     60
```

```
aatgccacaa tcgcaaacca tgtcgtgtac gggaaccatt ttacataata ggccggtgtt    120
tccgtttgct gttttctcga ttttaaatga gcgaatccga tgatcagcca aatgaataaa    180
acggtatatc ccaatgatcc cattaaataa ttaaatgttt ggcttcctgc gaacagagaa    240
atcaatacgc caatatagag agaagaagtg cacatcagaa tcgcaaacat cggtacgttt    300
ttcgatgaaa gcttcgagaa gatttttgga agccttccgt cacttgcctg tgtatacaaa    360
atgcgtgatg atccgtataa acctgaattc atagaagaaa tgatcgccag caggatgact    420
gcattcatga tatgatccgc gcccggaatg cctaccattt taaagaccat cacgaaagga    480
ctttccggaa ccgaattgac ttggttccat ggaatcaggc tgacgatgat gaaaaacggc    540
agcaggtaaa acgcgacaat ccgtgtcagt gtgctgcgga cagctttcgg gacaaccttt    600
tccggatttt ttgtctctgc aagcgttaca ccgataattt ctgtaccgcc gtaagagtag    660
atgacgacaa gcatcgccgt gatcagccct gtgccgccgt gcgggaaaaa tccgccgtgg    720
tctgtcaggt tggaaaatcc ggatgctgta tgatcaccga atgatacaaa taagagcagc    780
aatcccagaa taataaagat aataataacg gtaatcttga tcattgccag ccaatattca    840
gtttcggcga agattttaac agaaagcaag tttacaatcg tgacgataag agaaattcct    900
aatgccaaca cccagatcgg gcagcccggc agccaatatt gaatgaaaat cgcagctaca    960
acagcttcag ccgcaatgtt aagcacccac attttccagt agatccagtc caaaaagtaa   1020
gcagcgtaat ttcccaatac ctgctggaca agatcacgga aggttctggc gttacggttt   1080
cgaacagcca tttccgccag cccctgcata ataaacagca aaataatccc gccgagcagg   1140
tatgcgataa tgacagatgg ccctgccaca tcgatcgctg agctgctccc cttaaataaa   1200
cctgcgccga ttgctccgcc cagcgccatc atcataatat ggcgggacgt catcgtgcgt   1260
tttaacgttt gattgtcgtt tttcatcctc ttctacctct cattctcgtt ttcaaaaaca   1320
aaaaagcccg ccgtctccta cctaatctaa tagataaaga gacgacgagc cttcggctga   1380
ccgcggtacc actcttgttg attcttcatg aagaatcctg cttttgacct gtaacgaagg   1440
ttagccgtta aaacataggg aatattcaat ctattccgtt ccgtcttacc actcccgggc   1500
gagttcaaag aagaatcagg ctgcgtcgca ccaccccgca gctctctgtt ctgatcactt   1560
tcttttactg ctcccaatct atgtgtttta gttttctgaa aaactcaaat tttatgatct   1620
gaatatatta acataatata cgtgcttctc ttttaactgt caataacttc agagaaaaaa   1680
gaaactgtta ttttgtccct tttcgaatgg ctttccaaaa ggattctgac tcgtttccta   1740
atgcgtaaac tgaaacacct gctattttat attgctttgc cagatggctt ttcgtttgaa   1800
cggttttttc gttttcatac cacacgacat gtttatgctt ctttttgtca acataagaaa   1860
atgtcatcga gcctgatttt ttgttgaatg ccggctttgc tttttgtttt ttgatgaggg   1920
atttgagctc attccattcc cttattgtgc tggtacttcc gtcttttaca tcccagtcat   1980
agccgtacgc agggattccc atgatgact                                     2009
```

<210> SEQ ID NO 31
<211> LENGTH: 2009
<212> TYPE: DNA
<213> ORGANISM: Bacillus subtilis

<400> SEQUENCE: 31

```
gcagtaatgc cagtaatgac aattgatgtt gtcatgatga ccccgatcag aatggcgagt     60
aatgccacaa tcgcaaacca tgtcgtgtac gggaaccatt ttacataata agccggtgtt    120
```

```
tccgtttgct gttttctcga ttttaaatga gcgaatccga tgatcagcca aatgaataaa    180
acggtatatc ccaatgatcc cattaaataa ttaaatgttt ggcttcctgc gaacagagaa    240
atcaatacgc caatatagag agaagaagtg cacatcagaa tcgcaaacat cggtacgttt    300
ttcgatgaaa gcttcgagaa gacctttgga agccttccgt cacttgcctg tgtatacaaa    360
atgcgtgatg atccgtataa acctgaattc atagaagaaa tgatcgccag caggatgact    420
gcattcatga tatgatccgc gcccggaatg cctaccattt taaagaccat cacgaaagga    480
ctttccggaa cggaattgac ttggttccat ggaatcaggc tgacgatgat gaaaaacggc    540
agcaggtaaa acgcgacaat ccgtgtcagt gtgctgcgga cagctttcgg gacaaccttt    600
tccggatttt ttgtctctgc aagcgttaca ccgataattt ctgtaccgcc gtaagagtag    660
atgacgacaa gcatcgccgt gatcagccct gtgccgccgt gcgggaaaaa tccgccgtgg    720
tctgtcagat ttgaaaatcc ggatgctgta tgatcaccga atgatacaaa taagagcagc    780
aatcccagaa taataaagat aataataacg gtaatcttga tcattgccag ccaatattcg    840
gtttcggcga agattttaac agaaagcaag tttacaatcg tgacgataag agaaattcct    900
aatgccaaca cccagatcgg gcagcccggc agccaatatt gaatgaaaat cgcagctaca    960
acagcttcag ccgcaatgtt aagcacccac attttccagt agatccagtc caaaaagtaa   1020
gcggcgtagt ttcccaatac ctgctggaca agatcacgga aggttctggc gttacggttt   1080
cgaacagcca tttccgccag cccctgcata ataaacagca aaataatccc gccgagcaga   1140
tatgcgataa tgacagatgg ccctgccaca tcgatcgctg agctgctccc cttaaataaa   1200
cctgcgccga ttgctccgcc cagcgccatc atcataatat ggcgggacgt catcgtgcgt   1260
tttaacgttt gattgtcgtt tttcatcctc ttctacctct ccttctcgtt ttcaaaaaca   1320
aaaaagcccg ccgtctccta cctaatctaa tagataaaga gacgacgagc cttcggctga   1380
ccgcggtacc actcttgttg attcttcatg aagaatcctg cttttgacct gtaacgaagg   1440
ttagccgtta aaacataggg aatattcaat ctattccgtt ccgtcttacc actcccgggc   1500
gagttcaaag aagaatcagg ctgcgtcgca ccaccccgca gctctctgtt ctgatcactt   1560
tcttttactg ctcccaatct atgtgtttta gttttctgaa aaactcaaat tttatgatct   1620
gaatatatta acataatata cgtgcttctc ttttaactgt caataacttc agagaaaaaa   1680
gaaactgtta ttttgtccct tttcgaatgg ctttccaaaa ggattctgac tcgtttccta   1740
atgcgtaaac tgaaacacct gctattttat attgctttgc cagatggctt ttcgtttgaa   1800
cggtttttc gttttcatac cacacgacat gtttatgctt ctttttgtca acataagaaa    1860
acgtcatcga gcctgatttt ttgttgaatg ccggctttgc tttttgtttt ttgatgaggg   1920
atttgagctc attccattcc cttattgtgc tggtacttcc gtcttttaca tcccagtcat   1980
agccgtacgc agggattccc atgatgact                                     2009
```

<210> SEQ ID NO 32
<211> LENGTH: 2009
<212> TYPE: DNA
<213> ORGANISM: Bacillus subtilis

<400> SEQUENCE: 32

```
gcagtaatgc cggtaatgac aattgatgtt gtcatgatga ccccgatcag aatggcgagt     60
aatgccacaa tcgcaaacca tgtcgtgtac gggaaccatt ttacataata ggccggtgtt    120
tccgtttgct gttttctcga ttttaaatga gcgaatccga taatcagcca aatgaataaa    180
acggtatatc ccaatgatcc cattaaataa ttaaatgttt ggcttcctgc gaacagagaa    240
```

```
atcaatacgc caatatagag agaagaagtg cacatcagaa tcgcaaacat cggtacgttt    300
ttcgatgaaa gcttagagaa gacctttgga agccttccgt cacttgcctg tgtatacaaa    360
atgcgtgatg atccgtataa acctgaattc atagaagaaa tgatcgccag caggatgact    420
gcattcatga tatgatccgc gcccggaatg cctaccattt taaagaccat tacgaaagga    480
ctttccggaa cggaattgac ttggttccat ggaatcaggc tgacgatgat gaaaaacggc    540
agcaggtaaa acgcgacaat ccgtgtcagt gtgctgcgga cagctttcgg gacaaccttt    600
tccggatttt ttgtctctgc aagcgttaca ccgataattt ctgtaccgcc gtaagagtag    660
atgacgacaa gcatcgccgt gatcagccct gtgccgccgt gcgggaaaaa tccgccgtgg    720
tctgtcagat ttgaaaatcc ggatgctgta tgatcaccga atgatacaaa taagagcagc    780
aatcccagaa taataaagat aataataacg gtaatcttga tcattgccag ccaatattcg    840
gtttcggcga agattttaac agaaagcaag tttacaatcg tgacgataag agaaattcct    900
aatgccaaca cccagatcgg gcagcccggc agccaatatt gaatgaaaat cgcagctaca    960
acagcttcag ccgcaatgtt aagcacccac attttccagt agatccagtc caaaaagtaa   1020
gcggcgtaat ttcccaatac ctgctggaca agatcacgga aggttctggc gttacggttt   1080
cgaacagcca tttccgccag cccctgcata ataaacagca aaataatccc gccgagcaga   1140
tatgcgagaa tgacagatgg ccctgccaca tcgatcgctg agctgctccc cttaaataaa   1200
cctgcgccga ttgctccgcc cagcgccatc atcataaatat ggcgggacgt catcgtgcgt   1260
tttaacgttt gattgtcgtt tttcatcctc ttctacctct ccttttcgtt ttcaaaaaca   1320
aaaaagcccg ccgtctccta cctaatctaa tagataaaga gacgacgagc cttcggctga   1380
ccgcggtacc actcttgttg attcttcatg aagaatcctg cttttgacct gtaacgaagg   1440
ttagccgtta aaacataggg aatatttaat ctattccgtt ccgtcttacc actcccgggc   1500
gagttcaaag aagaatcagg ctgcgtcgca ccaccccgca gctctctgtt ctgatcactt   1560
tcttttactg ctcccaatct atgtgtttta gttttctgaa aaactcaaat tttatgatct   1620
gaatatatta acataatata cgtgcttctc ttttaactgt caataacttc agagaaaaaa   1680
gaaactgtta ttttgtccct tttcgaatgg ctttccaaaa ggattctgac tcgtttccta   1740
atgcgtaaac tgaaacacct gctattttat attgctttgc cagatggctt ttcgtttgaa   1800
cggtttttc gttttcatac cacacgacat gtttatgctt ctttttgtca acataagaaa    1860
acgtcatcga acctgatttt ttgttgaatg ccggctttgc tttttgtttt tggatgaggg   1920
atttgagctc attccattcc cttattgtgc tggtacttcc gtcttttaca tcccagtcat   1980
agccgtacgc agggattccc atgatgact                                     2009
```

<210> SEQ ID NO 33
<211> LENGTH: 2009
<212> TYPE: DNA
<213> ORGANISM: Bacillus subtilis

<400> SEQUENCE: 33

```
gcagtaatgc cggtaatgac aattgatgtt gtcatgatga ccccgatcag aatggcgagt     60
aatgccacaa tcgcaaacca tgtcgtgtac gggaaccatt ttacataata ggccggtgtt    120
tccgtttgct gttttctcga ttttaaatga gcgaatccga tgatcagcca aatgaataaa    180
acggtatatc ccaatgatcc cattaaataa ttaaatgttt ggcttcctgc gaacagagaa    240
atcaatacgc caatatagag agaagaagtg cacatcagaa tcgcaaacat cggtacgttt    300
```

```
ttcgatgaaa gcttcgagaa gatttttgga agccttccgt cacttgcctg tgtatacaaa    360
atgcgtgatg atccgtataa acctgaattc atagaagaaa tgatcgccag caggatgact    420
gcattcatga tatgatccgc gcccggaatg cctaccattt taaagaccat cacgaaagga    480
ctttccggaa ccgaattgac ttggttccat ggaatcaggc tgacgatgat gaaaaacggc    540
agcaggtaaa acgcgacaat ccgtgtcagt gtgctgcgga cagctttcgg gacaaccttt    600
tccggatttt ttgtctctgc aagcgttaca ccgataattt ctgtaccgcc gtaagagtag    660
atgacgacaa gcatcgccgt gatcagccct gtgccgccgt gcgggaaaaa tccgccgtgg    720
tctgtcaggt tggaaaatcc ggatgctgta tgatcaccga atgatacaaa taagagcagc    780
aatcccagaa taataaagat aataataacg gtaatcttga tcattgccag ccaatattca    840
gtttcggcga agattttaac agaaagcaag tttacaatcg tgacgataag agaaattcct    900
aatgccaaca cccagatcgg gcagcccggc agccaatatt gaatgaaaat cgcagctaca    960
acagcttcag ccgcaatgtt aagcacccac attttccagt agatccagtc caaaaagtaa   1020
gcagcgtaat ttcccaatac ctgctggaca agatcacgga aggttctggc gttacggttt   1080
cgaacagcca tttccgccag cccctgcata ataaacagca aaataatccc gccgagcagg   1140
tatgcgataa tgacagatgg ccctgccaca tcgatcgctg agctgctccc cttaaataaa   1200
cctgcgccga ttgctccgcc cagcgccatc atcataatat ggcgggacgt catcgtgcgt   1260
tttaacgttt gattgtcgtt tttcatcctc ttctacctct cattctcgtt ttcaaaaaca   1320
aaaaagcccg ccgtctccta cctaatctaa tagataaaga gacgacgagc cttcggctga   1380
ccgcggtacc actcttgttg attcttcatg aagaatcctg cttttgacct gtaacgaagg   1440
ttagccgtta aaacataggg aatattcaat ctattccgtt ccgtcttacc actcccgggc   1500
gagttcaaag aagaatcagg ctgcgtcgca ccaccccgca gctctctgtt ctgatcactt   1560
tcttttactg ctcccaatct atgtgtttta gttttctgaa aaactcaaat tttatgatct   1620
gaatatatta acataatata cgtgcttctc ttttaactgt caataacttc agagaaaaaa   1680
gaaactgtta ttttgtccct tttcgaatgg ctttccaaaa ggattctgac tcgtttccta   1740
atgcgtaaac tgaaacacct gctattttat attgctttgc cagatggctt ttcgtttgaa   1800
cggttttttc gttttcatac cacacgacat gtttatgctt ctttttgtca acataagaaa   1860
atgtcatcga gcctgatttt ttgttgaatg ccggctttgc tttttgtttt ttgatgaggg   1920
atttgagctc attccattcc cttattgtgc tggtacttcc gtcttttaca tcccagtcat   1980
agccgtacgc agggattccc atgatgact                                     2009
```

```
<210> SEQ ID NO 34
<211> LENGTH: 2009
<212> TYPE: DNA
<213> ORGANISM: Bacillus subtilis

<400> SEQUENCE: 34
```

```
gcagtaatgc cggtaatgac aattgatgtt gtcatgatga ccccgatcag aatggcgagt     60
aatgccacaa tcgcaaacca tgtcgtgtac gggaaccatt ttacataata ggccggtgtt    120
tccgtttgct gttttctcga ttttaaatga gcgaatccga tgatcagcca aatgaataaa    180
acggtatatc ccaatgatcc cattaaataa ttaaatgttt ggcttcctgc gaacagagaa    240
atcaatacgc caatatagag agaagaagtg cacatcagaa tcgcaaacat cggtacgttt    300
ttcgatgaaa gcttcgagaa gatttttgga agccttccgt cacttgcctg tgtatacaaa    360
atgcgtgatg atccgtataa acctgaattc atagaagaaa tgatcgccag caggatgact    420
```

```
gcattcatga tatgatccgc gcccggaatg cctaccattt taaagaccat cacgaaagga    480
ctttccggaa ccgaattgac ttggttccat ggaatcaggc tgacgatgat gaaaaacggc    540
agcaggtaaa acgcgacaat ccgtgtcagt gtgctgcgga cagctttcgg gacaaccttt    600
tccggatttt ttgtctctgc aagcgttaca ccgataattt ctgtaccgcc gtaagagtag    660
atgacgacaa gcatcgccgt gatcagccct gtgccgccgt gcgggaaaaa tccgccgtgg    720
tctgtcaggt tggaaaatcc ggatgctgta tgatcaccga atgatacaaa taagagcagc    780
aatcccagaa taataaagat aataataacg gtaatcttga tcattgccag ccaatattca    840
gtttcggcga agattttaac agaaagcaag tttacaatcg tgacgataag agaaattcct    900
aatgccaaca cccagatcgg gcagcccggc agccaatatt gaatgaaaat cgcagctaca    960
acagcttcag ccgcaatgtt aagcacccac attttccagt agatccagtc caaaaagtaa   1020
gcagcgtaat ttcccaatac ctgctggaca agatcacgga aggttctggc gttacggttt   1080
cgaacagcca tttccgccag cccctgcata ataaacagca aaataatccc gccgagcagg   1140
tatgcgataa tgacagatgg ccctgccaca tcgatcgctg agctgctccc cttaaataaa   1200
cctgcgccga ttgctccgcc cagcgccatc atcataatat ggcgggacgt catcgtgcgt   1260
tttaacgttt gattgtcgtt tttcatcctc ttctacctct cattctcgtt ttcaaaaaca   1320
aaaaagcccg ccgtctccta cctaatctaa tagataaaga gacgacgagc cttcggctga   1380
ccgcggtacc actcttgttg attcttcatg aagaatcctg cttttgacct gtaacgaagg   1440
ttagccgtta aaacataggg aatattcaat ctattccgtt ccgtcttacc actcccgggc   1500
gagttcaaag aagaatcagg ctgcgtcgca ccaccccgca gctctctgtt ctgatcactt   1560
tcttttactg ctcccaatct atgtgtttta gttttctgaa aaactcaaat tttatgatct   1620
gaatatatta acataatata cgtgcttctc ttttaactgt caataacttc agagaaaaaa   1680
gaaactgtta ttttgtccct tttcgaatgg ctttccaaaa ggattctgac tcgtttccta   1740
atgcgtaaac tgaaacacct gctattttat attgctttgc cagatggctt ttcgtttgaa   1800
cggtttttttc gttttcatac cacacgacat gtttatgctt ctttttgtca acataagaaa   1860
atgtcatcga gcctgatttt ttgttgaatg ccggctttgc tttttgtttt ttgatgaggg   1920
atttgagctc attccattcc cttattgtgc tggtacttcc gtcttttaca tcccagtcat   1980
agccgtacgc agggattccc atgatgact                                     2009
```

<210> SEQ ID NO 35
<211> LENGTH: 2009
<212> TYPE: DNA
<213> ORGANISM: Bacillus subtilis

<400> SEQUENCE: 35

```
gcagtaatgc cggtaatgac aattgatgtt gtcatgatga ccccgatcag aatggcgagt     60
aatgccacaa tcgcaaacca tgtcgtgtac gggaaccatt ttacataata ggccggtgtt    120
tccgtttgct gttttctcga ttttaaatga gcgaatccga tgatcagcca aatgaataaa    180
acggtatatc ccaatgatcc cattaaataa ttaaatgttt ggcttcctgc gaacagagaa    240
atcaatacgc caatatagag agaagaagtg cacatcagaa tcgcaaacat cggtacgttt    300
ttcgatgaaa gcttcgagaa gatttttgga agccttccgt cacttgcctg tgtatacaaa    360
atgcgtgatg atccgtataa acctgaattc atagaagaaa tgatcgccag caggatgact    420
gcattcatga tatgatccgc gcccggaatg cctaccattt taaagaccat cacgaaagga    480
```

```
ctttccggaa ccgaattgac ttggttccat ggaatcaggc tgacgatgat gaaaaacggc    540
agcaggtaaa acgcgacaat ccgtgtcagt gtgctgcgga cagctttcgg gacaaccttt    600
tccggatttt ttgtctctgc aagcgttaca ccgataattt ctgtaccgcc gtaagagtag    660
atgacgacaa gcatcgccgt gatcagccct gtgccgccgt gcgggaaaaa tccgccgtgg    720
tctgtcaggt tggaaaatcc ggatgctgta tgatcaccga atgatacaaa taagagcagc    780
aatcccagaa taataaagat aataataacg gtaatcttga tcattgccag ccaatattca    840
gtttcggcga agattttaac agaaagcaag tttacaatcg tgacgataag agaaattcct    900
aatgccaaca cccagatcgg gcagcccggc agccaatatt gaatgaaaat cgcagctaca    960
acagcttcag ccgcaatgtt aagcacccac attttccagt agatccagtc caaaaagtaa   1020
gcagcgtaat ttcccaatac ctgctggaca agatcacgga aggttctggc gttacggttt   1080
cgaacagcca tttccgccag cccctgcata ataaacagca aaataatccc gccgagcagg   1140
tatgcgataa tgacagatgg ccctgccaca tcgatcgctg agctgctccc cttaaataaa   1200
cctgcgccga ttgctccgcc cagcgccatc atcataaatat ggcgggacgt catcgtgcgt   1260
tttaacgttt gattgtcgtt tttcatcctc ttctacctct cattctcgtt ttcaaaaaca   1320
aaaaagcccg ccgtctccta cctaatctaa tagataaaga gacgacgagc cttcggctga   1380
ccgcggtacc actcttgttg attcttcatg aagaatcctg cttttgacct gtaacgaagg   1440
ttagccgtta aaacataggg aatattcaat ctattccgtt ccgtcttacc actcccgggc   1500
gagttcaaag aagaatcagg ctgcgtcgca ccaccccgca gctctctgtt ctgatcactt   1560
tcttttactg ctcccaatct atgtgtttta gttttctgaa aaactcaaat tttatgatct   1620
gaatatatta acataatata cgtgcttctc ttttaactgt caataacttc agagaaaaaa   1680
gaaactgtta ttttgtccct tttcgaatgg ctttccaaaa ggattctgac tcgtttccta   1740
atgcgtaaac tgaaacacct gctattttat attgctttgc cagatggctt ttcgtttgaa   1800
cggtttttttc gttttcatac cacacgacat gtttatgctt ctttttgtca acataagaaa   1860
atgtcatcga gcctgatttt ttgttgaatg ccggctttgc tttttgtttt ttgatgaggg   1920
atttgagctc attccattcc cttattgtgc tggtacttcc gtcttttaca tcccagtcat   1980
agccgtacgc agggattccc atgatgact                                     2009
```

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

```
Pro Gly Pro Gly Pro Gly Pro Gly Pro Gly
1               5                   10
```

<210> SEQ ID NO 37
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 37

```
agatcttacc gatagttaaa agtacta                                  27


<210> SEQ ID NO 38
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38

cctaggttat ctgccccgct tgcctaac                                 28


<210> SEQ ID NO 39
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39

agatcttacc gatagttaaa agtacta                                  27


<210> SEQ ID NO 40
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40

cctaggttat ctgccccgct tgcctaac                                 28
```

COMPOSITIONS AND METHODS FOR IMPROVING SKIN HEALTH AND FOR THE TREATMENT AND PREVENTION OF DISEASES, DISORDERS AND CONDITIONS ASSOCIATED WITH FUNGI AND OTHER PATHOGENIC MICROBES

CROSS-REFERENCE TO RELATED APPLICATIONS

This application is a National Stage Entry of PCT Application PCT/US2021/054856, filed Oct. 13, 2021, which claims priority to U.S. Provisional Application 63/091,783, filed on Oct. 14, 2020, both of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Oct. 12, 2021, is named DER-004WO_SL.txt and is 75,569 bytes in size.

FIELD

Among other things, the present disclosure provides certain beneficial compositions and methods for the improvement of skin health and inhibition, treatment and prevention of diseases, disorders and conditions associated with pathogenic microbes or microorganisms using *Janthinobacterium lividum, Alcaligenes faecalis, Bacillus altitudinis, Bacillus pumilus* or *Bacillus subtilis*, and combinations thereof, each strain of which was initially isolated from healthy human skin, and/or, metabolites, cell lysates, or postbiotic metabolites of *Janthinobacterium lividum, Alcaligenes faecalis, Bacillus altitudinis, Bacillus pumilus* or *Bacillus subtilis* and combinations thereof containing compositions, formulations, and products, may be used for cosmetic and consumer uses.

BACKGROUND

Topical infections of the skin, nails, mucosa and mucous cavities by pathogenic microorganisms are a health problem for a large number of human and non-human subjects. These microorganisms cause a variety of bacterial, viral, and fungal infections. These conditions may arise out of a dysbiosis of the skin, nails, mucosa and mucous cavities, allowing for a pathogenic microorganism or a community of pathogenic microorganisms to establish.

There are a variety of infections, such as bacterial, viral, parasitic, archaeal, and fungal infections, that affect a relatively large number of the human population. These human infections may be a result of a single microbial species or strain or a combination of species or strains.

Human infection by *Malassezia* affects a large part of the population. *Malassezia* are common, mostly lipophilic, fungi, that grow on the sebaceous areas of human skin, including the face, scalp, and upper trunk; and the sebaceous areas of other mammals' skin. Although *Malassezia* species are a part of the normal human skin flora, they may also cause or exacerbate several skin diseases with varied clinical manifestations ranging from benign skin conditions, such as *versicolor*, to fungemia in immunocompromised hosts. There are presently 14 described species, namely *M. furfur, M. pachydermatis, M. sympodialis, M.globosa, M. obtusa,*

*M. restricta, M. slooffiae, M. equina*, M. dermatis, M. *japonica*, M. nana, M. capre, M. yamatoensis, and *M. cuniculi*. Dandruff, atopic eczema, dermatitis, *pityriasis versicolor*, seborrheic dermatitis, and folliculitis are all conditions associated with *Malassezia* infection. *Pityriasis versicolor*, or *tinea versicolor*, is a prototype *Malassezia* infection that is a commonly encountered superficial mycosis, which can be a chronically recurring infection ofthe stratum corneum. It is characterized by fine white scaly, hypo or hyperpigmented macules that are irregular and most often occurring on the oily parts of the body, trunk, and extremities. Some patients may experience pruritus, but most are asymptomatic. Seborrheic dermatitis, the second most common infection associated with *Malassezia*, is a superficial eczematous dermatitis, either sub-acute or chronic, characterized by erythematous plaques with dry or oily scale. It occurs in sebaceous areas like the scalp, face, ears, chest, and axillary areas. Topical antifungals are a common method of treating *Malassezia*-related diseases and continuous prophylaxis is often required to prevent recurrences.

Other potentially pathogenic dermatophytic fungi can be yeasts, filamentous, or dimorphic (e.g., *Candida albicans*). Dermatophytes are fungi that require keratin for nutritionand live on the stratum corneum, hair, or nails to survive. Human dermatophytic infections are often caused by *Trichophyton, Microsporum* and *Epidermophyton* species. *Trichophyton rubrum* is responsible for approximately 46% to 72% of cutaneous and nail mycoses worldwide. Research studies have established that *Trichophyton rubrum*, the most common dermatophyte, is also the causal agent for *Tinea pedis*. Onychomycosis, a common and persistent fungal infection, is diagnosed in two to eight percent of the global population. The disease causes disfigurement of nails and/or pain. Treatments for dermatophytoses include antifungal topical products (e.g., terbinafine, itraconazole, miconazole, etc.) and/or systemic therapy.

SUMMARY

Ineffectiveness and toxicity of some long-term treatments for certain pathogens (e.g., fungi) as well as anti-fungal drug resistance and recurrence of infection has resulted in a need for an alternative treatment to those currently available.

Among other things, the present disclosure provides compositions comprising and methods for one or more bacterium (e.g., a probiotic) for treating, inhibiting, or preventing infection with one or more pathogenic microorganisms.

In some embodiments, the present disclosure provides pharmaceutical compositions comprising a probiotic, which probiotic comprises (i) human-isolated or synthetic *Alcaligenes faecalis, Bacillus altitudinis, Bacillus pumilus, Bacillus subtilis, Janthinobacterium lividum*, in an amount effective to treat a disease, disorder, or condition associated with a pathogenic microorganism and (ii) at least one first excipient, wherein said first excipient is a cryoprotectant.

In some embodiments, the disease disorder or condition is present in a mammal. In some embodiments, the mammal is a human. In some embodiments, the pharmaceutical composition is administered to a human in need thereof, in an amount effective to treat the human skin disease, disorder, or condition. In some embodiments, the disease, disorder, or condition comprises a skin disease. In some embodiments, the pharmaceutical composition is administered in an amount effective to treat growth of a topical pathogenic microorganism present on or in the skin of the human. In some embodiments, the topical pathogenic microorganism comprises or consists of *Malassezia*. In some embodiments, the disease, disorder, or condition is associated with *Malassezia*. In some embodiments, the *Malassezia* comprises or consists of one or more of *Malassezia restricta, Malassezia* furfur, or *Malassezia globosa*. In some such embodiments, the disease, disorder, or condition is selected from dandruff, atopic eczema, dermatitis, *pityriasis versicolor, Tinea versicolor*, seborrheic dermatitis, folliculitis or any combinations thereof. In some embodiments, the topical pathogenic microorganism comprises or consists of a dermatophyte. In some embodiments, the disease, disorder, or condition is associated with a dermatophyte. In some embodiments, the dermatophyte comprises or consists of *Trichophyton*. In some embodiments, *Trichophyton* comprises or consists of *Trichophyton mentagrophytes*. In some embodiments, *Trichophyton* comprises or consists of *Trichophyton rubrum*. In some embodiments, the disease, disorder, or condition is selected from *Tinea barbae, Tinea capitis, Tinea corporis, Tinea cruris, Tinea pedis, Tinea versicolor*, onychomycosis or any combination thereof. In some embodiments, the disease, disorder, or condition is associated with gram positive bacteria and *Staphylococcus*. In some embodiments, the disease, disorder, or condition is selected from atopic dermatitis, impetigo, skin infections, soft tissue infections, or any combination thereof. In some embodiments, the disease, disorder, or condition is associated with *Candida*. In some embodiments, the disease, disorder, or condition is selected from oral thrush, urinary tract infection, genital infection, mucocutaneous candidiasis or any combination thereof. In some embodiments, the disease, disorder, or condition is associated with *Tricophyton*. In some embodiments, the disease, disorder, or condition is selected from *Tinea barbae, Tinea capitis, Tinea corporis, Tinea cruris, Tinea pedis, Tinea versicolor, onychomycosis* or any combination thereof.

In some embodiments, the probiotic comprises one or more of human-isolated or synthetic *Alcaligenes faecalis, Bacillus altitudinis, Bacillus pumilus, Bacillus subtilis*, or *Janthinobacterium lividum* that comprises or consists of a nucleic acid sequence at least 95% identical to that set forth in SEQ ID NO: 1, SEQ ID NO: 2, SEQ ID NO: 3, SEQ ID NO: 4, or SEQ ID NO: 5. In some embodiments, the percent identity is at least 99%.

In some embodiments, the pharmaceutical composition is formulated for topical application to a mammal to for treating at least one symptom arising from an infection with a pathogenic microorganism. In some embodiments, the pharmaceutical composition comprising the least one first excipient further comprises a second excipient. In some embodiments, the pharmaceutical composition is frozen or lyophilized. In some embodiments, the cryoprotectant of the pharmaceutical composition results in a greater percent recovery of the probiotic after freezing or lyophilization as compared to a composition comprising the same probiotic without the cryoprotectant. In some such embodiments, the cryoprotectant results in greater efficacy, stability, and/or viability of the pharmaceutical composition against a pathogenic organism as compared to a pharmaceutical composition comprising the same probiotic without the cryoprotectant. In some such embodiments, the percent recovery in the composition with a cryoprotectant is between one to three logs greater after 20 days, as compared to the composition without the cryoprotectant. In some embodiments, the cryoprotectant comprises a disaccharide. In some embodiments, the disaccharide comprises trehalose. In some embodiments, the trehalose comprises D-trehalose at 2-20%.

In some embodiments, the pharmaceutical composition further comprises at least one additional isolated or synthetic probiotic. In some such embodiments, the additional isolated probiotic comprises human-isolated or synthetic *Alcaligenes faecalis, Bacillus altitudinis, Bacillus pumilus, Bacillus subtilis*, or *Janthinobacterium lividum*. In some embodiments, the additional isolated microbe comprises one or more members of a genera selected from *Lactobacillus, Lactococcus, Cutibacterium*, or *Propionibacterium*. In some embodiments, the pharmaceutical composition further comprises a first additional isolated microbe and a second additional isolated microbe, wherein the first and second additional isolated microbes are independently selected from bacteria, virus, yeast, fungus, or any combination thereof. In some embodiments, the pharmaceutical composition further comprising a plurality of additional isolated microbes, which microbes are selected from bacteria, virus, yeast, fungus, or any combination thereof. In some such embodiments, the isolated microbes are human-isolated or synthetic microbes.

In some embodiments, the pharmaceutical composition further comprises an anti-fungal compound. In some embodiments, the anti-fungal compound is present in the composition in a therapeutic amount. In some embodiments, the anti-fungal compound is present in the composition in a sub-therapeutic amount.

In some embodiments, the pharmaceutical composition further comprises an anti-bacterial compound. In some embodiments, the anti-bacterial compound is present in the composition in a therapeutic amount. In some embodiments, the anti-bacterial compound is present in the composition in a sub-therapeutic amount.

In some embodiments, the pharmaceutical composition further comprises a prebiotic. In some embodiments, the pharmaceutical composition further comprises at least one postbiotic.

In some embodiments, the pharmaceutical composition further comprises a topically acceptable carrier. In some embodiments, the topically acceptable carrier further comprises a prebiotic, metabolite, postbiotic, cell lysate, probiotic or any combination thereof.

In some embodiments, the pharmaceutical composition is dried to powder format by lyophilization. In some embodiments, the probiotic comprising is at least 10% viable upon rehydration. In some embodiments, the probiotic is at least 90% viable at refrigerated conditions for at least about 164 days.

In some embodiments, the pharmaceutical composition is formulated for topical administration to a human or non-human subject. In some embodiments, the pharmaceutical composition is formulated as a cream, gel, foam, ointment, powder or lotion. In some embodiments, the pharmaceutical composition is formulated as a liquid, tincture, spray, mister, or inhaler. In some embodiments, the pharmaceutical composition is formulated for topical administration to human skin. In some embodiment, the pharmaceutical composition is formulated for topical administration to human mucosa.

In some embodiments, the present disclosure provides synthetic compositions comprising human-isolated or synthetic *Alcaligenes faecalis, Bacillus altitudinis, Bacillus pumilus, Bacillus subtilis*, or *Janthinobacterium lividum* comprising a nucleic acid sequence 95% identical to SEQ ID NO: 1, SEQ ID NO: 2, SEQ ID NO: 3, SEQ ID NO: 4 or SEQ ID NO: 5, wherein the composition is formulated for topical application. In some embodiments, the *Alcaligenes faecalis, Bacillus altitudinis, Bacillus pumilus, Bacillus subtilis*, or *Janthinobacterium lividum* nucleic acid sequence identity is 99% identical to that of SEQ ID NO: 1, SEQ ID NO: 2, SEQ ID NO: 3, SEQ ID NO: 4, or SEQ ID NO: 5. In some embodiments, the composition is formulated for application to a material that will be in contact with human skin, nails, hair, or mucosa. In some embodiments, the composition is formulated for application to human skin, nails, hair, or mucosa. In some embodiments, the composition is formulated in an aqueous formulation. In some embodiments, the composition is formulated for topical application to a surface that is contacted by a human. In some embodiments, the composition is formulated for use as a cosmetic composition. In some embodiments, the composition is formulated as a toothpaste, mouthwash, shampoo, soap, dental floss, eye drops, or nasal spray composition. In some embodiments, the composition is formulated as a sunscreen, moisturizer, anti-aging, probiotic, or health promoting composition.

In some embodiments, the present disclosure provides, pharmaceutical compositions comprising *Alcaligenes faecalis, Bacillus altitudinis, Bacillus pumilus, Bacillus subtilis*, or *Janthinobacterium lividum* comprises a nucleic acid sequence at least 98% identical to SEQ ID NO: 1, SEQ ID NO: 2, SEQ ID NO: 3, SEQ ID NO:4 or SEQ ID NO: 5 at the 16s rRNA gene sequence in an amount effective to treat, inhibit or prevent a disease, disorder, or condition associated with a pathogenic microorganism.

In some embodiments, the present disclosure provides, pharmaceutical compositions comprising *Alcaligenes* or *Bacillus* comprising a nucleic acid sequence comprising SEQ ID NO: 1, SEQ ID NO: 2, SEQ ID NO: 3, or SEQ ID NO: 4 in an amount effective to treat, inhibit or prevent a disease, disorder, or condition associated with a pathogenic microorganism.

In some embodiments, the present disclosure provides methods of treating or preventing a pathogenic microorganism, the method comprising administering an effective amount of human-isolated or synthetic *Alcaligenes faecalis, Bacillus altitudinis, Bacillus pumilus, Bacillus subtilis*, or *Janthinobacterium lividum* to a subject in need thereof.

In some embodiments, the present disclosure provides methods of treating a skin condition in a subject in need thereof, comprising administering topically to the subject a therapeutically effective amount of a pharmaceutical composition that comprises a probiotic of the genus *Alcaligenes, Bacillus*, or *Janthinobacterium*, wherein the probiotic comprises a polynucleotide having a nucleic acid sequence at least 95% identical to the 16s rRNA gene sequence of SEQ ID NO: 1, SEQ ID NO: 2, SEQ ID NO: 3, SEQ ID NO: 4, or SEQ ID NO: 5.

In some embodiments, the present disclosure provides methods of improving efficacy of a probiotic comprising *Alcaligenes* comprising a probiotic having a methyltransferase at least 95% identical to that of SEQ ID NO: 6.

In some embodiments, the present disclosure provides isolated *Alcaligenes, Bacillus*, or *Janthinobacterium* probiotics comprising a 16s rRNA nucleic acid molecule having a sequence at least 95% identical to SEQ ID NO: 1, SEQ ID NO: 2, SEQ ID NO: 3, SEQ ID NO:4, or SEQ ID NO: 5. In some such embodiments, the isolated *Alcaligenes* probiotic comprises a methyltransferase having at least 95% identity to SEQ ID NO: 6. In some embodiments, a pharmaceutical composition comprises the isolated *Alcaligenes, Bacillus*, or *Janthinobacterium* probiotic comprising a 16s rRNA nucleic acid molecule having a sequence at least 95% identical to SEQ ID NO: 1, SEQ ID NO: 2, SEQ ID NO: 3, SEQ ID NO:4, or SEQ ID NO: 5 and, optionally, comprises a methyltransferase having an amino acid sequence as set forth in SEQ ID NO: 6. In some embodiments, a synthetic composition comprises the isolated *Alcaligenes, Bacillus*, or *Janthinobacterium* probiotic comprising a 16s rRNA nucleic acid molecule having a sequence at least 95% identical to SEQ ID NO: 1, SEQ ID NO: 2, SEQ ID NO: 3, SEQ ID NO:4, or SEQ ID NO: 5 and, optionally, comprises a methyltransferase having an amino acid sequence as set forth in SEQ ID NO: 6. In some embodiments, a cosmetic composition comprises the isolated *Alcaligenes, Bacillus*, or *Janthinobacterium* probiotic comprising a 16s rRNA nucleic acid molecule having a sequence at least 95% identical to SEQ ID NO: 1, SEQ ID NO: 2, SEQ ID NO: 3, SEQ ID NO:4, or SEQ ID NO: 5 and, optionally, comprises a methyltransferase having an amino acid sequence as set forth in SEQ ID NO: 6.

In some embodiments, the present disclosure provides isolated *Alcaligenes, Bacillus*, or *Janthinobacterium* probiotics comprising a 16s rRNA nucleic acid sequence at least 98% identical to SEQ ID NO: 1, SEQ ID NO: 2, SEQ ID NO: 3, SEQ ID NO: 4, or SEQ ID NO: 5.

In some embodiments, the present disclosure provides a combination composition comprising at least two probiotics selected from any of the *Alcaligenes, Bacillus* or *Janthinobacterium* comprising a 16s rRNA nucleic acid sequence at least 98% identical to SEQ ID NO: 1, SEQ ID NO: 2, SEQ ID NO: 3, SEQ ID NO: 4, or SEQ ID NO: 5.

In some embodiments, the present disclosure provides pharmaceutical compositions comprising at least one species of human-isolated or synthetic *Alcaligenes faecalis, Bacillus altitudinis, Bacillus pumilus, Bacillus subtilis*, or *Janthinobacterium lividum* present in an amount effective to treat or prevent a disease, disorder, or condition associated with a pathogenic microorganism in a subject in need thereof, wherein the pharmaceutical composition is in a topical dosage form.

In some embodiments, the present disclosure provides pharmaceutical compositions comprising a metabolite from at least one species of human-isolated or synthetic, *Alcaligenes faecalis, Bacillus altitudinis, Bacillus pumilus*, or *Bacillus subtilis*, wherein the metabolite is present in an amount sufficient for treatment, inhibition or prevention of a disease, disorder or condition associated with a pathogenic microorganism in a subject in need thereof, wherein the pharmaceutical composition is in a topical dosage form.

In some embodiments, the present disclosure provides pharmaceutical compositions comprising a cell lysate of at least one species of human-isolated or synthetic *Alcaligenes faecalis, Bacillus altitudinis, Bacillus pumilus, Bacillus subtilis*, or *Janthinobacterium lividum* present in an amount effective to treat or prevent a disease, disorder, or condition associated with a pathogenic microorganism in a subject in need thereof, wherein the pharmaceutical composition is in a topical dosage form.

In some embodiments, the present disclosure provides pharmaceutical compositions, comprising a postbiotic of at least one species of human-isolated or synthetic *Alcaligenes faecalis, Bacillus altitudinis, Bacillus pumilus, Bacillus subtilis*, or *Janthinobacterium lividum* present in an amount effective to treat, inhibit or prevent a disease, disorder, or condition associated with a pathogenic microorganism in a subject in need thereof, wherein the pharmaceutical composition is in a topical dosage form.

In some embodiments, the present disclosure provides methods for treating a skin disorder in a subject in need thereof, wherein the methodcomprises topically administering a formulation comprising an effective amount of probiotic bacteria, a metabolite of probiotic bacteria, postbiotic of probiotic bacteria, and/or cell lysate of probiotic bacteria; wherein the probiotic bacteria are human-isolated or synthetic *Alcaligenes faecalis, Bacillus* altitudinis, *Bacillus pumilus, Bacillus subtilis*, or *Janthinobacterium lividum*; and the disorder is associated with the presence of a topical pathogenic microorganism. In some such embodiments, the formulation is formulated for administration to skin, nails, or hair. In some embodiments, the formulation is formulated for administration to mucosa. In some embodiments, the mucosa is selected from the group consisting of mucosa of a vagina, penis, urethra, bladder, anus, mouth, nose, throat, bronchi, lungs, eye, and ear and nasal cavity.

In some embodiments, the present disclosure provides pharmaceutical compositions comprising a metabolite produced from at least one human-isolated or synthetic *Alcaligenes faecalis, Bacillus altitudinis, Bacillus pumilus, Bacillus subtilis*, or *Janthinobacterium lividum* in an amount effective to treat, inhibit or prevent a disease, disorder, or condition associated with a pathogenic microorganism. In some such embodiments, the *Janthinobacterium lividum Alcaligenes faecalis, Bacillus altitudinis, Bacillus pumilus, Bacillus subtilis* or *Janthinobacterium lividum*, comprises a 16S rRNA gene sequence that is at least 95% identical to SEQ ID NO: 1, SEQ ID NO: 2, SEQ ID NO:3, SEQ ID NO: 4 or SEQ ID NO: 5.

In some embodiments, the present disclosure provides pharmaceutical compositions comprising a cell lysate from at least one human-isolated or synthetic *Alcaligenes faecalis, Bacillus altitudinis, Bacillus pumilus, Bacillus subtilis*, or *Janthinobacterium lividum* in an amount effective to treat or prevent a disease, disorder, or condition associated with a pathogenic microorganism. In some such embodiments, the *Alcaligenes faecalis, Bacillus altitudinis, Bacillus pumilus, Bacillus subtilis*, or *Janthinobacterium lividum* comprises a 16S rRNA gene sequence that is at least 95% identical to SEQ ID NO: 1, SEQ ID NO: 2, SEQ ID NO:3, SEQ ID NO: 4, or SEQ ID NO: 5.

In some embodiments, the present disclosure provides pharmaceutical compositions comprising a postbiotic from at least one human-isolated or synthetic *Alcaligenes faecalis, Bacillus altitudinis, Bacillus pumilus, Bacillus subtilis*, or *Janthinobacterium lividum* in an amount effective to treat, inhibit or prevent a disease, disorder, or condition associated with a pathogenic microorganism. In some such embodiments, the *Alcaligenes faecalis, Bacillus altitudinis, Bacillus pumilus, Bacillus subtilis*, or *Janthinobacterium lividum* comprises a 16S rRNA gene sequence that is at least 95% identical to SEQ ID NO: 1, SEQ ID NO: 2, SEQ ID NO:3, SEQ ID NO: 4, or SEQ ID NO: 5.

In some embodiments, the present disclosure provides synthetic compositions comprising an effective amount of at least one human-isolated *Alcaligenes faecalis, Bacillus altitudinis, Bacillus pumilus, Bacillus subtilis*, or *Janthinobacterium lividum* metabolite, formulated for topical application. In some such embodiments, the *Alcaligenes faecalis, Bacillus altitudinis, Bacillus pumilus, Bacillus subtilis*, or *Janthinobacterium lividum* comprises a 16S rRNA gene sequence that is at least 95% identical to SEQ ID NO: 1, SEQ ID NO: 2, SEQ ID NO:3, SEQ ID NO: 4, or SEQ ID NO: 5. In some embodiments, the synthetic composition is a cosmetic composition. In some embodiments, the cosmetic composition is formulated as a toothpaste, mouthwash, shampoo, soap, moisturizer, or dental floss. In some embodiments, the cosmetic composition comprises a sunscreen, moisturizer, anti-aging, probiotic or health-promoting composition.

In some embodiments, the present disclosure provides synthetic compositions comprising an effective amount of *Janthinobacterium lividum, Alcaligenes faecalis, Bacillus altitudinis, Bacillus pumilus*, or *Bacillus subtilis* cell lysate, formulated for topical application. In some embodiments, the *Janthinobacterium lividum Alcaligenes faecalis, Bacillus altitudinis, Bacillus pumilus, Bacillus subtilis*, or *Janthinobacterium lividum* comprises a 16S rRNA gene sequence that is at least 95% identical to SEQ ID NO: 1, SEQ ID NO: 2, SEQ ID NO:3, SEQ ID NO: 4, or SEQ ID NO: 5. In some embodiments, the synthetic composition is a cosmetic composition. In some embodiments, the composition is formulated as a toothpaste, mouthwash, shampoo, soap, moisturizer, or dental floss. In some embodiments, the composition is formulated as a sunscreen, moisturizer, anti-aging, probiotic or health-promoting composition.

In some embodiments, the present disclosure provides synthetic compositions comprising an effective amount of human-isolated or synthetic *Janthinobacterium lividum, Alcaligenes faecalis, Bacillus altitudinis, Bacillus pumilus*, or *Bacillus subtilis* postbiotic, formulated for topical application. In some such embodiments, the *Alcaligenes faecalis, Bacillus altitudinis, Bacillus pumilus, Bacillus subtilis* or *Janthinobacterium lividum* comprises a 16S rRNA gene sequence that is at least 95% identical to SEQ ID NO: 1, SEQ ID NO: 2, SEQ ID NO: 3, SEQ ID NO: 4, OR SEQ ID NO: 5. In some embodiments, the synthetic composition is a cosmetic composition. In some embodiments, the composition is formulated as a toothpaste, mouthwash, shampoo, soap, moisturizer, lip balm, or dental floss. In some embodiments, the composition is formulated as a sunscreen, moisturizer, anti-aging, probiotic or health-promoting composition.

In some embodiments, the present disclosure provides methods of treating a subject in need thereof comprising administering to the subject a composition comprising a probiotic selected from *Alcaligenes faecalis, Bacillus altitudinis, Bacillus pumilus, Bacillus subtilis* or *Janthinobacterium lividum* or derivative thereof and at least one cryoprotectant, which cryoprotectant increases a level of at least one metabolite of the probiotic, wherein the increased level of the at least one metabolite is associated with treatment of a diseases, disorder, or condition associated with a pathogenic microorganism.

In some embodiments, the present disclosure provides methods of treating a subject in need thereof comprising administering to the subject a composition comprising a probiotic selected from *Alcaligenes faecalis, Bacillus altitudinis, Bacillus pumilus, Bacillus subtilis* or *Janthinobacterium lividum* or derivative thereof and at least one cryoprotectant, which cryoprotectant decreases a level of least one metabolite of the probiotic, wherein the at least one decreased level of the at least one metabolite is associated with treatment of a diseases, disorder, or condition associated with a pathogenic microorganism.

In some embodiments, the present disclosure provides lyophilized probiotic compositions comprising at least one probiotic selected from *Alcaligenes faecalis, Bacillus* altitudinis, *Bacillus pumilus, Bacillus subtilis* or *Janthinobacterium lividum* or derivative thereof and at least one cryoprotectant. In some such embodiments, the cryoprotectant comprises a disaccharide. In some embodiments, the cryoprotectant results in a composition with improved efficacy, stability, and/or viability as compared to a composition not comprising the cryoprotectant. In some embodiments, the lyophilized formulation further comprises at least one prebiotic.

In some embodiments, the present disclosure provides probiotic compositions comprising at least one of *Alcaligenes faecalis, Bacillus altitudinis, Bacillus pumilus, Bacillus subtilis* or *Janthinobacterium lividum* and at least one cryoprotectant for use as a medicament. In some such embodiments, the composition is for use in the treatment of a disease, disorder, or condition associated with at least one pathogenic microorganism.

In some embodiments, the present disclosure provides probiotic compositions comprising at least one of *Alcaligenes faecalis, Bacillus altitudinis, Bacillus pumilus, Bacillus subtilis* or *Janthinobacterium lividum* for use in the treatment of an infection associated with a pathogenic microorganism. In some such embodiments, the infection is a skin infection. In some embodiments, the pathogenic microorganism comprises or consists of *Malassezia*. In some embodiments, the pathogenic microorganism is associated with dandruff, atopic eczema, dermatitis, *pityriasis versicolor, Tinea versicolor*, seborrheic dermatitis, folliculitis or any combinations thereof. In some embodiments, the pathogenic microorganism comprises or consists of dermatophytes. In some embodiments, the pathogenic microorganism is associated with *Tinea barbae, Tinea capitis, Tinea corporis, Tinea cruris, Tinea pedis, Tinea versicolor, onychomycosis* or any combinations thereof. In some embodiments, the probiotic composition is for use in treatment of *Tinea pedis* or *Tinea versicolor.*

In some embodiments, the present disclosure provides compositions comprising at least one metabolite of *Alcaligenes faecalis, Bacillus altitudinis, Bacillus pumilus, Bacillus subtilis* or *Janthinobacterium lividum*. In some embodiments, the composition is for use in the treatment of an infection associated with a pathogenic microorganism.

In some embodiments, the present disclosure provides kits comprising (i) at least one vial comprising a composition, which composition comprises at least one stabilized human-isolated or synthetic *Alcaligenes faecalis, Bacillus altitudinis, Bacillus pumilus, Bacillus subtilis* or *Janthinobacterium lividum*, and at least one first excipient, wherein the at least one first excipient is a cryoprotectant; and (ii) instructions. In some embodiments, the kit further comprises at least one vial of formulation buffer for reconstitution. In some embodiments, the kit further comprises instructions for mixing and application, and, optionally, one or more implements of mixing and/or application. In some embodiments, the composition is in a powdered format. In some embodiments, the composition is in a liquid format.

In some embodiments, the present disclosure provides a bacterium. In some embodiments, the bacterium comprises or consists of a probiotic selected from *Janthinobacterium lividum, Alcaligenes faecalis, Bacillus altitudinis, Bacillus pumilus*, or *Bacillus subtilis*, which bacteria are or were initially isolated from healthy human skin. Without limitation, in some embodiments, compositions and methods provided herein may be useful in modulating the microbiome of a host to effectively inhibit, treat or prevent microbial infections. In some embodiments, these compositions and methods comprise or consist of one or more probiotic products (e.g., compositions, pharmaceutical compositions, etc.) provided by the present disclosure. In some such embodiments a probiotic product of the present disclosure comprises or consists of a probiotic selected from *Janthinobacterium lividum, Alcaligenes faecalis, Bacillus altitudinis, Bacillus pumilus*, or *Bacillus subtilis* and/or active components or metabolites thereof. In some embodiments, the bacteria provided by the present disclosure are isolated from a human or are synthetic.

Also provided herein are topical and cosmetic compositions and methods. In some embodiments, these topical and cosmetic compositions may be useful for improving skin health, reducing the effects of exposure to sun, and aging. In some embodiments, these topical and cosmetic compositions comprise or consist of a probiotic selected from *Janthinobacterium lividum, Alcaligenes faecalis, Bacillus altitudinis, Bacillus pumilus*, or *Bacillus subtilis* and/or active components or metabolites thereof.

The present disclosure provides, in some embodiments, pharmaceutical compositions comprising or consisting essentially of at least one strain of probiotic selected from *Janthinobacterium lividum, Alcaligenes faecalis, Bacillus altitudinis, Bacillus pumilus*, or *Bacillus subtilis*. In some such embodiments, a pharmaceutical composition further comprises one or more excipients. In some embodiments, the pharmaceutical compositions are used in an amount effective to generally improve health, and/or for inhibition, treatment or prevention of topical microorganisms and/or the diseases they cause. In some embodiments, a pharmaceutical composition comprising a probiotic selected from *Janthinobacterium lividum, Alcaligenes faecalis, Bacillus altitudinis, Bacillus pumilus*, or *Bacillus subtilis* and at least one excipient is more effective than a pharmaceutical composition not comprising the at least one excipient.

In some embodiments a composition comprises or consists essentially of a probiotic selected from *Janthinobacterium lividum, Alcaligenes faecalis, Bacillus altitudinis, Bacillus pumilus*, or *Bacillus subtilis*, and/or one or more materials originating therefrom.

In some embodiments, pharmaceutical compositions provided by the present disclosure comprising or consisting essentially of one or more metabolites of *Janthinobacterium lividum, Alcaligenes faecalis, Bacillus altitudinis, Bacillus pumilus*, or *Bacillus subtilis* of human origin. In some embodiments, the metabolites are administered in an amount effective for use in the inhibition, treatment or prevention of a topical microorganism.

Also provided herein are pharmaceutical compositions comprising, consisting essentially of, or consisting of a cell lysate of *Janthinobacterium lividum, Alcaligenes faecalis, Bacillus altitudinis, Bacillus pumilus*, or *Bacillus subtilis*. In some embodiments, the cell lysate is administered in an amount effective for use in the inhibition, treatment or prevention of a topical pathogenic microorganism. In some such embodiments, a pharmaceutical composition further comprises an excipient. In some embodiments, the excipient and/or materials originating from a probiotic provided herein are administered in an amount effective for use in the inhibition, treatment or prevention of infection with a topical microorganism. In some embodiments, the excipient and/or materials originating from probiotics provided herein are part of a method for using these pharmaceutical compositions to inhibit, treat, or prevent pathogenic microorganisms and/or the diseases they cause. In some embodiments, these human-isolated probiotics can be formulated into compositions for application to a subject in need thereof (e.g. skin, mucosa, hair, nails) or for application to objects that come in contact with the subject (e.g. cloth, floors, etc.). In some embodiments, the pharmaceutical compositions are formulated for application to the skin, mucosa, hair, and/or nails. In some embodiments, the pharmaceutical compositions are applied to, included in, or formulated as, e.g., bandages, sunscreen, toothpaste, mouthwash, shampoo, soap, moisturizer, lip balm, or dental floss.

In some embodiments, provided herein are synthetic compositions comprising a probiotic selected from *Janthi-*

*nobacterium lividum, Alcaligenes faecalis, Bacillus altitudinis, Bacillus pumilus*, or *Bacillus subtilis* or combinations thereof, one or more metabolites from a probiotics selected from *Janthinobacterium lividum, Alcaligenes faecalis, Bacillus altitudinis, Bacillus pumilus*, or *Bacillus subtilis* or combinations thereof, cell lysate of a probiotic *Janthinobacterium lividum, Alcaligenes faecalis, Bacillus altitudinis, Bacillus pumilus*, or *Bacillus subtilis* or combinations thereof; and/or one or more postbiotics selected from *Janthinobacterium lividum, Alcaligenes faecalis, Bacillus altitudinis, Bacillus pumilus*, or *Bacillus subtilis* or combinations thereof, formulated for topical application. In some embodiments, these synthetic compositions can be formulated for application to a subject in need thereof (e.g. skin, mucosa, hair, nails) or to objects that come in contact with the subject (e.g. cloth, floors, etc.). In some embodiments these synthetic compositions are cosmetic compositions.

In some embodiments, compositions of this disclosure further comprise a prebiotic. In some embodiments, the prebiotic is selected from one or more of an amino acid, biotin, glycerol, fructooligosaccharide, galactooligosaccharides, inulin, lactulose, mannan oligosaccharide, oligofructose-enriched inulin, oligofructose, oligodextrose, tagatose, trans-galactooligosaccharide, non-natural glycans and xylooligosaccharide.

In some embodiments, a pharmaceutical composition provided herein comprises a probiotic selected from *Janthinobacterium lividum, Alcaligenes faecalis, Bacillus altitudinis, Bacillus pumilus*, or *Bacillus subtilis* and further comprises at least one isolated additional microbe. In some embodiments, the additional isolated microbe is selected from a *Lactobacillus* species, a *Lactococcus* species, a benign fungal species typically found on human skin, or a *Propionibacterium* or *Cutibacterium* species.

In some embodiments, compositions (including pharmaceutical compositions) disclosed herein are formulated for administration with at least one additional antifungal or antibacterial compound. In some embodiments, the pharmaceutical composition is formulated for topical administration to skin or mucosa. In some embodiments, the compositions are part of a delivery device manufactured for mucosal cavities.

In some embodiments, the human-isolated *Janthinobacterium lividum, Alcaligenes faecalis, Bacillus altitudinis, Bacillus pumilus*, or *Bacillus subtilis* nucleic acid sequence is identified by SEQ ID NO: 1 corresponding with *Alcaligenes faecalis*, SEQ ID NO: 2 corresponding with *Bacillus altitudinis*, SEQ ID NO: 3 corresponding with *Bacillus pumilus*, SEQ ID NO: 4 corresponding with *Bacillus subtilis*, or SEQ ID NO: 5 corresponding with *Janthinobacterium lividum*, respectively. In some embodiments, human-isolated *Alcaligenes faecalis, Bacillus altitudinis, Bacillus pumilus, Bacillus subtilis* or *Janthinobacterium lividum* comprises or consists of a polynucleotide comprising a nucleic acid sequence at least 90% identical to SEQ ID NO: 1, SEQ ID NO: 2, SEQ ID NO: 3, SEQ ID NO: 4, or SEQ ID NO: 5 respectively; or at least 93% identical to, at least 95%, at least 97%, at least 98%, at least 99%, or 100% identical to SEQ ID NO: 1, SEQ ID NO: 2, SEQ ID NO: 3, SEQ ID NO: 4, or SEQ ID NO: 5 respectively, relative to its 16s rRNA gene sequence (i.e., as provided in SEQ ID NOs: 1-5).

In some embodiments, a pharmaceutical composition provided by the present disclosure is used to treat or prevent infection with a fungal microorganism, such as *Candida albicans, C. glabrata, C. parapsilosis, C. tropicalis, C. auris, C. krusei* or *C. kefyr.*

In some embodiments, the pharmaceutical composition is used to treat a fungal pathogenic microorganism, such as a *Trichophyton* or a *Malassezia* species.

In some embodiments a pharmaceutical composition is used to treat infection with a fungal pathogenic microorganism such as *T. rubrum, T. verrucosum, T. tonsurans, T. terrestre, T. interdigitale*, or *T. mentagraphytes.*

In some embodiments, a pharmaceutical composition is used to treat infection with a bacterial pathogenic microorganism, such as *Staphylococcus, Pseudomonas, Enterococcus*, and *Staphylococcus aureus.*

In some embodiments, a pharmaceutical composition is used to treat infection with a viral pathogenic microorganism, such as poliovirus, herpes simplex virus, hepatitis A virus, rotavirus, adenovirus, coronavirus, and influenza type A virus.

In some embodiments, a pharmaceutical composition is used to treat infection with a pathogenic microorganism selected from the group consisting of *Gardnerella vaginalis, Candida albicans, Atopobium vaginae, Staphylococcus aureus, Escherichia coli, Pseudomonas*, and *Salmonella.*

In some embodiments, an isolated metabolite of *Janthinobacterium lividum, Alcaligenes faecalis, Bacillus altitudinis, Bacillus pumilus* or *Bacillus subtilis* is provided for use in or as a composition with a soluble formulation appropriate for topical application. In some embodiments, the metabolite is selected from ectoine, betalactone, terpene, resorcinol, T1PKS, quilolobactin, burkhoderic acid, bacillibactin, hydroxylamine, cyclo-(L-Pro-Gly)5 (SEQ ID NO: 36), phenylacetic acid, p-hydroxyphenylacetylamide, amylase, protease, cellulase, iturin, chitinase, tunicamycin, butyrolactone, phosphonate, siderophores, indole acetic acid, thermostable keratinase, indole-3-acetic acid, osmolytes, producing catalase, amylase, ACC deaminase, guanyl-preferring RNase, binase, bacteriocin, nonribosomal peptide synthetase, sactipeptide, bacilysin, pseudomonine, fengycin, surfactin, lichenysin, sporulation killing factor, 4-phenylbutanoic acid, Butanal, 3-methyl-, Propene, 2-butene, 2-heptanone, 6-methyl-5-methylene-, and 6-oxabicyclo[3.1.0] hexane, Diketopiperazines cordycedipeptide, pumilacidins, a bacteriolytic, 4-dipentylhexane-2,5-diol, 1,1'-(4,5-dibutylcyclohexane-1,2-diyl)bis(ethan-1-ol), 1,1'-(4,5-dibutyl-3,6-dimethylcyclohexane-1,2-diyl)bis(ethan-1-one), antifungal cyclic lipopeptides, polyketides (PKs), ribosomally and non-ribosomally synthesized peptides, and any combinations thereof.

In some embodiments, a human-isolated *Janthinobacterium lividum, Alcaligenes faecalis, Bacillus altitudinis, Bacillus pumilus*, or *Bacillus subtilis* produces an antimicrobial metabolite, selected from ectoine, betalactone, terpene, resorcinol, betalactone, T1PKS, quilolobactin, burkhoderic acid, bacillibactin, hydroxylamine, cyclo-(L-Pro-Gly)5 (SEQ ID NO: 36), phenylacetic acid, p-hydroxyphenylacetylamide, amylase, protease, cellulase, iturin, chitinase, tunicamycin, butyrolactone, phosphonate, polyketides, siderophores, indole acetic acid, thermostable keratinase, indole-3-acetic acid, osmolytes, producing catalase, amylase, ACC deaminase, guanyl-preferring RNase, binase, bacteriocin, nonribosomal peptide synthetase, sactipeptide, bacilysin, pseudomonine, fengycin, surfactin, lichenysin, sporulation killing factor, 4-phenylbutanoic acid, Butanal, 3-methyl-, Propene, 2-butene, 2-heptanone, 6-methyl-5-methylene-, and 6-oxabicyclo[3.1.0] hexane, Diketopiperazines cordycedipeptide, pumilacidins, bacteriolytic, 4-dipentylhexane-2,5-diol, 1,1'-(4,5-dibutylcyclohexane-1,2-diyl)bis(ethan-1-ol), 1,1'-(4,5-dibutyl-3,6-dimethylcyclohexane-1,2-diyl)bis(ethan-1-one), antifungal cyclic lipopeptides, polyketides (PKs), terpenes, ribosomally and non-ribosomally synthesized peptides or any combinations thereof. In some embodiments, such an antimicrobial metabolite can be used for topical application or application to the mucosa to prevent, inhibit, or treat conditions, diseases, or disorders caused by microorganisms.

In some embodiments, a metabolite produced by a probiotic as provided herein is not isolated from a human reference strain. In some such embodiments, the metabolite from a human-isolated strain is present or detected at a level higher than another reference strain of *Janthinobacterium lividum, Alcaligenes faecalis, Bacillus altitudinis, Bacillus pumilus*, or *Bacillus subtilis* that was not isolated from a human. In some embodiments, the metabolite of human-isolated *Janthinobacterium lividum, Alcaligenes faecalis, Bacillus altitudinis, Bacillus pumilus*, or *Bacillus subtilis* is selected from bacillibactin, bacilysin, carotenoid lichenysin, fengycin, ectoine, quinolobactin and any combinations thereof.

In some embodiments, the pharmaceutical composition comprising the human-isolated *Janthinobacterium lividum, Alcaligenes faecalis, Bacillus altitudinis, Bacillus pumilus*, or *Bacillus subtilis* or one or more metabolites thereof is lyophilized, frozen at −20° C., or frozen at −80° C., before reconstitution with a separately-stored sterile formulation buffer.

In some embodiments, a formulation comprises one or more of eye lubricant, amino acids such as, e.g., tryptophan, dipeptides, oligopeptides, polypeptides, Casaminoacids, monosaccharides including glucose, sugar alcohol including mannitol, simple alcohols including glycerol, oligo-alcohols, simple polyols, complex polyols, disaccharides including sucrose and trehalose and isomers of, polysaccharides, modified polysaccharides including λ-Carrageenan, cellulose and modified celluloses including carboxymethyl cellulose, starch and modified starch including 2 Hydroxyethylstarch (HES), other bioadhesion agents including Carbopol polymers, thickeners and rheology modifiers such as, e.g., CMC, suspension and and/or emulsion stabilizers, and any combination thereof. In some such embodiments, one or more such components are included in a buffer for reconstitution.

In some embodiments, compositions comprising human-isolated or synthetic *Janthinobacterium lividum, Alcaligenes faecalis, Bacillus altitudinis, Bacillus pumilus*, or *Bacillus subtilis*, or metabolites thereof, are used in a method of treating or preventing diseases or disorders caused by a pathogenic microorganism. In some embodiments, methods of treatment comprise or consists of methods of inhibiting, slowing, or ceasing the growth of the pathogenic microorganism. In some embodiments the method comprises administering an effective amount of a human-isolated or synthetic probiotic selected from *Janthinobacterium lividum, Alcaligenes faecalis, Bacillus altitudinis, Bacillus pumilus*, or *Bacillus subtilis*, metabolite and/or cell lysate thereof to a subject in need thereof, wherein the human-isolated or synthetic probiotic, metabolite and/or cell lysate thereof is present in an amount effective for inhibiting, slowing, or ceasing the growth of microorganisms to treat or prevent diseases or disorders caused by such microorganisms. In some embodiments, the human-isolated or synthetic probiotic selected from *Janthinobacterium lividum, Alcaligenes faecalis, Bacillus altitudinis, Bacillus pumilus*, or *Bacillus subtilis* is applied in conjunction with an additional antifungal, antiviral, or antibacterial agent. In some embodiments the compositions comprise at least one additional probiotic or non-pathogenic microorganism.

In some embodiments, the pharmaceutical, synthetic, cosmetic, and probiotic compositions of this disclosure contain at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ colonizing forming units (CFUs) per milliliter or milligram of human-isolated or synthetic *Janthinobacterium lividum, Alcaligenes faecalis, Bacillus altitudinis, Bacillus pumilus*, or *Bacillus subtilis*.

Provided herein are methods of manufacturing a pharmaceutical composition comprising an effective amount of human-isolated or synthetic *Janthinobacterium lividum, Alcaligenes faecalis, Bacillus altitudinis, Bacillus pumilus*, or *Bacillus subtilis*, an optional metabolite, cell lysate, and/or prebiotic, and a pharmaceutically acceptable excipient. The method comprises preserving a human-isolated or synthetic *Janthinobacterium lividum, Alcaligenes faecalis, Bacillus altitudinis, Bacillus pumilus*, or *Bacillus subtilis* by lyophilization in the presence of a drug substance formulation containing an excipient which enhances preservation and packaging the preserved human-isolated or synthetic *Janthinobacterium lividum, Alcaligenes faecalis, Bacillus altitudinis, Bacillus pumilus*, or *Bacillus subtilis* for reconstitution with a second excipient formulation to generate the formulation immediately prior to administration. In some embodiments, the excipient is chosen from the group consisting of without limitation, DMSO, natural tears, eye lubricant, amino acids, peptides, glycerol, other simple polyols, complex polyols, modified polyols, sugar alcohols, glucose, monosaccharides, disaccharides, oligosaccharides, polysaccharides and modified oligosaccharides and polysaccharides, vitamins, proteins, buffers and combinations thereof.

Provided herein are kits comprising at least one vial of stabilized human-isolated or synthetic *Janthinobacterium lividum, Alcaligenes faecalis, Bacillus altitudinis, Bacillus pumilus*, or *Bacillus subtilis* and at least one optional vial of formulation buffer for reconstitution of stabilized human-isolated or synthetic *Janthinobacterium lividum, Alcaligenes faecalis, Bacillus altitudinis, Bacillus pumilus*, or *Bacillus subtilis*, instructions for mixing and application, and optionally one or more implements of mixing and application. In some embodiments, implements of mixing and application are included and comprise one or more elements selected from a syringe, an empty sterile container, and an atomizer or mister. In some embodiments, the kit contains multiple vials of stabilized human-isolated or synthetic *Janthinobacterium lividum, Alcaligenes faecalis, Bacillus altitudinis, Bacillus pumilus*, or *Bacillus subtilis* and at least one vial of liquid for reconstitution of stabilized human-isolated or synthetic *Janthinobacterium lividum, Alcaligenes faecalis, Bacillus altitudinis, Bacillus pumilus*, or *Bacillus subtilis*, for multiple applications to one or more subjects in need thereof. In some embodiments, the kit is prepared for application by a medical professional. In some embodiments, the kit is prepared for application by a subject in need thereof.

BRIEF DESCRIPTION OF FIGURES

FIGS. 2A and 2D show zones of inhibition around DB05646 grown on *Malassezia furfur* and *Malassezia restricta* as compared to the antifungal Terbinafine (TRB). FIG. 2B shows zones of inhibition around DB05646 grown on *S. aureus* as compared to the antibacterial Oxacillin. FIG. 2C shows inhibition of *Trichophyton rubrum* by crossed streaks of DB05646 as compared to growth of *T. rubrum* without crossed streaks of DB05646. One spot of *T. rubrum* was added to each quadrant for a total of 4 spots.

FIGS. 3A and 3D show zones of inhibition around DB10033 grown on *Malassezia furfur* as compared to the antifungal Terbinafine (TRB). FIG. 3B shows zones of inhibition around DB10033 grown on *S. aureus* as compared to the antibacterial Oxacillin. FIG. 3C shows widths of *Trichophyton rubrum* colonies grown with and without (mock) streaks of DB10033 surrounding two sides of the colony.

FIGS. 4A and 4D show zones of inhibition around DB03376 grown on *Malassezia furfur* as compared to the antifungal Terbinafine (TRB). FIG. 4B shows zones of inhibition around DB03376 grown on *S. aureus* as compared to the antibacterial Oxacillin. Three replicates were performed for each experiment. FIG. 4C shows widths of *Trichophyton rubrum* colonies grown with and without (mock) streaks of DB03376 surrounding two sides of the colony.

FIGS. 5A and 5D show zones of inhibition around DB02475 grown on *Malassezia furfur* as compared to the antifungal Terbinafine (TRB). FIG. 5B shows zones of inhibition around DB02475 grown on *S. aureus* as compared to the antibacterial Oxacillin. Three replicates were performed for each experiment. FIG. 5C shows widths of *Trichophyton rubrum* colonies grown with and without (mock) streaks of DB02475 surrounding two sides of the colony.

DETAILED DESCRIPTION

Figure 1:
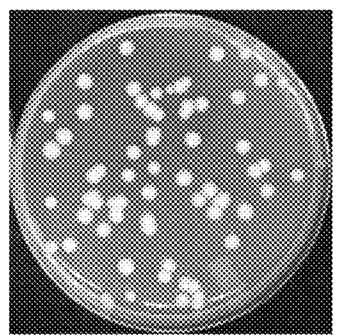
FIG. 1 shows representative examples of *Alcaligenes faecalis, Bacillus altitudinis, Bacillus pumilus*, and *Bacillus subtilis*, all grown on petri dishes.
Figure 1:
Figure 1:
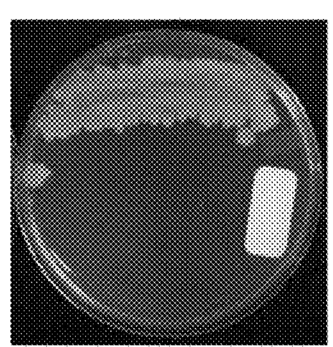
Figure 1:
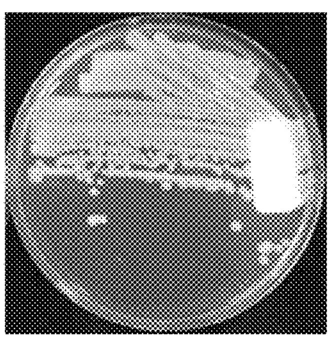

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

Certain Terminology

Throughout this application, various embodiments of this disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range.

It is appreciated that certain features of the disclosure, which are, for clarity, described in the context of separate embodiments, can also be provided in combination in a single embodiment. Conversely, various features of the disclosure, which are, for brevity, described in the context of a single embodiment, can also be provided separately or in any suitable sub-combination or as suitable in any other described embodiment of the disclosure. Certain features described in the context of various embodiments are not to be considered essential features of those embodiments, unless the embodiment is inoperative without those elements.

As used herein all percentages are weight percent unless otherwise indicated.

It must be noted that, as used in the specification and the appended claims, the singular forms "a," "an" and "the" include plural referents unless the context clearly dictates otherwise.

As used herein, the term "about" includes variation of up to approximately +/−10% and that allows for functional equivalence in the product.

As used herein an "acceptable" excipient refers to an excipient that must be compatible with the active ingredient and not deleterious to the subject to which it is administered.

As used herein the term "ameliorating" refers to any therapeutically beneficial result in the treatment of a disease state, (e.g., a metabolic disease state), including prophylaxis, lessening the severity or progression, remission, or cure thereof.

As used herein "colonization" of a host organism includes the non-transitory residence of a bacterium or other microscopic organism. As used herein, "reducing colonization" of a host subject's skin (or any other microbial niche) by a pathogenic bacterium includes a reduction in the residence time of the pathogen on the skin, reduction in replication on the skin, as well as a reduction in the number (or concentration) of the pathogen on the skin or adhered to the skin. Measuring reductions of adherent pathogens may be demonstrated, e.g., by a biopsy sample, by swabbing, scrubbing, or scraping the skin, or reductions may be measured indirectly.

As used herein, the term "colony-forming unit" or "CFU" is an individual cell that is able to divide itself into an entire colony of identical cells.

As used herein, a "combination" of two or more bacteria includes the physical co-existence of the two bacteria, either in the same material or product or in physically connected products, as well as the temporal co-administration or co-localization of the two bacteria.

As used herein, the phrase "without the cryoprotectant" refers to a composition that with otherwise identical components or as an otherwise identical formulation, the cryoprotectant is removed and replaced with water. In other words, "without the cryoprotectant" is used to describe presence or absence of a particular cryoprotectant from an otherwise identical composition.

As used herein, the term "derived from" includes microbes, microorganisms or other living culture immediately taken from an environmental sample, and also microbes, microorganisms or other living culture isolated from an environmental source and subsequently grown in a pure culture or isolate. Something that is derived from something else includes material isolated from the recited source, and materials obtained using the isolated materials (e.g., cultures of microorganisms grown from microorganisms isolated from the recited source). Similarly, as used herein, the term "derivative" when referring to a probiotic includes anything that originated or is a product of a probiotic such as, but not limited to, one or more polynucleotides or polypeptides having similarity to a parental strain polynucleotide or polypeptide, one or more metabolites, cell lysates, etc.

As used herein, dosage for compositions provided herein are deemed to be "effective doses," when the probiotic or prebiotic composition is administered in a sufficient quantity to alter the physiology of a pathogenic microorganism and/or a subject (e.g., a subject afflicted with a disease, disorder or condition associated with a pathogenic microorganism) in a desired manner.

As used herein, the term "human-isolated" is defined as bacteria or other microbes isolated from a human source.

As used herein, the term "inhibit", "inhibiting" or "inhibition" includes stopping, slowing, delaying, pausing, weakening, decreasing, the progression of a condition or growth, or preventing a condition or growth, or substantially treating a condition or undesired growth.

As used herein the term "in vitro" refers to processes that occur in a living cell growing separate from a living organism, e.g., growing in tissue culture.

As used herein, the term "in vivo" refers to processes that occur in a living organism.

As used herein the term "mammal" as used herein includes both humans and non-human mammals and includes but is not limited to humans, non-human primates, canines, felines, murines, bovines, equines, and porcines.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, a "microbe" refers to a microorganism, that is, a microscopic organism, and may be used to describe, for example, any type of bacteria, fungi including yeasts and molds, archae, protists, and viruses.

As used herein "microbiome" refers to the genetic content of the communities of microbes, microorganisms or living cultures that live in and on the human body, both sustainably and transiently, including micro-eukaryotes, fungi, archaea, bacteria, and viruses (including bacterial viruses i.e., phage), wherein "genetic content" includes genomic DNA, RNA such as ribosomal RNA, the epigenome, plasmids, and all other types of genetic information.

As used herein "microbiota" refers to the community of microorganisms or microbes that occur (sustainably or transiently) in and on an animal subject, typically a mammal such as a human, including micro-eukaryotes, archaea, bacteria, and viruses (including bacterial viruses i.e., phage).

As used, the terms "over produce" and "over express" refers to production of one or more compounds (e.g., metabolites) by an organism, and the term "over expresses" refers to the expression of a gene that produces the one or more compounds (e.g., metabolites). Over produce or over express refers to at least about 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 1.5-fold, 2-fold, 2.5-fold, 3-fold, 4-fold, 5-fold, or more production or more expression (respectively) relative to other strains (e.g., a reference strain).

As used herein, the term "pathogen" refers to a microorganism associated with the disease or infection. For example: *Tinea barbae* is a dermatophyte infection of the beard area most often caused by *Trichophyton mentagro-*

*phytes* or *T. verrucosum*. *Tinea capitis* is a dermatophytosis caused by *Trichophyton tonsurans, Microsporum canis* and *M. audouinii* or other *Trichophyton* species (e.g., T. schoenleinii. *T. violaceum*). *Tinea corporis* is a dermatophyte infection of the face, trunk, and extremities commonly caused by *Trichophyton mentagrophytes, T. rubrum*, and *Microsporum canis*. *Tinea cruris* is a dermatophytosis that is commonly caused by *Trichophyton rubrum* or *T. mentagrophytes*. *Tinea pedis* is a dermatophyte infection of the feet commonly caused by *T. rubrum*. *Tinea versicolor* is a dermatophyte infection of the chest, back, torso or other areas of the body most commonly caused by fungi of the genus *Malassezia*, and in some instances *M. furfur*. Onychomycosis is a dermatophyte infection of the fingernail or toenail, bed or plate, and is commonly caused by *T. rubrum, Microsporum species*, or *Trichophyton tonsurans*, but can also be caused by *Aspergillus, Fusarium, Acremonium, Scytalidium, Scopulariopsis, Paecilomyces, Syncephalastrum, Neoscytalidium, Chaetomium, Alternaria*, and *Onychocola* species or yeasts such as *Candida albicans* and *Candida parapsilosis*. Dermatophytid reactions are protean; they are not related to localized growth of the fungus but rather are an inflammatory reaction to a dermatophytosis elsewhere on the body. Other diseases, disorders, or conditions related, but not limited to, are atopic dermatitis, impetigo, skin and soft tissue infections, and are often caused by gram positive bacterium *Staphylococcus*.

As used herein, the term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

As used herein the term "postbiotic" refers to functional bioactive compounds, generated by a microbe, which may be used to promote health.

As used herein, the term "preventing" or "prevention" includes completely or substantially reducing the likelihood or occurrence or the severity of initial clinical or aesthetical symptoms of a condition, disease, or disorder.

As used herein the term "probiotic" refers to a live microorganism, microbe or living culture (including bacterium or fungi for example) which, provided in sufficient numbers, beneficially affects the host organism, i.e.by conferring one or more demonstrable health benefits on the host organism. Probiotics of the present disclosure are, at least initially, human-derived (i.e., collected from human skin samples), even if, at some point later, synthetic, or otherwise engineered compositions comprising the probiotic are provided.

As used herein "probiotic bacterium" or "probiotic microorganism" or "probiotic microbe" or "probiotic culture" or "probiotic bacteria" is a bacterium, microorganism, microbe, fungus, culture or bacteria which, provided in sufficient numbers, beneficially affects the host organism, i.e. by conferring one or more demonstrable health benefits on the host organism.

As used herein, the term "reference strain" refers to a strain isolated from the same genus (e.g., *Janthinobacterium, Alcaligenes, Bacillus*, etc) and may or may not be a variant of the same species (e.g., *J. lividum, A. faecalis, B. subtilis, B. pumilus, B. altitudinis*, etc.) A reference strain may be a strain isolated from a different environmental niche, for example, if a test strain is isolated from human skin, a reference strain may also be isolated from human skin, or it may be isolated from skin of another organism (e.g., salamander), or another source such as produce, dirt, wastewater, or the like.

As used herein, the term "soluble metabolite" refers to a metabolite or metabolites present in the supernatant of a cell culture from which the viable cells have been removed. In preferred embodiments the culture is grown to a cell density of at least about $OD_{600}$ 0.5. In a further preferred embodiment, the cells are removed by centrifugation and the embodiment can be called a "cell-free supernatant." In a more preferred embodiment, the supernatant is filtered and can be called a "cell-free filtrate." It will be apparent that the supernatant may be used directly in the formulations of the present disclosure, or that one or more of the metabolites may be isolated from the supernatant by any suitable means prior to use.

As used herein, the term "strain" is defined as any nucleic acid sequence that is 97% or greater identical to a defined 16s rRNA nucleic acid sequence. More preferred embodiments of strain are a nucleic acid sequence that is greater than 98%, greater than 99% identical to a defined 16s rRNA nucleic acid sequence.

As used herein the term "percent identical," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identical" can exist over a region of the sequence being compared, e.g., over a functional domain, or, alternatively, exist over the full length of the two sequences to be compared. In some aspects, percent identical is defined with respect to a region useful for characterizing phylogenetic similarity of two or more organisms, including two or more microorganisms. Percent identical in these circumstances can be determined by identifying such sequences within the context of a larger sequence, that can include sequences introduced by cloning or sequencing manipulations such as, e.g., primers, adapters, etc., and analyzing the percent identical in the regions of interest, without including in those analyses introduced sequences that do not inform phylogenetic similarity. For sequence comparison, typically one sequence acts as a reference sequence to which test sequences are compared. When using a sequence comparison algorithm, test and reference sequences are input into a computer for purposes of analyses using programs suchas BLASTP and BLASTN or other algorithms available to persons of skill, subsequent coordinates are designated, if necessary, and sequence algorithm program parameters are designated. The sequence comparison algorithm then calculates the percent sequence identical for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by thesearch for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identical and sequence similarity is the BLAST algorithm, which is described in Altschul et al., J. Mol. Biol. 215:403-410 (1990). Software for performing BLAST analyses is publicly available through the National Center for Biotechnology Information.

As used herein, the term "subject" refers to any animal subject including humans, laboratory animals (e.g., primates, rats, mice), livestock (e.g., cows, sheep, goats, pigs, turkeys, and chickens), aquatic animals (e.g. fish, crustaceans, cetaceans, and cephalopods), and household pets (e.g., dogs, cats, and rodents). The subject may be suffering from a dysbiosis, including, but not limited to, an infection due to a pathogenic microorganism or may be at risk of developing or transmitting to others an infection due to a pathogenic microorganism.

As used herein, the term "sufficient amount" means an amount sufficient to produce a desired effect, e.g., an amount sufficient to alter the microbial content of a subject's microbiota.

As used herein, "synthetic" refers to anything that is lab-produced or non-naturally derived in whole or in part, such that it mimics, in whole or in part, a naturally existing or derived counterpart in one or more aspects. For instance, a synthetic bacterium can be an engineered bacterium which has one or more components made or altered, in whole or in part, such that it mimics or changes (e.g., improves upon) a bacterium found in nature.

As used herein, the term "therapeutic amount" is an amount of an anti-microbial, for example an anti-fungal or anti-bacterial, compound that is prescribed, e.g., to achieve a therapeutic effect. Concentrations below those typically prescribed are termed "sub-therapeutic" amounts. Sub-therapeutic amounts are typically with reference to an agent (e.g., anti-microbial, e.g., anti-fungal, e.g., anti-bacterial) used as a monotherapy.

As used herein, the term "therapeutically effective amount" is an amount that is effective to ameliorate a symptom of a disease. A therapeutically effective amount can be a "prophylactically effective amount" as prophylaxis can be considered therapy.

As used herein, the term "topical" includes references to formulations that are adapted for application to body surfaces (e.g. the skin, mucosa or mucous membranes). Skin includes exterior surfaces such as hair, finger and toenails. Mucous membranes, or mucosa, that may be mentioned in this respect include the mucosa of the vagina, the penis, the urethra, the bladder, the anus, the colon, the mouth (including the mucosa of the cheek, the soft palate, the gums, the under surface of tongue and the floor of the mouth), the nose, the throat (including the mucosa of the pharynx, the larynx, the trachea and the esophagus), the bronchi, the lungs, the eye and the ear.

As used herein, the term "treat," "treating" or "treatment" includes abrogating, ameliorating, inhibiting, slowing, preventing, or reversing, either substantially or completely, the progression of a condition, disease, or disorder, and/or substantially or completely abrogating, ameliorating, inhibiting, slowing, preventing, or reversing one or more clinical or aesthetical symptoms of a condition, disease, or disorder.

As used herein "viable organisms" are organisms that are capable of growth and multiplication. In some embodiments, viability can be assessed by numbers of colony-forming units that can be cultured. In some embodiments, viability can be assessed by other means, such as live/dead staining and microscopy, or flow cytometry and quantitative polymerase chain reaction.

Compositions

Provided herein are probiotics comprising, consisting essentially of, or consisting of human-isolated *Alcaligenes faecalis, Bacillus altitudinis, Bacillus pumilus, Bacillus subtilis* or *Janthinobacterium lividum* strains or any combination thereof. In some embodiments the probiotics comprise or consist of a polynucleotide represented by a 16s rRNA sequence set forth in SEQ ID NO: 1, 2, 3, 4, and/or 5. In some embodiments, the present disclosure provides compositions comprising a probiotic selected from human-isolated *Alcaligenes faecalis, Bacillus altitudinis, Bacillus pumilus, Bacillus subtilis* or *Janthinobacterium lividum* or any combination thereof, which probiotics comprise antimicrobial and/or other beneficial properties. In some embodiments, the probiotic is adapted to a human host, ensuring that the compositions are safe for human application and equipped to survive on a human host at least long enough to be therapeutically effective. In some embodiments, the composition modulates the microbiome of the object of application (e.g., a host, e.g., a subject in need thereof).

In some embodiments, the composition comprises a probiotic, metabolite, postbiotic and/or cell lysate of one or more of *Janthinobacterium lividum, Alcaligenes faecalis, Bacillus altitudinis, Bacillus pumilus*, or *Bacillus subtilis* or any combination thereof. In some embodiments, the probiotic comprises, consists essentially of or consists of DB02473, DB02475, DB03376, DB10033, DB05646, or any combination thereof.

In some embodiments, soluble metabolites of, and for use in, the present disclosure include, but are not limited to, soluble metabolites from human-isolated or synthetic *Janthinobacterium lividum, Alcaligenes faecalis, Bacillus altitudinis, Bacillus pumilus*, or *Bacillus subtilis* and any additional microbe such as, *Bifidobacterium, Brevibacterium, Propionibacterium, Lactococcus, Streptococcus, Lactobacillus* (e.g., *L. acidophilus*), *Enterococcus, Pediococcus, Leuconostoc*, Oenococcus, and combinations thereof.

In some embodiments, cell lysates of, and for use in, the present disclosure include, but are not limited to, cell lysates from human-isolated or synthetic *Janthinobacterium lividum, Alcaligenes faecalis, Bacillus altitudinis, Bacillus pumilus*, or *Bacillus subtilis* and any additional microbe such as, *Bifidobacterium, Brevibacterium, Propionibacterium, Lactococcus, Streptococcus, Lactobacillus* (e.g., *L. acidophilus*), *Enterococcus, Pediococcus, Leuconostoc, Oenococcus*, or any combination thereof.

In some embodiments, a composition comprising a human-isolated or synthetic *Janthinobacterium lividum, Alcaligenes faecalis, Bacillus altitudinis, Bacillus pumilus*, or *Bacillus subtilis* or component or derivative thereof is improved by addition of one or more additional components. In some embodiments, an improvement is greater efficacy, stability, and/or viability as compared to the composition without the one or more additional components. In some embodiments, one or more additional components may include, but is not limited to an excipient such as, e.g., a cryoprotectant.

Probiotics

In some embodiments, a probiotic provided by the present disclosure comprises or consists of one or more genus of bacteria. Probiotic bacteria provided by and useful in methods provided herein of the present disclosure include, but are not limited to, human-isolated or synthetic (i.e., lab produced, e.g., engineered bacterium) *Janthinobacterium lividum, Alcaligenes faecalis, Bacillus altitudinis, Bacillus pumilus*, or *Bacillus subtilis*, and any additional microbe such as, *Bifidobacterium, Brevibacterium, Propionibacterium, Lactococcus, Streptococcus, Lactobacillus* (e.g., *L.*

*acidophilus*), *Enterococcus, Pediococcus, Leuconostoc*, Oenococcus, or any combinations thereof.

In some embodiments, the strain of *Janthinobacterium lividum, Alcaligenes faecalis, Bacillus altitudinis, Bacillus pumilus*, or *Bacillus subtilis* is originally derived from a human source. In some embodiments, a human-isolated or synthetic *Janthinobacterium lividum, Alcaligenes faecalis, Bacillus altitudinis, Bacillus pumilus*, or *Bacillus subtilis* strain demonstrates superior persistence on human skin compared to a reference strain, e.g., non-human strain. In some embodiments, a human-isolated or synthetic *Janthinobacterium lividum, Alcaligenes faecalis, Bacillus altitudinis, Bacillus pumilus*, or *Bacillus subtilis* strain demonstrates superior production or overproduction of a metabolite or metabolites or postbiotics compared to a reference strain. In such embodiments, a reference *Janthinobacterium lividum, Alcaligenes faecalis, Bacillus altitudinis, Bacillus pumilus*, or *Bacillus subtilis* strain may be a strain isolated from a different environmental niche, such as salamander skin, produce, or the like.

In some embodiments, a probiotic genus comprises or consists of *Alcaligenes, Bacillus*, and/or *Janthinobacterium.*

In some embodiments, the *Alcaligenes* comprises or consists of *A. faecalis.*

In some embodiments, the *Bacillus* comprises or consists of *B. altitudinis, B. pumilus*, and/or *B. subtilis.*

In some embodiments, the *Janthinobacterium* comprises or consists of J *lividum.*

In some embodiments, the probiotic comprises, consists essentially of or consists of a probiotic *A. faecalis*. In some such embodiments, the probiotic comprises or consists of DB05646. In some embodiments, the probiotic is characterized in that it comprises or consists of a nucleic acid sequence as set forth in SEQ ID NO: 1.

In some embodiments, the probiotic comprises, consists essentially of or consists of a probiotic *B. altitudinis*. In some such embodiments, the probiotic comprises or consists of DB10033. In some embodiments the probiotic comprises or consists of DB02448, DB02457, DB02461, DB02478, DB02549, or DB02623. In some embodiments, the probiotic is characterized in that it comprises or consists of a nucleic acid sequence as set forth in SEQ ID NO: 2. In some embodiments, the probiotic is characterized in that it comprises or consists of a nucleic acid sequence as set forth in any one of SEQ ID NOs 7-12:

In some embodiments, the probiotic comprises, consists essentially of or consists of a *B. pumilus*. In some such embodiments, the probiotic comprises or consists of DB03376. In some embodiments the probiotic comprises or consists of DB01269, DB02420, DB02429, DB02430, DB02485, DB02492, DB02548, DB02622, DB02626, DB02680, DB02681, DB02708, DB03355, DB03366, or DB03376. In some embodiments, the probiotic is characterized in that it comprises or consists of a nucleic acid sequence as set forth in SEQ ID NO: 3. In some embodiments, the probiotic is characterized in that it comprises or consists of a nucleic acid sequence as set forth in any one of SEQ ID NOs 13-16 and 18-26.

In some embodiments, the probiotic comprises, consists essentially of or consists of a probiotic comprising *B. subtilis*. In some such embodiments, the probiotic comprises or consists of DB02475. In some embodiments the probiotic comprises or consists of DB01270, DB01298, DB02460, DB02462, DB02946, DB03347, DB03351, DB03353, or DB03376. In some embodiments, the probiotic is characterized in that it comprises or consists of a nucleic acid sequence as set forth in SEQ ID NO: 4. In some embodiments, the probiotic is characterized in that it comprises or consists of a nucleic acid sequence as set forth in any one of SEQ ID NOs 27-35.

In some embodiments, the probiotic comprises, consists essentially of or consists of a probiotic comprising *J. lividum*. In some such embodiments, the probiotic comprises or consists of DB02473. In some embodiments, the probiotic is characterized in that it comprises or consists of a nucleic acid sequence as set forth in any one of SEQ ID NO: 5.

*Janthinobacterium*

*Janthinobacterium* is a genus of Gram negative, betaproteobacteria that are commonly found in many environmental niches, including the human body. *Janthinobacterium lividum* was identified for its ability to protect amphibians from fungal infection.

In some embodiments one or more species of *Janthinobacterium* is isolated from an environmental source. In some embodiments, one or more species of *Janthinobacterium* is isolated from a human source. In some embodiments, the human source is human skin. In some embodiments, the human skin is healthy human skin (e.g., no disease, disorder or condition present on the location of collection). In some embodiments, the human skin is diseased human skin (e.g., disease, disorder or condition present on the location of the collection).

In some embodiments, the *Janthinobacterium* comprises or consists of DB02473 In some embodiments, the *Janthinobacterium* is selected from an NCBI reference strain. In some embodiments, a species is *Janthinobacterium lividum*. In some embodiments, the *J. lividum* is characterized in that its 16s rRNA sequence comprises or consists of that set forth in SEQ ID NO: 5.

In some embodiments, the *Janthinobacterium lividum* strain is compared to a reference strain (e.g., an NCBI reference strain). In some embodiments, the reference strain is another *Janthinobacterium lividum* strain isolated from the same (e.g., human skin) or different (e.g., soil, insect, aquatic, etc.) environmental niche. In some embodiments, a reference *Janthinobacterium lividum* strain may be a strain isolated from a different environmental niche, such as an animal (e.g., a vertebrate), produce, soil, water, or the like.

In some embodiments, a human-derived *Janthinobacterium lividum* strain demonstrates superior persistence on human skin as compared to a reference strain. In some embodiments, a human-derived *Janthinobacterium lividum* strain demonstrates a benefit, such as superior persistence, production, or overproduction, of a metabolite or postbiotics compared to a reference strain. In some embodiments, the benefit is increased longevity on human skin. In some embodiments, the benefit is associated with increased production of a metabolite. In some embodiments, the benefit is associated with decreased production of a metabolite. In some embodiments, a human-derived *Janthinobacterium lividum* or an isolated human-derived *Janthinobacterium lividum* over produces or over expresses its metabolites relative to other strains (e.g., a reference strain).

*Alcaligenes*

*Alcaligenes* is a genus of Gram negative, aerobic, rod-shaped bacteria, commonly found in intestinal tracts (e.g., *A. faecalis*) or respiratory tracts of vertebrates (e.g., humans), water, soil, decaying materials, etc. This genus does not consume carbohydrates. that are commonly found in many environmental niches, including the human body.

In some embodiments one or more species of *Alcaligenes* is isolated from an environmental source. In some embodiments, one or more species of *Alcaligenes* is isolated from a human source. In some embodiments, the human source is human skin. In some embodiments, the human skin is healthy human skin (e.g., no disease, disorder or condition present on the location of collection). In some embodiments, the human skin is diseased human skin (e.g., disease, disorder or condition present on the location of the collection).

In some embodiments, the *Alcaligenes* is selected from a DB strain DB05646 (e.g., as provided in Tables 1 and 19). In some embodiments, the *Alcaligenes* is selected from an NCBI reference strain (e.g., as provided, but not limited to those in Table 19.) In some embodiments, a species is *Alcaligenes faecalis*. In some embodiments, the *A. faecalis* is characterized in that its 16s rRNA sequence comprises or consists of that set forth in SEQ ID NO: 1.

In some embodiments, the *A. faecalis* further comprises a gene comprising or consisting of a nucleic acid sequence as set forth in SEQ ID NO: 6. In some such embodiments, the nucleic acid comprising or consisting of SEQ ID NO: 6 confers advantageous properties on a composition comprising a probiotic with the gene represented by SEQ ID NO: 6. In some embodiments, the *A. faecalis* does not comprises a nucleic acid having the sequence of SEQ ID NO: 6, nor any nucleic acid with 90%, 91%, 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% identity or greater to SEQ ID NO: 6.

In some embodiments, the *Alcaligenes faecalis* strain is compared to a reference strain (e.g., an NCBI reference strain). In some embodiments, the reference strain is another *Alcaligenes faecalis* strain isolated from the same (e.g., human skin) or different (e.g., amphibian skin) environmental niche. In some embodiments, a reference *Alcaligenes faecalis* strain may be a strain isolated from a different environmental niche, such as salamander skin, produce, or the like.

In some embodiments, a human-derived *Alcaligenes faecalis* strain demonstrates superior persistence on human skin as compared to a reference strain. In some embodiments, a human-derived *Alcaligenes faecalis* strain demonstrates a benefit, such as superior persistence, production, or overproduction, of a metabolite or postbiotics compared to a reference strain. In some embodiments, the benefit is increased longevity on human skin. In some embodiments, the benefit is associated with increased production of a metabolite. In some embodiments, the benefit is associated with decreased production of a metabolite. In some embodiments, a human-derived *Alcaligenes faecalis* or an isolated human-derived *Alcaligenes faecalis* over produces or over expresses its metabolites relative to other strains (e.g., a reference strain).

*Bacillus*

*Bacillus* is a genus of Gram positive, rod-shaped and generally aerobic bacteria. In some embodiments, *Bacillus* is anaerobic. *Bacillus* is widely found in locations such as soil and water.

In some embodiments one or more species of *Bacillus* is isolated from an environmental source. In some embodiments, one or more species of *Bacillus* is isolated from a human source. In some embodiments, the human source is human skin. In some embodiments, the human skin is healthy human skin (e.g., no disease, disorder or condition present on the location of collection). In some embodiments, the human skin is diseased human skin (e.g., disease, disorder or condition present on the location of the collection).

In some embodiments, *Bacillus* (e.g., *B. altitudinis, B. pumilus, B. subtilis*, etc.) produces several metabolites with that may, in some embodiments, have antimicrobial effects.

In some embodiments, the *Bacillus* comprises or consists of a DB strain selected from DB10033 (*B. altitudinis*), DB03376 (*B. pumilus*), or DB02475 (*B. subtilis*). In some embodiments, the *Bacillus* is selected from a DB strain as provided in Tables 21, 23, and/or 25. In some embodiments, the *Bacillus* is selected from an NCBI reference strain (e.g., as provided, but not limited to those in Tables 21, 23, and 25). In some embodiments, a species is *Bacillus* altitudinis. In some embodiments, a species is *Bacillus pumilus*. In some embodiments, a species is *Bacillus subtilis*. In some embodiments, the *Bacillus* is characterized in that its 16s rRNA sequence comprises or consists of that set forth in any one of SEQ ID NOs: 2, 3, or 4. In some embodiments, the *Bacillus* is characterized in that its 16s rRNA sequence comprises or consists of that set forth in any one of SEQ ID NOs: 7-37.

In some embodiments, the DB10033 (*B. altitudinis*), DB03376 (*B. pumilus*), or DB02475 (*B. subtilis*) strain is compared to a reference strain (e.g., an NCBI reference strain). In some embodiments, the reference strain is another *Bacillus* strain isolated from the same (e.g., human skin) or different (e.g., amphibian skin) environmental niche. In some embodiments, a reference *Bacillus* strain may be a strain isolated from a different environmental niche, such as salamander skin, produce, or the like.

In some embodiments, a human-derived *Bacillus* (e.g., *B. altitudinis, B. pumilus, B. subtilis*) strain demonstrates superior persistence on human skin as compared to a reference strain. In some embodiments, a human-derived *Bacillus* (e.g., *B. altitudinis, B. pumilus, B. subtilis*) strain demonstrates a benefit, such as superior persistence, production, or overproduction, of a metabolite or postbiotics compared to a reference strain. In some embodiments, the benefit is increased longevity on human skin. In some embodiments, the benefit is associated with increased production of a metabolite. In some embodiments, the benefit is associated with decreased production of a metabolite. In some embodiments, a human-derived *Bacillus* (e.g., *B. altitudinis, B. pumilus, B. subtilis*) an isolated human-derived *Bacillus* (e.g., *B. altitudinis, B. pumilus, B. subtilis*) over produces or over expresses its metabolites relative to other strains (e.g., a reference strain).

Prebiotics

Prebiotics, in accordance with the teachings of this disclosure, comprise or consist of one or more componentsthat promote growth of beneficial bacteria. In some embodiments, prebiotic substances can be consumed by a relevant probiotic, or otherwise assist in keeping the relevant probiotic alive or stimulate its growth. In some embodiments, when applied or consumed in an effective amount, prebiotics also beneficially affecta subject's naturally occurring microbiome and thereby impart health benefits. In some embodiments, foods consumed by a host, that are prebiotics themselves or comprise one or more prebiotics, enter the colon and serve as substrate for endogenous bacteria, thereby indirectly providing the host with energy, metabolic substrates, and/or essential micronutrients. In some embodiments, prebiotics can also be added to any probiotic composition to enhance effectiveness or longevity of the probiotic strains.

Prebiotics help probiotics persist and even flourish in their environment, and accordingly, their health benefits are largely indirect. For example, metabolites generated by colonic fermentation by intestinal microflora, such as short-chain fatty acids, can play important functional roles in the health of the host. Prebiotics can be useful agents for enhancing the ability of human microflora to provide benefits to their host.

Prebiotics, in accordance with the embodiments of this disclosure may comprise prebiotic compositions comprising without limitation, amino acids, peptides, glycerol, other simple polyols, sugar alcohols, glucose, monosaccharides, disaccharides polysaccharides and oligosaccharides polysaccharides and modified polysaccharides, polysorbates vitamins, nutrient precursors, proteins, and combinations thereof.

In some embodiments, compositions comprising prebiotics comprise, without limitation, amino acids, glycerol, sugar alcohols, monosaccharides, disaccharides oligosaccharides, polysaccharides, modified polysaccharides and polysorbates.

In some such embodiments, these compounds have the ability to increase the number of probiotics and augment their associated benefits. Non-limiting examples of oligosaccharides that are categorized as prebiotics in accordance with particular embodiments of the present disclosure include galactooligosaccharides, fructooligosaccharides, inulins, isomalto-oligosaccharides, lactilol, lactosucrose, lactulose, pyrodextrins, soy oligosaccharides, transgalacto-oligosaccharides, and xylo-oligosaccharides.

In some embodiments, compositions comprise a prebiotic comprising an amino acid or peptide.

In some embodiments, a prebiotic is included to increase production of one or more beneficial metabolites.

In some embodiments, a prebiotic is added that additionally serves as a cryoprotectant.

Preferred embodiments comprise prebiotics that improve the growth of human-isolated or synthetic, *Janthinobacterium lividum, Alcaligenes faecalis, Bacillus altitudinis, Bacillus pumilus*, or *Bacillus subtilis*. In some such embodiments, a prebiotic comprises or consists of one or more polysorbates. In some embodiments, a prebiotic comprises or consists of one or more of D-Mannitol, Tween 20, Tween 40 and Cytidine.

Preferred embodiments comprise prebiotics that enhance the function of human-isolated orsynthetic *Janthinobacterium lividum, Alcaligenes faecalis, Bacillus altitudinis, Bacillus pumilus*, or *Bacillus subtilis.*

More preferred embodiments comprise prebiotics that enhance the function of human-isolated *Janthinobacterium lividum, Alcaligenes faecalis, Bacillus altitudinis, Bacillus pumilus*, or *Bacillus subtilis.*

Postbiotics

In some embodiments, postbiotics can be regarded as an umbrella term for all synonyms and related terms of these microbial components. In some embodiments, postbiotics can include many different constituents including metabolites, short-chain fatty acids (SCFAs, e.g. acetic, propionic and butyric acid), microbial cell fractions, functional proteins, extracellular polysaccharides (EPS), cell lysates, teichoic acid, phenyllactic acid, volatile organic compounds (VOCs), B-vitamin synthesis (biotin, cobalamin, folates, nicotinic acid, pantothenic acid, pyridoxine, riboflavin, and thiamine), peptidoglycan-isolated muropeptides, antimicrobial peptides (AMP) and pili-type structures.

Metabolites

In some embodiments, probiotics provided by the present disclosure produce one or more metabolites. In some embodiments, such metabolites may confer one or more benefits on a probiotic provided herein. In some embodiments, a probiotic as provided herein produces several metabolites. In some embodiments, one or more metabolites may have certain antimicrobial effects. For example, in some embodiments, a metabolite may be or comprise one or more of ectoine, betalactone, terpene, resorcinol, T1PKS, quilolobactin, burkhoderic acid, bacillibactin, hydroxylamine, cyclo-(L-Pro-Gly)5, phenylacetic acid, p-hydroxyphenylacetylamide, amylase, protease, cellulase, iturin, chitinase, tunicamycin, butyrolactone, phosphonate, siderophores, indole acetic acid, thermostable keratinase, indole-3-acetic acid, osmolytes, producing catalase, amylase, ACC deaminase, guanyl-preferring RNase, binase, bacteriocin, nonribosomal peptide synthetase, sactipeptide, bacilysin, pseudomonine, fengycin, surfactin, lichenysin, sporulation killing factor, 4-phenylbutanoic acid, Butanal, 3-methyl-, Propene, 2-butene, 2-heptanone, 6-methyl-5-methylene-, and 6-oxabicyclo[3.1.0] hexane, Diketopiperazines cordycedipeptide, pumilacidins, a bacteriolytic, 4-dipentylhexane-2,5-diol, 1,1'-(4,5-dibutylcyclohexane-1,2-diyl)bis(ethan-1-ol), 1,1'-(4,5-dibutyl-3,6-dimethylcyclohexane-1,2-diyl)bis(ethan-1-one), antifungal cyclic lipopeptides, polyketides (PKs), and ribosomally and non-ribosomally synthesized peptides, N1-tetrahydrofuran-2-ylmethyl-2-cyanoacetamide, Lys-Pro, 6-Oxo-pipecolinic acid, (1Z)—N-(4-Aminobutyl)ethanimidic acid, Valyl-4-hydroxyproline, 2-(1-Ethoxyethoxy)propanoic acid, 1-pyrroline-5-carboxylic acid, METHYLTHIO 2-(PROPIONYLOXY) PROPIONATE, 5-guanidino-2-oxopentanoic acid, Ethyl acetoacetate, Ribulose-5-phosphate, 1-Methyl-1H-pyrrole, N-Acetylornithine, D-1-Piperideine-2-carboxylic acid, (2S)-4-Acetamido-2-aminobutanoic acid, N6-Acetyl-L-lysine, N-Acetylmethionine,6-Oxo-pipecolinic acid, 2-Methylthiazolidine, Histamine, Acetylarginine, Diethyl malonate, 6-Oxo-pipecolinic acid, (Dimethylamino)acetonitrile, N-Acetylglutamic acid, 3-Methylcrotonylglycine, Putrescine, Vanillin, N-Acetylcadaverine, 1-pyrroline, 8-Azabicyclo[3.2.1]octan-3-ol, 2-[(1S)-1, Hydroxyethyl]-4(1H)-quinazolinone, 4-Morpholinylacetic acid, Aminoethylethanolamine, 4-Morpholinylacetic acid, Urocanic acid, (2S)-6-Amino-2-[(E)-(hydroxymethylene)amino]hexanimidic acid, (Z)-Norendoxifen, Ser-Leu, 5-Methylcytosine, Nikethamide, pentoxyl, Pilocarpine, Prolinamide, Pipecolinic acid, Aminoadipic acid, Gly-Phe, 2-Ethylnicotinamide, (2R,3S)-3-Hydroxy-8-methyl-8-azabicyclo[3.2.1]octane-2-carboxylic acid, 3-hydroxyquinuclidine-3-carbonitrile hydrochloride, Valeronitrile, Isopropyl methoxy pyrazine, 2-sec-Butyl-3-methoxypyrazin, 4-Piperidone, (1S,3R,4s)-1,3,4,5-Tetrahydroxycyclohexanecarboxylic acid, 2,3,5,6-Tetramethylpyrazine, N Acetylprocainamide, Aprobarbital, Leu-Val, N-Acetylaspartic acid, gamma-Glutamyl-3-(2-methylenecyclopropyl)alanine, 4-Guanidinobutyric acid, Methyl acetoacetate, Methyl indole-3-acetate, 3-amino-2-phenyl-2H-pyrazolo[4,3-c]pyridine-4,6-diol, N8-Acetylspermidine, Uridine, Hexose dimer1, N(6)-Methyladenosine, Guanosine, Inosine, 4 Morpholinepropanesulfonic acid, Suxibuzone, Uracil, L-gamma-Glutamyl-L-leucine, 5-Hydroxy-2-furoic acid, 15,16-DiHODE, 3-Hydroxybutyric acid, Thymine, NP-008993, N-Acetyltryptophan, 4-Deoxy-5-C-(3,5-di-sec-butyl-1-cyclopenten-1-yl)pentonic acid, Furfural, 4-[(3-Acetamidopropyl)amino]butanoic acid, Cytosine, Aprobarbital, 5-methyl-tryptophan, Acetylserine, N-Acetyltryptophan, N-Iso-Valerylglycine, Ribulose-5-phosphate, Guanosine, 3-Methylcrotonylglycine, 2-Pyrrolidone, 8-Azabicyclo[3.2.1]octan-3-ol, 6-Oxo-pipecolinic acid, Tetraacetylethylenediamine, 2-(hydroxymethyl)butanoic acid, N6-Acetyl-L-lysine, Prostaglandine E2, Furaneol, Myriocin, 3-Hydroxy-5,8-tetradecadiencarnitine, Acetylarginine, Hypoxanthine, Tropic acid/acetovanillone/

3-phenyllactic acid, Uracil, 3-Hydroxyoctanoic acid, Desmeninol, Kynurenic acid, 2-Hydroxyfelbamate, (1S,3R,4s)-1,3,4,5-Tetrahydroxycyclohexanecarboxylic acid, Levulinic acid, 4,5-Dideoxy-3-C-methyl-D-erythro-pentonic acid, 3,13,13,17-Tetramethyl-21-oxa-12-azahexacyclo [10.7.1.1~2,17~0.0~5,20~0.0~6,11~0.0~14,19~]henicosa-1 (20),2,4,6,8,10-hexaene, 2-Acetamidooctanoic acid, 4-Methyl-2-oxovaleric acid (ketoleucine), L-5-Hydroxytryptophan, Pyruvic acid, DL-Glyceric acid, 5-Methylcytidine, Edaravone, 3 Hydroxybutyric acid, Thr-Val, 4-Indolecarbaldehyde, Methyl 2-[(2-methoxy-2-oxoethyl) amino]acetate, Benzene, L-gamma-Glutamyl-L-leucine, Alanylleucine, 1-pyrroline, Thymine, Indole-3-acetic acid, Levulinic acid Glutaric acid/Ethylmalonic acid, pterin, N-Acetyl-L-leucine, 4-Deoxy-5-C-(3,5-di-sec-butyl-1-cyclopenten-1-yl)pentonic acid, 4-(METHYLNITROSAMINO)-1-(3-PYRIDYL-N-OXIDE)-1-BUTANOL, N-Acetyl-L-phenylalanine, Tyramine, Acetophenone, Nicotinic acid, Indole-3-carboxylate, asp-leu, Histidine, 3,3'-(1,4-Butanediyldiimino)dipropanoic acid, 8-Hydroxyquinoline, Alanylleucine, 4-hydroxybenzaldehyde, 2-Amino-4-methylpyrimidine, Fomepizole, 3-Isopropylmalic acid, Methyl 2-[(2-methoxy-2-oxoethyl)amino]acetate, Homo-L-arginine, 1-(4-Aminobutyl)urea, N-(2-hydroxyphenyl)acetamide, Acetylhistidine, 1-Vinylimidazole, 2-[(8E,11E,14Z)-8,11,14-Heptadecatrien-1-yl]-6-hydroxybenzoic acid, 4-coumaric-acid, Prolinamide, or ile-ala.

In some embodiments, soluble metabolites of, and for use in, the present disclosure include, but are not limited to, soluble metabolites from human-isolated or synthetic *Janthinobacterium lividum, Alcaligenes faecalis, Bacillus altitudinis, Bacillus pumilus*, or *Bacillus subtilis* and any additional microbe such as, *Bifidobacterium, Brevibacterium, Propionibacterium, Lactococcus, Streptococcus, Lactobacillus* (e.g., *L. acidophilus*), *Enterococcus, Pediococcus, Leuconostoc*, Oenococcus, or any combinations thereof.

In some embodiments, the *Janthinobacterium lividum, Alcaligenes faecalis, Bacillus altitudinis, Bacillus pumilus*, or *Bacillus subtilis* strain is compared to a reference strain. In some embodiments, the reference strain is another *Janthinobacterium lividum, Alcaligenes faecalis, Bacillus altitudinis, Bacillus pumilus*, or *Bacillus subtilis* strain isolated from another environmental niche.

In some embodiments, a human-isolated or synthetic *Janthinobacterium lividum, Alcaligenes faecalis, Bacillus altitudinis, Bacillus pumilus*, or *Bacillus subtilis* or a human-isolated or synthetic *Janthinobacterium lividum, Alcaligenes faecalis, Bacillus altitudinis, Bacillus pumilus*, or *Bacillus subtilis* over produces or over expresses its compounds (e.g., metabolites) relative to other strains (e.g., a reference strain). As used, the terms "over produce" and "over express" refer to at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 1.5-fold, 2-fold, 2.5-fold, or 3-fold more production or more expression (respectively) relative to other strains (e.g., a reference strain). In some such embodiments, a reference *Janthinobacterium lividum, Alcaligenes faecalis, Bacillus altitudinis, Bacillus pumilus*, or *Bacillus subtilis* strain may be a strain isolated from a different environmental niche, such as salamander skin, produce, or the like. As used, the term "over produce" refers to the production of the compounds (e.g., metabolites) by the organism, and the term "over expresses" refers to the expression of a gene that produces the compounds (e.g., metabolites).

In some embodiments, a probiotic produces one or more metabolites. In some embodiments, a metabolite may be a prebiotic. In some embodiments, a metabolite may be a postbiotic. In some embodiments, a metabolite is produced from a monoculture. In some embodiments, a metabolite is produced from a co-culture. In some embodiments, certain metabolites are produces at higher levels (e.g., 1, 2, 3, 4, 5-fold or higher) than other metabolites. In some embodiments, certain metabolites are produced at lower levels (e.g., 1, 2, 3, 4, 5-fold or less) than other metabolites. In some embodiments, a metabolite is increased (relative to other metabolite levels) in a monoculture and stays the same or is decreased in a coculture (relative the monoculture). In some embodiments, a metabolite is decrease in a monoculture (relative to other metabolite levels), and stays the same or is increased in a coculture (relative to a monoculture). In some embodiments, a coculture comprises a culture with *M. furfur.*

*Janthinobacterium* (e.g., *J. lividum*) produces several metabolites with that may, in some embodiments, have antimicrobial effects. In some embodiments, increased production of one or more metabolites confers a beneficial effect (e.g., greater therapeutic efficacy versus a pathological microbe, etc.) In some embodiments, a metabolite is produced by a single strain of *Janthinobacterium*. In some embodiments, a metabolite concentration is increased in a coculture (e.g., with another microbe, e.g., with *M. furfur*, etc.). In some embodiments, an increase in a metabolite confers additional benefit on therapeutic use of the probiotic and/or metabolite.

In some embodiments, a metabolite of *Janthinobacterium* comprises or consists of violacein, indole-3-carboxaldehyde, prodigiosin, salicylate, 2,4-diamabutyrate, one or more lantibiotics or any combinations thereof. As will be known to those of skill in the art, violacein is a bisindole compound known for its purple color and, in some embodiments, displays one or more antimicrobial properties. In some embodiments, indole-3-carboxaldehye (a heteroarene carbaldehyde, indole alkaloid, and member of indoles) has a role as a plant metabolite, a human xenobiotic metabolite, a bacterial metabolite and a marine metabolite. In some embodiments, prodigiosin (an alkaloid, red-pigmented, secondary metabolite) is associated with *Serratia* species. In some such embodiments, prodigiosin molecules are identified by their common pyrrolyl pyrromethene skeleton, and have been shown to have a variety of biological activities, including antimicrobial activity. In some embodiments, lantibiotics, a subset of bacteriocins, are genetically-encoded peptides containing intramolecular ring structures, many of which have been shown to have antimicrobial properties. In some embodiments, lantibiotic peptides are modified post-translationally to create their characteristic ring structures. As will be known to those in the art, one of the most well-known lantibiotics is nisin.

In some embodiments, the metabolite comprises or consists of violacein, indole-3-carboxaldehyde, prodigiosin, salicylate, 2,4-diamabutyrate and one or more lantibiotics. In some embodiments, the benefit is increased production of 2-(alpha-D-mannosyl)-D-glyceric acid, 2-ketogluconate, 2-O-ethyl ascorbic acid, anthramycin, Aprobarbital, bendiocarb, Bis(2-ethylhexyl) phthalate, cis-5-Tetradecenoylcarnitine, Dibutyl phthalate, imidazole propionate, indole-3-carboxylate, indolin-2-one, N-Acetyl-L-aspartic acid, Phosphoric acid, Phthalic acid, Pimilprost, trimethadione, and Vernolate.

In some embodiments, *Alcaligenes* (e.g., *A. faecalis*) produces several metabolites with that may, in some embodiments, have antimicrobial effects. In some embodiments, *Alcaligenes* (e.g., *A. faecalis*) produces several metabolites with that may, in some embodiments, have antimicrobial effects. In some embodiments, increased production of one or more metabolites confers a beneficial effect (e.g., greater therapeutic efficacy versus a pathological microbe, etc.) In some embodiments, a metabolite is produced by a single strain of *Alcaligenes*. In some embodiments, a metabolite concentration is increased in a coculture (e.g., with another microbe, e.g., with *M. furfur*, etc.). In some embodiments, an increase in a metabolite confers additional benefit on therapeutic use of the probiotic and/or metabolite.

In some embodiments, an *Alcaligenes* metabolite comprises or consists of N1-tetrahydrofuran-2-ylmethyl-2-cyanoacetamide, Lys-Pro, 6-Oxo-pipecolinic acid, (1Z)—N-(4-Aminobutyl)ethanimidic acid, Valyl-4-hydroxyproline or any combination thereof. In some embodiments, a metabolite is selected from 2-(1-Ethoxyethoxy)propanoic acid, 1-pyrroline-5-carboxylic acid, Methylthio 2-(Propionyloxy) Propionate, 5-guanidino-2-oxopentanoic acid, Ethyl acetoacetate, Ribulose-5-phosphate, 1-Methyl-1H-pyrrole, N-Acetylornithine, D-1-Piperideine-2-carboxylic acid, (2S)-4-Acetamido-2-aminobutanoic acid, N6-Acetyl-L-lysine, N-Acetylmethionine, 6-Oxo-pipecolinic acid, 2-Methylthiazolidine, Histamine, Acetylarginine, Diethyl malonate, (Dimethylamino)acetonitrile, N-Acetylglutamic acid, 3-Methylcrotonylglycine, Putrescine, vanillin, N-Acetylcadaverine, 1-pyrroline, 8-Azabicyclo[3.2.1]octan-3-ol, 2-[(1S)-1-Hydroxyethyl]-4(1H)-quinazolinone, 4-Morpholinylacetic acid, Aminoethylethanolamine, 4-Morpholinylacetic acid, Urocanic acid, (2S)-6-Amino-2-[(E)-(hydroxymethylene) amino]hexanimidic acid, (Z)-Norendoxifen, Ser-Leu, 5-Methylcytosine, Nikethamide, pentoxyl, Pilocarpine, Prolinamide, Pipecolinic acid, Aminoadipic acid, Gly-Phe, 2-Ethylnicotinamide, (2R,3S)-3-Hydroxy-8-methyl-8-azabicyclo[3.2.1]octane-2-carboxylic acid, 3-hydroxyquinuclidine-3-carbonitrile hydrochloride, Valeronitrile, Isopropyl methoxy pyrazine, 2-sec-Butyl-3-methoxypyrazin, 4-Piperidone, (1S,3R,4s)-1,3,4,5-Tetrahydroxycyclohexanecarboxylic acid, 2,3,5,6-Tetramethylpyrazine, N-Acetylprocainamide, Aprobarbital, Leu-Val, N-Acetylaspartic acid, gamma-Glutamyl-3-(2-methylenecyclopropyl)alanine, 4-Guanidinobutyric acid, Methyl acetoacetate, Methyl indole-3-acetate, 3-amino-2-phenyl-2H-pyrazolo[4,3-c] pyridine-4,6-diol, N8-Acetylspermidine, Uridine, Hexose dimer1, N(6)-Methyladenosine, Guanosine, Inosine, 4-Morpholinepropanesulfonic acid, Suxibuzone, Uracil, L-gamma-Glutamyl-L-leucine, 5-Hydroxy-2-furoic acid, 15,16-DiHODE, 3-Hydroxybutyric acid, Thymine, NP-008993, N-Acetyltryptophan, 4-Deoxy-5-C-(3,5-di-sec-butyl-1-cyclopenten-1-yl)pentonic acid, Furfural, 4-[(3-Acetamidopropyl)amino]butanoic acid, Cytosine or any combination thereof.

In some embodiments, *Bacillus* (e.g., *B. altitudinis, B. pumilus, B. subtilis*) produces several metabolites with that may, in some embodiments, have antimicrobial effects. In some embodiments, *Bacillus* (e.g., *B. altitudinis, B. pumilus, B. subtilis*) produces several metabolites with that may, in some embodiments, have antimicrobial effects. In some embodiments, increased production of one or more metabolites confers a beneficial effect (e.g., greater therapeutic efficacy versus a pathological microbe, etc.) In some embodiments, a metabolite is produced by a single strain of *Bacillus*. In some embodiments, a metabolite concentration is increased in a coculture (e.g., with another microbe, e.g., with *M. furfur*, etc.). In some embodiments, an increase in a metabolite confers additional benefit on therapeutic use of the probiotic and/or metabolite.

In some embodiments, a *Bacillus* (e.g. *B. altitudinis, B. pumilus, B. subtilis*, etc.) metabolite comprises or consists of 5-methyl-tryptophan, Acetylserine, N-Acetyltryptophan, N-Iso-Valerylglycine, Ribulose-5-phosphate, Guanosine, 3-Methylcrotonylglycine, 2-Pyrrolidone, 8-Azabicyclo [3.2.1]octan-3-ol, 6-Oxo-pipecolinic acid, Tetraacetylethylenediamine, 2-(hydroxymethyl)butanoic acid, N6-Acetyl-L-lysine, Prostaglandine E2, Furaneol, Myriocin, 3-Hydroxy-5, 8-tetradecadiencamitine, Acetylarginine, Hypoxanthine, Tropic acid/acetovanillone/3-phenyllactic acid, Uracil, 3-Hydroxyoctanoic acid, Desmeninol Kynurenic acid, 2-Hydroxyfelbamate, (1S,3R,4s)-1,3,4,5-Tetrahydroxycyclohexanecarboxylic acid, Levulinic acid, 4,5-Dideoxy-3-C-methyl-D-erythro-pentonic acid, 3,13,13,17-Tetramethyl-21-oxa-12-azahexacyclo[10.7.1.1~2,17~0.0~5,20~0.0~6, 11~0.0~14,19~]henicosa-1(20),2,4,6,8,10-hexaene, 2-Acetamidooctanoic acid, 4-Methyl-2-oxovaleric acid (ketoleucine), L-5-Hydroxytryptophan, Pyruvic acid, DL-Glyceric acid, 5-Methylcytidine, Edaravone, 3-Hydroxybutyric acid, Thr-Val, 4-Indolecarbaldehyde, Methyl 2-[(2-methoxy-2-oxoethyl)amino]acetate, Benzene, L-gamma-Glutamyl-L-leucine, Alanylleucine, 1-pyrroline, Thymine, Indole-3-acetic acid, Levulinic acid, Glutaric acid/Ethylmalonic acid, pterin, N-Acetyl-L-leucine, 4-Deoxy-5-C-(3,5-di-sec-butyl-1-cyclopenten-1-yl)pentonic acid, 4-(Methylnitrosamino)-1-(3-Pyridyl-N-Oxide)-1-Butanol, N-Acetyl-L-phenylalanine, Tyramine, Acetophenone, Nicotinic acid, Indole-3-carboxylate, asp-leu, Histidine, 3,3'-(1,4-Butanediyldiimino)dipropanoic acid, 8-Hydroxyquinoline, Alanylleucine, 4-hydroxybenzaldehyde, 2-Amino-4-methylpyrimidine, Fomepizole, 3-Isopropylmalic acid, Methyl 2-[(2-methoxy-2-oxoethyl)amino]acetate, Homo-L-arginine, 1-(4-Aminobutyl)urea, N-(2-hydroxyphenyl)acetamide, Acetylhistidine, 1-Vinylimidazole, 2-[(8E,11E,14Z)-8,11,14-Heptadecatrien-1-yl]-6-hydroxybenzoic acid, 4-coumaric-acid, Prolinamide, ile-ala, and any combinations thereof.

Genetic Analysis of Strains

Whole Genome Shotgun Sequencing and Genome Sequence Assembly

In some embodiments provided herein, one or more probiotic or other microbe strains is genetically analyzed using methods and resources known and available to those of skill in the art. In some embodiments genetic analysis comprises whole genome shotgun sequencing and/or genome sequence assembly. In some such embodiments, a shotgun sequencing library is created for each strain being analyzed (e.g., *Alcaligenes faecalis, Bacillus altitudinis, Bacillus pumilus, Bacillus subtilis*, etc.). In some embodiments, one or more shotgun libraries is pooled and sequences (e.g., using HiSeq X). In some embodiments, sequencing reads are demultiplexed (e.g., using standard bioinformatic analysis approaches). strain was generated using the Nextera Flex kit manufactured by Illumina according to the instructions. The shotgun libraries were pooled and sequenced in a HiSeq X platform. The sequencing reads were automatically demultiplexed into individual FASTA files, run through standard bioinformatic analysis procedures known and available to those of skill in the art. In some embodiments, such methods and approaches to genetic analysis yields a genome assembled from cleaned sequencing reads.

Nucleotide-Level Genome Similarity Analysis

In some embodiments, genome sequences (e.g., *Alcaligenes faecalis, Bacillus altitudinis, Bacillus pumilus, Bacillus subtilis*, etc.) are analyzed using Average Nucleotide Identify (ANI, found at img.jgi.doe.gov/docs/docs/ANI.pdf) analyses to determine the similarity and genetic diversity.

Phylogenomic Analysis

In some embodiments, phylogenomic relationships are determined and evaluated using approaches and methodologies know and available to those of skill in the art (e.g., RAxML package).

Pharmaceutical and Cosmetic Compositions

In some embodiments the present disclosure provides pharmaceutical compositions. In some embodiments the present disclosure provides cosmetic compositions. In some embodiments, a pharmaceutical or cosmetic composition comprises at least one probiotic and one or more additional components. In some embodiments, a pharmaceutical or cosmetic composition comprises or consists essentially of at least one probiotic (e.g., *Janthinobacterium lividum, Alcaligenes faecalis, Bacillus altitudinis, Bacillus pumilus*, or *Bacillus subtilis*), or derivative thereof (e.g., metabolite, cell lysate, etc.) and at least one excipient. In some embodiments, the pharmaceutical or cosmetic composition comprising the probiotic comprises a human isolated or synthetic probiotic as disclosed and provided herein. In some embodiments, the pharmaceutical or cosmetic composition comprises at least one human-isolated *Janthinobacterium lividum, Alcaligenes faecalis, Bacillus altitudinis, Bacillus pumilus*, or *Bacillus subtilis*. In some such embodiments, a composition comprises, consists essentially of, or consists of a probiotic selected from *Janthinobacterium lividum, Alcaligenes faecalis, Bacillus altitudinis, Bacillus pumilus*, or *Bacillus subtilis* or any combination thereof in an amount effective to treat, inhibit, or prevent a topical pathogenic microorganism.

In some embodiments, a pharmaceutical or cosmetic composition provided herein is a synthetic or human isolated composition comprising a probiotic comprising, consisting essentially of, or consisting of human-isolated or synthetic *Janthinobacterium lividum, Alcaligenes faecalis, Bacillus altitudinis, Bacillus pumilus*, or *Bacillus subtilis* or any combinations thereof and formulated for topical application.

In some embodiments, the composition of bacterial strains may be formulated for administration as a pharmaceutical or cosmetic composition. In some embodiments, the pharmaceutically or cosmetically acceptable excipient is selected based on the intended route of administration of the composition, for example a composition for oral or nasal administration may comprise a different pharmaceutically or cosmetically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

In some embodiments, pharmaceutical or cosmetic compositions provided herein may further comprise any carriers or stabilizers in the form of a lyophilized formulation or an aqueous solution. In some embodiments, acceptable excipients, carriers, or stabilizers may include, for example, buffers, antioxidants, preservatives, polymers, chelating reagents, and/or surfactants. Pharmaceutical or cosmetic compositions are preferably manufactured under GMP conditions. In some embodiments, pharmaceutical or cosmetic compositions provided herein can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

Also provided herein are pharmaceutical or cosmetic compositions comprising, consisting essentially of, or consisting of a cell lysate of *Janthinobacterium lividum, Alcaligenes faecalis, Bacillus altitudinis, Bacillus pumilus*, or *Bacillus subtilis*. In some embodiments, the cell lysate is administered in an amount effective for use treatment of a topical pathological microorganism. In some such embodiments, a pharmaceutical or cosmetic composition further comprises an excipient. In some embodiments, the excipient and/or materials originating from a probiotic provided herein are administered in an amount effective for use in treatment of a topical microorganism. In some embodiments, the excipient and/or materials originating from probiotics provided herein are part of a method for using these pharmaceutical or cosmetic compositions to treat pathogenic microorganisms and/or the diseases they cause. In some embodiments, these human-isolated probiotics can be formulated into compositions for application to a subject in need thereof (e.g. skin, mucosa, hair, nails) or for application to objects that come in contact with the subject (e.g. cloth, floors, etc.). In some embodiments, the pharmaceutical or cosmetic compositions are formulated for application to the skin, mucosa, hair, and/or nails. In some embodiments, the pharmaceutical or cosmetic compositions are applied to, included in, or formulated as, e.g., bandages, sunscreen, toothpaste, mouthwash, shampoo, soap, moisturizer, lip balm, or dental floss.

Formulations and Administration

Provided herein, in some embodiments, are compositions that comprise at least one of human-isolated or synthetic *Janthinobacterium lividum, Alcaligenes faecalis, Bacillus altitudinis, Bacillus pumilus*, or *Bacillus subtilis* disclosed herein, wherein the compositions are formulated for administration to a subject in need thereof.

In some embodiments, the composition is formulated to modulate the microbiome of the object of application (e.g., a host, e.g., a subject in need thereof).

In some embodiments, the composition of human-isolated or synthetic *Alcaligenes faecalis, Bacillus altitudinis, Bacillus pumilus, Bacillus subtilis* or *Janthinobacterium lividum* metabolite, postbiotic and/or cell lysate is formulated for administration to the skin. In another embodiment, the composition of human-isolated or synthetic *Alcaligenes faecalis, Bacillus altitudinis, Bacillus pumilus, Bacillus subtilis* or *Janthinobacterium lividum* metabolite, postbiotic and/or cell lysate is formulated for administration to the mucosa.

In some embodiments, the formulation may comprise one or more of at least one probiotic bacterium, at least one metabolite of a probiotic bacterium, at least one cell lysate of a probiotic bacterium or a postbiotic of a probiotic bacterium.

In some embodiments the formulation may comprise a combination of *Janthinobacterium lividum* and one or more of *Alcaligenes faecalis, Bacillus* altitudinis, *Bacillus pumilus*, or *Bacillus subtilis*. In some embodiments the formulation may comprise a combination of *Alcaligenes faecalis* and one or more of *Janthinobacterium lividum, Bacillus altitudinis, Bacillus pumilus*, or *Bacillus subtilis*. In some embodiments the formulation may comprise a combination of *Bacillus* altitudinis and one or more of *Janthinobacterium lividum, Alcaligenes faecalis, Bacillus pumilus*, or *Bacillus*

*subtilis*. In some embodiments the formulation may comprise a combination of *Bacillus pumilus* and one or more of *Janthinobacterium lividum, Alcaligenes faecalis, Bacillus* altitudinis or *Bacillus subtilis*. In some embodiments the formulation may comprise a combination of *Bacillus subtilis* and one or more of *Janthinobacterium lividum, Alcaligenes faecalis, Bacillus altitudinis*, or *Bacillus pumilus.*

In some embodiments, a formulation provided herein may further comprise more than one bacterium in combination with one or more of *Janthinobacterium lividum, Alcaligenes faecalis, Bacillus altitudinis, Bacillus pumilus*, or *Bacillus subtilis*. For example, in some embodiments, a formulation may comprise at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ bacteria of one or more of *Janthinobacterium lividum, Alcaligenes faecalis, Bacillus altitudinis, Bacillus pumilus*, and/or *Bacillus subtilis.*

In some embodiments, a formulation may further comprise more than one, soluble metabolite, cell lysate or postbiotic. For example, in some embodiments, a formulation may comprise at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ bacteria, a culture, their metabolites, cell lysates or postbiotics.

In some embodiments, a formulation may comprise one or more of at least one probiotic bacterium, at least one metabolite of a probiotic bacterium, at least one cell lysate of a probiotic bacterium or a postbiotic of a probiotic bacterium.

In some embodiments, a subject in need of one or more compositions provided by the present disclosure has or is at risk of having a topical infection. In some embodiments, the subject has an infection of the skin and/or mucosa caused by a at least one microorganism. In some embodiments, compositions of the present disclosure are formulated for topical administration to a subject in need thereof. In some embodiments, the compositions are formulated for topical administration to the skin of the subject. In some embodiments, the compositions are formulated for topical administration to the scalp of the subject. In some embodiments, the compositions are formulated for application to mucosal surfaces. In some embodiments, a composition is formulated for oral administration. In some embodiments, a composition is formulated for transdermal administration. In some embodiments, a composition is formulated for injectable administration. In some embodiments, the composition is a formulation selected from a gel, ointment, lotion, emulsion, paste, cream, foam, mousse, liquid, douche, gavage, spray, suspension, dispersion, nasal spray and aerosol.

In some embodiments, the formulation comprises one or more excipients to provide a desired form and a desired viscosity, flow or other physical or chemical characteristic for effective application, coverage and adhesion to skin.

In some embodiments the human-isolated or synthetic (e.g., including one or more lab-created components, e.g., engineered bacterium, etc.) *Janthinobacterium lividum, Alcaligenes faecalis, Bacillus altitudinis, Bacillus pumilus*, or *Bacillus subtilis* of this disclosure is dried (e.g. desiccated or dehydrated). Drying may be accomplished by standard methods of practice and can be select from such methods as lyophilization. Rehydration of the dried human-isolated or synthetic *Janthinobacterium lividum, Alcaligenes faecalis, Bacillus altitudinis, Bacillus pumilus*, or *Bacillus subtilis Alcaligenes faecalis, Bacillus altitudinis, Bacillus pumilus, Bacillus subtilis* at least 10%, 20% viable, at least 30% viable bacterium, at least 50% viable bacteria. In some embodiments rehydration of dried (e.g., via lyophilization) human-isolated or synthetic *Janthinobacterium lividum, Alcaligenes faecalis, Bacillus altitudinis, Bacillus pumilus*, or *Bacillus subtilis Alcaligenes faecalis, Bacillus altitudinis, Bacillus pumilus, Bacillus subtilis* produces at least 60% viable bacteria.

In some embodiments, materials are used in a lyophilization process to assist retention of viability of microorganisms. In some embodiments the material may be a cryoprotectant and/or thermal change stabilizers (e.g., a stabilizer to provide protection at, e.g., lower temperatures and/or during temperature transitions, etc.). In some embodiments, a cryoprotectant and/or thermal may be chosen from but is not limited to, amino acids, peptides, glycerol, other simple polyols, complex polyols, modified polyols, sugar alcohols, glucose, monosaccharides, disaccharides, oligosaccharides, polysaccharides and modified oligosaccharides and polysaccharides, vitamins, proteins, buffers and combinations thereof. In some embodiments the cryoprotectant and/or thermal change stabilizers comprise 0.001% to 50% of the lyophilization composition.

In some embodiments, the liquid lyophilization composition comprises disaccharides, sugar alcohols, simple polyols, amino acids, polysaccharides, modified polysaccharides, and combinations thereof. In certain embodiments the composition comprises trehalose, sucrose, phosphate-buffered saline, mannitol, glycerol, tryptophan, carboxy methyl cellulose (sodium salt), maltodextrin, isomers of the species separately or mixtures of, and combinations thereof. In some embodiments the materials comprise 0.001% to 50% of the lyophilization composition.

In some embodiments, a liquid lyophilization composition comprises 0.1% to 50% trehalose, 0.1% to 50% sucrose, 0.1% to 50% mannitol, 0.1% to 50% glycerol, 0.001% to 1% tryptophan, 0.1% to 6% carboxy methyl cellulose (sodium salt), 0.1% to 20% maltodextrin, 0.1% to 20% phosphate-buffered saline, isomers of the species separately or mixtures of, and combinations thereof. In some such embodiments, one or more components of a lyophilizate results in an improved composition upon rehydration (e.g., trehalose, etc.).

In some embodiments, lyophilization is performed in one or multiple steps within the ranges of −45° C. to 40° C. Lyophilization is initiated with frozen lyophilization solutions frozen at temperatures between −45° C. to −15° C. at 100-1500 Torr followed by up to three drying steps with starting ramp to primary drying cycle at −25° C. to −5° C. for 0.1-100 hours at 10-2000 mTorr, followed by ramp to secondary drying cycle at 0° C. to 30° C. for 0.1-100 hours at 10-2000 mTorr, followed by ramp to tertiary drying cycle at 5° C. to 40° C. for 0.1-100 hours at 10-2000 mTorr.

In some embodiments, a lyophilized dried product has a moisture content of up to 15%. In some embodiments a lyophilized dried product has a moisture content of 0.1% to 6%. In some embodiments a lyophilized dried product has a water activity up to 0.4, or a water activity between 0.05 and 0.20.

In some embodiments, the composition comprises at least 10% of viable microorganism at room temperature for at least thirty, 60, 90, 120, 150 or more days. In some embodiments, the composition comprises at least 10% of viable microorganism in refrigerated conditions for at least thirty, 60, 90, 120, 150 or more days. In some embodiments, the composition comprises at least 10% of viable microorganism in frozen conditions for at least thirty, 60, 90, 120, 150 or more days. Also disclosed are compositions in which at least 1%, at least 5%, at least 10%, at least 20%, at least 30%, at least 40%, at least 50%, at least 60%, at least 70%, at least 80%, at least 90%, of microorganisms in the composition are viable for at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180 or more up to at least 360 days.

In some embodiments lyophilized compositions comprise 0.001% to 90% of a microorganism. In some instances the viability of the microbes in the composition after drying is up to 100%. In some instances the viability of microbes in lyophilized composition upon storage at room temperature for up to 360 days is between 0.0001% to 100% at room temperature. In some instances the microbes are 0.0001% to 100% viable when stored at room temperature or 0-10° C. for up to 360 days in argon, nitrogen or ambient air.

In some embodiments, the microorganisms comprise 1% to 50% of the of lyophilized product. In some instances the viability of the microbes in the composition after drying is between 10% to 100%. In some instances the viability of microbes in the lyophilized composition upon storage at room temperature for up to 360 days is between 10% to 100% at room temperature. In some instances the microbes are 10% to 100% viable when stored at room temperature or 0-10° C. for up to 360 days in argon, nitrogen, with humidity not exceeding 40%.

In some embodiments, the microorganisms comprise 5% to 20% of the lyophilized product. In some instances the viability of the microbes in the composition after drying is between 50% and 100%. In some instances the viability of the microbes in the lyophilized composition upon storage at room temperature for up to 360 days is between 50% to 100%. In some instances the microbes are 50% to 100% viable when stored at room temperature or 0-10° C. for between 30-360 days in argon, nitrogen, with humidity not exceeding 30%.

In some embodiments the compositions are pharmaceutical compositions, comprisinga composition as described herein and a pharmaceutically acceptable excipient. In some embodiments the compositions are synthetic forms of the described human-isolated or synthetic compositions. In some embodiments the compositions are for use in cosmetic compositions.

Compositions disclosed herein may be presented in a formulation that includes one ormore excipients to improve any one or more of shelf-life, application, skin penetration, and therapeutic effect. In some embodiments, the excipient is necessary to improve any one or more of shelf-life, application, skin penetration, and therapeutic effect.

In some embodiments, compositions disclosed herein may be in a topical dosage form, wherein the topical dosage form provides easy application to a surface, such as skin, nails, hair, and/or mucosa. The surface may be a surface that comes in contact with a subject.

In certain embodiments, the *Janthinobacterium lividum, Alcaligenes faecalis, Bacillus altitudinis, Bacillus pumilus*, or *Bacillus subtilis* compositions described herein are formulated for oral ingestion. In some embodiments, the oral ingestion form may be a pill, tablet, capsule, paste, liquid suspension, colloid, or mixed with various foods such as candies, chews, yogurt, milk, cheese, cottage cheese or non-dairy based or lactose reduced substitutes. In some embodiments, the formulation may contain additional non-active ingredients that improve flavor, smell, or texture of the edible composition. In some embodiments, the formulation may also include binding agents, encapsulating films, or excipients that preserve shelf-life and bioavailability.

In some embodiments, an emulsion may be described as a preparation of one liquid distributed in small globules throughout the body of a second liquid. In some embodiments, the dispersed liquid is the discontinuous phase, and the dispersion medium is the continuous phase. In some embodiments, when oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. In some embodiments, an oil phase may consist at least in part of a propellant, such as an HFA propellant. In some embodiments, either or both of an oil phase and an aqueous phase may contain one or more surfactants, emulsifiers, emulsion stabilizers, buffers, and other excipients. In some embodiments, for example, an excipient comprises or consists of surfactants, especially non-ionic surfactants; emulsifying agents, especially emulsifying waxes; and liquid non-volatile non-aqueous materials, and particularly glycols such as propylene glycol. In some embodiments, an oil phase may contain other oily pharmaceutically approved excipients. For example, in some embodiments, materials such as hydroxylated castor oil or sesame oil may be used in the oil phase as surfactants or emulsifiers.

In some embodiments, a lotion may be described as a low-to-medium viscosity liquid formulation. In some embodiments, a lotion may contain finely powdered substances that are insoluble in the dispersion medium through the use of suspending agents and dispersing agents. In some embodiments, lotions can have as the dispersed phase liquid substances that are immiscible with the vehicle and are usually dispersed by means of emulsifying agents or other suitable stabilizers. In some embodiments, a lotion is in the form of an emulsion having a viscosity of between 100 and 1000 centistokes. In some embodiments, fluidity of lotions permits rapid and uniform application over a wide surface area. In some embodiments, lotions are typically intended to dry on the skin leaving a thin coat of their medicinal components on the skin's surface.

In some embodiments, a cream may be described as a viscous liquid or semi-solid emulsion of either the "oil-in-water" or "water-in-oil type". In some embodiments, creams may contain emulsifying agents and/or other stabilizing agents. In some embodiments, the formulation is in the form of a cream having a viscosity of greater than 1000 centistokes, typically in the range of 20,000-50,000 centistokes. In some embodiments, creams are often time preferred over ointments as they are generally easier to spread and easier to remove.

As will be understood by one of skill in the art, a difference between a cream and a lotion is viscosity. In some embodiments, viscosity depends on amount/use of various oils and percentage of water used to prepare a formulation. In some embodiments, creams are typically thicker than lotions and may have various uses and often one uses more varied oils/butters, depending upon the desired effect upon the skin. In some embodiments, where a formulation comprises or consists of a cream, the water-base percentage is about 60-75% and the oil-base is about 20-30% of the total, with the other percentages being the emulsifier agent, preservatives and additives for a total of 100%.

In some embodiments, an ointment may be described as a semisolid preparation containing an ointment base and optionally one or more active agents as provided in the present disclosure. For example, in some embodiments, suitable ointment bases include hydrocarbon bases (e.g., petrolatum, white petrolatum, yellow ointment, and mineral oil); absorption bases (hydrophilic c, anhydrous lanolin, lanolin, and cold cream); water-removable bases (e.g., hydrophilic ointment), and water-soluble bases (e.g., polyethylene glycol ointments). In some embodiments, pastes typically differ from ointments in that they contain a larger percentage of solids. In some embodiments, pastes are typically more absorptive and less greasy than ointments prepared with the same components.

In some embodiments, a gel may be described as a semisolid system containing dispersions of small or large molecules in a liquid vehicle that is rendered semisolid by the action of a thickening agent or polymeric material dissolved or suspended in the liquid vehicle. In some embodiments, a liquid may include a lipophilic component, an aqueous component or both. In some embodiments, emulsions may be gels or otherwise include a gel component. In some embodiments, gels are not emulsions because they do not contain a homogenized blend of immiscible components. In some embodiments, suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alkene glycols, such as propylene glycol; dimethyl isosorbide; alcohols, such as isopropyl alcohol and ethanol. In some embodiments, solvents are typically selected for their ability to dissolve the drug. In some embodiments, other additives, which improve the skin feel and/or emollience of the formulation, may also be incorporated. For example, in some embodiments, such additives may include, but are not limited, isopropyl myristate, ethyl acetate, C12-C15 alkyl benzoates, mineral oil, squalane, cyclomethicone, capric/caprylic triglycerides, and combinations thereof.

In some embodiments, foams may be described as an emulsion in combination with a gaseous propellant. In some embodiments, a gaseous propellant consists primarily of hydrofluoroalkanes (HFAs). Suitable propellantsinclude HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. In some embodiments, propellants preferably are not hydrocarbon propellant gases which can produce flammable or explosive vapors during spraying. Furthermore, in some embodiments, the compositions preferably contain no volatilealcohols, which can produce flammable or explosive vapors during use.

In some embodiments, emollients may be described as externally applied agents that soften or soothe skin and are generally known in the art and listed in compendia, such as the "Handbook of Pharmaceutical Excipients", 4th Ed., Pharmaceutical Press, 2003. In some embodiments, an emollient may be or comprise, for example, almond oil, castor oil, ceratonia extract, cetostearoyl alcohol, cetyl alcohol, cetyl esters wax, cholesterol, cottonseed oil, cyclomethicone, ethylene glycol palmitostearate,glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, emollients comprise ethylhexyl stearate and/or ethylhexyl palmitate.

In some embodiments, surfactants are surface-active agents that lower surface tension and thereby increase the emulsifying, foaming, dispersing, spreading and wetting properties of a product. In some embodiments, suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, a non-ionic surfactant is stearyl alcohol.

In some embodiments, emulsifiers are surface active substances which promote the suspension of one liquid in another and promote the formation of a stable mixture, or emulsion, of oil and water. In certain embodiments, the emulsifiers are metallic soaps, certain animal and vegetable oils, and various polar compounds. In some embodiments, suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, an emulsifier is glycerol stearate. In some embodiments, an emulsifier is glycerol. In some embodiments, an emulsifier is glycerin.

In some embodiments, compositions disclosed herein are formulated to be applied to a subject's scalp. In some embodiments, the composition is formulated to be used as a product selected from a shampoo, a conditioner, a mousse, a gel, and a spray. Such compositions would be useful for the treatment of seborrheic dermatitis. Treatment of seborrheic dermatitis with such compositions may result in the reduction of a symptom selected from dandruff and cradle cap. However, compositions disclosed herein may be used to treat seborrheic dermatitis at other areas of the body besides the scalp. Non-limiting examples of other areas include the chest, stomach, skin folds, arms, legs, groin area and under breasts.

In some embodiments, compositions disclosed herein comprise a buffer, wherein the buffer controls a pH of the composition. Preferably, the buffers maintain the composition from a pH of about 4 to a pH of about 7.5, from a pH of about 4 to a pH of about 7, and from a pH of about 5 to a pH of about 7.

In some embodiments, compositions disclosed herein are formulated to provide or maintain a desirable skin pH. In some embodiments, the desirable skin pH is between about 4.5 and about 6.5. In some embodiments, the desirable skin pH is between about 5 and about 6. In some embodiments, the desirable skin pH is about 5.5. In some embodiments, compositions disclosed herein are formulated with a skin pH modulating agent. Non-limiting examples of pH modulating agents include salicylic acid, glycolic acid, trichloroacetic acid, azeilic acid, lactic acid, aspartic acid, hydrochloride, stearic acid, glyceryl stearate, cetyl palmitate, urea phosphate, and tocopheryl acetate.

In some embodiments, compositions disclosed herein are formulated to provide more oxygen to the skin. In some embodiments, compositions disclosed herein are formulated to provide more oxygen exposure to the skin. In some embodiments, compositions disclosed herein are formulated to provide more oxygen diffusion into the skin. In some embodiments, compositions disclosed herein are formulated to provide more oxygen diffusion through the skin. In some embodiments, compositions disclosed herein are formulated with an agent that provides more oxygen to the skin. In some embodiments, compositions disclosed herein are used with an agent that provides more oxygen to the skin. In some embodiments, compositions disclosed herein are used before use of an agent that provides more oxygen to the skin. In some embodiments, compositions disclosed herein are used after use of an agent that provides more oxygen to the skin. A non-limiting example of an agent that provides oxygen to the skin is chlorophyll.

In some embodiments, preservatives can be used to prevent the growth of fungi and microorganisms. In some embodiments, suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridiniumchloride, chlorobutanol, phenol, phenylethyl alcohol, and thimerosal. In some embodiments, a concentration of a preservative that is effective to prevent fungal growth is selected, without affecting the effectiveness of the composition for its intended purposed upon topical application.

In some embodiments, excipients in the formulation are selected based on the type of formulation intended. In certain embodiments, the excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hy droxyethylcellulose, hydroxypropylcellulose, hydroxypropylmethy cellulose phthalate, noncrystalline cellulose, magnesium aluminum silicate, triethanolamine, polyvinyl alcohol, polyvinylpyrrolidone, sugars, and starches.

Provided herein are probiotic compositions comprising human-isolated or synthetic *Janthinobacterium lividum, Alcaligenes faecalis, Bacillus altitudinis, Bacillus pumilus*, or *Bacillus subtilis* in an aqueous formulation for topical application. In some embodiments the probiotic compositions are formulated for application to the skin. In some embodiments the probiotic compositions are formulated for application to the mucosa.

In some embodiments the *Janthinobacterium lividum, Alcaligenes faecalis, Bacillus altitudinis, Bacillus pumilus*, or *Bacillus subtilis* probiotic composition is co-formulated with one or more additional active agents. The probiotic composition can be co-formulated with one or more additional antimicrobial agents, as detailed in the combination section. Briefly, the additional antimicrobial agent can be an antifungal agent, an antibacterial agent, an anti-parasitic agent, or a combination of any of those agents.

In some embodiments, the *Janthinobacterium lividum, Alcaligenes faecalis, Bacillus altitudinis, Bacillus pumilus*, or *Bacillus subtilis* probiotic composition is co-formulated with one or more additional active agents that confer additional benefits, such as an agent to relieve itching, pain, discoloration or other undesirable effect.

In some embodiments, the *Janthinobacterium lividum, Alcaligenes faecalis, Bacillus altitudinis, Bacillus pumilus*, or *Bacillus subtilis Janthinobacterium lividum Alcaligenes faecalis, Bacillus altitudinis, Bacillus pumilus, Bacillus subtilis* probiotic composition further contains additional microbes. In some embodiments, the composition contains at least two, three, or four distinct human-isolated or synthetic *Janthinobacterium lividum, Alcaligenes faecalis, Bacillus altitudinis, Bacillus pumilus*, or *Bacillus subtilis*, wherein at least one is isolated from a human host. In some embodiments, the *Janthinobacterium lividum, Alcaligenes faecalis, Bacillus altitudinis, Bacillus pumilus*, or *Bacillus subtilis* probiotic further contains a *Lactobacillus* species or a *Lactococcus* species. In some embodiments, the *Janthinobacterium lividum, Alcaligenes faecalis, Bacillus altitudinis, Bacillus pumilus*, or *Bacillus subtilis* probiotic further contains a benign or beneficial fungal strain often found on human skin or a benign or beneficial strain of *Propionibacterium.*

In some embodiments, the *Janthinobacterium lividum, Alcaligenes faecalis, Bacillus altitudinis, Bacillus pumilus*, or *Bacillus subtilis* composition is in the form of an emulsion composition according to the disclosure is especially effective. In some embodiments the composition is for an emulsion form and used in cosmetic applications. In this case, the emulsion may be in the form of an oil-in-water emulsion, a water-in-oil emulsion, a water-in-oil-in-water emulsion or an oil-in-water-in-oil emulsion. Alternatively, the cosmetic composition of the disclosure may also be used in the form of a nonaqueous composition. The form of the nonaqueous composition is exemplified by solid, semisolid, pressed, mousse, powder and stick forms. In this disclosure, "non-aqueous composition" refers to compositions that are not formulated with water.

In some embodiments, the human-isolated or synthetic *Janthinobacterium lividum, Alcaligenes faecalis, Bacillus altitudinis, Bacillus pumilus*, or *Bacillus subtilis* compositions of this disclosure can be administered with other agents in a combination therapy mode, including anti-microbial agents, probiotics, postbiotics, and prebiotics. Administration can be sequential, over a period of hours or days, or simultaneously.

In one embodiment, the bacterial compositions are included in combination therapy with one or more anti-microbial agents, which include anti-bacterial agents, anti-fungal agents, anti-viral agents and anti-parasitic agents.

In some embodiments, anti-bacterial agents can include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

In some embodiments, anti-viral agents can include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, TenofovirTrifluridine, Valaciclovir, Valganciclovir, Vidarabine, Ibacitabine, Amantadine, Oseltamivir, Rimantidine, Tipranavir, Zalcitabine, Zanamivir and Zidovudine.

Non-limiting examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

Cryoprotectants

In some embodiments, a cryoprotectant is used to protect a probiotic. In some such embodiments, cryoprotectants are used to protect a probiotic during a process, such as a formulation process and/or process for preparing a composition (e.g., pharmaceutical composition). In some embodiments, a cryoprotectant may be chosen from but is not limited to, amino acids, peptides, glycerol, other simple polyols, complex polyols, modified polyols, sugar alcohols, glucose, monosaccharides, disaccharides, oligosaccharides, polysaccharides and modified oligosaccharides and polysaccharides, vitamins, proteins, buffers and combinations thereof. In some embodiments, a cryoprotectant comprises or consists of trehalose. In some embodiments, the trehalose is present at about 2-20%. In some embodiments, the trehalose is D-trehalose.

In some embodiments, compositions disclosed herein are formulated with glycerol. In some instances, a strain of bacterium in the composition ferments the glycerol, thereby producing short chain fatty acids. Non-limiting examples of short-chain fatty acids include acetic acid, lactic acid, and propionic acid. In some instances, human-isolated or synthetic *Janthinobacterium lividum, Alcaligenes faecalis, Bacillus altitudinis, Bacillus pumilus*, or *Bacillus subtilis* grown in the presence of glycerol enhances the production of one or more antimicrobial metabolites.

In some embodiments, penetration enhancers are used to promote transdermal delivery of drugs across the skin, in particular across the stratum corneum. In some embodiments, some penetration enhancers can cause dermal irritation, dermal toxicity and dermal allergies. However, in some embodiments, more commonly used penetration enhancers may include, for example, urea, (carbonyldiamide), imidurea, N,N-diethylformamide, N-methyl-2-pyrrolidine, 1-dodecal-azacyclopheptane-2-one, calcium thioglycate, 2-pyyrolidine,N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10) oxyethylene ether), BRIJ® 78 (stearyl poly(20)oxyethylene ether), BRIJ@96 (oleyl poly(10)oxyethyleneether), and BRIJ® 721 (stearyl poly (21) oxyethylene ether) (ICI Americas Inc. Corp.).

In some embodiments, a composition can be formulated to comprise *Janthinobacterium lividum, Alcaligenes faecalis, Bacillus altitudinis, Bacillus pumilus*, or *Bacillus subtilis* at a particular concentration. For example, in some embodiments, a composition can comprise an amount of probiotic such that the microorganisms may be delivered/administered in effective amounts. In some embodiments, the amount of probiotic delivered is at least $10^3$, $10^4$, $10^5$, $10^6$, $10^7$, $10^8$, $10^9$, $10^{10}$, $10^{11}$, or $10^{12}$ CFUs per unit dose. In some embodiments, a composition may be formulated with the *Janthinobacterium lividum, Alcaligenes faecalis, Bacillus altitudinis, Bacillus pumilus*, or *Bacillus subtilis* probiotic in a proportion of at least about 0.0001% (expressed by dry weight), from about 0.0001% to about 99%, from about 0.001% to about 90% by weight, from about 0.01% to about 80% by weight, and from about 0.1% to about 70% by weight, relative to the total weight of the composition. In some embodiments, a composition intended to be administered topically comprises at least $10^3$, $10^4$, $10^5$, $10^6$, $10^7$, $10^8$, $10^9$, or $10^{10}$, $10^{11}$, or $10^{12}$ microorganisms per gram of carrier, or at equivalent doses calculated for inactive or dead microorganisms or for bacterial fractions or for metabolites produced.

In some embodiments, microbes disclosed herein may be delivered in effective amounts per unit dose, of at least about $10^2$ CFU to about $10^{20}$ CFU. In some embodiments, compositions formulated for topical administration comprise a concentration of each bacterial strain and/or corresponding fraction and/or metabolite that is adjusted so as to correspond to doses (expressed as bacterialequivalent) ranging from about $10^5$ to about $10^{12}$ CFU/dose.

In some embodiments, compositions provided herein for topical application generally comprise from about $10^2$ to about $10^{15}$ CFU/g, from about $10^5$ to about $10^{12}$ CFU/g, or from about $10^6$ to about $10^{13}$ CFU/g of bacteria.

In some embodiments, compositions disclosed herein are delivered to a subject in an amount of at least $10^6$ microbes per square cm of skin. In some embodiments, the composition is formulated in order to deliver at least $10^7$ microbes per square cm of skin. In some embodiments, the composition is formulated in order to deliver at least $10^8$ microbes per square cm of skin. In some embodiments, the composition is formulated in order to deliver at least $10^9$ microbes per square cm of skin. In some embodiments, the composition is formulated in order to deliver less than $10^9$ microbes per square cm of skin. In some embodiments, the composition is formulated in order to deliver less than $10^8$ microbes per square cm of skin. In some embodiments, the composition is formulated in order to deliver less than $10^7$ microbes per square cm of skin. In some embodiments, the composition is formulated in order to deliver between about $10^7$ and $10^8$ microbes per square cm of skin. In some embodiments, the composition is formulated in order to deliver between about $10^6$ microbes per square cm of skin and about $10^{10}$ microbes per square cm of skin. In some embodiments, the composition is formulated in order to deliver between about $10^6$ microbes per square cm of skin and about $10^9$ microbes per square cm of skin. In some embodiments, the composition is formulated in order to deliver between about $10^7$ microbes per square cm of skin and about $10^{10}$ microbes per square cm of skin. In some embodiments, the composition is formulated in order to deliver between about $10^7$ microbes per square cm of skin and about $10^9$ microbes per square cm of skin.

In certain embodiments, compositions disclosed herein are formulated at a concentration of about $10^5$ microbes per milliliter to about $10^{12}$ microbes per milliliter. In certain embodiments, compositions disclosed herein are formulated at a concentration of about $10^6$ microbes per milliliter. In certain embodiments, compositions disclosed herein are formulated at a concentration of about $10^7$ microbes per milliliter. In certain embodiments, compositions disclosed herein are formulated at a concentration of about $10^8$ microbes per milliliter. In certain embodiments, compositions disclosed herein are formulated at a concentration of about $10^9$ microbes per milliliter. In certain embodiments, compositions disclosed herein are formulated at a concentration of about $10^{10}$ microbes per milliliter.

In certain embodiments, compositions disclosed herein for topical or oral use may contain biologic stability compounds including but not limited to amino acids including tryptophan, dipeptides, oligopeptides, polypeptides, Casaminoacids, monosaccharides including glucose, sugar alcohol including mannitol, simple alcohols including glycerol, oligo-alcohols, simple polyols, complex polyols, disaccharides including sucrose and trehalose and isomers of, polysaccharides, mannitol, modified polysaccharides including λ-Carrageenan, cellulose and modified celluloses including carboxymethyl cellulose, starch and modified starch including 2-Hydroxyethylstarch (HES), bioadhesion agents including Carbopol polymers, thickeners and rheology modifiers, suspension and/or emulsion stabilizers, surfactants, oils, modified oils, vitamins, proteins, buffers, salts, bovine-free media, (e.g., tryptic soy broth), lyophilized bacteria, or other inactive/killed bacteria and combinations thereof.

Formatting, Packaging and Kits

In some embodiments, after formulation, composition disclosed herein may be packaged in a manner suitable for delivery and use by an end user. In one embodiment, the composition is placed into an appropriate dispenser and shipped to the end user. Non-limiting examples of a final container may include a pump bottle, squeeze bottle, jar, tube, capsule or vial.

In some embodiments, compositions disclosed herein can be added to an applicator before packaging. Non-limiting examples of applicators include a cotton pad, a polyester pad, a Q-tip, a sponge, and a brush. In some embodiments, the applicator is placed in a package. Non-limiting examples of a package includes bags and foil or wax lined paper packets. In some embodiments, the interior of the package may be sterile. In some embodiments, air in the package is removed with a vacuum before sealing. In some embodiments, the package is heat-sealed. In some embodiments, the package is sealed with adhesive.

In another embodiment, compositions disclosed herein are prepared by being dehydrated or dried through lyophilization for reconstitution before application to the skin. In one embodiment, lyophilization is conducted with one or more additional agents such as glycerol or other sugar alcohols. In some embodiments, one or more additional agents improves the shelf life of the selected bacteria. In one embodiment, the formulation composition does not include trehalose (alpha-D-glucopyranosyl-1,1-alpha-D-glucopyranoside). In some embodiments, the composition does not have to be frozen.

In some embodiments, compositions provided herein may be packaged in one or more containers. For example, in some embodiments, a single bottle, tube, container, or capsule may be divided to two equal or unequal parts wherein one part contains the bacteria, in their packing form (desiccated, freeze dried, etc.), and the other part contains an activation material, which can be a liquid or a gel. In some such embodiments, the single bottle or container can be designed so that an end user can dispense with a single forceapplied to the container all or a portion of the contents in the two container parts, to dispense onto the skin or other surface the selected, transformed, or engineered bacterium and the activation material. In some embodiments, a kit may also be of the form that comprises two or more containers, one container with the population(s) of selected, transformed, or engineered bacterium and the other with a formulation for admixture with the populations of selected, transformed, or engineered bacteria.

In some embodiments, two or more containers, one container with the population of selected, transformed, or engineered bacteria, the other container with natural nonpathogenic skin bacteria that are not selected, transformed, or engineered, and a third container with a formulation for admixture with the populations of selected, transformed, or engineered bacteria. In another example, the two or more containers composing the single bottle have one pump connected to two separate tubes, each draining from a different chamber. The kit may also include one or more complementary products, such as soaps, body washes or moisturizing lotions with certain pH, lotions or creams. In another embodiment, the complementary product is a probiotic. The complementary product may include any compound beneficial to the activity of the original product and enhance its activity for lasting efficacy. Another contemplated packaging is one wherein the population of selected, transformed, or engineered bacteria is maintained as a layer on a bandage or film that is combined with a second layer of bandage/film that will allow activation of the bacteria, and that optionally may also limit reproduction/growth factors. In another embodiment, the final product is stored refrigerated, with the bacteria being in their active state. In another embodiment, the bacteria are stored in a small bead of water-soluble cellulose. The beads can be mixed in any solution such as sunscreen, moisturizer, body wash or soap.

Methods of Use

Methods and compositions provided herein can be used in one or more ways. In some embodiments, a method of use is or comprises a method of treatment. In some embodiments, compositions provided by the present disclosure are used to treat and/or prevent infections resulting from growth of parasitic microorganisms susceptible to metabolites produced by human-isolated or synthetic *Janthinobacterium lividum, Alcaligenes faecalis, Bacillus altitudinis, Bacillus pumilus*, or *Bacillus subtilis*. These microbes can be bacteria, viruses, yeast or fungi.

In an embodiment, the infection is an onychomycosis. In an embodiment, the infection is *Tinea pedis*. In an embodiment, the infection is atopic dermatitis. In an embodiment, the infection is impetigo. In an embodiment, the infection is of the skin or soft tissue.

In an embodiment, the infection is caused by a dermatophyte. In an embodiment, the infection is caused by a *Malassezia* species. In an embodiment, the infection is caused by a *Trichophyton* species. In an embodiment, the infection is caused by *Staphylococcus* species. In an embodiment, the infection is caused by *Trichophyton rubrum*. In an embodiment, the infection is caused by *Staphylococcus aureus*. In an embodiment the infection is caused by *Malassezia* furfur, *M. restricta*, or M. glabosa. In an embodiment, the infection is caused by a gram-positive bacterium.

Prior to administration of the compositions of the present disclosure, a subject may optionally have a pretreatment protocol to prepare the skin to receive the bacterial composition. In certain embodiments, the pretreatment protocol is advisable, such as when a patient has an acute infection with a highly resilient pathogen. In other embodiments, the pretreatment protocol is entirely optional, such as when the pathogen causing the infection is not resilient, or the patient has had an acute infection that has been successfully treated but where the physician is concerned that the infection may recur. In these instances, the pretreatment protocol may enhance the ability of the bacterial composition to affect the patient's microbiome.

As one way of preparing the patient for administration of the microbial community or species, at least one antibiotic or antifungal may be administered to alter the microbes on the patient. This may be applied orally or topically.

If a patient has received an antibiotic for treatment of an infection, or if a patient has received an antibiotic as part of a specific pretreatment protocol, in one embodiment the antibiotic should be stopped in sufficient time to allow the antibiotic to be substantially reduced in concentration on the skin before the bacterial composition is administered. In one embodiment, the antibiotic may be discontinued 1, 2, or 3 days before the administration of the bacterial composition. In one embodiment, the antibiotic may be discontinued 3, 4, 5, 6, or 7 antibiotic half-lives before administration of the bacterial composition. In another embodiment, the antibiotic may be chosen so the constituents in the bacterial composition have an MIC50 that is higher than the concentration of the antibiotic on the skin.

MIC50 of a bacterial composition or the elements in the composition may be determined by methods well known in the art, see, e.g., Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic may be chosen so that the infection is sensitive to the antibiotic, but the constituents in the bacterial composition are not sensitive to the antibiotic.

In some embodiments, the skin of the subject is pretreated with a detergent substance to decrease the amount of skin pathogen prior to application of the *Janthinobacterium lividum, Alcaligenes faecalis, Bacillus altitudinis, Bacillus pumilus*, or *Bacillus subtilis* probiotic composition.

In some embodiments, the *Janthinobacterium lividum, Alcaligenes faecalis, Bacillus altitudinis, Bacillus pumilus*, or *Bacillus subtilis* probiotic is pretreated with a substance to increase production of a beneficial metabolite.

In some embodiments, relative abundance of a probiotic (e.g., *Janthinobacterium lividum, Alcaligenes faecalis, Bacillus altitudinis, Bacillus pumilus*, or *Bacillus subtilis*) is measured on a subject or a surface. In some embodiments, for example, a sample is collected from a scalp, paranasal location, *glabella*, etc. from a subject. In some embodiments, relative abundance of a probiotic on a subject is compared to a population of subjects for determining diagnosis of or risk of developing a disease, disorder or condition.

Methods of Manufacture

Any compositions provided herein, including the pharmaceutical compositions, articles of manufacture, and food or household products comprising the compositions, may contain bacterial strains in any form, for example in an aqueous or oil form, such as a solution or a suspension, embedded in a semi-solid form, in a powdered form or lyophilized form. In some embodiments, the composition or the bacterial strains of the composition are lyophilized. In some embodiments, a subset of the bacterial strains in a composition is lyophilized. Lyophilization was conducted by freezing materials between −80° C. to −20° C. followed by primary drying and secondary drying with varying ramp speeds and hold times, as recommended by manufacturer instruction manual. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacterium may be lyophilized as a combination and/or the bacterium may be lyophilized separately and combined prior to administration. A bacterial strain may be combined with a pharmaceutical excipient prior to combining it with the other bacterial strain or multiple lyophilized bacterium may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake. A bacterial strain may be combined with a pharmaceutical excipient prior to combining it with the other bacterial strain or multiple lyophilized bacterium may be combined while in lyophilized form and the mixture of bacteria, once combined may be subsequently be combined with a pharmaceutical excipient. In some embodiments, the bacterial strain is a lyophilized powder. In some embodiments, the compositions comprising the one or more bacterial strains are lyophilizates.

In some embodiments, bacterial strains of a composition can be manufactured using fermentation techniques well known in the art. In some embodiments, the active ingredients are manufactured using fermentors, which can support the rapid growth of anaerobic bacterial species. The fermentors may be, for example, stirred tank reactors or disposable wave bioreactors. Culture media such as LB media and TB media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

Pharmaceutical or cosmetic compositions of the disclosure can be prepared in accordance with methods well known and routinely practiced in the art (see e.g., Remington: The Science and Practice of Pharmacy, Mack Publishing Co. 20th ed. 2000). Thus, in some embodiments, the present disclosure provides a composition for manufacture of a medicament comprising a probiotic and at least one additional component. In some embodiments, the one additional component comprises or consists of an excipient. In some embodiments, the excipient improves one or more features of the composition such as, for example, efficacy in treating or preventing one or more diseases, disorders, or conditions.

Articles of Manufacture

In some embodiments, the human-isolated or synthetic *Janthinobacterium lividum, Alcaligenes faecalis, Bacillus altitudinis, Bacillus pumilus*, or *Bacillus subtilis* is formulated into an article of manufacture, for example a substance impregnated with the human-isolated or synthetic *Janthino-*

*bacterium lividum, Alcaligenes faecalis, Bacillus altitudinis, Bacillus pumilus*, or *Bacillus subtilis* or postbiotics, or lysates, or metabolites of the human-isolated or synthetic *Janthinobacterium lividum, Alcaligenes faecalis, Bacillus altitudinis, Bacillus pumilus*, or *Bacillus subtilis.*

In some embodiments, the human-isolated or synthetic *Janthinobacterium lividum, Alcaligenes faecalis, Bacillus altitudinis, Bacillus pumilus*, or *Bacillus subtilis* is associated with cloth. Cloth generally refers to a flexible material suitable to be made into clothing, e.g., having enough material strength to withstand everyday motion by a wearer. Cloth can be fibrous, woven, or knit; it can be made of a naturally occurring material or a synthetic material. Exemplary cloth materials include cotton, flax, wool, ramie, silk, denim, leather, nylon, polyester, and spandex, and blends thereof.

In some embodiments, the human-isolated or synthetic *Janthinobacterium lividum, Alcaligenes faecalis, Bacillus altitudinis, Bacillus pumilus*, or *Bacillus subtilis* is associated with yarn. Yarn generally refers to a long, thin spun flexible material that is suitable for knitting or weaving. In some embodiments, yarn can be made of, e.g., wool, cotton, polyester, or one or more other suitable materials and blends thereof.

In some embodiments, the human-isolated or synthetic *Janthinobacterium lividum, Alcaligenes faecalis, Bacillus altitudinis, Bacillus pumilus*, or *Bacillus subtilis* is associated with thread. Thread generally refers to a long, thin spun flexible material that is suitable for sewing. Thread generally has a thinner diameter than yarn. Thread can be made of, e.g., cotton, polyester, nylon, silk, and blends thereof.

Articles of clothing such as, for example, shoes, shoe inserts, pajamas, sneakers, belts, hats, shirts, underwear, athletic garments, helmets, towels, gloves, socks, bandages, and the like, may also be treated with the human-isolated or synthetic *Janthinobacterium lividum, Alcaligenes faecalis, Bacillus altitudinis, Bacillus pumilus*, or *Bacillus subtilis*. Bedding, including sheets, pillows, pillowcases, and blankets may also be treated with *Janthinobacterium lividum, Alcaligenes faecalis, Bacillus altitudinis, Bacillus pumilus*, or *Bacillus subtilis*. In some embodiments, areas of skin that cannot be washed for a period of time may also be contacted with *Janthinobacterium lividum, Alcaligenes faecalis, Bacillus altitudinis, Bacillus pumilus*, or *Bacillus subtilis*. For example, skin enclosed in orthopedic casts which immobilize injured limbs during the healing process, areas of skin in contact with prosthetics or devices worn regularly such as hearing aids, and areas in proximity to injuries that must be kept dry for proper healing such as stitched wounds may benefit from contact with *Janthinobacterium lividum, Alcaligenes faecalis, Bacillus altitudinis, Bacillus pumilus*, or *Bacillus subtilis.*

In some embodiments, the present disclosure provides a wearable article comprising a human-isolated or synthetic *Janthinobacterium lividum, Alcaligenes faecalis, Bacillus altitudinis, Bacillus pumilus*, or *Bacillus subtilis* as described herein. A wearable article may be a light article that can be closely associated with a user's body, in a way that does not impede ambulation.

Examples of wearable articles include a wristwatch, wristband, headband, hair elastic, hair nets, shower caps, hats, hairpieces, and jewelry. The wearable article comprising a human-isolated or synthetic *Janthinobacterium lividum, Alcaligenes faecalis, Bacillus altitudinis, Bacillus pumilus*, or *Bacillus subtilis* described herein may provide, e.g., at a concentration that provides one or more of a treatment or prevention of a skin disorder, a treatment or prevention of a disease or condition associated with low nitrite levels, a treatment or prevention of body odor, a treatment to supply nitric oxide to a subject, or a treatment to inhibit microbial growth.

In some embodiments, the human-isolated or synthetic *Janthinobacterium lividum, Alcaligenes faecalis, Bacillus altitudinis, Bacillus pumilus*, or *Bacillus subtilis* is associated with a product intended to contact the hair, for example, a brush, comb, shampoo, conditioner, headband, hair elastic, hair nets, shower caps, hats, and hairpieces. Articles contacting the surface of a human subject, such as a diaper, may be associated with the *Janthinobacterium lividum, Alcaligenes faecalis, Bacillus altitudinis, Bacillus pumilus*, or *Bacillus subtilis* of this disclosure.

In some embodiments, the human-isolated or synthetic *Janthinobacterium lividum, Alcaligenes faecalis, Bacillus altitudinis, Bacillus pumilus*, or *Bacillus subtilis* is associated with a household item, which may otherwise function as a reservoir for a human skin pathogen. In some embodiments, a shower curtain, bathmat, shower mat, or drainage tile is impregnated with *Janthinobacterium lividum, Alcaligenes faecalis, Bacillus altitudinis, Bacillus pumilus*, or *Bacillus subtilis* or postbiotics, or lysates, or metabolites of the human-isolated or synthetic *Janthinobacterium lividum, Alcaligenes faecalis, Bacillus altitudinis, Bacillus pumilus*, or *Bacillus subtilis.*

In some embodiments, the human-isolated or synthetic *Janthinobacterium lividum, Alcaligenes faecalis, Bacillus altitudinis, Bacillus pumilus*, or *Bacillus subtilis* is associated with a household or industrial cleaning substance, such as a cleaning substance intended for cleaning a gym shower.

In some embodiments, the product comprising the human-isolated or synthetic *Janthinobacterium lividum, Alcaligenes faecalis, Bacillus altitudinis, Bacillus pumilus*, or *Bacillus subtilis* is packaged. The packaging may serve to compact the product or protect it from damage, dirt, or degradation. The packaging may comprise, e.g., plastic, paper, cardboard, or wood. In some embodiments the packaging is impermeable to bacteria. In some embodiments the packaging is permeable to oxygen and/or carbon dioxide.

TABLE 1

16s rRNA sequences of *Alcaligenes faecalis, Bacillus altitudinis, Bacillus pumilus*, or *Bacillus subtilis.*

| Seq ID No: | Name | Sequence |
|---|---|---|
| 1 | DB05646 *A. faecalis* | GAACGGCAGCGCGAGAGAGCTTGCTCTCTTGGCGGCGAGTGGCGGACGG GTGAGTAATATATCGGAACGTGCCCAGTAGCGGGGGATAACTACTCGAA AGAGTGGCTAATACCGCATACGCCCTACGGGGGAAAGGGGGGGATCGCA AGACCTCTCACTATTGGAGCGGCCGATATCGGATTAGCTAGTTGGTGGG GTAAAGGCTCACCAAGGCAACGATCCGTAGCTGGTTTGAGAGGACGACC AGCCACACTGGGACTGAGACACGGCCCAGACTCCTACGGGAGGCAGCAG TGGGGAATTTTGGACAATGGGGGAAACCCTGATCCAGCCATCCCGCGTG |

TABLE 1-continued 16s rRNA sequences of *Alcaligenes faecalis*, *Bacillus altitudinis*, *Bacillus pumilus*, or *Bacillus subtilis*.

| Seq ID No:Name | | Sequence |
|---|---|---|
| | | TATGATGAAGGCCTTCGGGTTGTAAAGTACTTTTGGCAGAGAAGAAAAG<br>GTACCTCCTAATACGAGGTACTGCTGACGGTATCTGCAGAATAAGCACC<br>GGCTAACTACGTGCCAGCAGCCGCGGTAATACGTAGGGTGCAAGCGTTA<br>ATCGGAATTACTGGGCGTAAAGCGTGTGTAGGCGGTTCGGAAAGAAAGA<br>TGTGAAATCCCAGGGCTCAACCTTGGAACTGCATTTTTAACTGCCGAGC<br>TAGAGTATGTCAGAGGGGGGTAGAATTCCACGTGTAGCAGTGAAATGCG<br>TAGATATGTGGAGGAATACCGATGGCGAAGGCAGCCCCCTGGGATAATA<br>CTGACGCTCAGACACGAAAGCGTGGGGAGCAAACAGGATTAGATACCCT<br>GGTAGTCCACGCCCTAAACGATGTCAACTAGCTGTTGGGGCCGTTAGGC<br>CTTAGTAGCGCAGCTAACGCGTGAAGTTGACCGCCTGGGGAGTACGGTC<br>GCAAGATTAAAACTCAAAGGAATTGACGGGGACCCGCACAAGCGGTGGA<br>TGATGTGGATTAATTCGATGCAACGCGAAAAACCTTACCTACCCTTGAC<br>ATGTCTGGAAAGCCGAAGAGATTTGGCCGTGCTCGCAAGAGAACCGGAA<br>CACAGGTGCTGCATGGCTGTCGTCAGCTCGTGTCGTGAGATGTTGGGTT<br>AAGTCCCGCAACGAGCGCAACCCTTGTCATTAGTTGCTACGCAAGAGCA<br>CTCTAATGAGACTGCCGGTGACAAACCGGAGGAAGGTGGGGATGACGTC<br>AAGTCCTCATGGCCCTTATGGGTAGGGCTTCACACGTCATACAATGGTC<br>GGGACAGAGGGTCGCCAACCCGCGAGGGGGAGCCAATCTCAGAAACCCG<br>ATCGTAGTCCGGATCGCAGTCTGCAACTCGACTGCGTGAAGTCGGAATC<br>GCTAGTAATCGCGGATCAGAATGTCGCGGTGAATACGTTCCCGGGTCTT<br>GTACACACCGCCCGTCACACCATGGGAGTGGGTTTCACCAGAAGTAGGT<br>AGCCTAACCGTAAGGAGGGCGCTTACCACGGTGGGATTCAT |
| 2 | DB10033 *B. altitudinis* | GACTTCACCCCAATCATCTGCCCCACCTTCGGCGGCTGGCTCCATAAAG<br>GTTACCTCACCGACTTCGGGTGTTGCAAACTCTCGTGGTGTGACGGGCG<br>GTGTGTACAAGGCCCGGGAACGTATTCACCGCGGCATGCTGATCCGCGA<br>TTACTAGCGATTCCAGCTTCACGCAGTCGAGTTGCAGACTGCGATCCGA<br>ACTGAGAACAGATTTGTGGGATTGGCTAAACCTTGCGGTCTCGCAGCCC<br>TTTGTTCTGTCCATTGTAGCACGTGTGTAGCCCAGGTCATAAGGGGCAT<br>GATGATTTGACGTCATCCCCACCTTCCTCCGGTTTGTCACCGGCAGTCA<br>CCTTAGAGTGCCCAACTGAATGCTGGCAACTAAGATCAAGGGTTGCGCT<br>CGTTGCGGGACTTAACCCAACATCTCACGACACGAGCTGACGACAACCA<br>TGCACCACCTGTCACTCTGTCCCCGAAGGGAAAGCCCTATCTCTAGGGT<br>TGTCAGAGGATGTCAAGACCTGGTAAGGTTCTTCGCGTTGCTTCGAATT<br>AAACCACATGCTCCACCGCTTGTGCGGGCCCCCGTCAATTCCTTTGAGT<br>TTCAGTCTTGCGACCGTACTCCCCAGGCGGAGTGCTTAATGCGTTAGCT<br>GCAGCACTAAGGGGCGGAAACCCCCTAACACTTAGCACTCATCGTTTAC<br>GGCGTGGACTACCAGGGTATCTAATCCTGTTCGCTCCCCACGCTTTCGC<br>TCCTCAGCGTCAGTTACAGACCAGAGAGTCGCCTTCGCCACTGGTGTTC<br>CTCCACATCTCTACGCATTTCACCGCTACACGTGGAATTCCACTCTCCT<br>CTTCTGCACTCAAGTTTCCCAGTTTCCAATGACCCTCCCCGGTTGAGCC<br>GGGGGCTTTCACATCAGACTTAAGAAACCGCCTGCGAGCCCTTTACGCC<br>CAATAATTCCGGACAACGCTTGCCACCTACGTATTACCGCGGCTGCTGG<br>CACGTAGTTAGCCGTGGCTTTCTGGTTAGGTACCGTCAAGGTGCAAGCA<br>GTTACTCTTGCACTTGTTCTTCCCTAACAACAGAGCTTTACGATCCGAA<br>AACCTTCATCACTCACGCGGCGTTGCTCCGTCAGACTTTCGTCCATTGC<br>GGAAGATTCCCTACTGCTGCCTCCCGTAGGAGTCTGGGCCGTGTCTCAG<br>TCCCAGTGTGGCCGATCACCCTCTCAGGTCGGCTACGCATCGTCGCCTT<br>GGTGAGCCGTTACCTCACCAACTAGCTAATGCGCCGCGGGTCCATCTGT<br>AAGTGACAGCCGAAACCGTCTTTCATCCTTGAACCATGCGGTTCAAGGA<br>ACTATCCGGTATTAGCTCCGGTTTCCCGGAGTTATCCCAGTCTTACAGG<br>CAGGTTACCCACGTGTTACTCACCCGTCCGCCGCTAACATCCGGGAGCA<br>AGCTCCCTTCTGTCCGCTCGACTTGCATGTATTAGGCACGCCGCCAGCG<br>TTCGTCCTGAGC |
| 3 | DB03376 *B. pumilus* | TCATCTGTCCCACCTTCGGCGGCTGGCTCCATAAAGGTTACCTCACCGA<br>CTTCGGGTGTTACAAACTCTCGTGGTGTGACGGGCGGTGTGTACAAGGC<br>CCGGGAACGTATTCACCGCGGCATGCTGATCCGCGATTACTAGCGATTC<br>CAGCTTCACGCAGTCGAGTTGCAGACTGCGATCCGAACTGAGAACAGAT<br>TTATGGGATTGGCTAAACCTTGCGGTCTCGCAGCCCTTTGTTCTGTCCA<br>TTGTAGCACGTGTGTAGCCCAGGTCATAAGGGGCATGATGATTTGACGT<br>CATCCCCACCTTCCTCCGGTTTGTCACCGGCAGTCACCTTAGAGTGCCC<br>AACTAAATGCTGGCAACTAAGATCAAGGGTTGCGCTCGTTGCGGGACTT<br>AACCCAACATCTCACGACACGAGCTGACGACAACCATGCACCACCTGTC<br>ACTCTGTCCCCGAAGGGAAAGCCCTATCTCTAGGGTTGTCAGAGGATGT<br>CAAGACCTGGTAAGGTTCTTCGCGTTGCTTCGAATTAAACCACATGCTC<br>CACCGCTTGTGCGGGCCCCCGTCAATTCCTTTGAGTTTCAGTCTTGCGA<br>CCGTACTCCCCAGGCGGAGTGCTTAATGCGTTAGCTGCAGCACTAAGGG<br>GCGGAAACCCCCTAACACTTAGCACTCATCGTTTACGGCGTGGACTACC<br>AGGGTATCTAATCCTGTTCGCTCCCCACGCTTTCGCTCCTCAGCGTCAG<br>TTACAGACCAGAGAGTCGCCTTCGCCACTGGTGTTCCTCCACATCTCTA<br>CGCATTTCACCGCTACACGTGGAATTCCACTCTCCTCTTCTGCACTCAA<br>GTTTCCCAGTTTCCAATGACCCTCCCCGGTTGAGCCGGGGGCTTTCACA<br>TCAGACTTAAGAAACCGCCTGCGAGCCCTTTACGCCCAATAATTCCGGA<br>CAACGCTTGCCACCTACGTATTACCGCGGCTGCTGGCACGTAGTTAGCC |

TABLE 1-continued 16s rRNA sequences of *Alcaligenes faecalis*, *Bacillus altitudinis*, *Bacillus pumilus*, or *Bacillus subtilis*.

| Seq ID No | Name | Sequence |
|---|---|---|
| | | GTGGCTTTCTGGTTAGGTACCGTCAAGGTGCGAGCAGTTACTCTCGCAC |
| | | TTGTTCTTCCCTAACAACAGAGCTTTACGATCCGAAAACCTTCATCACT |
| | | CACGCGGCGTTGCTCCGTCAGACTTTCGTCCATTGCGGAAGATTCCCTA |
| | | CTGCTGCCTCCCGTAGGAGTCTGGGCCGTGTCTCAGTCCCAGTGTGGCC |
| | | GATCACCCTCTCAGGTCGGCTACGCATCGTCGCCTTGGTGAGCCATTAC |
| | | CCCACCAACTAGCTAATGCGCCGCGGGTCCATCTGTAAGTGACAGCCGA |
| | | AACCGTCTTTCATCCTTGAACCATGCGGTTCAAGGAACTATCCGGTATT |
| | | AGCTCCGGTTTCCCGGAGTTATCCCAGTCTTACAGGCAGGTTACCCACG |
| | | TGTTACTCACCCGTCCGCCGCTAACATCCGGGAGCAAGCTCCCTTCTGT |
| | | CCGCTCGACTTGCA |
| 4 | DB02475 | TTATCGGAGAGTTTGATCCTGGCTCAGGACGAACGCTGGCGGCGTGCCT |
| | *B. subtilis* | AATACATGCAAGTCGAGCGGACAGATGGGAGCTTGCTCCCTGATGTTAG |
| | | CGGCGGACGGGTGAGTAACACGTGGGTAACCTGCCTGTAAGACTGGGAT |
| | | AACTCCGGGAAACCGGGGCTAATACCGGATGCTTGTTTGAACCGCATGG |
| | | TTCAAACATAAAAGGTGGCTTCGGCTACCACTTACAGATGGACCCGCGG |
| | | CGCATTAGCTAGTTGGTGAGGTAACGGCTCACCAAGGCAACGATGCGTA |
| | | GCCGACCTGAGAGGGTGATCGGCCACACTGGGACTGAGACACGGCCCAG |
| | | ACTCCTACGGGAGGCAGCAGTAGGGAATCTTCCGCAATGGACGAAAGTC |
| | | TGACGGAGCAACGCCGCGTGAGTGATGAAGGTTTTCGGATCGTAAAGCT |
| | | CTGTTGTTAGGGAAGAACAAGTACCGTTCGAATAGGGCGGTACCTTGAC |
| | | GGTACCTAACCAGAAAGCCACGGCTAACTACGTGCCAGCAGCCGCGGTA |
| | | ATACGTAGGTGGCAAGCGTTGTCCGGAATTATTGGGCGTAAAGGGCTCG |
| | | CAGGCGGTTTCTTAAGTCTGATGTGAAAGCCCCCGGCTCAACCGGGGAG |
| | | GGTCATTGGAAACTGGGGAACTTGAGTGCAGAAGAGGAGAGTGGAATTC |
| | | CACGTGTAGCGGTGAAATGCGTAGAGATGTGGAGGAACACCAGTGGCGA |
| | | AGGCGACTCTCTGGTCTGTAACTGACGCTGAGGAGCGAAAGCGTGGGGA |
| | | GCGAACAGGATTAGATACCCTGGTAGTCCACGCCGTAAACGATGAGTGC |
| | | TAAGTGTTAGGGGGTTTCCGCCCCTTAGTGCTGCAGCTAACGCATTAAG |
| | | CACTCCGCCTGGGGAGTACGGTCGCAAGACTGAAACTCAAAGGAATTGA |
| | | CGGGGGCCCGCACAAGCGGTGGAGCATGTGGTTTAATTCGAAGCAACGC |
| | | GAAGAACCTTACCAGGTCTTGACATCCTCTGACAATCCTAGAGATAGGA |
| | | CGTCCCCTTCGGGGGCAGAGTGACAGGTGGTGCATGGTTGTCGTCAGCT |
| | | CGTGTCGTGAGATGTTGGGTTAAGTCCCGCAACGAGCGCAACCCTTGAT |
| | | CTTAGTTGCCAGCATTCAGTTGGGCACTCTAAGGTGACTGCCGGTGACA |
| | | AACCGGAGGAAGGTGGGGATGACGTCAAATCATCATGCCCCTTATGACC |
| | | TGGGCTACACACGTGCTACAATGGACAGAACAAAGGGCAGCGAAACCGC |
| | | GAGGTTAAGCCAATCCCACAAATCTGTTCTCAGTTCGGATCGCAGTCTG |
| | | CAACTCGACTGCGTGAAGCTGGAATCGCTAGTAATCGCGGATCAGCATG |
| | | CCGCGGTGAATACGTTCCCGGGCCTTGTACACACCGCCCGTCACACCAC |
| | | GAGAGTTTGTAACACCCGAAGTCGGTGAGGTAACCTTTTAGGAGCCAGC |
| | | CGCCGAAGGTGGGACAGATGATTGGGGTGAAGTCGTAACAAGGTAGCCG |
| | | TATCGGAAGGTGCGGCTGGATCACCTCCTTT |

EXAMPLES

Example 1: Isolation of *Alcaligenes faecalis*, *Bacillus altitudinis*, *Bacillus Pumilus*, and *Bacillus subtilis* from a Human Source

Summary

To identify new bacterial isolates with probiotic potential from the human skin, approximately 700 skin microbiome samples collected from 42 healthy young adults were screened for viable colony forming units. Individual isolates were purified through passage of single colonies. Primary screening of 454 of these individual bacterial isolates was completed, yielding 5 candidate species that show inhibition activity against *Malassezia*, *Staphylococcus aureus*, and/or *Trichophyton rubrum*.

Materials & Methods

Samples for Bioprospecting

Samples were sourced and collected from the skin of healthy human subjects or from the toes of human subjects with *T. pedis*. Skin microbiome samples were collected from human subjects following standard scrubbing/swabbing procedures known to those in the art, and using eSwab tubes (Fisher, Cat. No. 23-600-900). Samples were collected from forehead, lower leg, heel, and toes for each subject.

Strain Isolation

Samples collected from human skin were either processed directly or stored at −80° C. with 10% DMSO as cryoprotectant and thawed at room temperature for processing. Skin samples were plated onto BHI and R2A agar plates supplied with 1% glycerol following standard microbial practice after being diluted to the extent of 30-300 colonies per plate. Plates were incubated at ambient temperature for 3-5 days and visually checked for bacterial colonies.

Molecular Identification of *Alcaligenes faecalis, Bacillus Altitudinis, Bacillus Pumilus* and *Bacillus subtilis* Strains All samples were purified by sub-culturing and confirmed via 16S rRNA sequencing. DNA was extracted from purified colonies and amplified by polymerase chain reaction using a thermal cycler and the standard 27F/1492R primer pair. PCR products were checked on E-gel before submission for Sanger sequencing. Taxonomic information was determined by search obtained sequences against NCBI database.

Results, Interpretations and Conclusions

*Alcaligenes faecalis*, DB05646, was isolated from the great toe nail bed of a human subject with *T. pedis* moccasin and is a non-fermenting gram-negative (NFGN) rod-shaped bacteria (FIG. 1).

*Bacillus* altitudinis, DB10033 was isolated from the front lower leg of a healthy human subject, *Bacillus pumilus* DB03376, was isolated from the heel of a second healthy human subject, and *Bacillus subtilis* DB02475 was isolated from the forehead of another healthy human subject and are gram-positive rod-shaped bacteria (FIG. 1).

Example 2: Genetic Assessment Methods and Abundance of *Alcaligenes faecalis, Bacillus altitudinis, Bacillus pumilus, and Bacillus subtilis*

Summary

Genetic analyses and molecular evolution study of *Alcaligenes faecalis, Bacillus altitudinis, Bacillus pumilus*, or *Bacillus subtilis* strains disclosed herein together with strains with published genome sequences showed that *Alcaligenes faecalis, Bacillus altitudinis, Bacillus pumilus*, or *Bacillus subtilis* strains fell into at least four distinct subgroups and each subgroup includes *Alcaligenes faecalis, Bacillus altitudinis, Bacillus pumilus*, or *Bacillus subtilis* strains isolated from various sources including soil, plant, amphibian, and human skin. Relative abundances of *Alcaligenes faecalis, Bacillus altitudinis, Bacillus pumilus*, or *Bacillus subtilis* on human hosts were measured at anatomical sites.

Materials & Methods

Whole Genome Shotgun Sequencing and Genome Sequence Assembly

Shotgun sequencing library for each *Alcaligenes faecalis, Bacillus* altitudinis, *Bacillus pumilus*, or *Bacillus subtilis* strain was generated using the Nextera Flex kit manufactured by Illumina according to the instructions. The shotgun libraries were pooled and sequenced in a HiSeq X platform. The sequencing reads were automatically demultiplexed into individual FASTA files, run through standard bioinformatic analysis yielding a genome assembled from cleaned sequencing reads. Samples were also assessed for relative abundance of different microbial species.

Nucleotide-Level Genome Similarity of *Alcaligenes faecalis, Bacillus Altitudinis, Bacillus Pumilus*, or *Bacillus subtilis* Strains Genome sequences of *Alcaligenes faecalis, Bacillus altitudinis, Bacillus pumilus*, or *Bacillus subtilis* strains, along with several published *Alcaligenes faecalis, Bacillus altitudinis, Bacillus pumilus*, or *Bacillus subtilis* genomes (as set forth by reference numbers shown in Tables 17, 19, 22, and 24, for which sequences can be found at, e.g., world wide web at ncbi.nlm.nih.gov/genome/), were run through Average Nucleotide Identify ("ANI"; see hypertext transfer protocol secure//img.jgi.doe.gov/docs/docs/ANI.pdf) analyses to determine the similarity and genetic diversity.

Phylogenomic Analysis of *Alcaligenes faecalis, Bacillus Altitudinis, Bacillus Pumilus*, or *Bacillus subtilis* Genome Sequences Phylogenomic relationships of *Alcaligenes faecalis, Bacillus* altitudinis, *Bacillus pumilus*, or *Bacillus subtilis* strains described herein and strains with published genomic sequences (as set forth by reference numbers shown in Tables 19, 21 23, and 25, for which sequences can be found at, e.g., world wide web at ncbi.nlm.nih.gov/genome/), were evaluated using the RAxML package following accompanying instructions (see, e.g., cme.h-its.org/exelixis/web/software/raxml/; see also, e.g., A. Stamatakis: "RAxML Version 8: A tool for Phylogenetic Analysis and Post-Analysis of Large Phylogenies." 2014. Bioinformatics).

Relative Abundance of *Alcaligenes faecalis, Bacillus Altitudinis, Bacillus Pumilus*, or *Bacillus subtilis* on Human Hosts Microbiomes of 228 healthy subjects and 28 diseased subjects (subjects diagnosed as having an infection with a skin pathogen) were analyzed using 16s amplicon sequencing and metagenomic shotgun sequencing of gDNA as described above. Samples were collected from the scalp, paranasal location, and *glabella* from healthy and diseased participants. The mean relative abundance of *A. faecalis, B. altitudinis, B. pumilus*, and *B. subtilis* at each anatomical site was calculated as the mean percent of the total reads that were assigned to each species observed in the microbiome sample.

Results, Interpretations, and Conclusions

Once the identity of the strains of interest *A. faecalis, B. altitudinis, B. pumilus*, and *B. subtilis* were identified and run through standard genetic analysis procedures known and available to those in the art, the relative abundance of each species at difference anatomical sites was assessed. Entire microbial communities at different anatomical sites of 228 healthy subjects and 28 diseased subjects were analyzed to determine the abundance of*A. faecalis, B. altitudinis, B. pumilus*, and *B. subtilis* (Table 2). Subjects tested were found to have *Alcaligenes faecalis, Bacillus altitudinis, Bacillus pumilus, pumilus*, and/or *Bacillus subtilis* in different abundances on their skin. *B. subtilis* had the highest mean relative abundance at healthy anatomical sites and some diseased sites and *A. faecalis* had the highest relative abundance at diseased scalp and diseased *glabella* anatomical sites.

TABLE 2

Mean Relative Abundance at Anatomical Site (mean % of microbiome observed) based upon a sampling of N = 228 healthy patients and N = 28 diseased patients, based upon 16s amplicon sequencing and metagenomic shotgun sequencing of gDNA.

| | All Healthy Sites | ±sd | Healthyscalp | ±sd | Diseasescalp | ±sd | Healthy Paranasal |
|---|---|---|---|---|---|---|---|
| *A. faecalis* | 0.198 | 0.606 | 0.073 | 0.061 | 0.940 | 2.621 | 0.110 |
| *B. pumilus* | 0.210 | 0.399 | 0.295 | 0.386 | 0.389 | 0.801 | 0.169 |
| *B. subtilis* | 2.840 | 21.038 | 8.971 | 50.532 | 0.339 | 0.248 | 3.523 |
| *B. altitudinis* | 0.102 | 26.221 | 0.037 | 0.089 | 0.042 | 0.095 | 0.265 |

TABLE 2-continued

Mean Relative Abundance at Anatomical Site (mean % of microbiome observed) based upon a sampling of N = 228 healthy patients and N = 28 diseased patients, based upon 16s amplicon sequencing and metagenomic shotgun sequencing of gDNA.

| | ±sd | Disease Paranasal | ±sd | Healthy Glabella | ±sd | Disease Glabella | ±sd |
|---|---|---|---|---|---|---|---|
| *A. faecalis* | 0.200 | 0.168 | 0.210 | 0.094 | 0.111 | 0.521 | 1.407 |
| *B. pumilus* | 0.192 | 0.095 | 0.041 | 0.162 | 0.360 | 0.051 | 0.043 |
| *B. subtilis* | 17.612 | 0.411 | 0.269 | 0.759 | 1.659 | 0.334 | 0.221 |
| *B. altitudinis* | 1.711 | 0.024 | 0.028 | 0.027 | 0.045 | 0.039 | 0.041 |

Example 3: Pathogen Screening

Summary

*Alcaligenes faecalis, Bacillus altitudinis, Bacillus pumilus*, or *Bacillus subtilis* were tested for their ability to inhibit one to three *Malassezia* species, *T. rubrum*, and *S. aureus*. The strains being screened were grown in fermentors and then used in modified inhibition assays. The assays were tailored to the type of pathogen being tested but in each experiment the zone of inhibition induced by *Alcaligenes faecalis, Bacillus altitudinis, Bacillus pumilus*, or *Bacillus subtilis* was measured and compared to a control. All four strains were found to inhibit the growth of *M. globosa, M. furfur, T. rubrum* and/or *S. aureus*. DB05646 was also tested against *M. restricta* and found to inhibit it.

Materials & Methods

Microbial Strains

*M. restricta* MYA4611, *M. furfur* 12078, *M. globosa* MYA4794 were purchased from ATCC and maintained according to accompanying instructions. 16s rRNA sequences were used to confirm identity of all purchased microbial strains. Trichophytonrubrum strain 18754 was purchased from ATCC and maintained according to instructions. *Staphylococcus aureus* strain 25923 was purchased from ATCC and maintained according toinstructions. *Alcaligenes faecalis* DB05646, *Bacillus* altitudinis DB10033, *Bacillus pumilus* DB03376, or *Bacillus subtilis* DB02475 strains were stored at −80° C. with either DMSO or glycerol as cryoprotectant.

*Alcaligenes faecalis, Bacillus altitudinis, Bacillus pumilus*, or *Bacillus subtilis* were grown in fermentors at 5 L scale. Fermentors were inoculated from 14-15 h old shake flask cultures, and growth at 25° C. was monitored by measuring absorbance at 600 nm. Fermentor cultures were harvested aseptically and the cell pellet was resuspended in formulation buffer containing cryoprotectants and stabilizers, to prepare frozen or lyophilized formulations. The final formulated product, prior to freezing or lyophilizing, was tested for viability, purity, and functional activity against pathogens *M. restricta, M. furfur, M. globosa, T. rubrum*, and *S. aureus*, before and after dilution to $10^9$, $10^8$, $10^7$ and $10^6$ CFU/mL. Purity was >99.99%, and there was zero to minimal drop in viability and no change in activity between undiluted and diluted samples.

Purity Assay

Shake flask cultures were used to inoculate the fermentors, and harvested cultures were resuspended in the cryoprotectant vehicle and diluted such that plating of 100 μl would grow an estimated 30-300 colonies per plate. This estimate was based on the absorbance at 600 nm reading and previous experiments determining the CFU/mL of 1OD unit and such methodology is known and available to those of skill in the art. 6-10 plates of LB50 agar or BHI supplemented with 0.5% glycerol agar were spread plated with 100 μl of culture. Plates were incubated at room temperature for up to one week and were monitored for non-*Alcaligenes faecalis, Bacillus altitudinis, Bacillus pumilus*, or *Bacillus subtilis* growth.

Viability Assay

At harvest of cultures grown in shake flasks, the absorbance at 600 nm was measured, and the CFU/mL calculated using the previously calculated relationship between OD and CFU. One sample was plated immediately as described herein and another sample was analyzed for *M. restricta, M furfur, M. globosa* and *T. rubrum* growth. Growth was determined using a modified inhibition assay and the *Staphylococcus* growth was determined using an antibiosis assay. Additionally, 3 samples were then made from the harvest to equal $10^8$, $10^7$ and $10^6$ CFU/mL. 100 μl from each dilution was added to the first well of a 96 well plate in triplicate. 30 μl were removed from this well and added to 270 μl of sterile PBS in the second well of the 96 well plate. A pipette with 100 μl volume was used to mix the contents of the well before tips were changed and 30 μl removed from this second well and transferred in to a third well with 270 μl sterile PBS. A 100 μl volume was used to mix the culture. In this way, seven serial 10-fold dilutions were made to the original 10-fold dilution. 10 μl spots of each dilution were spotted on to an LB50 agar plate from each of the three replicate dilutions and allowed to dry. Plates were incubated at room temperature for 2 days and CFU were counted. CFU/mL was calculated using the dilution factors of the spot counts.

*Malassezia* Antibiosis Assay

In vitro assays were set up. Briefly, *Malassezia* was grown for 5-14 days on YPD-Mal agar plates then the fungal material from the plates was scraped into a cryotube containing 5 mm glass beads in 1 mL sterilized water. The tube was then vortexed to homogenize the material. The OD 600 was measured and diluted to 0.3.200 μl volumes of the scraped culture were then spread using the beads onto Media 22 agar plates and allowed to dry to create anew cultured plate. One 5 μl spot of *Alcaligenes faecalis* DB05646, *Bacillus* altitudinis DB10033, *Bacillus pumilus* DB03376, or *Bacillus subtilis* DB02475 from frozen sample or optimized culture (optimized growth time and optimized CFU/mL) were added to each plate and allowed to dry. Plates were incubated at 27° C. for 4 days. The width of the zone of inhibition was measured.

Results are semi quantitative as zones of inhibition can be measured. The width of the zones were first measured using ImageJ in pixels (straight line) and converted into mm based the pixel measurements of petri dishes.

*T. rubrum* Antibiosis Assay

In vitro assays were set up following a modified inhibition assay similar to the procedure reported by Ramsey et al. (2015) and optimized as described and provided herein. Briefly, *Alcaligenes faecalis* DB05646, *Bacillus altitudinis* DB10033, *Bacillus pumilus* DB03376, or *Bacillus subtilis* DB02475 cultures were grown for 24 hours in 50% LB-Lennox (LBS-50), to roughly $2\times10^9$ CFU/mL. Aliquots of cultures were applied onto 33% Tryptone agar plates in two straight perpendicular lines that ran from the edge of one side of the plate to the other. Each line bisected the plate and the two lines crossed in the center of the plate to make an even cross, and 4 sections separated by lines of bacterial inoculum. The lines were struck out using a sterile cotton swab.

Conidia of *T. rubrum* were harvested from an approximately 2-week old culture grown on Sabouraud Dextrose Agar, counted using a hemocytometer under a standard light microscope, and applied at a concentration of $10^6$ spores/mL in four replicate spots with 5 μl per spot. The fungal inoculum was added to the four empty sections on the plate separated by the lines of bacterial inoculum. In this way the fungal colonies were surrounded by bacteria (or the edge of the petri dish) and could not grow into each other to make one larger colony, unless the bacteria were ineffective at inhibiting the fungal growth. The fungi would have to grow over the bacteria to merge with a neighbor fungal colony. The positions of the *Alcaligenes faecalis, Bacillus altitudinis, Bacillus pumilus*, or *Bacillus subtilis* cross and spore spots were replicated on each plate using a template. Assay plates were incubated at ambient temperature or at 27° C. as indicated for 1 to 2 weeks. Images were taken at Day 7 and Day 14.

The inhibition of *T. rubrum* by the bacteria struck out on the plate in the cross formation, was determined by the reduction of fungal colony size in mm compared to controls that had 4 *T. rubrum* dots of inoculum but no bacterial cross. Radii of *T. rubrum* colonies were first measured using ImageJ in pixels (straight line) and converted into mm based the pixel measurements of petri dishes.

*S. aureus* Antibiosis Assay

In vitro assays were set up following standard experimental procedure. A research cell bank vial of *S. aureus* 25923 was thawed and diluted 100 fold in 50% LB-vegitone media (LB50). The final concentration of this suspension was $1\times10^6$ CFU/mL. 200 μl of this was added to LB50 agar plates, and a lawn of bacteria dispersed over the agar using five to ten 5 mm sterile glass beads. The beads were removed and the plates allowed to dry. One or two 5 l spots of *Alcaligenes faecalis, Bacillus altitudinis, Bacillus pumilus*, or *Bacillus subtilis* from frozen sample or 20-24 hr cultures were added to each plate and allowed to dry. A mock control plate was left untouched. All plates were incubated for 24 hours at 27° C.

Results are semi quantitative as zones can be measured. The widths of the zones were first measured using ImageJ in pixels (straight line) and converted into mm based the pixel measurements of petri dishes.

Results, Interpretations, and Conclusions

A successful outcome was a clear to mildly cloudy zone of inhibition on the experimental or control plate compared with a lawn on the mock control. The degree of inhibition was measured by the width of the zone of inhibition and the clarity of the zone.

*Alcaligenes faecalis*

Figure 2A:
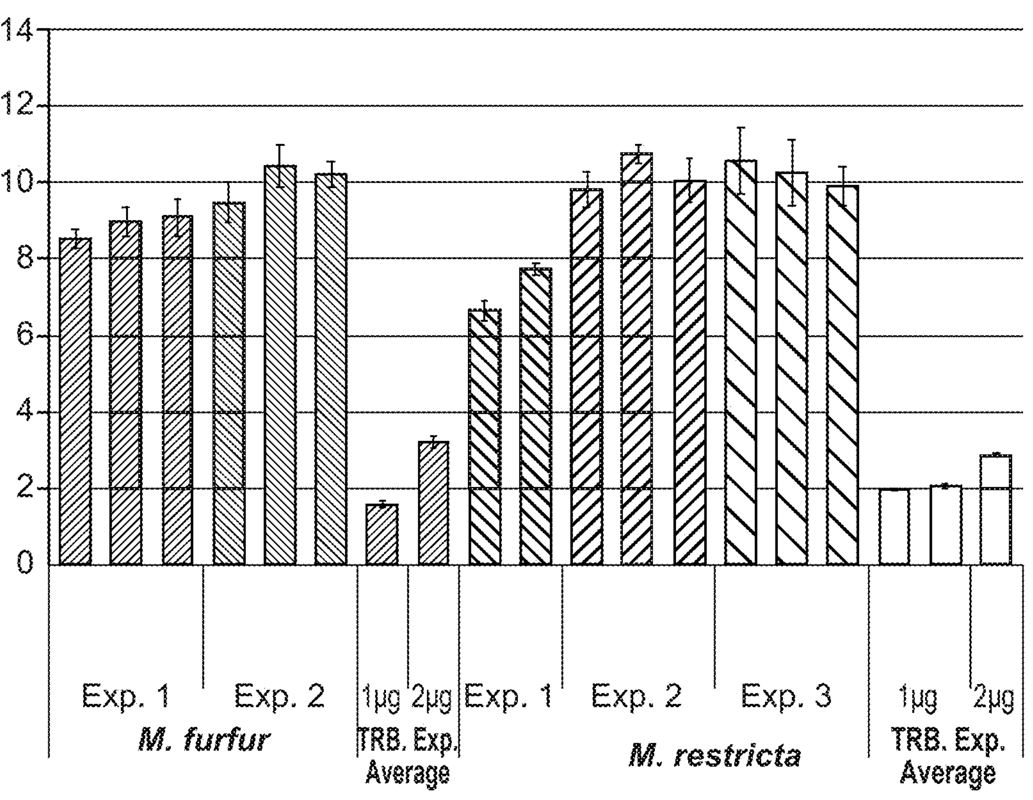
FIGS. 2A-2D show human-isolated *Alcaligenes faecalis* inhibited growth of *Malassezia, T. rubrum*, and *S. aureus* on agar plates.
Figure 2B:
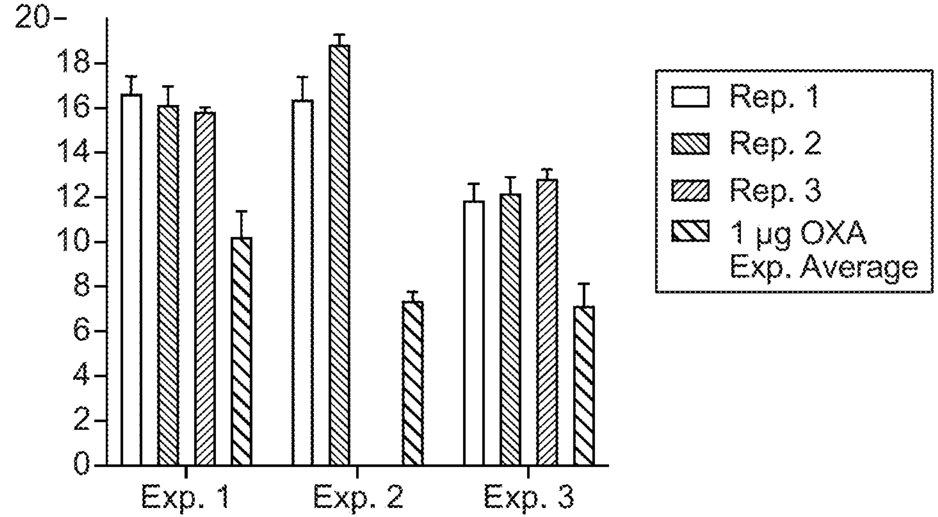
Figure 2C:
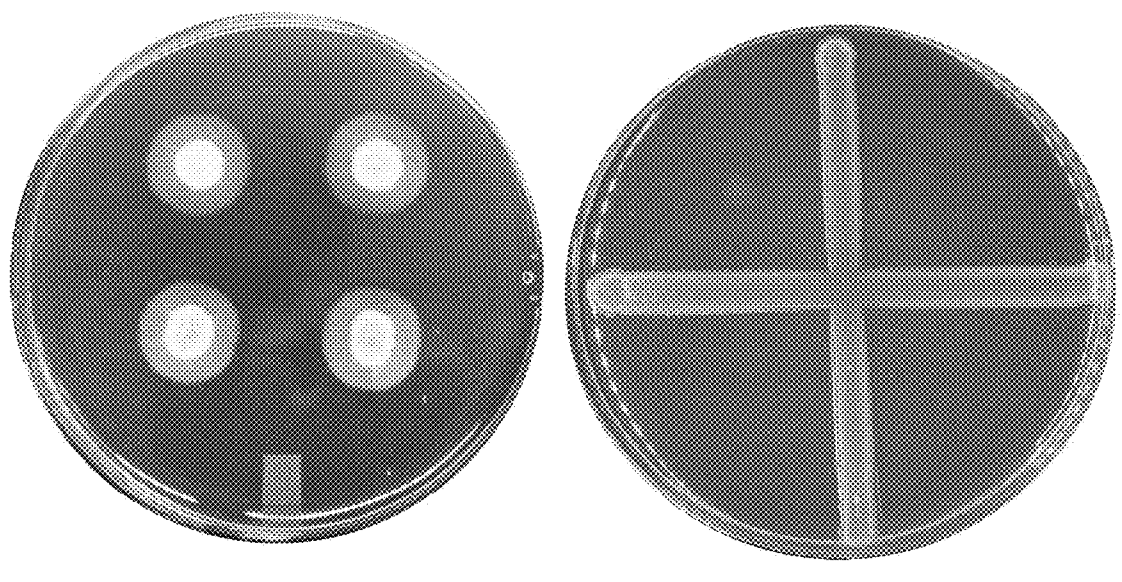
Figure 2D:
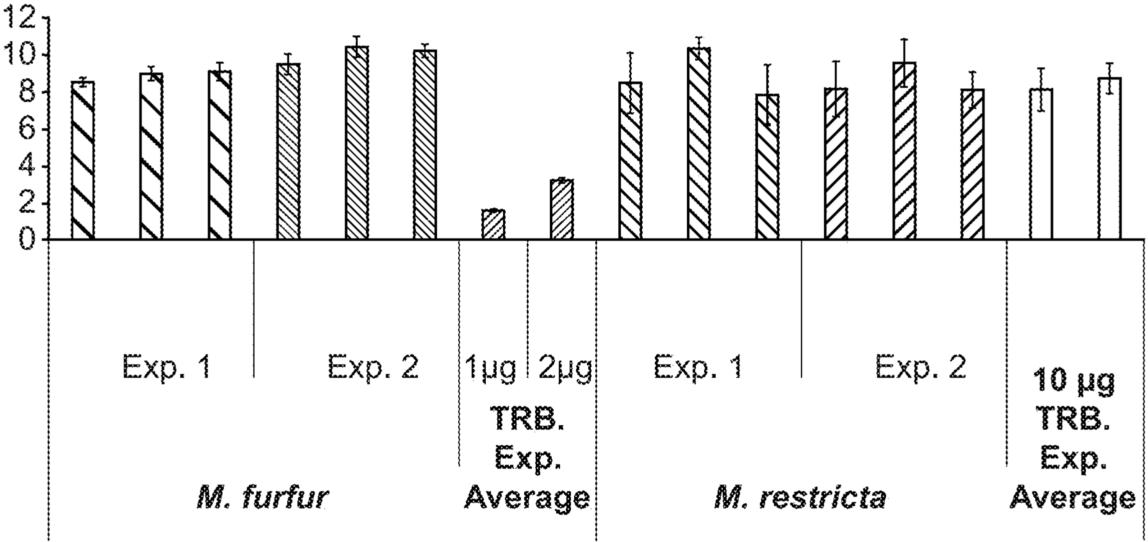

Assay results for *A. faecalis* are presented in FIGS. 2A-2D. *Alcaligenes faecalis* strain DB05646 showed high antimicrobial activity by inhibiting *Malassezia* species, *S. aureus*, and *T. rubrum*. In all experiments DB05646 inhibited the growth of these pathogens significantly better than an antifungal (FIGS. 2A and 2D) or antibiotic (FIG. 2B) and had a larger zone of inhibition. In a modified inhibition assay using a cross pattern of bacteria to create four quadrants, DB05646 stopped the growth of *T. rubrum* (FIG. 2C).

*Bacillus altitudinis*

Figure 3A:
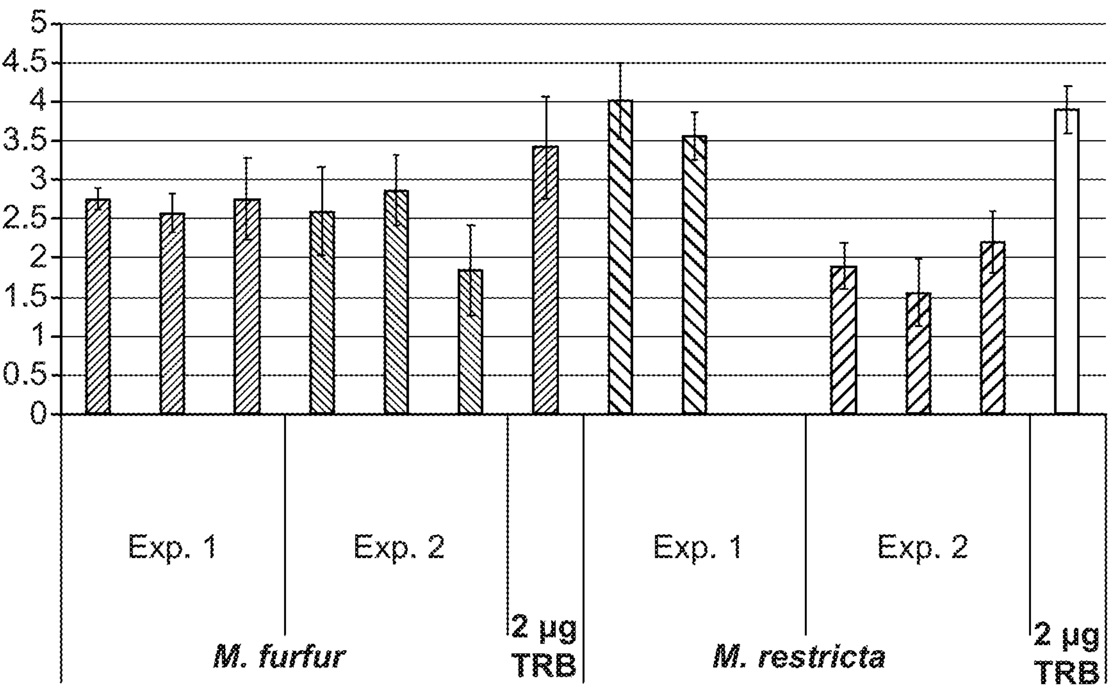
FIGS. 3A-3D show human-isolated *Bacillus* altitudinis inhibited growth of *Malassezia, T. rubrum*, and *S. aureus* on agar plates.
Figure 3B:
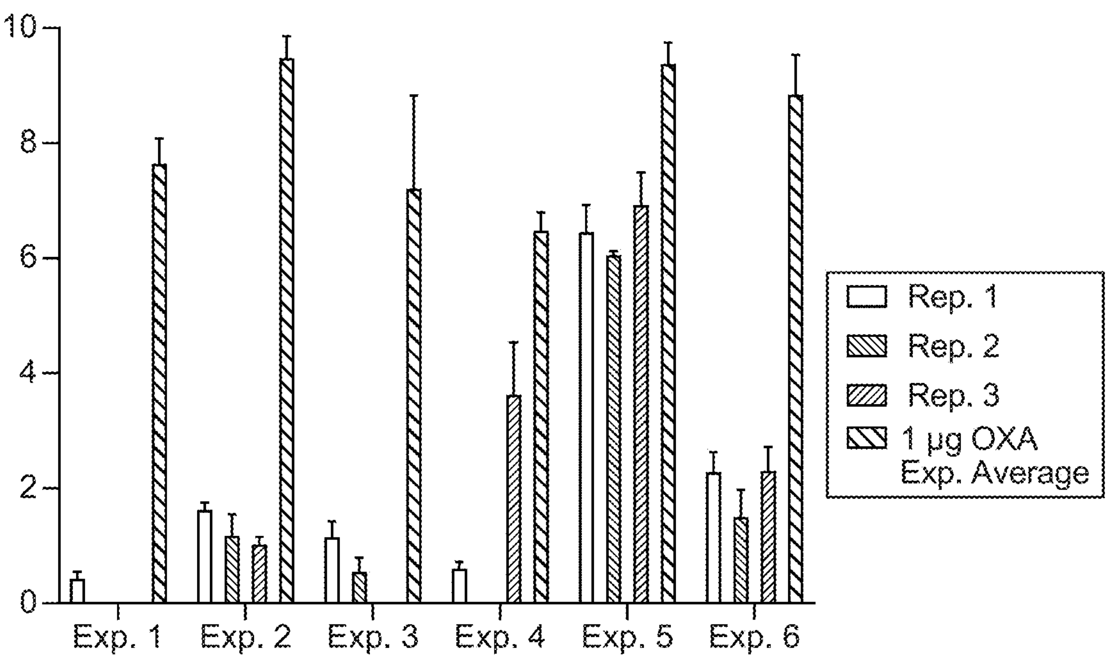
Figure 3C:
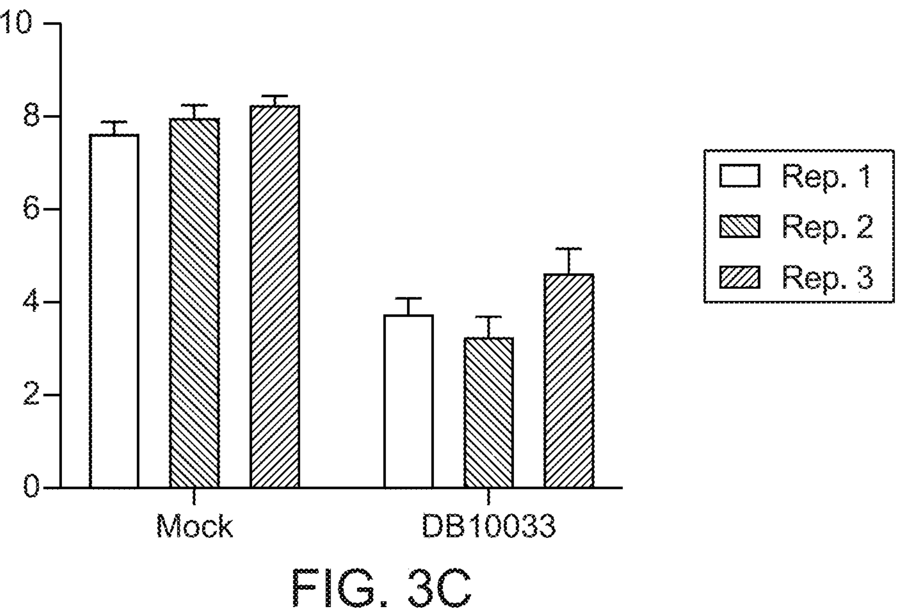
Figure 3D:
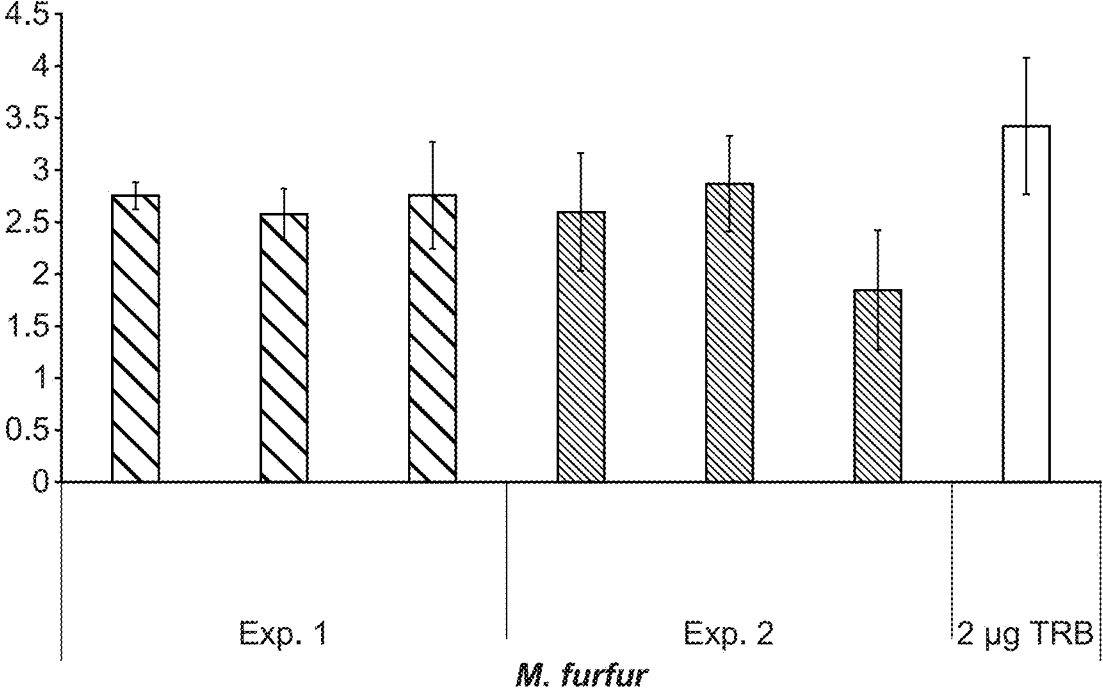

Assay results for *B. altitudinis* are presented in FIGS. 3A-3D. *Bacillus* altitudinis DB10033 showed inhibition of two *Malassezia* species, *S. aureus*, and *T. rubrum*. However it was not as effective as an antibiotic (FIGS. 3A and 3B) or antifungal (FIGS. 3A and 3D) and zones of inhibition of inhibition of *S. aureus* were variable (FIG. 3B). DB10033 decreased the size of *T. rubrum* colonies in a modified inhibition assay using a cross pattern of bacteria to create four quadrants, by approximately half (FIG. 3C).

*Bacillus pumilus*

Figure 4A:
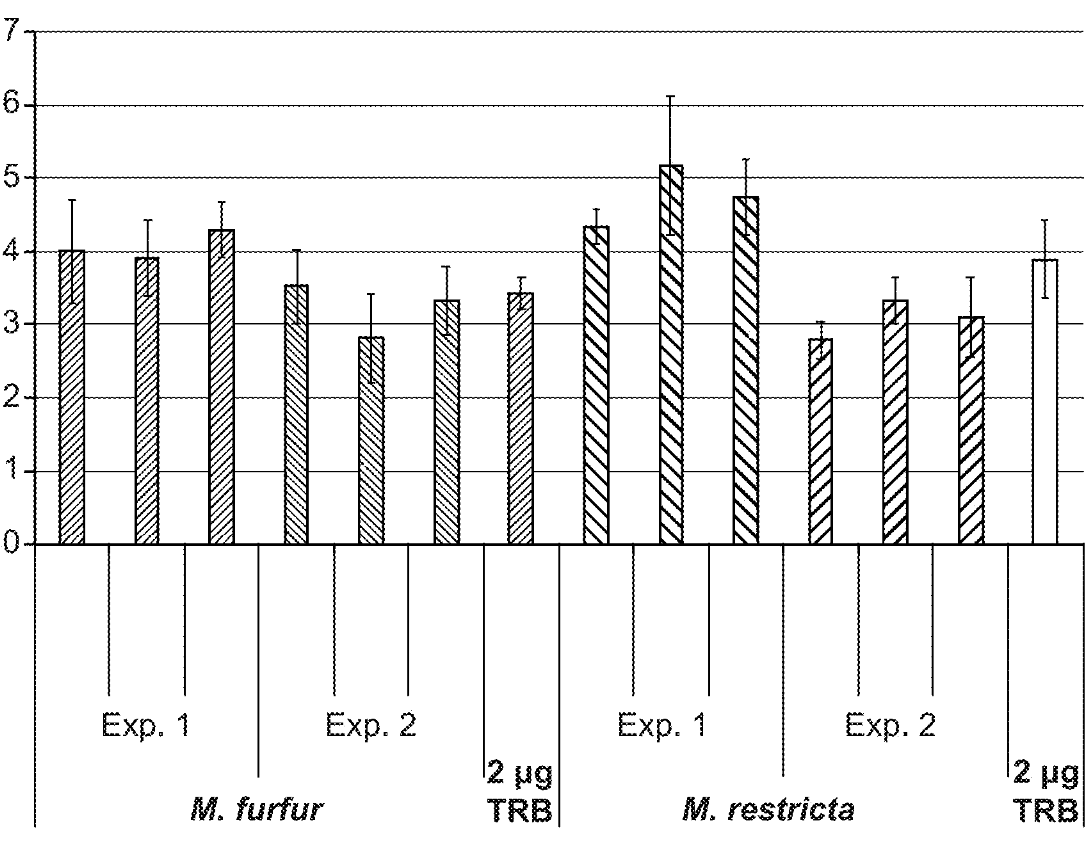
FIGS. 4A-4D show human-isolated *Bacillus pumilus* inhibited growth of *Malassezia, T. rubrum*, and *S. aureus* on agar plates.
Figure 4B:
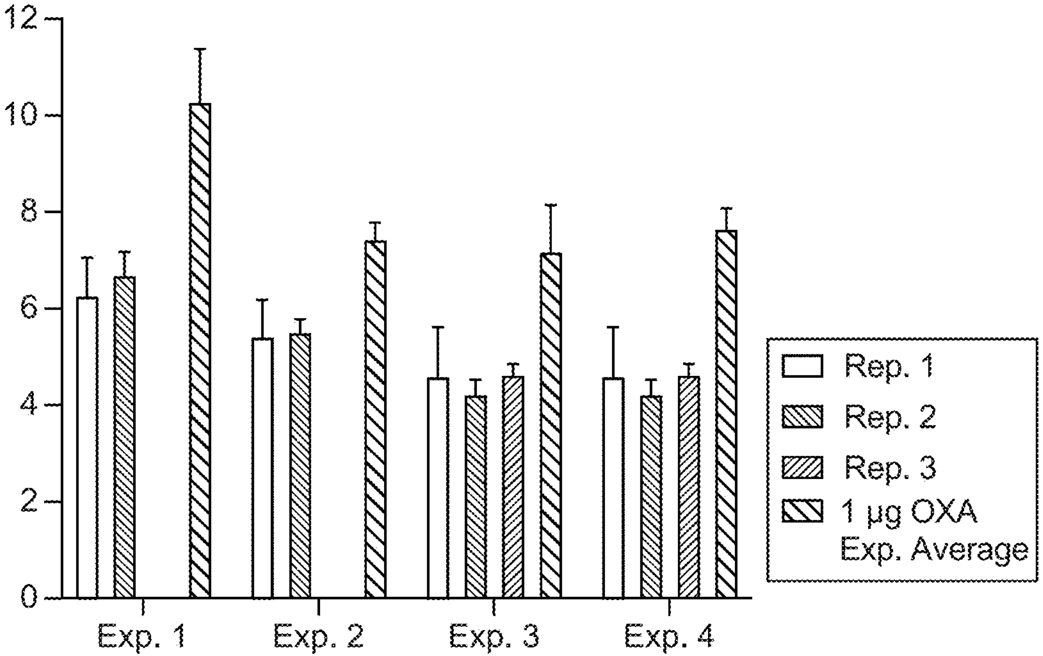
Figure 4C:
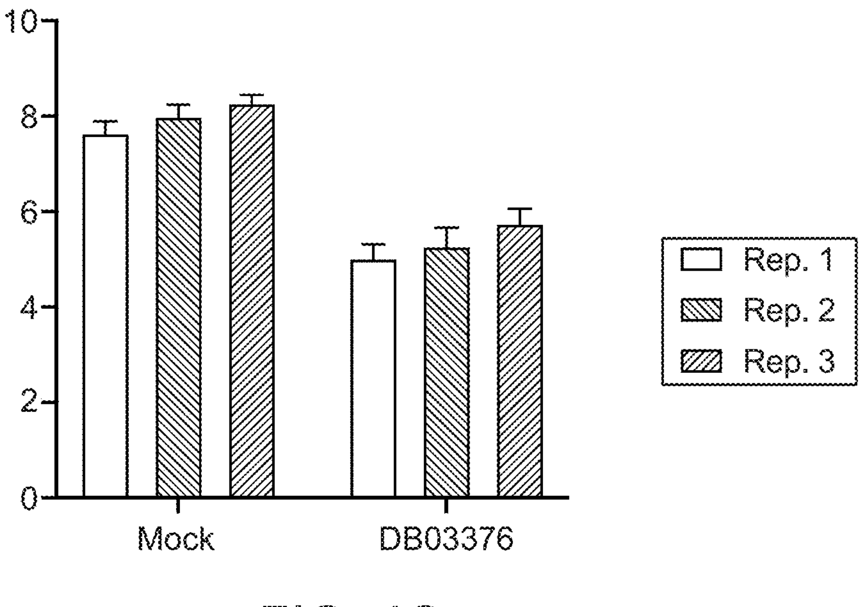
Figure 4D:
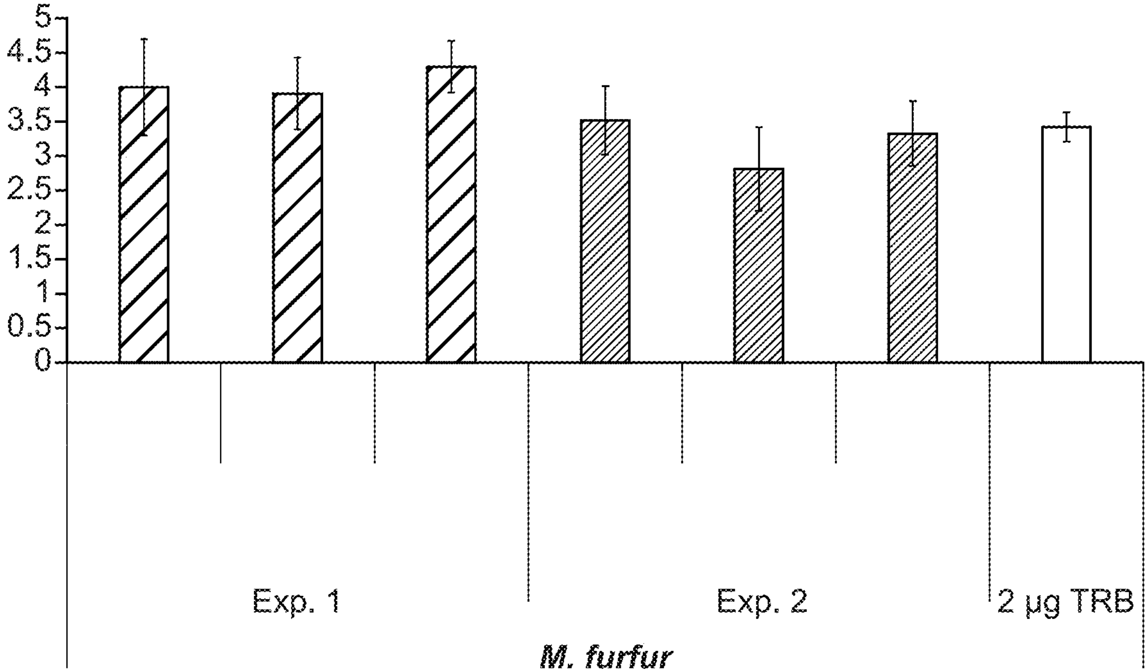

Assay results for *B. pumilus* are presented in FIGS. 4A-4D. *Bacillus pumilus* DB03376 showed inhibition of two *Malassezia* species, *S. aureus*, and *T. rubrum*. It was comparable or better at inhibiting *Malassezia* and *S. aureus* as compared to an antibiotic (FIG. 4B) or an antifungal (FIGS. 4A and 4B). DB03376 decreased the size of *T. rubrum* colonies in a modified inhibition assay using a cross pattern of bacteria to create four quadrants, by approximately three quarters (FIG. 4C).

*Bacillus subtilis*

Figure 5A:
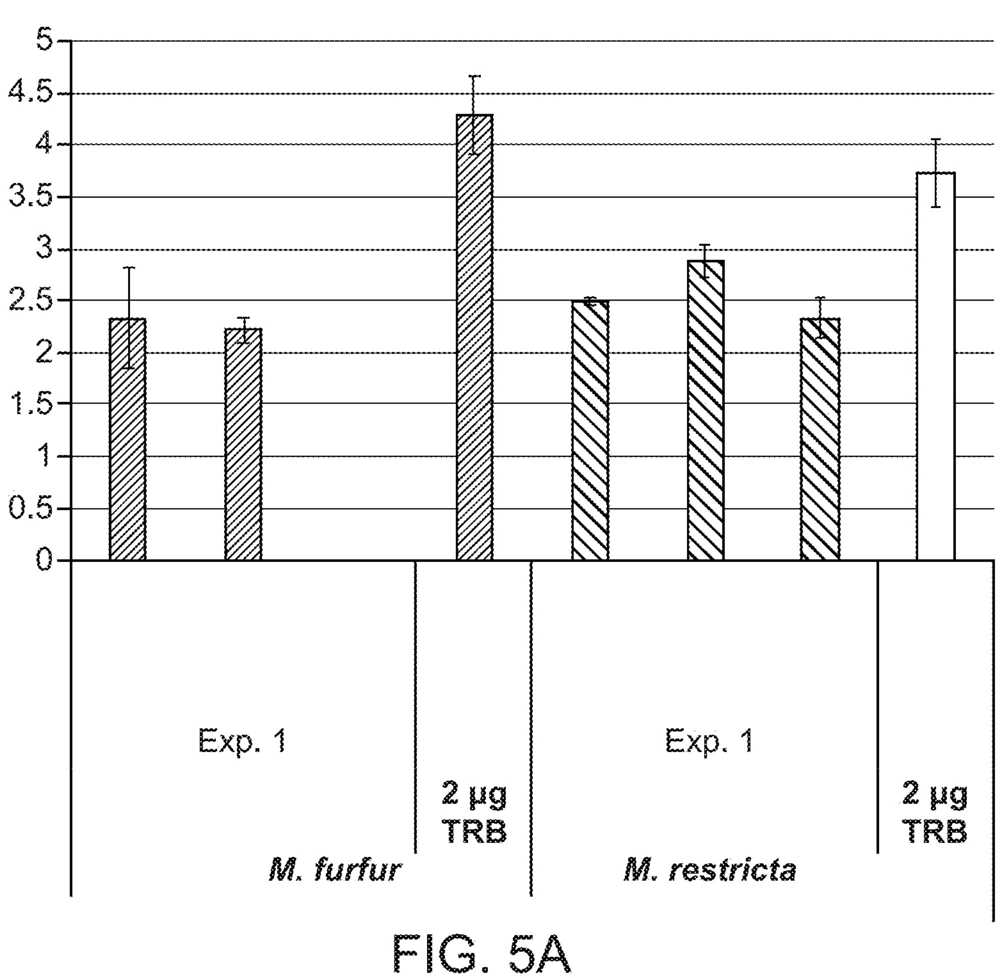
FIGS. 5A-5D show human-isolated *Bacillus subtilis* inhibited growth of *Malassezia, T. rubrum*, and *S. aureus* on agar plates.
Figure 5B:
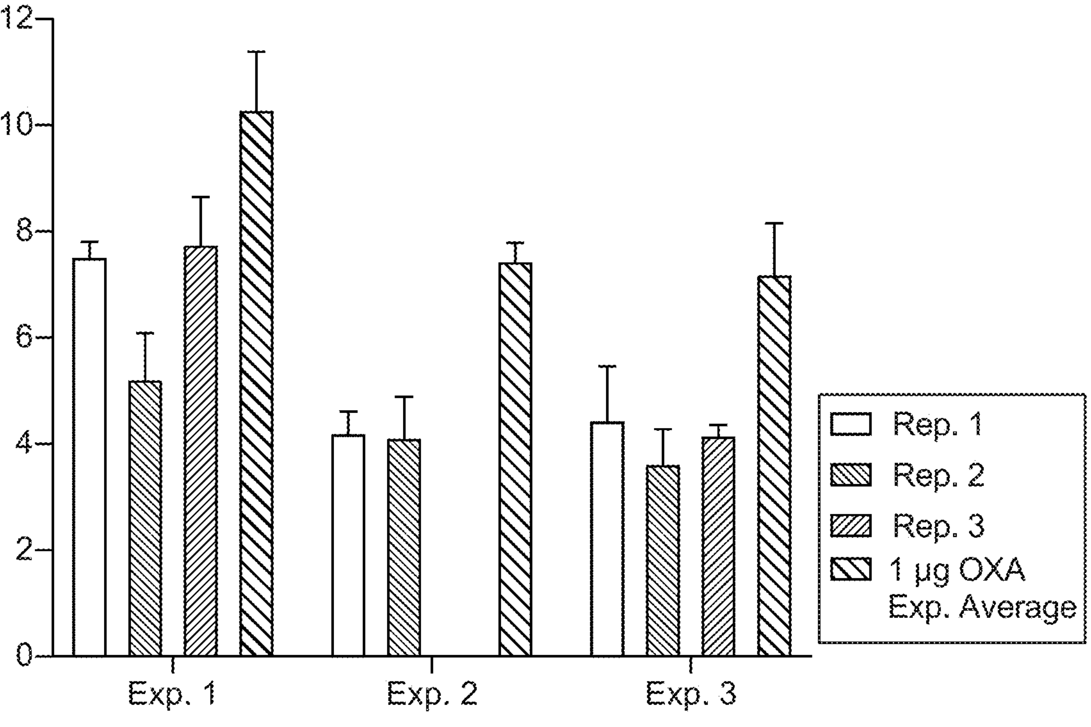
Figure 5C:
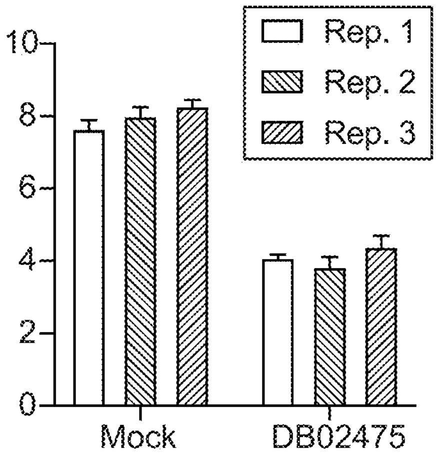
Figure 5D:
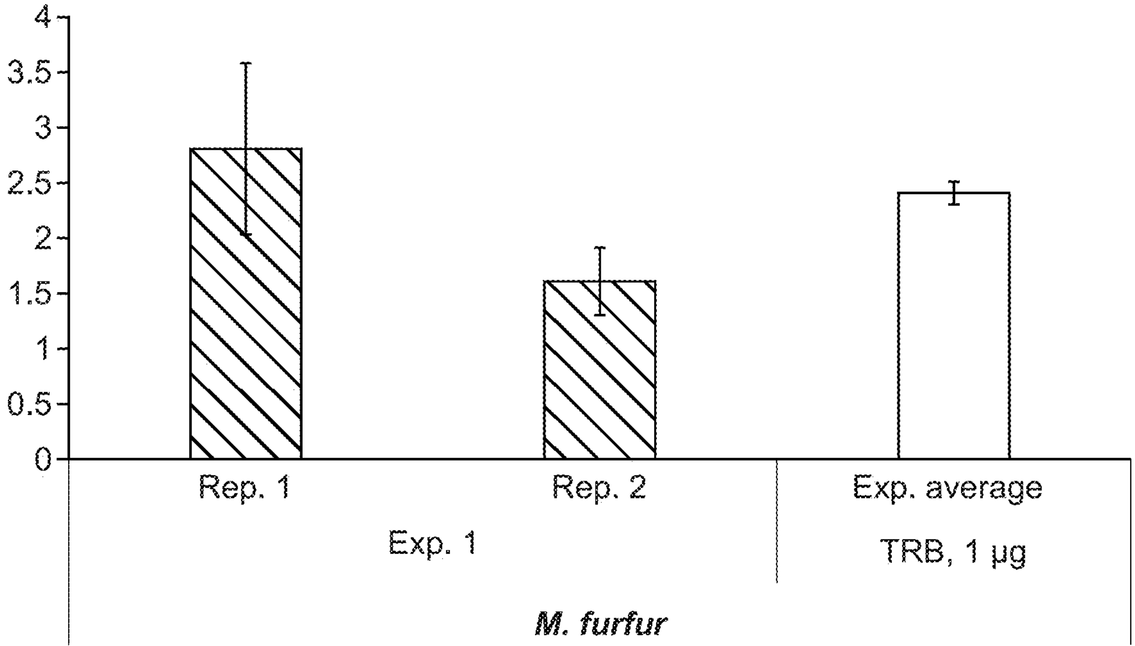

Assay results for *B. subtilis* are presented in FIGS. 5A-5D. *Bacillus subtilis* DB02475 showed inhibition of two *Malassezia* species, *S. aureus*, and *T. rubrum*. However, it was not as effective as an antibiotic (FIG. 5B) or an antifungal (FIGS. 5A and 5D) and zones of inhibition of inhibition of *S. aureus* were variable (FIG. 5B). DB02475 decreased the size of *T. rubrum* colonies in a modified inhibition assay using a cross pattern of bacteria to create four quadrants, by approximately half (FIG. 5C).

Example 4: Antibiotic and Antimicrobial Resistance, Plasmids, and Virulence Factors Summary To evaluate biosafety of *Alcaligenes faecalis* DB05646, *Bacillus* altitudinis DB10033, *Bacillus pumilus* DB03376, or *Bacillus subtilis* DB02475, these strains were tested for virulence factors and examined for their antibiotic resistance profiles by performing both in silico analyses and wet lab experimental confirmation. In silico genome mining revealed no known virulence factors and no antibiotic resistance genes in genomes of *Alcaligenes faecalis* DB05646, *Bacillus* altitudinis DB10033, *Bacillus pumilus* DB03376, or *Bacillus subtilis* DB02475. Antibiotic resistance tests, showed that the tested *Alcaligenes faecalis, Bacillus altitudinis, Bacillus pumilus*, or *Bacillus subtilis* strains are sensitive to over 24 antibiotics to various extents. *Alcaligenes faecalis* DB05646, *Bacillus* altitudinis DB10033, *Bacillus pumilus* DB03376, or *Bacillus subtilis* DB02475 strains are sensitive to cephalosporin, quinolone, and tetracycline classes of antibiotics, less sensitive to aminoglycosides, macrolides, aztreonam, carbapenem, meropenem, chloramphenicol, clindamycin, and amoxicillin/clavulanate (4:1), and are resistant to bacitracin.

Materials & Methods

Whole Genome Shotgun Sequencing and Bioinformatic Analyses

Shotgun sequencing libraries for each *Alcaligenes faecalis, Bacillus altitudinis, Bacillus pumilus*, or *Bacillus subtilis* strain were generated using the Nextera Flex kit (Illumina). The shotgun libraries were pooled and sequenced in a HiSeq X platform. The sequencing reads were automatically demultiplexed into individual FASTA files, and run standard bioinformatic analysis yielding a genome assembled from cleaned sequencing reads.

In Silico Tests for Virulence Factors, Plasmids, and Antibiotic Resistance

*Alcaligenes faecalis* DB05646, *Bacillus subtilis* DB02475, *Bacillus pumilus* DB03376, and *Bacillus* altitudinis DB10033 were analyzed using Abricate (Seemann T, Abricate, Github hypertext transfer protocol secure //github.com/tseemann/abricate). The databases used were CARD, Resfinder, VFDB, and plasmidfinder. The top-level analysis showed the strains have no virulence factors and plasmids. CARD=Comprehensive antibiotic resistance database; Resfinder=anti-microbial resistance database; VFDB=Virulence factor database; Plasmidfinder=database of collection of plasmid replicons.

Internal Antibiotic Resistance Tests

One *Alcaligenes faecalis* DB05646, *Bacillus altitudinis* DB10033, *Bacillus pumilus* DB03376, or *Bacillus subtilis* DB02475 colony was grown for 3 days on 50% BHI agar and then mixed well in 1 mL of 1×PBS buffer, diluted 10× and 100×, respectively. 200 μl of diluted *Alcaligenes faecalis, Bacillus altitudinis, Bacillus pumilus*, or *Bacillus subtilis* cells were evenly plated onto R2A/BHI agar plates in triplicate in 150 mm petri dishes. Antibiotic discs (BD BBL Sensi-Disc antimicrobial susceptibility test discs) were dispensed using a Disc dispenser (BD BBL Sensi-Disc Designer Dispenser System, 12-Place). Plates were incubated for 2-3 days at room temperature and imaged at the end of incubation.

A bacterial colony of each strain of 3-day old grown in vegitone LB broth was mixed well in 1 mL of 1×PBS buffer, diluted 10× and 100×, respectively. 200 μl of diluted bacterial cells were evenly plated onto vegitone agar plates in triplicate in 150 mm petri dishes. Antibiotic discs (BD BBL Sensi-Disc antimicrobial susceptibility test discs) were dispensed using a Disc dispenser (BD BBL Sensi-Disc Designer Dispenser System, 12-Place). Plates were incubated for 2-3 days at room temperature and imaged at the end of incubation.

The sensitivity of each strain to antibiotics is reflected by a clear zone of inhibition of cells surrounding the antibiotic discs. The zone of inhibition was measured using ImageJ and was transformed into cm for analysis.

Antibiotic MIC Tests

The antibiotic resistance profile and MICs tests were performed using *Alcaligenes faecalis* DB05646, *Bacillus* altitudinis DB10033, *Bacillus pumilus* DB03376, or *Bacillus subtilis* DB02475 grown from cultures purified and grown in LB broth-vegitone.

Results, Interpretations, & Conclusions

All four human-isolated *Alcaligenes faecalis* DB05646, *Bacillus* altitudinis DB10033, *Bacillus pumilus* DB03376, or *Bacillus subtilis* DB02475 strains were sequenced with a coverage of at least 100× of the genome size. Genome sequences were assembled into contigs and run through standard analysis procedures built on public databases including: the Comprehensive Antibiotic Resistance Database (CARD, hypertext transfer protocol secure//card.mcmaster.ca/), ResFinder 3.2 (identified acquired antimicrobial resistance genes and/or chromosomal mutations), Argannot (available at hypertext transfer protocol secure on the worldwide web atncbi.nlm.nih.gov/pubmed/24145532), PlasmidFinder 2.1, and Virulence Factorsof Pathogenic Bacteria (VFDB, hypertext transfer protocol //www.mgc.ac.cn/VFs/main.htm). In silico searches yielded no known genes coding for virulence factors.

None of the strains tested had plasmids or virulence factors in their genomes as analyzed using Abricate (Table 3). DB05646 has no antibiotic or antimicrobial resistance genes, however, DB10033 and DB03376 have 2 putative antibiotic resistance genes and 1 antimicrobial resistance gene. DB02475 has 6 putative antibiotic resistance genes and no antimicrobial resistance genes. (Tables 3 and 4)

TABLE 3

Results of in silico analysis of strains using CARD, Resfinder, VFDB, and Plasmidfinder.

| Strain ID | CARD/Resfinder | VFDB | Plasmidfinder |
|---|---|---|---|
| DB05646 | 0/0 | 0 | 0 |
| DB02475 | 6/0 | 0 | 0 |
| DB03376 | 2/1 | 0 | 0 |
| DB10033 | 2/1 | 0 | 0 |

TABLE 4

Specific antibiotic resistance and antimicrobial resistance genes identified in *Bacillus* strains.

| Strain ID | CARD | Resfinder |
|---|---|---|
| DB10033 | 1. Cat86_1(Phenicol) | 1. Cat86_1(Phenicol) |
| | 2. BPU_1(Phenam) | |
| DB03376 | 1. Cat86_1(Phenicol) | 3. Cat86_1(Phenicol) |
| | 2. BPU_1(Phenam) | |
| DB02475 | 1. Mprf(peptide) | — |
| | 2. MexQ | |
| | 3. Thin_B_beta-lactamase(carbapenam, penam) | |
| | 4. Ykkd(phenicol, aminoglycoside, tetracycline) | |
| | 5. Ykkc(Phenicol, aminoglycoside, tetracycline) | |
| | 6. Rm3_beta-lactamase (carbapenam, penam) | |

TABLE 5

Wet lab testing of antibiotic resistance as compared to a standard CLSI comparison strain.

| | *E. coli* ATCC 25922 CLSI QC Range | DB05646 | | DB02473 | | DB00376 | | DB10033 | |
|---|---|---|---|---|---|---|---|---|---|
| | (μg/mL) | 24 hr | 48 hr | 24 hr | 48 hr | 24 hr | 48 hr | 24 hr | 48 hr |
| **Antibiotic** | | | | | | | | | |
| Amikacin | 0.5-4 | 4 | 4 | 0.25 | 0.25 | 0.5 | 1 | 0.5 | 2 |
| Amoxicillin/ Clavulanate (4:1) | NBP | 32 | 32 | ≤0.06 | ≤0.06 | ≤0.06 | ≤0.06 | ≤0.06 | ≤0.06 |
| Azithromycin[1] | NBP | 2 | 2 | 0.5 | 1 | 0.25 | 1 | 0.2 | 0.2 |
| Aztreonam | 0.06-0.25 | 32 | 32 | >64 | >64 | 16 | >64 | >64 | >64 |
| Cefepime | 0.016-0.12 | 4 | 8 | 2 | 4 | 1 | 64 | 64 | 64 |
| Ceftriaxone | 0.03-0.12 | 0.25 | 0.25 | 4 | 16 | 2 | 4 | 16* | 16 |
| Ciprofloxacin | 0.004-0.016 | 2 | 2 | ≤0.06 | 0.125 | 0.0625 | 0.5 | 0.125* | 1 |
| Erythromycin | NBP | 16 | 64 | 0.125 | 0.125 | 0.125 | 0.5 | ≤0.06 | ≤0.06 |
| Polymyxin B | 0.25-2 | 1 | 1 | 4 | 8 | 8 | 16 | 8 | 16 |
| Clindamycin | NBP | >64 | >64 | 0.5 | 2 | 1 | 4 | 0.125 | 2* |
| Levofloxacin | 0.008-0.06 | 1 | 1 | ≤0.06 | 0.125 | ≤0.06 | 0.125 | ≤0.06 | 0.125 |
| Meropenem | 0.008-0.06 | ≤0.06 | ≤0.06 | ≤0.06 | ≤0.06 | ≤0.06 | ≤0.06 | ≤0.06 | 0.125 |
| Minocycline | 0.25-1 | 2 | 4 | 0.125 | 0.5 | 0.0625 | 0.25 | 2 | 2 |
| Chloramphenicol | 8-Feb. | 8 | 16 | 4 | 16 | 2 | 8 | 2 | 4 |
| Neomycin | NBP | 8 | 16 | ≤0.06 | 0.25 | 0.125 | 0.25 | 0.125 | 0.125 |
| Tetracycline | 0.5-2 | 4 | 16 | 0.125 | 0.25 | 0.0625 | 0.25 | 0.125 | 0.25 |
| **Topical Antibiotics** | | | | | | | | | |
| Chlorhexidine | NBP | 32 | 32 | 1 | 1 | 0.5 | 1 | 1 | 2 |
| Povidone-iodine | NBP | >1024 | >1024 | >1024 | >1024 | >1024 | >1024 | >1024 | >1024 |
| Mupirocin | NBP | 64 | 128 | ≤1 | ≤1 | 2 | 16 | 8 | 64 |

*MICs (μg/mL) tests were performed by Institute for Life Science Entrepreneurship NBP—no breakpoint information available.

Based on MIC (minimal inhibitory concentration) performed by a CRO (contract research organization), DB05646 is sensitive to the following parenteral antibiotics:

Beta-lactams: Cefepime, Ceftriaxone, Meropenem, BUT NOT Aztreonam or Amoxicillin/Clavulanate (4:1)

Aminoglycosides: Amikacin, Neomycin

Tetracycline: Tetracycline, Minocycline

Quinolones: Ciprofloxacin, Levofloxacin

Macrolide: Azithromycin, Erythromycin

Other: Chloramphenicol, Polymyxin B

Based on MIC, DB05646 was demonstrated to be sensitive to all the topical antibiotics at concentrations in which they exist in which they are commonly found. Mupirocin is used at 2% (20,000 μg/mL) in topical Bactroban cream or ointment. Topical chlorhexidine is used at 4% (40,000 μg/mL) in Hibiclens solution, Betasept surgical scrub (4%), and povidone-iodine in swabs at 7.5-10% (75,000-100,000 μg/mL) in Betadine swab sticks or surgical scrub solution. Except for povidone-iodine, the MICs are well below the topical treatment concentrations.

Example 5: Inhibition Assays with Combinations of Probiotics

Summary

*Janthinobacterium lividum* DB02473, *Alcaligenes faecalis* DB05646, *Bacillus* altitudinis DB10033, *Bacillus pumilus* DB03376, or *Bacillus subtilis* DB02475 were grown in shake flasks and either streaked or dotted onto a lawn of *M. restricta* or *M. furfur*. The ability of these bacteria to inhibit *M. restricta* or *M. furfur* alone or in combination was observed. Some of the strains tested had an increased ability to inhibit *M. restricta* or *M. furfur* when grown in combination with another bacterium.

Materials & Methods

Strains

*M. restricta* MYA4611, *M. furfur* 12078, M. globose MYA4794 were purchased from ATCC and maintained according to instructions. *Trichophyton rubrum* strain 18754 was purchased from ATCC and maintained according to instructions.

*Staphylococcus aureus* strain 25923 was purchased from ATCC and maintained according to instructions. *Janthinobacterium lividum* DB02473, *Alcaligenes faecalis* DB05646, *Bacillus* altitudinis DB10033, *Bacillus pumilus* DB03376, or *Bacillus subtilis* DB02475 strains were stored at −80° C. with either DMSO or glycerol as cryoprotectant.

In vitro assays were set up. This assay is a variation of standard inhibition assays for testing the ability of a bacterium, fungus, or small molecule to stop or limit the growth of a pathogen. The potential inhibitor was added to a lawn of pathogen and the zone of inhibition of pathogen growth surrounding the inhibitor was measured.

Briefly, *Malassezia* was grown for 5-14 days on YPD-Mal agar plates then the fungal material from the plates was scraped into a cryotube containing 5 mm glass beads in 1 mL sterilized water. The tube was then vortexed to homogenize the material. The OD 600 was measured and diluted to 0.3.200 μl volumes of the homogenized inoculum were then spread using the beads onto Media 22 agar plates and allowed to dry to create a new cultured plate.

*Janthinobacterium lividum* DB02473, *Alcaligenes faecalis* DB05646, *Bacillus* altitudinis DB10033, *Bacillus pumilus* DB03376, or *Bacillus subtilis* DB02475 were grown in shake flasks. An aliquot of frozen culture was inoculated into 50 mL BHI broth in a baffled 250-mL flask on and incubated overnight at 25° C., 200 rpm for about 20-22 hours.

Each bacterial strain was diluted to a predetermined CFU/mL in a 1 mL volume (~10^6, in a range of ~10^4-10^8). A swab was dipped into the dilution from *Janthinobacterium lividum, Alcaligenes faecalis, Bacillus altitudinis, Bacillus pumilus*, or *Bacillus subtilis* was streaked in a straight line from the center of the plate to the perimeter. Then a swab dipped in the dilution of one of the other strains chosen from *Janthinobacterium lividum, Alcaligenes faecalis, Bacillus altitudinis, Bacillus pumilus, Bacillus subtilis*, or sterile media was streaked in a straight line from the center of the plate to the perimeter to create a straight line across the plate comprising half of one strain and half of another strain. If two bacteria were used, the center of the plate was an interface where both bacterial strains were mixed on the lawn of pathogen.

In some instances, one 5 μl spot of probiotic inoculum (*Alcaligenes faecalis, Bacillus altitudinis, Bacillus pumilus, Bacillus subtilis*) was added to the center of a plate with a lawn of *Malassezia* prepared as described above. Directly next to the spot, an additional 5 μl spot of probiotic inoculum or sterile media was added.

The streaks or dots of *Janthinobacterium lividum* DB02473, *Alcaligenes faecalis* DB05646, *Bacillus* altitudinis DB10033, *Bacillus pumilus* DB03376, or *Bacillus subtilis* DB02475 from frozen sample or optimized culture (optimized growth time and optimized CFU/mL) were added to each plate and allowed to dry. Plates were incubated at 27° C. for 4 days. The width of the zone of inhibition was observed.

Results, Interpretations, and Conclusions

When Grown Together on a Lawn of *M. furfur, Bacillus Subtilis* DB02475 Grown in combination with *Bacillus pumilus* DB03376 resulted in greater inhibition of *M. furfur* than compared to the inhibition exhibited by each strain individually. This indicates that DB02475 and DB03376 work together to inhibit *M. furfur* by inhibiting to a greater extent than with either probiotic alone (Table 6). As shown in Table 6, strains DB02475 and DB03376 grown together inhibited *M. restricta* growth creating a larger zone of inhibition than each strain alone. Additionally, strains DB10033 and DB03376 in combination led to a larger zone of inhibition against *M. restricta* than each strain was able to individually. Additional clearing of fungal lawn was observed when DB10033 and DB3376 or DB3376 and DB02475 were present together (data not shown). These data support that certain combinations of the strains described herein may be effective at inhibiting *Malassezia* pathogens more than the individual strains alone.

TABLE 6

Test Groups for monoculture and coculture inhibition assays against *M. furfur* and *M. restricta* with *Bacillus altitudinis* DB10033, *Bacillus pumilus* DB03376 and/or *Bacillus subtilis* DB02475.

| Pathogen | Condition | Condition | Condition |
|---|---|---|---|
| *M. furfur* lawn | DB10033 + media | DB10033 + DB03376 | DB03376 + media |
| *M. furfur* lawn | DB02475 + media | DB02475 + DB03376 | DB03376 + media |
| *M. restricta* lawn | DB02475 + media | DB02475 + DB03376 | media + DB03376 |

Example 6: Ex Vivo Pig Skin Study

Summary

Ex vivo pig skin assays were developed to test the pathogen growth inhibition abilities of *Alcaligenes faecalis* (DB05646) and *Janthinobacterium lividum* (DB02473) in a system mimicking the human skin. Both bacteria were tested as probiotics on pig skin explants that had been colonized with *Staphylococcus aureus*. The presence ofAlcaligenes *faecalis, Janthinobacterium lividum*, and *Staphylococcus aureus* were measured by colony forming unit counting recovered from the explants. The *Staphylococcus aureus* inhibiting activity of DB05646 and DB02473 probiotics were observed in comparison to PBS and vehicle controls.

Materials & Methods

DB05646 and DB02473 were grown in fermentors at 5 L scale. Fermentors were inoculated from 14-15 h old shake flask cultures, and growth at 25° C. was monitored by measuring absorbance at 600 nm. Cells were harvested at 16 hours, spun down, and resuspended in liquid vehicles.

To prepare *Staphylococcus aureus* ATCC 43300 culture, a single colony was placed in 5 mL THB broth and placed in the shaking incubator at 37° C. overnight. Approximately 2.5 hours before pig skin explants were ready to infect, 20 μl of ATCC 43300 culture was transferred into 2 mL fresh THB broth and allow for continued growth in a shaker incubator at 37° C. Cell density is checked by optical density (OD) reading aiming for an OD of 0.6, which corresponding to 5×10^8 CFU/mL. An aliquot of the final culture was plated on MSA plates to verify colony count.

Pig skin explants were obtained from a local vendor. Dirt and debris were completely removed by scrubbing with a surgical scrub brush and water. Hair was removed by clipping and then repeated shaving with disposable razors. Explants of 8 mm in diameter were created and soaked in RPMI with 2% Penicillin/Streptomycin and 0.2% Fungizone, vortexed for 30 seconds, sonicated for 2 min, and vortexed again for 30 seconds. RPMI with 2% Penicillin/Streptomycin and 0.2% Fungizone was replaced, and tissues incubated submerged in solution for 30 minutes at 37° C. Explants were rinsed 3 times with ~10 mL of fresh RPMI to remove any other solutions and then incubated submerged in RPMI without antibiotics for 30 minutes. Explants were placed skin side up in a 6-well plate with a transwell and 2 mL RPMI in the bottom.

Explants were inoculated with 20 μl of *S. aureus* ATCC 43300 culture for a final concentration of 10^7 CFU/explant. *S. aureus* was allowed to grow at 37° C. for 2 hours before treatment with probiotic-based drug products. For each drug product, vehicle, and PBS, 5 μl was applied to each explant. Inoculated explants were incubated for 48 hours at 25° C. DB02473 drug product was formulated at a dose of 10^8 CFU/mL and DB05646 drug product was formulated at a dose of 10^10 CFU/mL. For the 10× or 100× diluted DB05646 drug products, the original drug product was diluted accordingly using the vehicle.

To determine the cell abundance, explants were removed from the plate and placed in a 2-mL tube filled with 1 mL of 1×PBS. Bacteria were liberated by vortexing for 30 seconds, sonicating for 2 minutes, and vortexing for another 30 seconds. The samples were plated onto BHI agar for probiotics CFU counting and onto MSA for *S. aureus* CFU counting. MSA plates were incubated at 37° C. and BHI plates were incubated at 25° C. Measurements of CFU/mL of *Staphylococcus aureus* ATCC 43300 were taken at 0, 7, and 24 hours using standard CFU counting methods. Three explant replicates were performed for each probiotic concentration or vehicle control. A 2-way ANOVA and Tukey's HSD posthoc test were used for statical analysis of results.

Results, Interpretations, & Conclusions

A total of four experiments have been performed to evaluate the treatment effect of DB02473 and DB05646 on *S. aureus* abundance per explant. Despite high variability in the data, in two experiments, presence of DB02473 and DB05646 significantly decreased the amount of CFU/mL of *S. aureus* on the pig skin explants compared to PBS and vehicle controls at 7 hours, 24 hours, and 48 hours after treatment. In contrast, the vehicle and PBS controls resulted in no change in CFU/mL of *S. aureus* on the pig skin explants at each time point (i.e., no detectable change or a non-significant increase).

Figure 6:
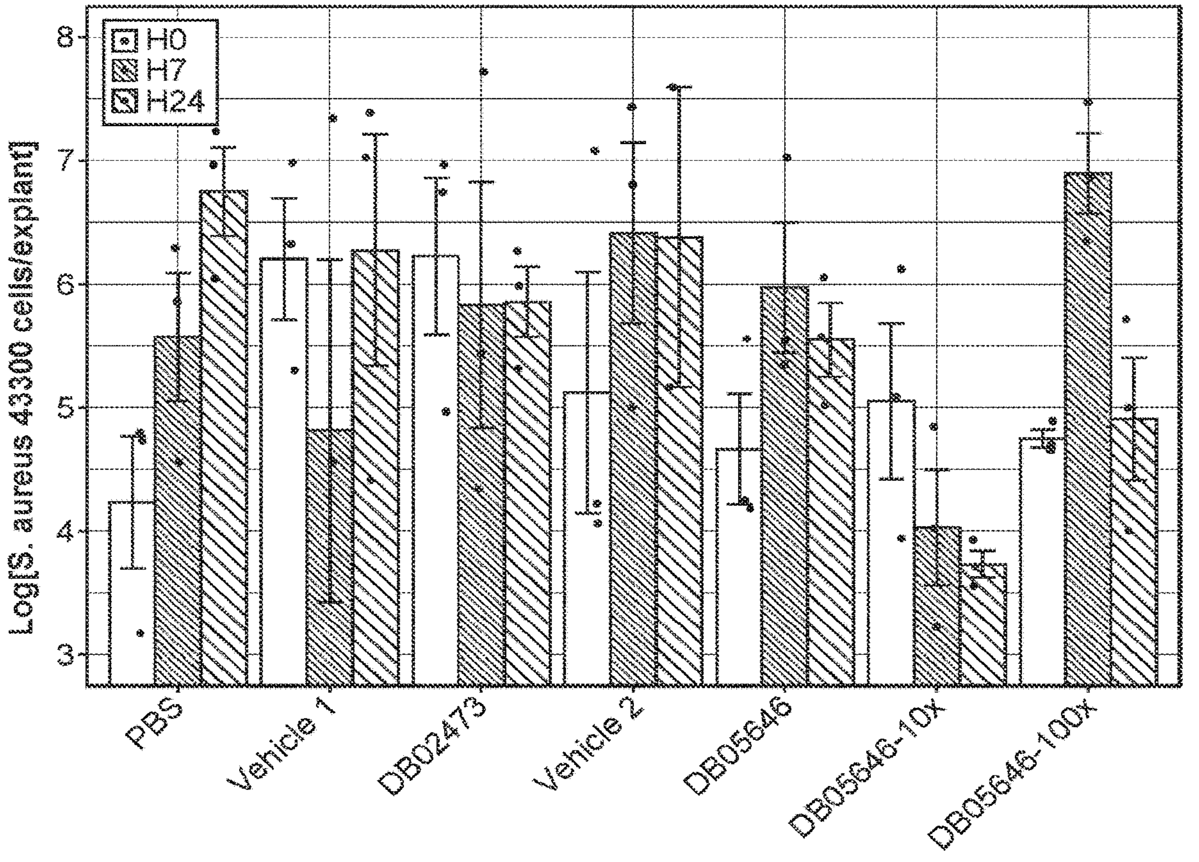
FIG. 6 shows abundance of *S. aureus* ATCC 43300 CFU/Explants by CFU plating on explants inoculated with both *S. aureus* and either *J. lividum* DB02473 or *A. faecalis* DB05646.

DB05646 at a concentration of 10^9 CFU/mL was the most effective at significantly decreasing *S. aureus* on the pig skin explants compared to the 0-hour control, whereas DB05646 and 10^10 and 10^8 CFU/mL did not significantly decrease *S. aureus* CFU count compared to 0-hour control. DB02473 at 10^9 CFU/mL slightly but not significantly decreased the amount of *S. aureus* on the explants compared to 0-hour control (FIG. 6). However, when compared to PBS and vehicle controls at the 24 hour time point, both DB02473 and DB05646 drug products significantly reduced *S. aureus* abundance on the pig skin explants.

These data show that both DB02473 and DB05646 have an inhibitory effect on the growth of *S. aureus* in an ex vivo skin model.

Example 7. Clinical Trial

Summary

*Alcaligenes faecalis*, strain DB05646 was tested for use in treating and preventing skin diseases. DB05646 showed initial trends in improving signs and symptoms of *Tinea versicolor* in a Phase IIa, randomized, double-blinded, vehicle and aqueous gel controlled within-patient comparison, clinical trial. This clinical trial demonstrated that probiotic treatment with *Alcaligenes faecalis* DB05646 isolated from a human source is correlated with reduction in *Malassezia* abundance in some subjects, when *A. faecalis* DB05646 is applied in the proximity of *Malassezia*. Some subjects demonstrated persistence of DB05646 up to one week post-final treatment application.

Materials & Methods

Subjects meeting inclusion/exclusion criteria at screening were enrolled into one of four cohorts of the study. Each subject was randomly assigned to have doses of DB05646 probiotic, vehicle gel, or aqueous gel applied to *Tinea versicolor* affected skin located on their chest and back. Cohort 1 had six subjects who received DB05646 at 10^6 CFU/ml test article on one *Tinea versicolor* affected torso location and aqueous gel on another. Cohort 2 had six subjects who received DB05646 at 10^8 CFU/ml test article on one *Tinea versicolor* affected torso location and aqueous gel on another. Cohort 3 had six subjects who received DB05646 at 10^10 CFU/ml test article on one *Tinea versicolor* affected torso location and aqueous gel on another. Two subjects in each of these three cohorts received a single dose of the test article and 4 subjects received doses on 5 consecutive days (multiple doses). Cohort 4 had four subjects who received the vehicle on one *Tinea versicolor* affected torso location and aqueous gel on another. The subjects received a drug product containing DB05646 probiotic, vehicle, and/or aqueous gel applied at the clinic to different anatomical locations with *Tinea versicolor* affected skin on a subject's chest or back. The vehicle gel vs. aqueous gel cohort had four subjects enrolled to receive a once daily treatment dose for five consecutive days.

Subjects were seen at clinic visits and had drug product applied for up to 5 consecutive days then had a follow-up visit approximately one week after the final drug product administration. Swabs for microbial abundance, both fungal and bacterial, were collected at each visit. Clinical evaluations were performed using a 5-point scale for signs and symptoms of *Tinea versicolor*, and evaluation of local tolerability was performed. as well as an evaluation for local tolerability.

Absolute abundance of *Malassezia* and *A. faecalis* were measured using standard qPCR methods. Relative microbial abundance of the microbiome was assessed using whole genome sequencing.

Results, Interpretations, & Conclusions

This clinical trial demonstrated that *Alcaligenes faecalis* DB05646 is correlated with the reduction in clinical scores of *Tinea versicolor* and *Malassezia* abundance in some subjects, when *Alcaligenes faecalis* DB05646 is applied in the proximity of *Malassezia*.

Figure 7:
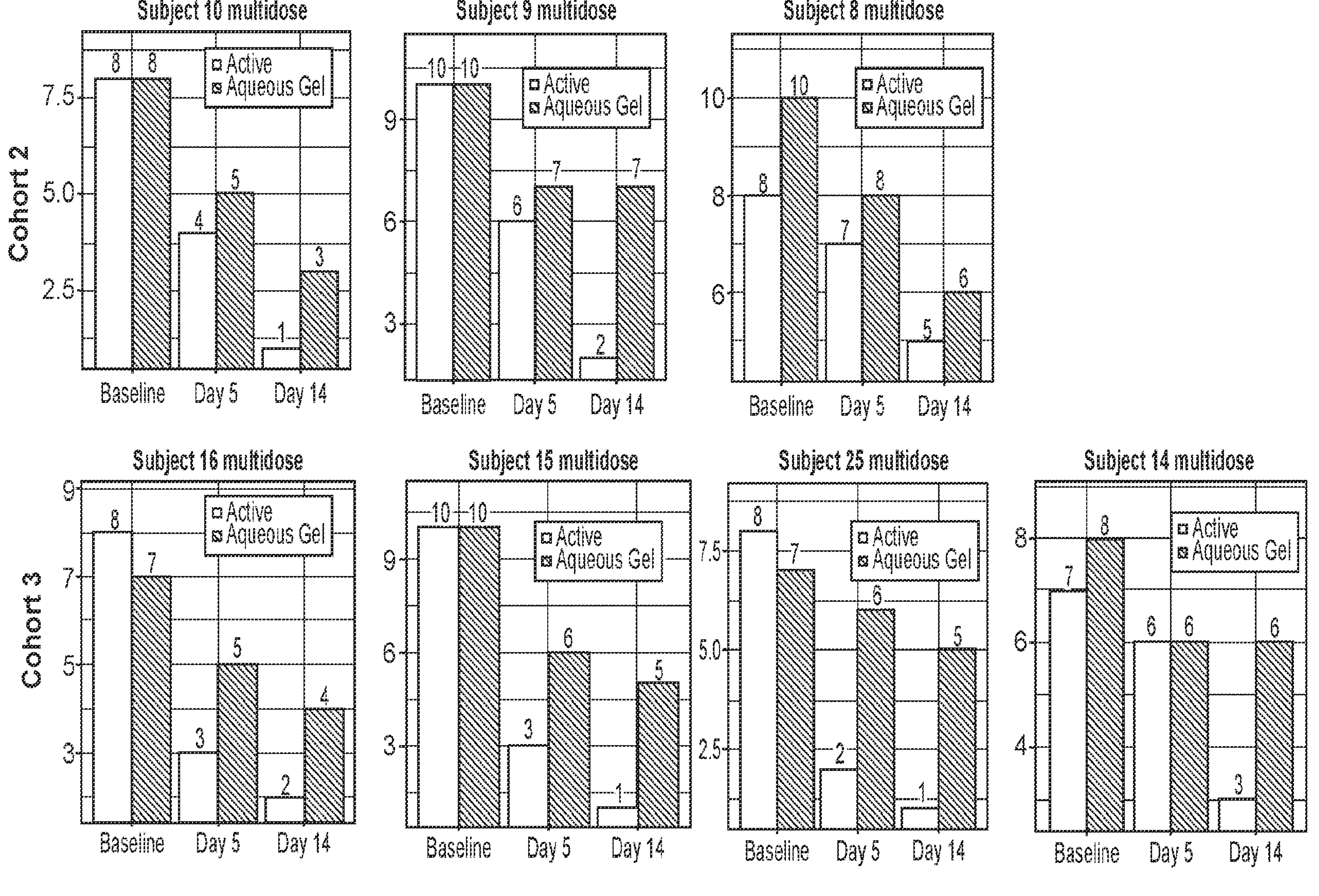
FIG. 7 shows clinical scores of signs and symptoms of *Tinea Versicolor* in subjects treated with active DB05646 *A. faecalis* (white) and control (aqueous gel, diagonal black lines) conditions. A decrease in score (as compared to an earlier timepoint) indicates clinical improvement. Scores are shown for 7 individuals.
Figure 8:
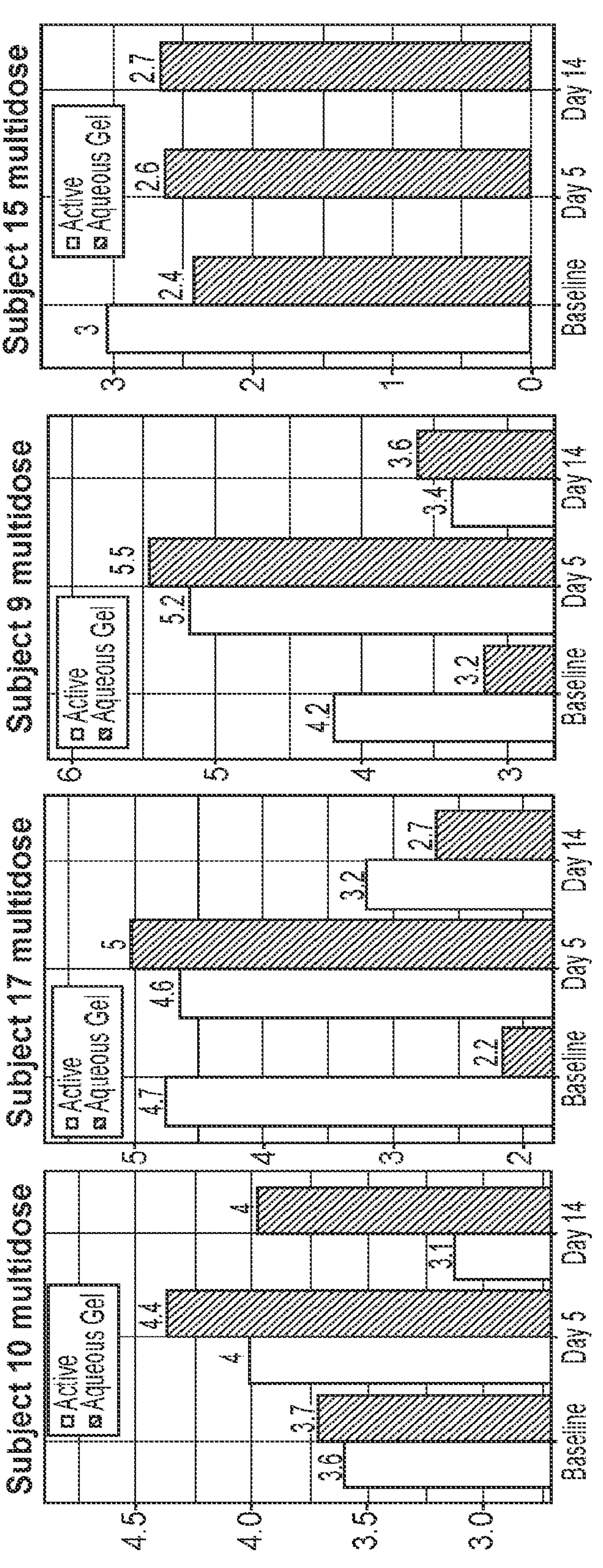
FIG. 8 shows abundance of *Malassezia* by qPCR in subjects treated with active DB05646 *A. faecalis* (white) and control (aqueous gel, diagonal black lines) shown as *Malassezia* levels relative to baseline in active treatment locations compared to control locations FIG. 9 demonstrates persistence of DB05646 presence up to a week (Day 14) after final treatment application to a subject with abundance measured via qPCR. Active (white) and control (aqueous gel, diagonal black lines) treatment groups show DB05646 levels at baseline, Day 5, and Day 14.
Figure 9:
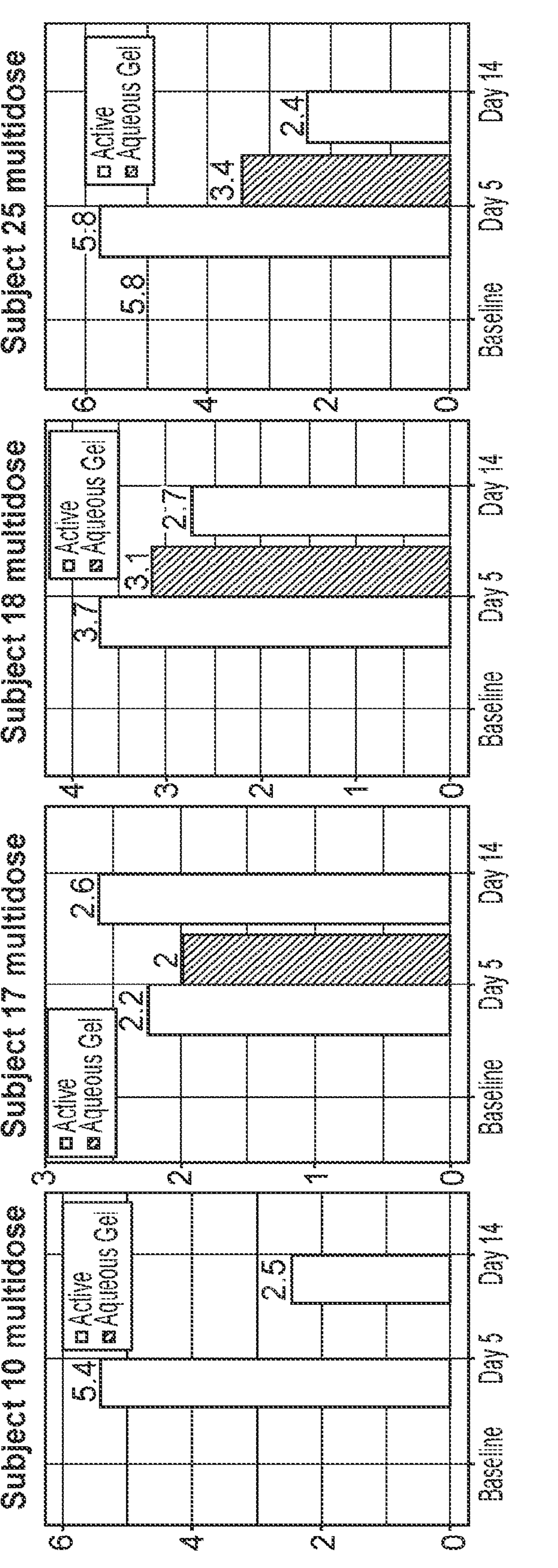

As shown in FIG. 7, certain concentrations of active drug product containing DB05646 resulted in lower scores, indicating improved clinical signs and symptoms, as compared to treatment with a control of aqueous gel. Active drug product was administered to 6 subjects in Cohort 2 (2 single dose subjects and 4 multidose subjects) and 6 subjects in Cohort 3 (2 single dose subjects and 4 multidose subjects) at concentrations of 10^9 or 10^10 CFU/mL respectively. Of 12 subjects, 7 experienced a quantifiable decrease in clinical scores and 5 subjects had a greater decrease in clinical scores at the anatomical locations treated with DB05646 probiotic as compared to the anatomical locations treated with aqueous gel control (FIG. 7). This difference was most notable at Day 14 in all subjects (FIG. 7, all panels). Additionally, a number of subjects experienced a decrease in the absolute abundance of *Malassezia* at the site of treatment as measured by qPCR over the course of the trial (FIG. 8). Some subjects also demonstrated persistence of DB05646 presence up to one week post final treatment application (FIG. 9).

Example 8. Metabolites

Summary

*Alcaligenes faecalis* DB05646 and *Bacillus pumilus* DB03376 extracts were analyzed for metabolites. The metabolic profile of *Alcaligenes faecalis* in the presence and absence of *Malassezia furfur* culture was analyzed by liquid chromatography-mass spectrometry (LC-MS). A full spectrum panel of metabolites produced by *Alcaligenes faecalis* isolate and those metabolites upregulated by *Alcaligenes faecalis* in the presence of *M. furfur* culture was developed and is shown in Tables 7-16.

Materials & Methods

The separated co-incubation of *A. faecalis* DB05646 and *B. pumilus* DB03376 with *Malassezia* used a 0.4 μm filter insert to separate the two cultures from each other in a well of 12-well plate. 2 mL of each probiotic culture in Media 22 at an OD600 of 5 was added to 4 duplicate wells of a 12-well plate. 2 mL of Media 22 was added to 4 duplicate wells of a 12-well plate as negative controls. An insert with a 0.4 μm filter (Greiner Bio One, Cat. No. 700388) was placed in each well. To set up probiotic-*Malassezia* co-incubation, *Malassezia* from a freshly grown agar plate was scraped into a volume of RPMI containing 5-10 5 mm glass beads. This was vortexed and the OD600 of the suspension measured. A fresh suspension was made to and OD600 of 0.05 in Media 22 and 1 mL was added to duplicate inserts. As a control, 1 mL of Media 22 broth was added into each insert. Plates were shaken at 180 rpm at 27° C. for 48 hours at which two 1 mL samples were collected from each well to separate tubes.

The 1.2-mL samples were sonicated using a probe sonicator set at 40% intensity for 3×40s with 20s on ice between sonication bursts. This procedure lysed the *Alcaligenes faecalis*. The sonicated material was centrifuged at 14,000×g for 2 minutes. 700 μl of the supernatant was transferred to a fresh tube. The tubes were capped, flash frozen in liquid nitrogen and stored at −80° C. The remainder of the lysate supernatant was stored in the −80° C. in freezer boxes after being flash frozen.

Semi-polar metabolites detection was performed according to standard methods. Each sample of the spent media was diluted 20 times using 10 mM ammonium formate with 0.1% formic acid prior to LC-MS analysis. The LC-MS analysis was carried out using a UPLC system (Vanquish, Thermo Fisher Scientific) coupled with a high-resolution quadrupole-orbitrap mass spectrometer (Q Exactive HF Hybrid Quadrupole-Orbitrap, Thermo Fisher Scientific). An electrospray ionization interface was used as ionization source. Analysis was performed in negative and positive mode. A QC sample was analyzed in MS/MS mode for identification of compounds. The UPLC was performed using a slightly modified version of the protocol described by Catalin et al., UPLC/MS monitoring of water-soluble vitamin Bs in cell culture media in minutes, Water Application note 2011, 720004042en.

LS-MS data were processed using the Compound Discoverer 3.1 (ThermoFisher Scientific). The compounds were identified with three level of annotation, from level 1 to level 3 (compounds labeled with "Compound ID" in Tables 7-16). A quantitative value was generated for each compound in a given sample based on the area of the chromatogram.

Results, Interpretations, & Conclusions

Compounds that were significantly greater (produced at 5-fold or more) by DB05646 or DB03376 were of particular interest. Five groups of compounds were over-produced by DB05646/DB03376, either in DB05646/DB03376 single culture and/or in co-culture with *M. furfur*.

A total of 89 compounds was found to be significantly produced by DB05646.

Group 1 compounds were significantly produced in DB05646 single culture only (Table 7).

Group 2 compounds were significantly produced in DB05646 single culture, *M. furfur* single culture, and the coculture (Table 8). Of particular interest within group 2 compounds were six compounds that were significantly produced in DB05646*M. furfur* co-culture when compared to *M. furfur* single culture: 2-(1-ethoxyethoxy)propanoic acid; 1-pyrroline-5-carboxylic acid; methylthio 2-(propionyloxy) propionate: 5-guanidino-2-oxopentanoic acid; ethyl acetoacetate; and ribulose-5-phosphate.

Group 3 compounds were significantly produced in DB05646 single culture and co-culture (Table 9). Notably, of the 29 compounds in group 3, 24 compounds were also significantly produced in co-culture when compared to *M. furfur* single culture. This supports that DB05646 contributes significantly to the production of these 22 compounds in the co-culture.

Group 4 compounds were significantly produced in both DB05646 single culture and *M. furfur* single culture, but not in the co-culture (Table 10). Of the six compounds in group 4, two compounds, guanosine and inosine, werre significantly decreased in the co-culture, supporting that these two compounds are critical for interaction in the co-culture.

Group 5 compounds were upregulated in co-culture only (Table 11). Nine of the 14 compounds in group 5 were not significantly higher in co-culture when compared to Media 22, but were significantly higher in co-culture when compared to *M. furfur*, supporting that these compounds are produced by DB05646, but consumed by *M. furfur* in the co-culture.

For the 44 compounds that were significantly decreased five-fold or more in co-culture in the presence of DB05646, two compounds, homocitrulline and malonic acid, were of particular interest. These two compounds were slightly lower in DB05656 single culture when compared to Media 22, but were significantly lower in the co-culture when compared to *M. furfur*. These two compounds may play an important role in *M. furfur* growth inhibition such as via a mechanism of nutritional starvation for *M. furfur.*

Similarly, there were a total of 77 compounds that were significantly produced by DB03376 in various conditions.

Group 1 compounds were significantly produced in DB03376 single culture only (Table 12).

Group 2 compounds were significantly produced in DB03376 single culture, *M. furfur* single culture, and the coculture (Table 13).

Group 3 compounds are significantly produced in DB03376 single culture and co-culture (Table 14). Notably, all eight of the group 3 compounds were also significantly produced in co-culture when compared to *M. furfur* single culture. This supports that DB03376 contributes significantly to the production of these compounds in the co-culture.

There were only two compounds in group 4 that were significantly produced in both DB03376 single culture and *M. furfur* single culture, but not in the co-culture (Table 15). Of the two compounds, hypoxanthine, was significantly decreased in the co-culture, supporting that these two compounds are critical for interaction in the co-culture.

Group 5 compounds were upregulated in co-culture only (Table 16). The majority of the group 5 compounds (50/157), were not significantly higher in co-culture when compared to Media 22, but were significantly higher in coculture when compared to *M. furfur*, suggesting that these compounds were produced by DBC5646 but consumed by *M. furfur* in the co-culture.

Similarly, for compounds that were significantly decreased in the presence of DB03376, four compounds, mudifloramide, N,N'-di[4-(2,6-dimethylmorpholino)phenyl]thiourea, choline phosphate, and (Z)-norendoxifen, were of particular interest. These four compounds were detected at low levels in DB03376 single culture when compared to Media 22, but were significantly lower in the co-culture when compared to *M. furfur*. These compounds may play an important role in *M. furfur* growth inhibition such as via a mechanism of nutritional starvation for *M. furfur*.

TABLE 7

Compounds significantly produced in DB05646 single culture only.

| Compound Name | Group | Fold of change* DB05646 vs Media | Coculture vs Media | *M.furfur* vs Media | Coculture vs DB05646 | Coculture vs *M.furfur* | Compound ID | Annotation Level** |
|---|---|---|---|---|---|---|---|---|
| N1-tetrahydrofuran-2-ylmethyl-2-cyanoacetamide | Group1a | 7.8 | 3.3 | 0.8 | 0.4 | 4.3 | X02253 | 2b |
| Lys-Pro | Group1a | 6.2 | 2.7 | 1.5 | 0.4 | 1.8 | X02664 | 3 |
| 6-Oxo-pipecolinic acid | Group1a | 5.5 | 4.7 | 2.1 | 0.9 | 2.3 | X01346 | 3 |
| (1Z)-N-(4-Amino-butyl)ethanimidic acid | Group1a | 5.6 | 3.3 | 3.7 | 0.6 | 0.9 | X02808 | 3 |
| Valyl-4-hydroxyproline | Group1b | 5.8 | 4.7 | 0.9 | 0.8 | 5.4 | X02417 | 3 |

*The fold of change cutoff is set at 5x.

**Level of confidence on compound annotation with level 1 being the most confident.

*** Light grey indicates a 5x increase or more with a fold of change equal to or greater than 5.

TABLE 8

Compounds significantly produced in DB05646 single culture, *M. furfur* single culture and co-culture.

| Compound Name | Group | Fold of change* DB05646 vs Media | Coculture vs Media | *M.furfur* vs Media | Coculture vs DB05646 | Coculture vs *M.furfur* | Compound ID | Annotation Level** |
|---|---|---|---|---|---|---|---|---|
| 2-(1-Ethoxy-ethoxy)propanoic acid | Group2a | 462.0 | 416.4 | 18.2 | 0.9 | 22.9 | X00281 | 3 |
| 1-pyrroline-5-carboxylic acid | Group2a | 191.4 | 128.9 | 7.6 | 0.7 | 16.9 | X00623 | 3 |
| METHYLTHIO 2-(PROPIONYLOXY) PROPIONATE | Group2a | 175.0 | 141.3 | 10.3 | 0.8 | 13.7 | X02354 | 3 |
| 5-guanidino-2-oxopentanoic acid | Group2a | 3090.7 | 1424.5 | 109.8 | 0.5 | 13.0 | X00188 | 3 |
| Ethyl acetoacetate | Group2a | 164.8 | 125.1 | 10.0 | 0.8 | 12.5 | X00811 | 3 |
| Ribulose-5-phosphate | Group2a | 126.7 | 305.2 | 30.7 | 2.4 | 9.9 | TF00528 | 2a |
| 1-Methyl-1H-pyrrole | Group2b | 511.2 | 426.1 | 88.7 | 0.8 | 4.8 | X00853 | 3 |
| N-Acetylornithine | Group2b | 21.0 | 23.7 | 5.0 | 1.1 | 4.7 | TF00499 | 2a |
| D-1-Piperideine-2-carboxylic acid | Group2b | 2874.9 | 1865.8 | 434.3 | 0.6 | 4.3 | X00049 | 3 |
| (2S)-4-Acetamido-2-aminobutanoic acid | Group2b | 146.2 | 157.1 | 39.6 | 1.1 | 4.0 | X00796 | 3 |
| N6-Acetyl-L-lysine | Group2b | 57.5 | 38.9 | 13.3 | 0.7 | 2.9 | X00745 | 2b |
| N-Acetylmethionine | Group2b | 78.1 | 68.4 | 24.1 | 0.9 | 2.8 | X00512 | 1 |
| 6-Oxo-pipecolinic acid | Group2b | 100.5 | 80.3 | 29.3 | 0.8 | 2.7 | X00741 | 3 |
| 2-Methylthiazolidine | Group2b | 89.0 | 75.1 | 28.6 | 0.8 | 2.6 | X02009 | 3 |
| Histamine | Group2b | 227.9 | 193.9 | 87.4 | 0.9 | 2.2 | X00969 | 3 |
| Acetylarginine | Group2b | 17.5 | 13.6 | 6.2 | 0.8 | 2.2 | X00587 | 1 |
| Diethyl malonate | Group2b | 1040.6 | 903.6 | 439.0 | 0.9 | 2.1 | X01118 | 3 |
| 6-Oxo-pipecolinic acid | Group2b | 158.2 | 126.2 | 70.1 | 0.8 | 1.8 | X00983 | 3 |
| (Dimethylamino)aceto-nitrile | Group2b | 72.8 | 63.6 | 44.6 | 0.9 | 1.4 | X01719 | 3 |
| N-Acetylglutamic acid | Group2b | 17.6 | 12.6 | 9.2 | 0.7 | 1.4 | X02016 | 1 |
| 3-Methylcrotonylglycine | Group2b | 7.8 | 21.0 | 16.1 | 2.7 | 1.3 | X01255 | 2b |
| Putrescine | Group2b | 19.9 | 14.3 | 12.1 | 0.7 | 1.2 | X00320 | 2b |
| vanillin | Group2b | 384.0 | 363.4 | 312.5 | 0.9 | 1.2 | X02269 | 1 |
| N-Acetylcadaverine | Group2b | 266.7 | 245.3 | 215.9 | 0.9 | 1.1 | X00232 | 3 |
| 1-pyrroline | Group2b | 129.6 | 78.9 | 70.1 | 0.6 | 1.1 | X01595 | 3 |
| 8-Azabicy-clo[3.2.1]octan-3-ol | Group2b | 551.2 | 395.0 | 399.0 | 0.7 | 1.0 | X01149 | 3 |

TABLE 8-continued

Compounds significantly produced in DB05646 single culture, *M. furfur* single culture and co-culture.

| Compound Name | Group | Fold of change* DB05646 vs Media | Coculture vs Media | *M.furfur* vs Media | Coculture vs DB05646 | Coculture vs *M.furfur* | Compound ID | Annotation Level** |
|---|---|---|---|---|---|---|---|---|
| 2-[(1S)-1-Hydroxyethyl]-4(1H)-quinazolinone | Group2b | 479.8 | 376.8 | 412.0 | 0.8 | 0.9 | X01857 | 2b |
| 4-Morpholinylacetic acid | Group2b | 196.9 | 188.6 | 247.0 | 1.0 | 0.8 | X02697 | 3 |
| Aminoethylethanolamine | Group2b | 10.2 | 7.2 | 15.4 | 0.7 | 0.5 | X00626 | 2b |
| 4-Morpholinylacetic acid | Group2c | 109.4 | 65.3 | 366.5 | 0.6 | 0.2 | X02265 | 3 |
| Urocanic acid | Group2c | 28.6 | 17.3 | 271.3 | 0.6 | 0.1 | X00095 | 1 |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2.

TABLE 9

Compounds significantly produced in DB05646 single culture and co-culture.

| Compound Name | Group | Fold of change* DB05646 vs Media | Coculture vs Media | *M.furfur* vs Media | Coculture vs DB05646 | Coculture vs *M.furfur* | Compound ID | Annotation Level** |
|---|---|---|---|---|---|---|---|---|
| (2S)-6-Amino-2-[(E)-(hydroxymethylene)amino]hexanimidic acid | Group3a | 8.0 | 5.9 | 1.4 | 0.7 | 4.3 | X02906 | 3 |
| (Z)-Norendoxifen | Group3a | 22.4 | 13.3 | 3.1 | 0.6 | 4.2 | X00903 | 3 |
| Ser-Leu | Group3a | 17.6 | 6.9 | 1.9 | 0.4 | 3.7 | X00847 | 3 |
| 5-Methylcytosine | Group3a | 6.8 | 7.5 | 2.1 | 1.1 | 3.6 | X02794 | 2a |
| Nikethamide | Group3b | 579.2 | 210.5 | 0.9 | 0.4 | 238.5 | X01364 | 2b |
| pentoxyl | Group3b | 444.9 | 204.8 | 1.0 | 0.5 | 200.0 | X01877 | 3 |
| Pilocarpine | Group3b | 214.5 | 106.9 | 0.8 | 0.5 | 139.1 | X01930 | 3 |
| Prolinamide | Group3b | 20.6 | 13.8 | 0.1 | 0.7 | 123.7 | X02680 | 2b |
| Pipecolinic acid | Group3b | 230.6 | 228.5 | 2.3 | 1.0 | 101.2 | TF00254 | 2a |
| Aminoadipic acid | Group3b | 106.4 | 68.0 | 0.7 | 0.6 | 90.8 | X01703 | 1 |
| Gly-Phe | Group3b | 305.2 | 91.8 | 1.2 | 0.3 | 79.2 | X02647 | 3 |
| 2-Ethylnicotinamide | Group3b | 81.3 | 49.4 | 0.9 | 0.6 | 56.4 | X00360 | 3 |
| (2R,3S)-3-Hydroxy-8-methyl-8-azabicyclo[3.2.1]octane-2-carboxylic acid | Group3b | 216.8 | 45.7 | 0.9 | 0.2 | 53.1 | X01904 | 3 |
| 3-hydroxyquinuclidine-3-carbonitrile hydrochloride | Group3b | 21.9 | 11.7 | 0.3 | 0.5 | 45.7 | X02067 | 2b |
| Valeronitrile | Group3b | 57.5 | 62.8 | 1.4 | 1.1 | 44.8 | X00395 | 3 |
| Isopropyl methoxy pyrazine | Group3b | 85.1 | 39.3 | 1.1 | 0.5 | 37.4 | X02606 | 3 |
| 2-sec-Butyl-3-methoxypyrazin | Group3b | 135.2 | 31.4 | 1.3 | 0.2 | 24.2 | X01994 | 2b |
| 4-Piperidone | Group3b | 36.0 | 20.2 | 0.9 | 0.6 | 23.6 | X00193 | 2b |
| (1S,3R,4s)-1,3,4,5-Tetrahydroxycyclohexane-carboxylic acid | Group3b | 61.3 | 52.5 | 3.2 | 0.9 | 16.3 | X02207 | 3 |
| 2,3,5,6-Tetramethylpyrazine | Group3b | 31.4 | 14.0 | 0.9 | 0.4 | 16.2 | X01373 | 2b |
| N-Acetylprocainamide | Group3b | 178.8 | 13.1 | 1.1 | 0.1 | 11.8 | X02952 | 3 |
| Aprobarbital | Group3b | 39.0 | 11.2 | 1.0 | 0.3 | 11.7 | X00689 | 3 |
| Leu-Val | Group3b | 16.2 | 8.6 | 0.9 | 0.5 | 9.8 | X00967 | 3 |
| N-Acetylaspartic acid | Group3b | 13.6 | 12.7 | 1.4 | 0.9 | 8.9 | TF00498 | 2a |
| gamma-Glutamyl-3-(2-methylenecyclopropyl)alanine | Group3b | 198.2 | 18.6 | 2.2 | 0.1 | 8.4 | X02842 | 3 |
| 4-Guanidinobutyric acid | Group3b | 15.8 | 10.6 | 1.3 | 0.7 | 8.3 | TF00345 | 2a |
| Methyl acetoacetate | Group3b | 23.2 | 14.2 | 1.8 | 0.6 | 8.1 | TF00218 | 2a |
| Methyl indole-3-acetate | Group3b | 10.3 | 9.1 | 1.2 | 0.9 | 7.5 | X02893 | 2b |
| 3-amino-2-phenyl-2H-pyrazolo[4,3-c]pyridine-4,6-diol | Group3b | 26.7 | 12.0 | 1.8 | 0.5 | 6.6 | X00904 | 2b |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2.

TABLE 10

| Compounds significantly produced in both DB05646 single culture and *M. furfur* single culture, but not in co-culture. | | | | | | | | |
|---|---|---|---|---|---|---|---|---|
| | | Fold of change* | | | | | | |
| Compound Name | Group | DB05646 vs Media | Coculture vs Media | *M.furfur* vs Media | Coculture vs DB05646 | Coculture vs *M.furfur* | Compound ID | Annotation Level** |
| N8-Acetylspermidine | Group4a | 16.8 | 3.1 | 4.0 | 0.2 | 0.8 | X00384 | 1 |
| Uridine | Group4a | 32.0 | 1.9 | 26.1 | 0.1 | 0.1 | X00213 | 1 |
| Hexose dimer1 | Group4a | 8.2 | 1.1 | 6.3 | 0.1 | 0.2 | X01321 | 1 |
| N(6)-Methyladenosine | Group4a | 19.3 | 0.7 | 16.3 | 0.0 | 0.0 | X02458 | 3 |
| Guanosine | Group4b | 41.6 | 0.1 | 21.1 | 0.0 | 0.0 | X02111 | 2a |
| Inosine | Group4b | 303.5 | 0.1 | 124.0 | 0.0 | 0.0 | TF00187 | 2a |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2

TABLE 11

| Compounds significantly produced in DB05646-M. furfur co-culture only. | | | | | | | | |
|---|---|---|---|---|---|---|---|---|
| | | Fold of change* | | | | | | |
| Compound Name | Group | DB05646 vs Media | Coculture vs Media | *M.furfur* vs Media | Coculture vs DB05646 | Coculture vs *M.furfur* | Compound ID | Annotation Level** |
| 4-Morpholine-propanesulfonic acid | Group5a | 1.4 | 9151.4 | 10458.3 | 6713.0 | 0.9 | X00050 | 2b |
| Suxibuzone | Group5a | 1.1 | 74.2 | 167.0 | 68.4 | 0.4 | X02976 | 3 |
| Uracil | Group5b | 0.7 | 55.3 | 0.7 | 78.1 | 76.7 | X00735 | 1 |
| L-gamma-Glutamyl-L-leucine | Group5c | 3.3 | 15.3 | 3.8 | 4.6 | 4.0 | X01300 | 3 |
| 5-Hydroxy-2-furoic acid | Group5c | 2.3 | 5.1 | 2.0 | 2.2 | 2.6 | X00925 | 3 |
| 15,16-DiHODE | Group5d | 0.1 | 0.1 | 0.0 | 1.2 | 18.8 | X02542 | 3 |
| 3-Hydroxybutyric acid | Group5d | 0.2 | 0.2 | 0.0 | 0.9 | 17.3 | TF00337 | 2a |
| Thymine | Group5d | 0.1 | 0.8 | 0.1 | 11.5 | 14.1 | X00109 | 2a |
| NP-008993 | Group5d | 0.2 | 0.2 | 0.0 | 1.0 | 12.8 | X00473 | 2b |
| N-Acetyltryptophan | Group5d | 0.2 | 0.2 | 0.0 | 1.1 | 12.4 | TF00236 | 2a |
| 4-Deoxy-5-C-(3,5-di-sec-butyl-1-cyclopenten-1-yl)pentonic acid | Group5d | 0.0 | 0.1 | 0.0 | 3.7 | 7.5 | X00740 | 3 |
| Furfural | Group5d | 4.7 | 2.3 | 0.3 | 0.5 | 7.1 | X00763 | 3 |
| 4-[(3-Acetamido-propyl)amino]butanoic acid | Group5d | 0.8 | 2.7 | 0.4 | 3.2 | 6.6 | X01604 | 3 |
| Cytosine | Group5d | 2.7 | 0.9 | 0.2 | 0.3 | 5.5 | X00023 | 1 |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2

TABLE 12

| Compounds significantly produced in DB03376 single culture only. | | | | | | | | |
|---|---|---|---|---|---|---|---|---|
| | | Fold of change* | | | | | | |
| Compound Name | Group | DB03376 vs Media | Coculture vs Media | *M.furfur* vs Media | Coculture vs DB03376 | Coculture vs *M.furfur* | Compound ID | Annotation Level** |
| Aprobarbital | Group1a | 5.6 | 0.4 | 1.0 | 0.1 | 0.4 | X00689 | 3 |
| 5-methyl-tryptophan | Group1a | 13.7 | 0.2 | 0.4 | 0.0 | 0.5 | TF00042 | 2a |
| Acetylserine | Group1b | 5.4 | 4.3 | 0.0 | 0.8 | 161.0 | TF00052 | 2a |
| N-Acetyltryptophan | Group1b | 5.7 | 0.1 | 0.0 | 0.0 | 7.4 | TF00236 | 2a |
| N-Iso-Valerylglycine | Group1b | 6.1 | 4.4 | 0.4 | 0.7 | 10.1 | X00907 | 2a |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2

TABLE 13

Compounds significantly produced in DB03376 single culture, *M. furfur* single culture and co-culture.

| Compound Name | Group | Fold of change* DB03376 vs Media | Coculture vs Media | *M.furfur* vs Media | Coculture vs DB03376 | Coculture vs *M.furfur* | Compound ID | Annotation Level** |
|---|---|---|---|---|---|---|---|---|
| Ribulose-5-phosphate | Group2a | 18.9 | 25.4 | 30.7 | 1.3 | 0.8 | TF00528 | 2a |
| Guanosine | Group2a | 21.9 | 17.1 | 21.1 | 0.8 | 0.8 | X02111 | 2a |
| 3-Methylcrotonylglycine | Group2a | 12.1 | 10.1 | 16.1 | 0.8 | 0.6 | X01255 | 2b |
| 2-Pyrrolidone | Group2b | 7.8 | 5.5 | 38.9 | 0.7 | 0.1 | X00454 | 3 |
| 8-Azabicyclo[3.2.1]octan-3-ol | Group2b | 5.4 | 5.0 | 399.0 | 0.9 | 0.0 | X01149 | 3 |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2

TABLE 14

Compounds significantly produced in DB03376 single culture and co-culture.

| Compound Name | Group | Fold of change* DB03376 vs Media | Coculture vs Media | *M.furfur* vs Media | Coculture vs DB03376 | Coculture vs *M.furfur* | Compound ID | Annotation Level** |
|---|---|---|---|---|---|---|---|---|
| 6-Oxo-pipecolinic acid | Group3a | 42.6 | 52.5 | 2.1 | 1.2 | 25.3 | X01346 | 3 |
| Tetraacetylethylenediamine | Group3a | 5.4 | 6.7 | 1.0 | 1.2 | 6.7 | X01901 | 3 |
| 2-(hydroxymethyl)butanoic acid | Group3a | 9.7 | 8.5 | 0.4 | 0.9 | 21.3 | X02104 | 2a |
| N6-Acetyl-L-lysine | Group3a | 108.2 | 116.0 | 0.3 | 1.1 | 381.3 | X00633 | 2b |
| Prostaglandine E2 | Group3a | 15.3 | 9.5 | 0.2 | 0.6 | 45.7 | TF00259 | 2a |
| Furaneol | Group3b | 5.7 | 5.0 | 0.1 | 0.9 | 66.2 | X02465 | 3 |
| Myriocin | Group3b | 6.5 | 5.8 | 0.1 | 0.9 | 96.8 | X01114 | 2b |
| 3-Hydroxy-5, 8-tetradecadiencarnitine | Group3b | 11.2 | 10.7 | 0.1 | 1.0 | 196.4 | X02183 | 3 |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2

TABLE 15

Compounds significantly produced in both DB03376 single culture and *M. furfur* single culture, but not in co-culture.

| Compound Name | Group | Fold of change* DB03376 vs Media | Coculture vs Media | *M.furfur* vs Media | Coculture vs DB03376 | Coculture vs *M.furfur* | Compound ID | Annotation Level** |
|---|---|---|---|---|---|---|---|---|
| Acetylarginine | Group4 | 5.5 | 4.5 | 6.2 | 0.8 | 0.7 | X00587 | 1 |
| Hypoxanthine | Group4 | 257.6 | 1.4 | 22.8 | 0.0 | 0.1 | X00039 | 1 |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2

TABLE 16

Compounds significantly produced in DB03376-*M. furfur* co-culture only.

| Compound Name | Group | Fold of change* DB03376 vs Media | Coculture vs Media | *M.furfur* vs Media | Coculture vs DB03376 | Coculture vs *M.furfur* | Compound ID | Annotation Level** |
|---|---|---|---|---|---|---|---|---|
| Tropic acid/acetovanillone/3-phenyllactic acid | Group5a | 2.1 | 25.2 | 0.1 | 12.0 | 297.7 | X02575 | 2a |
| Uracil | Group5a | 0.9 | 11.9 | 0.7 | 13.8 | 16.5 | X00735 | 1 |
| 3-Hydroxyoctanoic acid | Group5a | 1.3 | 26.4 | 1.0 | 20.5 | 26.7 | X01388 | 3 |
| Desmeninol | Group5a | 1.0 | 216.8 | 1.0 | 211.9 | 215.6 | X02752 | 3 |
| Kynurenic acid | Group5a | 0.6 | 13.1 | 3.2 | 22.5 | 4.0 | X02806 | 1 |
| 2-Hydroxyfelbamate | Group5a | 2.7 | 8.0 | 2.0 | 3.0 | 3.9 | X02195 | 3 |
| (1S,3R,4s)-1,3,4,5-Tetrahydroxycyclohexane-carboxylic acid | Group5a | 3.5 | 6.8 | 3.2 | 1.9 | 2.1 | X02207 | 3 |
| Levulinic acid | Group5b | 1.1 | 3.5 | 0.0 | 3.1 | 854.5 | X01509 | 3 |
| 4,5-Dideoxy-3-C-methyl-D-erythro-pentonic acid | Group5b | 4.7 | 3.8 | 0.0 | 0.8 | 763.0 | X01317 | 3 |
| 3,13,13,17-Tetramethyl-21-oxa-12-azahexacyclo[10.7.1.1⁻2,17⁻.0⁻5,20⁻.0⁻6,11⁻.0⁻14,19⁻]henicosa-1(20),2,4,6,8,10-hexaene | Group5b | 0.9 | 1.1 | 0.0 | 1.2 | 365.4 | X01479 | 3 |
| 2-Acetamidooctanoic acid | Group5b | 1.1 | 1.0 | 0.0 | 0.9 | 229.4 | X02244 | 3 |
| 4-Methyl-2-oxovaleric acid (ketoleucine) | Group5b | 0.4 | 2.0 | 0.0 | 4.5 | 192.3 | X00493 | 2a |
| L-5-Hydroxytryptophan | Group5b | 1.1 | 1.2 | 0.0 | 1.1 | 178.6 | X00783 | 2b |
| Pyruvic acid | Group5b | 0.3 | 0.3 | 0.0 | 1.0 | 177.8 | X00377 | 2a |
| DL-Glyceric acid | Group5b | 1.6 | 1.6 | 0.0 | 1.0 | 169.4 | X02926 | 3 |
| 5-Methylcytidine | Group5b | 0.6 | 0.7 | 0.0 | 1.0 | 114.5 | X02519 | 3 |
| Edaravone | Group5b | 1.1 | 1.0 | 0.0 | 0.9 | 74.6 | X02766 | 2b |
| 3-Hydroxybutyric acid | Group5b | 0.8 | 0.8 | 0.0 | 1.0 | 67.5 | TF00337 | 2a |
| Thr-Val | Group5b | 0.3 | 0.4 | 0.0 | 1.1 | 66.6 | X00775 | 3 |
| 4-Indolecarbaldehyde | Group5b | 1.0 | 1.5 | 0.0 | 1.4 | 53.7 | X01468 | 2b |
| Methyl 2-[(2-methoxy-2-oxoethyl)amino]acetate | Group5b | 2.3 | 0.9 | 0.0 | 0.4 | 42.4 | X00567 | 2b |
| Benzene | Group5b | 1.0 | 0.9 | 0.0 | 0.9 | 37.2 | X00036 | 3 |
| L-gamma-Glutamyl-L-leucine | Group5b | 0.2 | 0.4 | 0.0 | 2.0 | 33.8 | X02900 | 3 |
| Alanylleucine | Group5b | 3.0 | 2.7 | 0.1 | 0.9 | 33.8 | X02703 | 3 |
| 1-pyrroline | Group5b | 2.1 | 1.4 | 0.0 | 0.6 | 32.8 | X00481 | 3 |
| Thymine | Group5b | 2.0 | 1.7 | 0.1 | 0.9 | 31.1 | X00109 | 2a |
| Indole-3-acetic acid | Group5b | 0.9 | 0.7 | 0.0 | 0.7 | 31.1 | X01343 | 2a |
| Levulinic acid | Group5b | 2.5 | 2.3 | 0.1 | 0.9 | 31.0 | X02357 | 3 |
| Glutaric acid/Ethylmalonic acid | Group5b | 1.0 | 1.0 | 0.0 | 1.0 | 31.0 | X02885 | 1 |
| pterin | Group5b | 2.5 | 2.0 | 0.1 | 0.8 | 27.6 | X02947 | 3 |
| N-Acetyl-L-leucine | Group5b | 3.5 | 2.6 | 0.1 | 0.7 | 25.6 | X00576 | 2b |
| 4-Deoxy-5-C-(3,5-di-sec-butyl-1-cyclopenten-1-yl)pentonic acid | Group5b | 0.3 | 0.3 | 0.0 | 0.9 | 22.1 | X00740 | 3 |
| 4-(METHYLNITROSAMINO)-1-(3-PYRIDYL-N-OXIDE)-1-BUTANOL | Group5b | 1.2 | 0.4 | 0.0 | 0.4 | 21.8 | X02493 | 3 |
| N-Acetyl-L-phenylalanine | Group5b | 3.3 | 2.1 | 0.1 | 0.6 | 19.7 | X01164 | 3 |
| Tyramine | Group5b | 1.1 | 1.0 | 0.1 | 1.0 | 18.0 | X00595 | 2b |
| Acetophenone | Group5b | 1.0 | 1.0 | 0.1 | 1.0 | 17.6 | X00714 | 2b |
| Nicotinic acid | Group5b | 0.1 | 0.2 | 0.0 | 2.4 | 17.1 | X00239 | 1 |
| Indole-3-carboxylate | Group5b | 0.9 | 1.2 | 0.1 | 1.4 | 16.0 | TF00466 | 2a |
| asp-leu | Group5b | 0.2 | 0.3 | 0.0 | 1.7 | 14.1 | X00908 | 3 |
| Histidine | Group5b | 1.1 | 1.0 | 0.1 | 0.9 | 11.6 | X00170 | 1 |
| 3,3'-(1,4-Butanediyldiimino)dipropanoic acid | Group5b | 0.3 | 0.4 | 0.0 | 1.4 | 11.0 | X02375 | 3 |
| 8-Hydroxyquinoline | Group5b | 1.0 | 0.9 | 0.1 | 0.9 | 10.9 | X01414 | 2b |
| Alanylleucine | Group5b | 0.0 | 0.1 | 0.0 | 4.3 | 10.9 | X02205 | 3 |
| 4-hydroxybenzaldehyde | Group5b | 1.2 | 1.2 | 0.1 | 1.0 | 10.4 | X01530 | 2a |
| 2-Amino-4-methylpyrimidine | Group5b | 1.1 | 0.9 | 0.1 | 0.9 | 10.4 | X00531 | 2b |
| Fomepizole | Group5b | 1.1 | 0.9 | 0.1 | 0.9 | 9.7 | X02749 | 3 |
| 3-Isopropylmalic acid | Group5b | 4.2 | 3.2 | 0.4 | 0.8 | 8.9 | X02587 | 2b |
| Methyl 2-[(2-methoxy-2-oxoethyl)amino]acetate | Group5b | 4.3 | 3.5 | 0.4 | 0.8 | 8.3 | X01693 | 2b |

TABLE 16-continued

Compounds significantly produced in DB03376-*M. furfur* co-culture only.

| Compound Name | Group | Fold of change* DB03376 vs Media | Coculture vs Media | *M.furfur* vs Media | Coculture vs DB03376 | Coculture vs *M.furfur* | Compound ID | Annotation Level** |
|---|---|---|---|---|---|---|---|---|
| Homo-L-arginine | Group5b | 0.9 | 2.5 | 0.3 | 2.7 | 8.1 | X02657 | 3 |
| 1-(4-Aminobutyl)urea | Group5b | 1.9 | 2.1 | 0.3 | 1.1 | 6.4 | X02222 | 3 |
| N-(2-hydroxy-phenyl)acetamide | Group5b | 2.3 | 1.4 | 0.2 | 0.6 | 5.9 | X00076 | 2b |
| Acetylhistidine | Group5b | 0.6 | 0.4 | 0.1 | 0.6 | 5.7 | X00433 | 1 |
| 1-Vinylimidazole | Group5b | 1.0 | 1.0 | 0.2 | 1.0 | 5.5 | X02841 | 2b |
| 2-[(8E,11E,14Z)-8,11,14-Heptadecatrien-1-yl]-6-hydroxybenzoic acid | Group5b | 0.9 | 1.2 | 0.2 | 1.3 | 5.0 | X00823 | 3 |
| 4-coumaric-acid | Group5b | 0.3 | 4.1 | 0.4 | 12.4 | 11.6 | X02182 | 2a |
| Prolinamide | Group5b | 0.1 | 1.0 | 0.1 | 10.2 | 8.9 | X02680 | 2b |
| ile-ala | Group5b | 0.0 | 0.0 | 0.0 | 6.7 | 7.2 | X01302 | 3 |

*The fold of change cutoff is set at 5x.

**Level of confidence on compound annotation with level 1 being the most confident.

*** Light grey indicates a 5x increase or more with a fold of change equal to or greater than 5. Dark grey indicates a 5x decrease or more with a fold of change equal to or less than 0.2

Example 9: Genome Comparison Studies of *A. faecalis*

Summary

To identify new bacterial isolates with probiotic potential from the human skin, approximately 700 skin microbiome samples collected from 42 healthy young adults were screened for viable colony forming units. Individual isolates were purified through passage of single colonies. Primary screening of 454 of these individual bacterial isolates was performed, yielding 5 candidate species that show inhibition activity against *Malassezia, Staphylococcus aureus*, and/or *Trichophyton rubrum.*

To perform bioinformatics analysis on an *Alcaligenes faecalis* DB05646, various analyses including strain assembly, taxonomic classification, identity and safety were performed against NCBI reference strains (Table 19). Analysis included assembly of the sequencing data of the strains with taxonomic classification, along with alignment of the whole genomes with publicly and commercially available genomes to assess the phylogeny of the strains. Strain identity was evaluated with average nucleotide identity (ANI; known to those in the art and described further herein for reference) and a secondary metabolite profile with potential pharmaceutical applications was established.

TABLE 17

*Alcaligenes faecalis* DB05646 and strains from the NCBI data base used in analyses.

| DermBiont strains | NCBI reference strains |
|---|---|
| DB05646 (*A. faecalis*) (SEQ ID NO: 1) | GCA_002242175.1 |
| | GCA_004319585.1 |
| | GCA_016807785.1 |
| | GCF_002443155.1 |
| | GCF_010092625.1 |
| | GCA_002443155.1 |
| | GCA_010092625.1 |
| | GCF_000967305.2 |
| | GCF_003716855.1 |
| | GCF_016128035.1 |
| | GCA_000967305.2 |
| | GCA_003716855.1 |
| | GCA_016128035.1 |
| | GCF_001641975.2 |
| | GCF_003813085.1 |
| | GCF_016446305.1 |
| | GCA_001641975.2 |
| | GCA_003813085.1 |
| | GCA_016446305.1 |
| | GCF_002242175.1 |
| | GCF_004319585.1 |
| | GCF_016807785.1 |

Materials & Methods

Whole Genome Shotgun Sequencing and Genome Sequence Assembly

Shotgun sequencing for DB05646 was performed using the Nextera Flex kit manufactured by Illumina according to manufacturer's instructions. The shotgun libraries were pooled and sequenced in a HiSeq X platform. The sequencing reads were automatically demultiplexed into individual FASTA files and standard bioinformatic analyses performed, yielding a genome assembled from cleaned sequencing reads.

Whole Genome Alignment/Phylogeny

Figure 10:
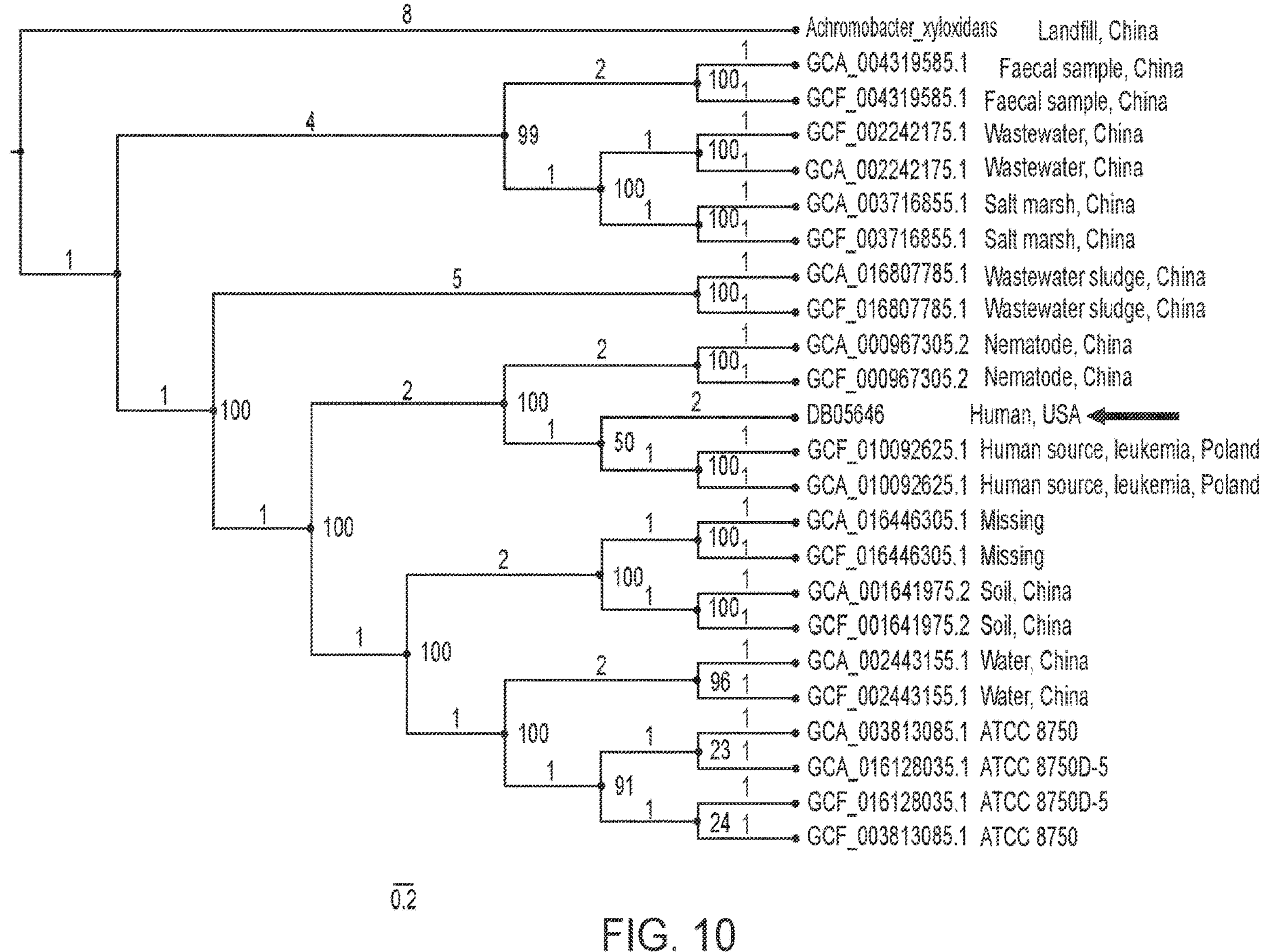
FIG. 10 is an exemplary phylogenetic analysis of DB05646.

Whole genome analysis was performed. Assembled genomes along with reference genomes (i.e., in Table 17) and an outgroup from public databases were used in the whole genome alignment. Homblocks was used to perform whole genome alignment, which used progressive mauve in the background to perform the alignment and extract the Locally collinear blocks (LCBs). LCBs are conserved segments that appear to be free from genome rearrangements. Whole genome alignment was used to establish phylogeny. Once the alignment file was produced a phylogenetic tree was built using RaxML for DB05646 and NCBI reference strains (Table 17), along with *Achromobacter xylosoxidans* as a reference bacterium from a different genus used as an outgroup, to produce a tree showing an evolutionary relationship of the strains (see FIG. 10).

Average Nucleotide Identity

Average nucleotide identity (ANI) is similar to whole genome alignment, but instead uses BLAST to perform a nucleotide genomic similarity between the genomes. ANI is widely used in comparing prokaryotic genomes which gives the strain level identity resolution of the species. Average nucleotide identity python script was used to perform the ANI. All strains in Table 17 were used for the comparison. A cutoff of 95% is used to establish species level identity and 100% is used to establish strain level identity.

Pangenome Analysis

Roary was used for pan genome analysis. It requires annotated gff files (generated by prokka) of the assemblies to isolate the genes that fall into Core genome (100% coverage and 99% identity or more), accessory genome, or variable (below 99% identity but still some match or genes specific to strains). Pan genome analysis was performed on assemblies in Table 17. All the genomes assemblies (DB specific, refseq and genbank) used in the analysis were annotated using prokka (Prokaryotic annotation tool). Resultant gff files were used in the Roary for building pangenomes. Variable genes were assessed specifically to establish genetic differences between DB05646 and reference strains.

Antismash

Antismash is a web browser-based tool for identification and annotation of secondary metabolite biosynthetic gene clusters in the bacterial genomes. It can mine genomic assemblies for secondary metabolic profiles that can have potential pharmaceutical applications. Antismash analysis was performed on whole genome assemblies of *A. faecalis* strains LK36, MB207, NBIB-017, HPC1271 and MUB14 (GCF_010092625.1).

Results, Interpretations, Amd Conclusions

Phylogeny

DB05646 showed a clear separation from the outgroup *Achromobacter xylosoxidans* (a different species). DB05646 is also separated from all 22 reference strains and does not share a clade with another strain from the same species.

Average Nucleotide Identity

Figure 11:
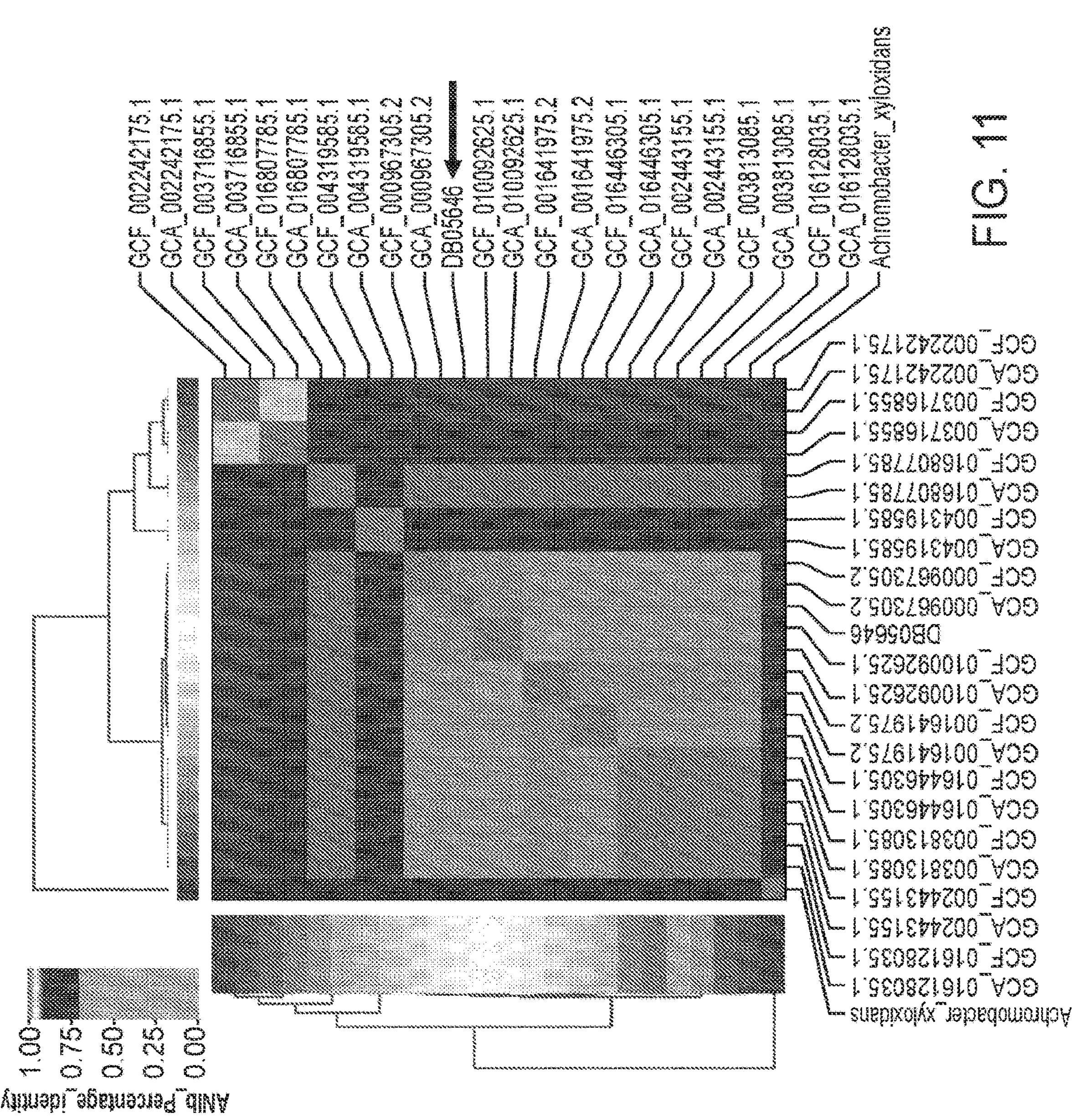
FIG. 11 shows results from an ANI whole genome analysis of DB05646 compared to *A. faecalis* reference strains.

Data represented in the heatmap shown in FIG. 11 show that DB05646 has species level identity of over 95% to some of the reference strains from NCBI including a strain isolated from a human host, and shows clear separation from outgroup *Achromobacter xylosoxidans* by a greater percent difference than other *A. faecalis* reference strains. DB05646 groups with confidence with other species of *Alcaligenes faecalis*, but at a strain level it is genetically different than the reference strains and has well under 100% identity to any of them. DB05646 is an *Alcaligenes faecalis* species, but is a genetically different strain than the reference strains.

Pangenome Analysis

Figure 12A:
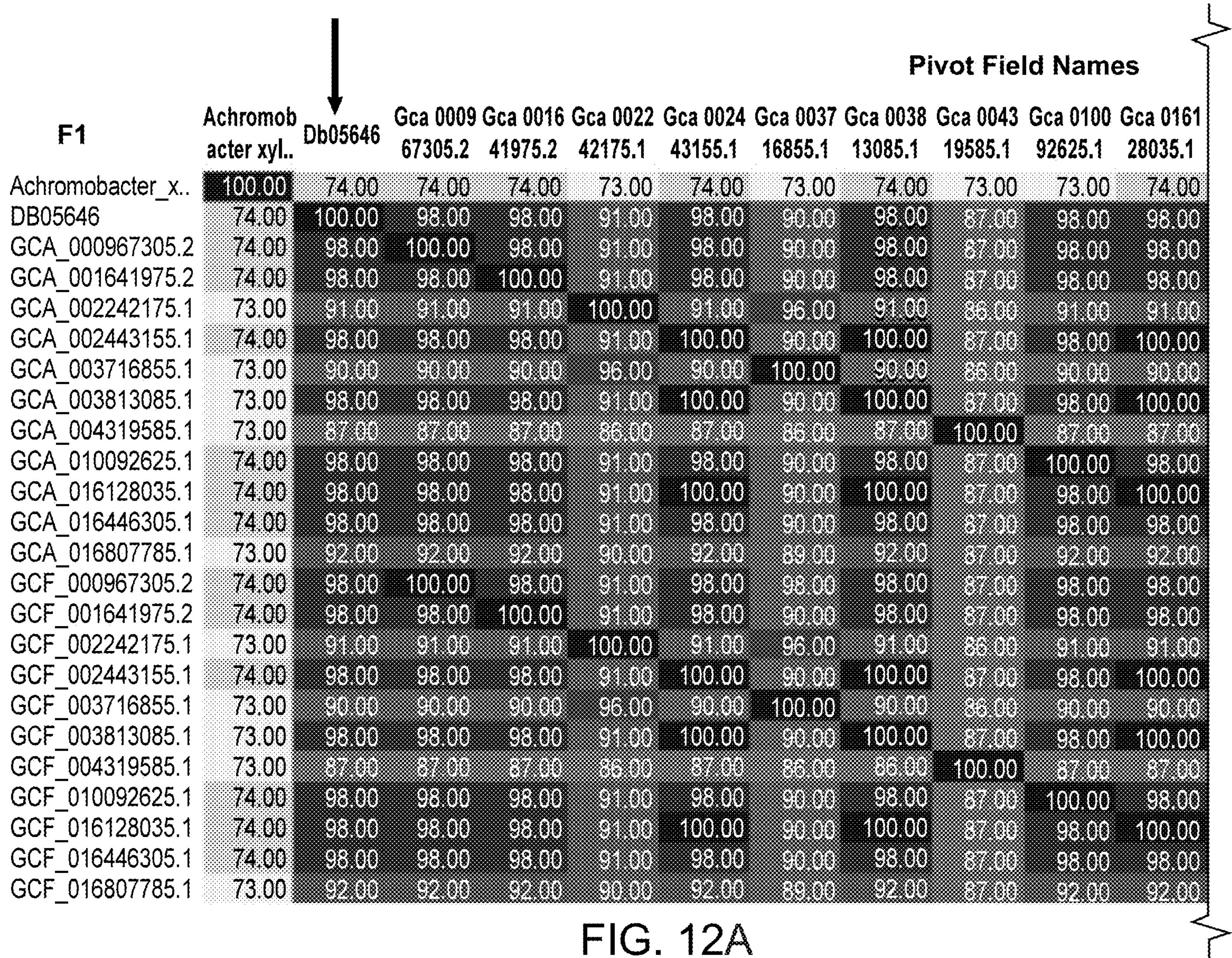
FIGS. 12A-12B show percent similarities between DB05646 and 34 variable genes of known functionality compared to other *A. faecalis* reference genomes using pan genome analysis.
Figure 12B:
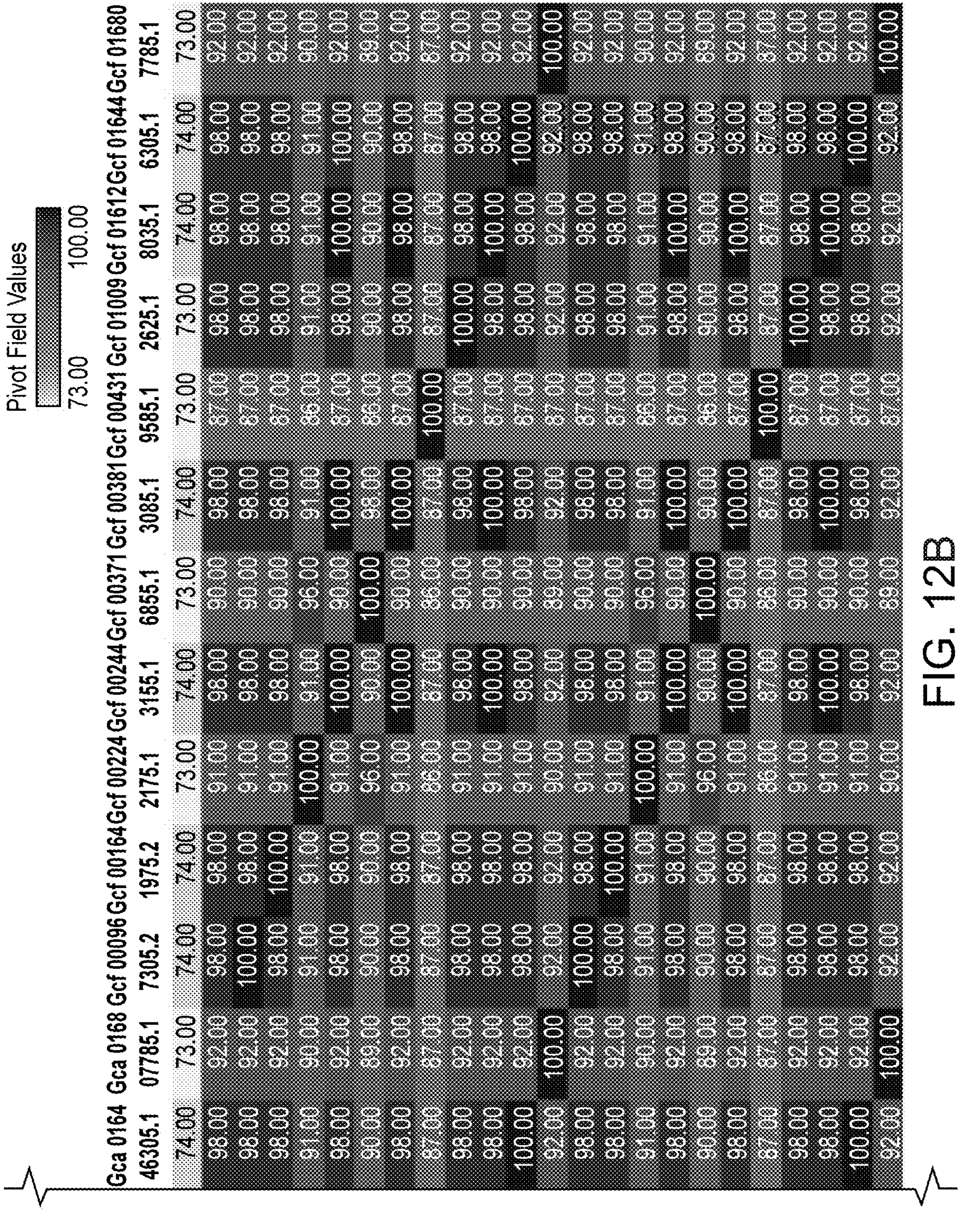

Percent similarities between DB05646 and 34 variable genes of known functionality were determined using pangenome analysis. From this set of 34 variable genes 33 genes were found in other strains or blastdb coverage and percent identity lower than as to be classified as a core gene, but still present in all genomes (FIGS. 12A-12B).

Interestingly, one gene from DB05646, ycgJ (putative methyltransferase; SEQ ID NO: 6)) was found only in DB05646 and not in any other *Alcaligenes faecalis* strains from NCBI. This was confirmed by local BLAST to all the *A. faecalis* reference strains and online BLAST to the entire NCBI nr/nt database. No similarity was found between this newly discovered gene to any other known strain. In some embodiments, this methyltransferase may play a role in epigenetics. In some embodiments, this methyltransferase gene may play a role the ability of DB05646 to be used in effective treatments against pathogens. Thus use of this methyltransferase gene may be considered as an additive to an *A. faecalis* and/or one or more other strains in order to develop additional *A. faecalis*-based treatments of one or more pathogens.

```
>HDLJNHPI_02397 ycgJ putative
methyltransferase
                                        (SEQ ID NO: 6)
ATGGCTATCAATTTTCATGATCAAAAGAATCGCAAAACCTACGCCACTCG

TGAGGCGGACGGCTCCTGGGTGCAAGCTATCGAAACCCTGATCAACCTGT

TCGGTTTGCGTGTGGCCGATATAGGTTGCGGCGGCGGGATTTATTCCTCG

GCCTTTCTGGATCAGGGCGCAAGCAGCGTGGTGGGCGTGGATTTTTCTCA

GGCCATGATTTCTGGCGCTCAAGAACGCAATGCGGGCCGGGAGGGGATTG

AGTTCCGTCAGGGGGACGCGACGGCGACCGGCTTGCCCTCTGAGAGTGTG

GACCTGGTTTTTCAGCGCGCCTTGATTCATCACCTGACAGACTATGAGGC

CTGCTTTACCGAAGCCAAGCGTTTGCTGGTTCCGGGTGGCGCTTTGCTGG

TGCAGGACCGGACGGCGGTGGATGTGCAGCAGCCTGCTTCAGCCTCTCAT

TTGCGGGGCTACTTCTTTGAATGTTTCCCCCGCCTGTTGGAGGTGGAGCT

GAAACGCCGCCCCGATACGTCCAAGGTACAGGCAGCACTGCAGGCCGTCG

GTTTTGTGGATCTGCAATCCAGCACCGTGTGGGAAGACCGGCGCTACTAC

AACAGCTTTGAGGACTATGCTCAGGAGCTGGTCCAGCGTACCGGGCGCTC

TATCTTGCATGAGCTAAGTGACGCCGAGCTGCAAGAGCTGATCGACTATA

TTCGCGCCCGAGTTCCTGCGAATCAGTCCTTTGTGGAGCGTGATTGCTGG

ACCTTGTGGTTAGGCAAGCGGGGCAGATAA
```

Conserved Genes and Metabolites

Antismash-mined whole genome assemblies for secondary metabolite profiles. DB05646 was found to have Ectoine, Bacillibactin Quinolobactin, Burkhoderic acid, and Emulsan metabolite profiles. As shown in Table 18A, these profiles were also found in the genomes NCBI reference strains (isolated from humans and/or having antimicrobial activity) LK36, MB207, NBIB-017, HPC1271 and MUB14 (GCF_010092625.1).

TABLE 18A

Secondary metabolite profiles found in whole genome assemblies of *A. faecalis* strains.

| | | | | | |
|---|---|---|---|---|---|
| DB05646 | Ectione | Bacillibactin | Quinolobactin | Burkholderic acid | Emulsan |
| LK36 (human, wound healing) | Ectione | Bacillibactin | Quinolobactin | Burkholderic acid | Emulsan |
| MB207 (effluent, biodegradation) | Ectione | Bacillibactin | Quinolobactin | Burkholderic acid | |

TABLE 18A-continued

| Secondary metabolite profiles found in whole genome assemblies of *A. faecalis* strains. | | | | | |
|---|---|---|---|---|---|
| NBIB-017 (soil, antimicrobial) | Ectione | Bacillibactin | Quinolobactin | Burkholderic acid | Emulsan |
| HPC1271 (wastewater, antimicrobial) | Ectione | Bacillibactin | Quinolobactin | Burkholderic acid | Emulsan |
| GCF_010092625.1 (urine, human) | Ectione | Bacillibactin | Quinolobactin | Burkholderic acid | Emulsan |

To further assess conserved pathways, all the bacterial genome assemblies for the conserved pathway comparison were first annotated with the PROKKA annotation tool. The resultant .faa files, which contain the functional amino acid sequences, were used as input for blastkoala search. The file was uploaded on the blastkoala server and run using the genus level taxa KEGG orthology database. The tool assigned K numbers to the amino acid sequences based on orthology based on orthology based search. These K numbers represent molecular functions in terms of functional orthologs. Using this methods K numbers were generated to all genomes.

The common K numbers (functional amino acids) between genomes of comparison of taxa were isolated using custom R script. Resultant common K numbers from the genomes comparison were reconstructed into pathways using KEGG pathway reconstructed web server (hypertext transfer protocol secure on the world-wide web at mLkeg-g.jp/kegg/mapper/reconstruct.htmL). Once the common K numbers were uploaded, the pathways representing these K numbers were generated from the common conserved pathways, those with antibiotic and antifungal properties based on literature review were further explored.

Based on analysis for conserved antimicrobial pathways in *Alcaligenes faecalis* strains LK36, MB207, NBIB-017, HPC1271 and MUB14 (GCF_010092625.1), data showed that terpenoid and polyketide biosynthesis pathways as well as Xenobiotics degradation pathways were conserved (Table 18B). The K numbers mapped inside each pathway are marked behind the pathway number. For example, the pathway "M00793 dTDP-L-rhamnose biosynthesis (4) (complete 3/4)" has four K numbers mapped inside the pathway; and out of the four K numbers, three of them are common in these strains.

TABLE 18B

| Conserved pathways in *Alcaligenes faecalis* |
|---|
| Biosynthesis of terpenoids and polyketides |
| Polyketide sugar unit biosynthesis |
| M00793 dTDP-L-rhamnose biosynthesis (4) (complete 3/4) |
| Xenobiotics biodegradation |
| Aromatics degradation |
| M00548 Benzene degradation, benzene => catechol (6) (complete 1/6) |
| M00551 Benzoate degradation, benzoate => catechol/methylbenzoate => methylcatechol (4) (complete 2/4) |
| M00568 Catechol ortho-cleavage, catechol => 3-oxoadipate (4) (complete 4/4) |
| M00545 Trans-cinnamate degradation, trans-cinnamate => acetyl-CoA (11) (complete 6/11) |

Example 10: Genome Comparison Studies of *B. altitudinis*

Summary

To perform bioinformatics analysis on *Bacillus* altitudinis isolated from human skin samples (DB strains), various analyses including strain assembly, taxonomic classification, identity and safety were performed, within the DB group and against reference strains (Table 19). Analysis included assembly of the sequencing data of the strains with taxonomic classification, along with alignment of the whole genomes with a few publicly and commercially available genomes to assess the phylogeny of the strains.

Strain identity was evaluated with average nucleotide identity (ANI; known to those in the art and described further herein for reference) and a secondary metabolite profile with potential pharmaceutical applications was established.

TABLE 19

*Bacillus altitudinis* strains isolated by DermBiont and strains from the NCBI data base used in analyses.

| DermBiont strains | NCBI reference strains |
|---|---|
| DB10033 (*B. altitudinis*) (SEQ ID NO: 2) | GCF_000299555.1.fasta |
| DB02448 (SEQ ID NO: 7) | GCF_000691145.1.fasta |
| DB02457 (SEQ ID NO: 8) | GCF_000949525.1.fasta |
| DB02461 (SEQ ID NO: 9) | GCF_000972685.1.fasta |
| DB02478 (SEQ ID NO: 10) | GCF_001191605.1.fasta |
| DB02549 (SEQ ID NO: 11) | GCF_001431145.1.fasta |
| DB02623 (SEQ ID NO: 12) | GCF_001431785.1.fasta |
| | GCF_001457015.1.fasta |
| | GCF_001543165.1.fasta |
| | GCF_001700735.1.fasta |
| | GCF_002443015.2.fasta |
| | GCF_002741745.1.fasta |
| | GCF_004563755.2.fasta |
| | GCF_005849435.1.fasta |
| | GCF_006007905.1.fasta |
| | GCF_007671735.1.fasta |
| | GCF_007681095.1.fasta |
| | GCF_007923025.1.fasta |
| | GCF_008764185.1.fasta |
| | *Halobacillus*284515.fasta |

Materials & Methods

Whole Genome Shotgun Sequencing and Genome Sequence Assembly

Shotgun sequencing for all DB strains in Table 21 was performed using the Nextera Flex kit manufactured by Illumina according to the manufacturer's instructions. The shotgun libraries were pooled and sequenced in a HiSeq X platform. The sequencing reads were automatically demultiplexed into individual FASTA files and standard bioinformatic analysis performed, yielding a genome assembled from cleaned sequencing reads.

Whole Genome Alignment/Phylogeny

Whole genome analysis was performed. Assembled genomes along selected reference genomes and an outgroup from public databases were used in the whole genome alignment. Homblocks was used to perform whole genome alignment, which used progressive mauve in the background to perform the alignment and extract the Locally collinear blocks (LCBs). LCBs are conserved segments that appear to be free from genome rearrangements. Whole genome alignment was used to establish phylogeny. Once the alignment file was produced a phylogenetic tree was built using RaxML for all DB strains and NCBI reference strains (Table 19), along with Halobacillus *halophilus* as a reference bacterium from a different genus used as an outgroup, to produce a tree showing an evolutionary relationship of the strains (see FIG. 13).

Average Nucleotide Identity:

Average nucleotide identity (ANI) is similar to whole genome alignment, but instead uses BLAST to perform a nucleotide genomic similarity between the genomes. ANI is widely used in comparing prokaryotic genomes which gives the strain level identity resolution of the species. Average nucleotide identity python script was used to perform the ANI. All strains in Table 19 were used for the comparison. A cutoff of 95% is used to establish species level identity and 100% is used to establish strain level identity.

Antismash

Antismash is a web browser-based tool for identification and annotation of secondary metabolite biosynthetic gene clusters in the bacterial genomes. It can mine genomic assemblies for secondary metabolic profiles that can have potential pharmaceutical applications. Antismash analysis was performed on whole genome assemblies of all Derm-Biont (DB) strains in Table 19.

Results, Interpretations, Amd Conclusions

Phylogeny

Figure 13:
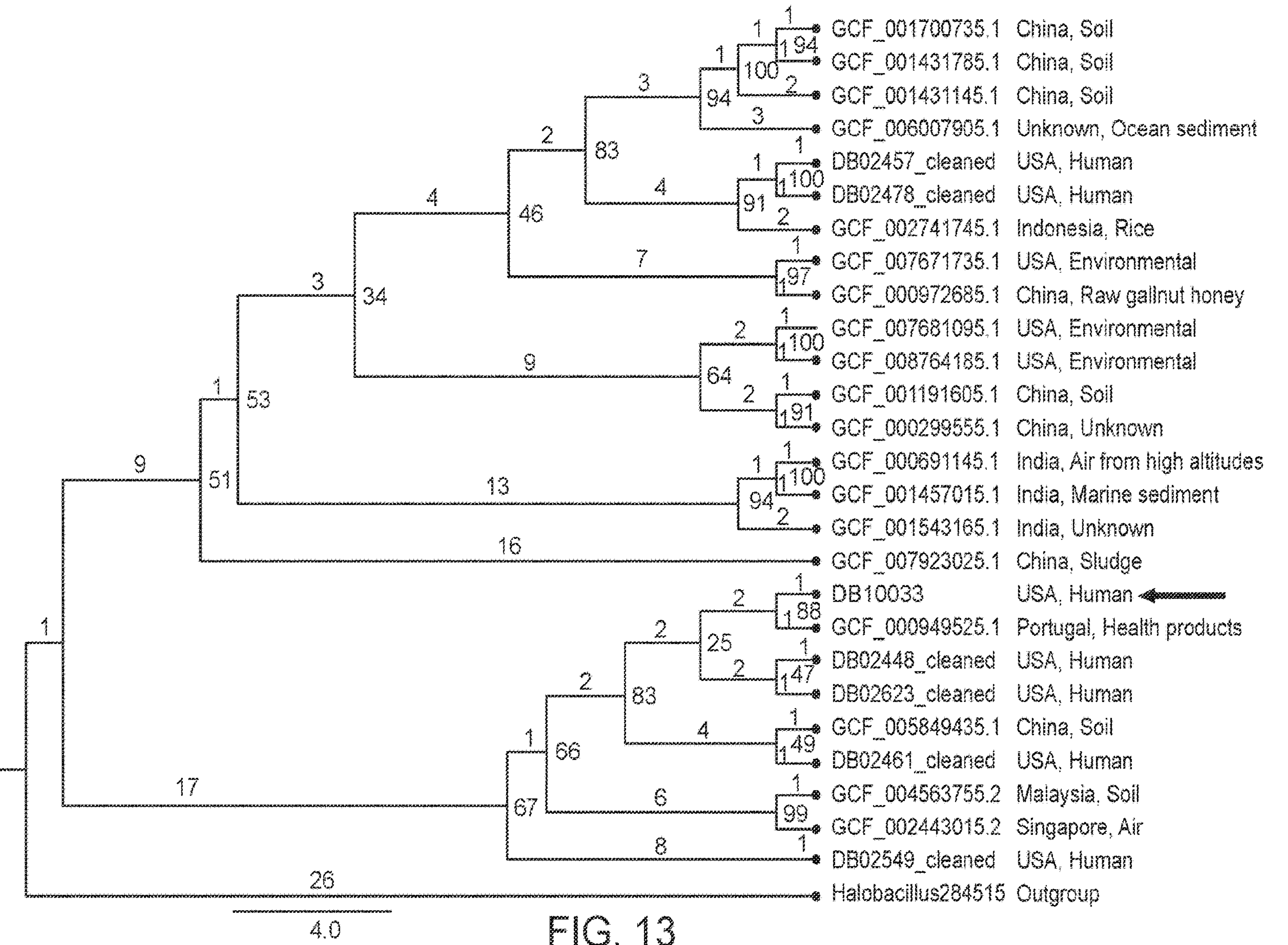
FIG. 13 is an exemplary phylogenetic analysis of DB10033.

A phylogenetic tree was generated, showing genomic differences between various DB strains of *B. altitudinis* (FIG. 13). DB10033 (*B. altitudinis*; SEQ ID NO: 2), DB02448 (SEQ ID NO: 7), DB02457 (SEQ ID NO: 8), DB02461 (SEQ ID NO: 9), DB02478 (SEQ ID NO: 10), DB02549 (SEQ ID NO: 11), and DB02623 (SEQ ID NO: 12) showed clear separation from outgroup Halobacillus *halophilus*. Halobacillus is a genus closely related to *bacillus*. All "DB" strains tested also show differences in sharing clades from the 19 publicly available genomes used in the phylogenetic analysis (FIG. 13).

Figure 14:
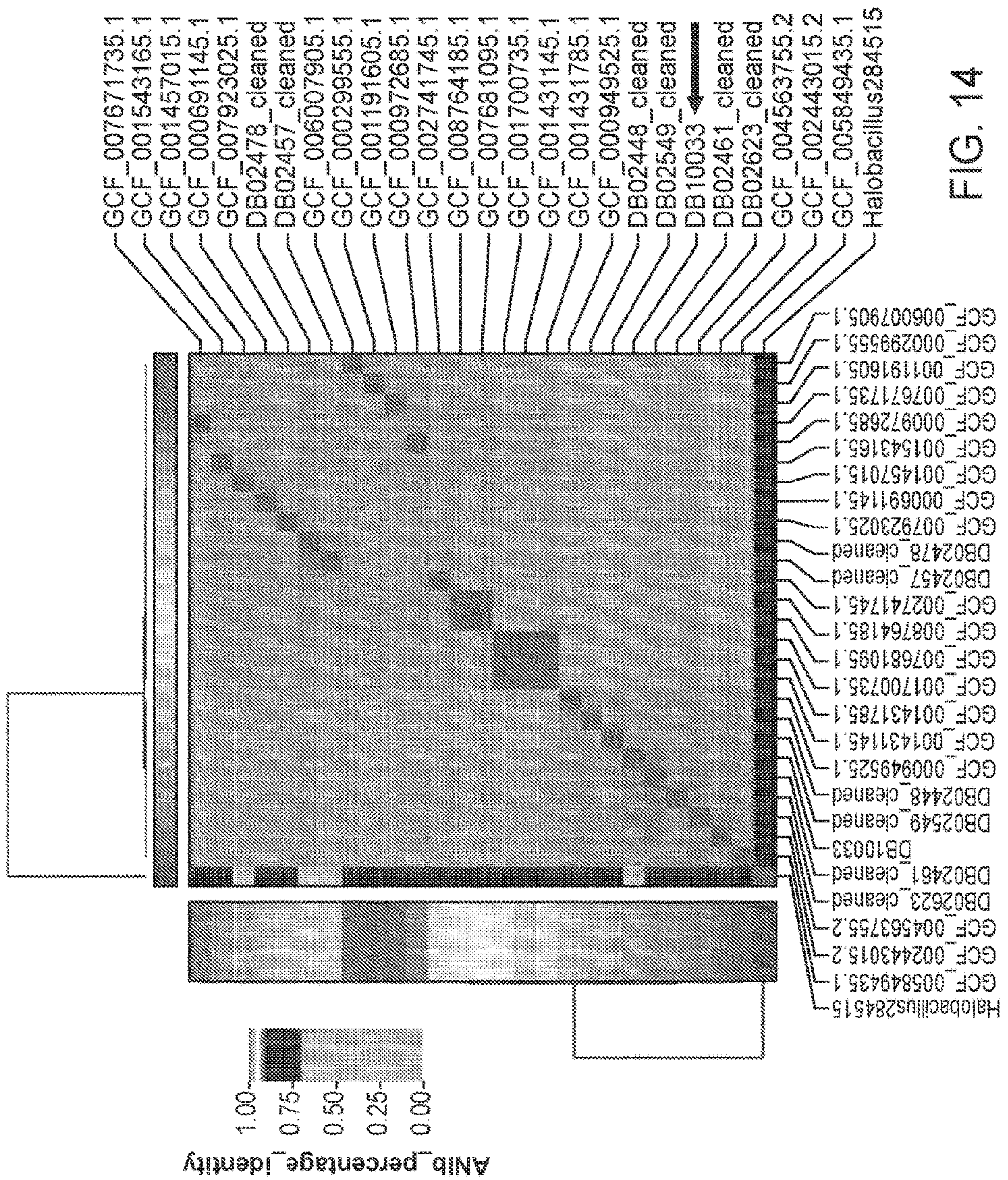
FIG. 14 shows results from an ANI analysis of whole genome analysis of DB10033 as compared to DB *B. altitudinis* strains and publicly-available *B. altitudinis* reference strains.

Average Nucleotide Identity:

Data represented in the heatmap shown in FIG. 14 show that all seven DB *B. altitudinis* strains have identity ranges around 98-99% similarity within the DB group and when compared to the reference *B. altitudinis* genomes. This confirms *B. altitudinis* as the species of all seven DB strains tested. None of the DB strains shares 100% identity with the DB group or when compared to the reference genomes, demonstrating clear strain level differences (FIG. 14).

Antismash

Antismash was used to produce lists of common compounds present in all DB *B. altitudinis* strains (i.e., as provided in Table 21). DB *B. altitudinis* strains showed profiles with potential pharmaceutical applications as antibiotics, anti-tumor drugs or cholesterol lowering drugs (Table 20A).

Common compounds present in DB *B. altitudinis* strains included Bacilysin, Carotenoid, Lichenysin and Fengycin. In addition, antibacterial compounds including Baclillibactin (DB02461) or Sporulation killing factor (DB02478 and DB02623) were detected in three DB strains.

TABLE 20A

Conserved secondary metabolite profiles in DB *B. altitudinis* strains.

| | | | | | |
|---|---|---|---|---|---|
| DB10033 | Bacilysin | Carotenoid | Lichenysin | Fengycin | |
| DB2448 | Bacilysin | Carotenoid | Lichenysin | Bacillibactin | |
| DB02457 | Bacilysin | Carotenoid | Lichenysin | Fengycin | |
| DB02461 | Bacilysin | Carotenoid | Lichenysin | Fengycin | Bacillibactin |
| DB02478 | Bacilysin | Carotenoid | Lichenysin | Fengycin | Sporulation killing factor |
| DB02549 | Bacilysin | Carotenoid | Lichenysin | Fengycin | |
| DB02623 | Bacilysin | Carotenoid | Lichenysin | Fengycin | Sporulation killing factor |

To further assess conserved pathways, all the bacterial genome assemblies for the conserved pathway comparison were first annotated with the PROKKA annotation tool. The resultant .faa files, which contain the functional amino acid sequences, were used as input for blastkoala search. The file was uploaded on the blastkoala server and run using the genus level taxa KEGG orthology database. The tool assigned K numbers to the amino acid sequences based on orthology based on orthology based search. These K numbers represent molecular functions in terms of functional orthologs. Using this methods K numbers were generated to all genomes.

The common K numbers (functional amino acids) between genomes of comparison of taxa were isolated using custom R script. Resultant common K numbers from the genomes comparison were reconstructed into pathways using KEGG pathway reconstructed web server (hypertext transfer protocol secure on the world-wide web at kegg.jp/kegg/mapper/reconstruct.htmL). Once the common K numbers were uploaded, the pathways representing these K numbers was generated from the common conserved pathways, those with antibiotic and antifungal properties based on literature review were further explored.

Based on analysis for conserved antimicrobial pathways in strains DB10033, DB2448, DB02457, DB02461, DB02478, DB02549, DB02623 data showed that terpenoid, polyketide, and secondary metabolite pathways were conserved between all DB *B. altitudinis* pathways (Table 20B). The K numbers mapped inside each pathway are marked behind the pathway number. For example, the pathway "M00096 C5 isoprenoid biosynthesis, non-mevalonate pathway (8) (Complete 8/8)" has eight K numbers mapped inside the pathway; and out of the eight K numbers, all of them are common in these strains.

TABLE 20B

| Conserved pathways in *Bacillus altitudinis*. |
| --- |
| Biosynthesis of terpenoids and polyketides |
| Terpenoid backbone biosynthesis |
| M00096 C5 isoprenoid biosynthesis, non-mevalonate pathway (8) (complete 8/8) |
| M00364 C10-C20 isoprenoid biosynthesis, bacteria (2) (complete 2/2) |
| Polyketide sugar unit biosynthesis |
| M00793 dTDP-L-rhamnose biosynthesis (4) (complete 3/4) |
| Biosynthesis of other secondary metabolites |
| Biosynthesis of other antibiotics |
| M00877 Kanosamine biosynthesis glucose 6-phosphate => kanosamine (3) (complete 3/3) |
| M00787 Bacilysin biosynthesis, prephenate => bacilysin (6) (complete 6/6) |

Example 11: Genome Comparison Studies of *Bacillus pumilus* Strains

Summary

To perform bioinformatics analysis on *Bacillus pumilus* strains isolated from human skin samples (DB strains), various analyses including strain assembly, taxonomic classification, identity and safety were performed, within the DB group and against reference strains (Table 22). Analysis included assembly of the sequencing data of the strains with taxonomic classification, along with alignment of the whole genomes with a few publicly and commercially available genomes to assess the phylogeny of the strains.

Strain identity was evaluated with average nucleotide identity (ANI; known to those in the art and described further herein for reference) and a secondary metabolite profile with potential pharmaceutical applications was established.

TABLE 22

*Bacillus pumilis* strains isolated by DermBiont and strains from the NCBI data base used in analyses.

| DermBiont strains | NCBI reference strains |
| --- | --- |
| DB01269 (SEQ ID NO: 13) | GCF_000017885.4.fasta |
| DB02420 (SEQ ID NO: 14) | GCF_000590455.1.fasta |
| DB02429 (SEQ ID NO: 15) | GCF_000691485.2.fasta |
| DB02430 (SEQ ID NO: 16) | GCF_001183525.1.fasta |
| DB02485 (SEQ ID NO: 17) | GCF_001548215.1.fasta |
| DB02492 (SEQ ID NO: 18) | GCF_001578165.1.fasta |
| DB02548 (SEQ ID NO: 19) | GCF_001578205.1.fasta |
| DB02622 (SEQ ID NO: 20) | GCF_001687085.1.fasta |
| DB02626 (SEQ ID NO: 21) | GCF_001704975.1.fasta |
| DB02680 (SEQ ID NO: 22) | GCF_001908475.1.fasta |
| DB02681 (SEQ ID NO: 23) | GCF_002998415.1.fasta |
| DB02708 (SEQ ID NO: 24) | GCF_003020795.1.fasta |
| DB03355 (SEQ ID NO: 25) | GCF_003034105.1.fasta |
| DB03366 (SEQ ID NO: 26) | GCF_003431975.1.fasta |
| DB03376 (SEQ ID NO: 3 | GCF_003571425.1.fasta |
| (*B. pumilus*) | GCF_004006455.1.fasta |
| | GCF_007678395.1.fasta |
| | GCF_009937765.1.fasta |
| | GCF_900186955.1.fasta |
| | *Bacillus_pumilus*_ATCC_7061.fasta |
| | *Halobacillus*284515.fasta |

Materials & Methods

Whole Genome Shotgun Sequencing and Genome Sequence Assembly

Shotgun sequencing for all DB strains in Table 22 was performed using the Nextera Flex kit manufactured by Illumina according to the manufacturer's instructions. The shotgun libraries were pooled and sequenced in a HiSeq X platform. The sequencing reads were automatically demultiplexed into individual FASTA files and standard bioinformatics analysis performed, yielding a genome assembled from cleaned sequencing reads.

Whole Genome Alignment/Phylogeny

Whole genome analysis was performed. Assembled genomes along with a reference genomes in Table 22 and an outgroup from public databases were used in the whole genome alignment. Homblocks was used to perform whole genome alignment, which used progressive mauve in the background to perform the alignment and extract the Locally collinear blocks (LCBs). LCBs are conserved segments that appear to be free from genome rearrangements. Whole genome alignment was used to establish phylogeny. Once the alignment file was produced a phylogenetic tree was built using RaxML for all DB strains and NCBI reference strains (Table 22), along with Halobacillus *halophilus* as a reference bacterium from a different genus used as an outgroup, to produce a tree showing an evolutionary relationship of the strains (see FIG. 15).

Average Nucleotide Identity

Average nucleotide identity (ANI) is similar to whole genome alignment, but instead uses BLAST to perform a nucleotide genomic similarity between the genomes. ANI is widely used in comparing prokaryotic genomes which gives the strain level identity resolution of the species. Average nucleotide identity python script was used to perform the ANI. All strains in Table 22 were used for the comparison. A cutoff of 95% is used to establish species level identity and 100% is used to establish strain level identity.

Antismash

Antismash is a web browser-based tool for identification and annotation of secondary metabolite biosynthetic gene clusters in the bacterial genomes. It can mine genomic assemblies for secondary metabolic profiles that can have potential pharmaceutical applications. Antismash analysis was performed on whole genome assemblies of all DermBiont (DB) strains in Table 22.

Results, Interpretations, and Conclusions

Phylogeny

Figure 15:
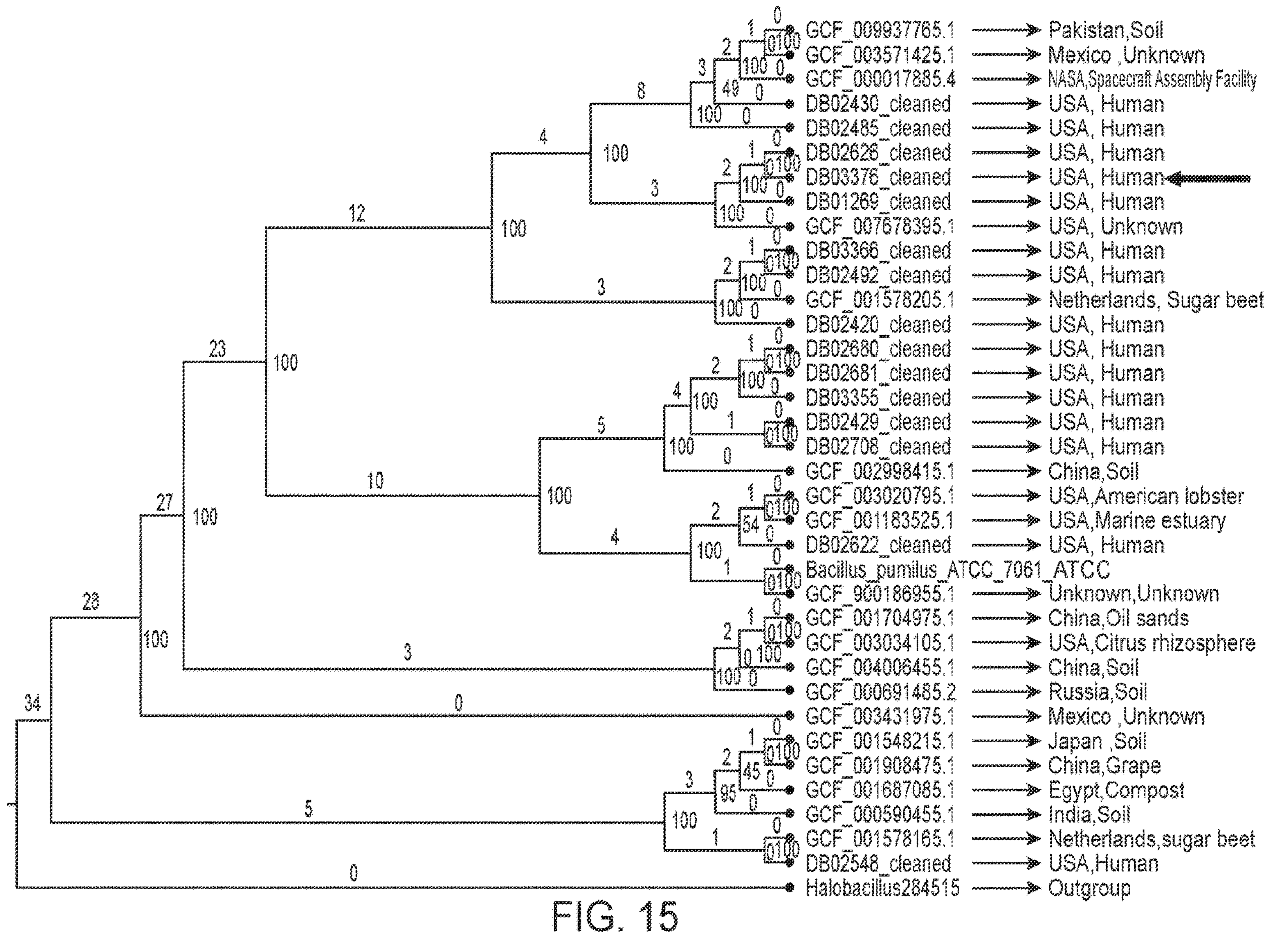
FIG. 15 shows an exemplary phylogenetic analysis of DB03376.
Figure 16:
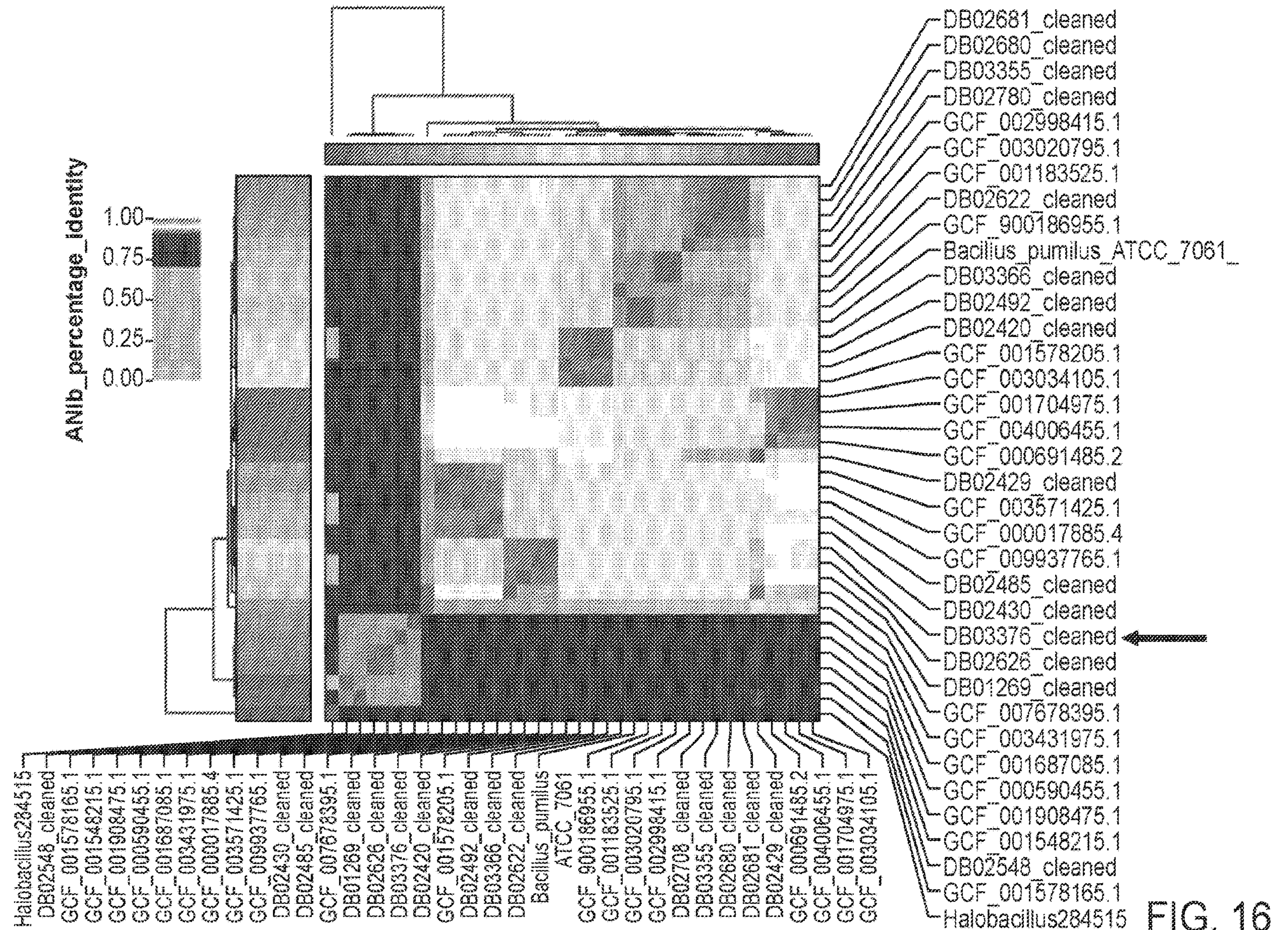
FIG. 16 shows results from an ANI analysis of whole genome sequences of *B. pumilus* DB03376 as compared to other DB *B. pumilus* strains and publicly-available *B. pumilus* reference strains.

A phylogenetic tree was generated, showing genomic differences between various DB strains of *B. pumilus* (FIG. 15). DB01269 (SEQ ID NO: 13), DB02420 (SEQ ID NO: 14), DB02429 (SEQ ID NO: 15), DB02430 (SEQ ID NO: 16), DB02485 (SEQ ID NO: 17), DB02492 (SEQ ID NO: 18), DB02548 (SEQ ID NO: 19), DB02622 (SEQ ID NO: 20), DB02626 (SEQ ID NO: 21), DB02680 (SEQ ID NO: 22), DB02681 (SEQ ID NO: 23), DB02708 (SEQ ID NO: 24), DB03355 (SEQ ID NO: 25), DB03366 (SEQ ID NO: 26), DB03376 (SEQ ID NO: 3) showed clear separation from outgroup Halobacillus *halophilus*. Halobacillus is a genus closely related to *bacillus*. All "DB" strains tested also show differences in sharing clades from the 19 publicly available genomes used in the phylogenetic analysis Average Nucleotide Identity Data represented in the heatmap shown in FIG. 16 show that 14 of 15 DB *B. pumilus* strains have an identity range around 95-99% similarity within that DB group and when compared to the reference *B. pumilus* genomes with the exception DB02548. This confirms *B. pumilus* as the species of 14 of the 15 DB genomes tested. None of the DB strains shares 100% identity within the DB group or when compared to the reference genomes, demonstrating clear strain level differences (FIG. 16). DB *B. pumilus* strains in Table 22, except for DB02548 (SEQ ID NO: 19), also show a range of 96-98% identity to genomes from commercially available ATCC strains, which provided enough information to infer species level identity but not strain level (FIG. 16).

Antismash

Antismash was used to produce lists of common compounds present in all DB *B. pumilus* strains (i.e., as provided in Table 22).

Common compounds present in several of the provided DB *B. pumilus* strains were Bacilysin, Carotenoid, Lichenysin, Fengycin and Bacillibactin (Table 23A). Two secondary metabolites, Plantazolicin and Deserrioxamine E, were present in some of the DB strains, but not DB03376.

TABLE 23A

Conserved secondary metabolite profiles in *B. pumilus* DermBiont strains.

| | | | | | | |
|---|---|---|---|---|---|---|
| DB01269 | Bacilysin | Carotenoid | Lichenysin | Plantazolicin | Fengycin | — |
| DB02420 | Bacilysin | Carotenoid | Lichenysin | — | Fengycin | BacilliBactin |
| DB02429 | — | Carotenoid | — | — | — | Deserrioxamine E |
| DB02430 | Bacilysin | Carotenoid | — | — | — | — |
| DB02485 | Bacilysin | Carotenoid | Lichenysin | — | Fengycin | — |
| DB02492 | Bacilysin | Carotenoid | Lichenysin | — | Fengycin | BacilliBactin |
| DB02548 | Bacilysin | Carotenoid | Lichenysin | — | Fengycin | BacilliBactin |
| DB02622 | Bacilysin | Carotenoid | Lichenysin | — | Fengycin | BacilliBactin |
| DB02626 | Bacilysin | Carotenoid | Lichenysin | — | Fengycin | — |
| DB02680 | Bacilysin | Carotenoid | Lichenysin | Plantazolicin | Fengycin | BacilliBactin |
| DB02681 | Bacilysin | Carotenoid | Lichenysin | Plantazolicin | Fengycin | BacilliBactin |
| DB02708 | Bacilysin | Carotenoid | Lichenysin | Plantazolicin | Fengycin | BacilliBactin |
| DB03355 | Bacilysin | Carotenoid | Lichenysin | Plantazolicin | Fengycin | BacilliBactin |
| DB03366 | Bacilysin | Carotenoid | Lichenysin | — | Fengycin | BacilliBactin |
| DB03376 | Bacilysin | Carotenoid | Lichenysin | — | Fengycin | — |

To further assess conserved pathways, all the bacterial genome assemblies for the conserved pathway comparison were first annotated with the PROKKA annotation tool. The resultant .faa files, which contain the functional amino acid sequences, were used as input for blastkoala search. The file was uploaded on the blastkoala server and run using the genus level taxa KEGG orthology database. The tool assigned K numbers to the amino acid sequences based on orthology based on orthology based search. These K numbers represent molecular functions in terms of functional orthologs. Using this methods K numbers were generated to all genomes.

The common K numbers (functional amino acids) between genomes of comparison of taxa were isolated using custom R script. Resultant common K numbers from the genomes comparison were reconstructed into pathways using KEGG pathway reconstructed web server (hypertext transfer protocol secure on the world-wide web at kegg.jp/kegg/mapper/reconstruct.htmL). Once the common K numbers were uploaded, the pathways representing these K numbers was generated, from the common conserved pathways, those with antibiotic and antifungal properties based on literature review were further explored.

Based on analysis for conserved antimicrobial pathways in strains DB01269, DB02420, DB02429, DB02430, DB02485, DB02492, DB02548, DB02622, DB02626, DB02680, DB02681, DB02708, DB03355, DB03366, DB03376, data showed that terpenoid and polyketide and secondary metabolite biosynthesis pathways were conserved (Table 23B). The K numbers mapped inside each pathway are marked behind the pathway number. For example, the pathway "M00096 C5 isoprenoid biosynthesis, non-mevalonate pathway (8) (Complete 8/8)" has eight K numbers mapped inside the pathway; and out of the eight K numbers, all of them are common in these strains.

TABLE 23B

| Conserved antimicrobial pathways in *Bacillus pumilus* |
|---|
| Biosynthesis of terpenoids and polyketides |
| Terpenoid backbone biosynthesis |
| M00096 C5 isoprenoid biosynthesis, non-mevalonate pathway (8) (complete 8/8) |
| M00364 C10-C20 isoprenoid biosynthesis, bacteria (2) (complete 2/2) |
| Polyketide sugar unit biosynthesis |
| M00793 dTDP-L-rhamnose biosynthesis (4) (complete 3/4) |
| Biosynthesis of other secondary metabolites |
| Biosynthesis of other antibiotics |
| M00877 Kanosamine biosynthesis glucose 6-phosphate => kanosamine (3) (complete 3/3) |

Example 13: Genome Comparison Studies of *B. subtilis*

Summary

To perform bioinformatics analysis on *Bacillus subtilis* strains isolated from human skin samples (DB strains), various analyses including strain assembly, taxonomic classification, identity and safety were performed, within the DB group and against reference strains (Table 24). Analysis included assembly of the sequencing data of the strains with taxonomic classification, along with alignment of the whole genomes with a few publicly and commercially available genomes to assess the phylogeny of the strains.

Strain identity was evaluated with average nucleotide identity (ANI; known to those in the art and described further herein for reference) and a secondary metabolite profile with potential pharmaceutical applications was established.

TABLE 24

*Bacillus subtilis* strains isolated by DermBiont and strains from the NCBI data base used in analyses.

| Strain IDS | References Used |
|---|---|
| DB01270 (SEQ ID NO: 27) | GCF_000009045.1.fasta |
| DB01298 (SEQ ID NO: 28) | GCF_000227465.1.fasta |
| DB02460 (SEQ ID NO: 29) | GCF_000344745.1.fasta |
| DB02462 (SEQ ID NO: 30) | GCF_000789275.1.fasta |
| DB02475 (*B. subtilis*) | GCF_000953615.1.fasta |
| (SEQ ID NO: 4) | GCF_001704095.1.fasta |
| DB02946 (SEQ ID NO: 31) | GCF_002055965.1.fasta |
| DB03347 (SEQ ID NO: 32) | GCF_002163815.1.fasta |
| DB03351 (SEQ ID NO: 33) | GCF_003148415.1.fasta |
| DB03353 (SEQ ID NO: 34) | GCF_003665215.1.fasta |
| DB03367 (SEQ ID NO: 35) | GCF_004119775.1.fasta |
| | GCF_004328925.1.fasta |
| | GCF_006088795.1.fasta |
| | GCF_006741845.1.fasta |
| | GCF_009363835.1.fasta |
| | GCF_009662175.1.fasta |
| | GCF_009662195.1.fasta |
| | GCF_009662255.1.fasta |
| | GCF_009913275.1.fasta |
| | GCF_009914705.1.fasta |
| | *Bacillus_subtilis*_ATCC_6051_.fasta |
| | *Halobacillus*284515.fasta |

Materials & Methods

Whole Genome Shotgun Sequencing and Genome Sequence Assembly

Shotgun sequencing for all DB strains in Table 24 was performed using the Nextera Flex kit manufactured by Illumina according to the manufacturer's instructions. The shotgun libraries were pooled and sequenced in a HiSeq X platform. The sequencing reads were automatically demultiplexed into individual FASTA files and standard bioinformatics analysis performed, yielding a genome assembled from cleaned sequencing reads.

Whole Genome Alignment/Phylogeny

Whole genome analysis was performed. Assembled genomes along with a reference genomes as provided in Table 24 and an outgroup from public databases were used in the whole genome alignment. Homblocks was used to perform whole genome alignment, which used progressive mauve in the background to perform the alignment and extract the Locally collinear blocks (LCBs). LCBs are conserved segments that appear to be free from genome rearrangements. Whole genome alignment was used to establish phylogeny. Once the alignment file was produced a phylogenetic tree was built using RaxML for all DB strains and NCBI reference strains (Table 24), along with Halobacillus *halophilus* as a reference bacterium from a different genus used as an outgroup, to produce a tree showing an evolutionary relationship of the strains (see FIG. 17).

Average Nucleotide Identity

Average nucleotide identity (ANI) is similar to whole genome alignment, but instead uses BLAST to perform a nucleotide genomic similarity between the genomes. ANI is widely used in comparing prokaryotic genomes which gives the strain level identity resolution of the species. Average nucleotide identity python script was used to perform the ANI. All strains in Table 24 were used for the comparison. A cutoff of 95% is used to establish species level identity and 100% is used to establish strain level identity.

Antismash

Antismash is a web browser-based tool for identification and annotation of secondary metabolite biosynthetic gene clusters in the bacterial genomes. It can mine genomic assemblies for secondary metabolic profiles that can have potential pharmaceutical applications. Antismash analysis was performed on all DB strains provided in Table 24.

Results, Interpretations, and Conclusions

Phylogeny

Figure 17:
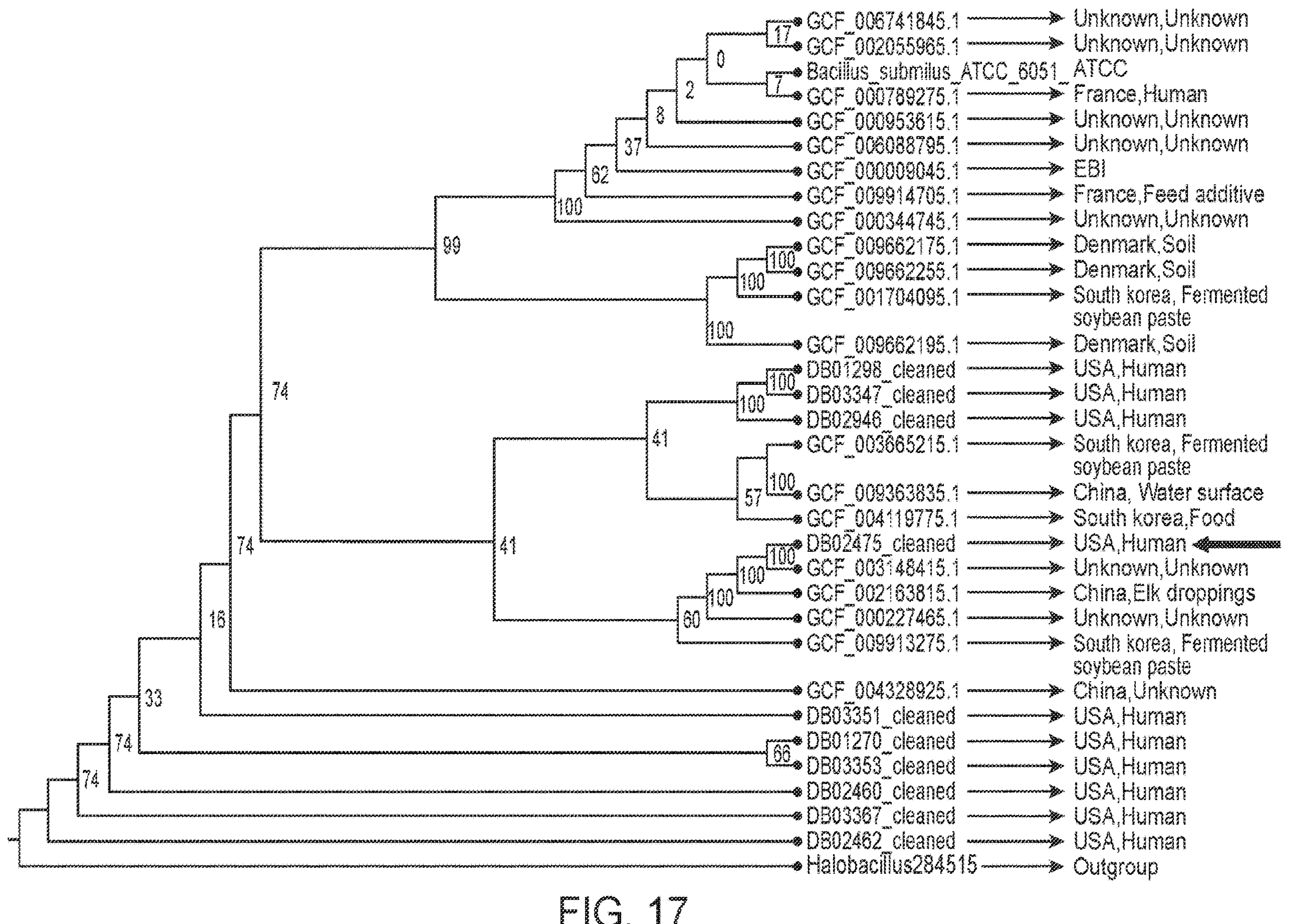
FIG. 17 shows an exemplary phylogenetic analysis of DB02475.

A phylogenetic tree was generated, showing genomic differences between various DB strains of *B. subtilis* (FIG. 17). DB01270 (SEQ ID NO: 27), DB01298 (SEQ ID NO: 28), DB02460 (SEQ ID NO: 29), DB02462 (SEQ ID NO: 30), DB02946 (SEQ ID NO: 31), DB03347 (SEQ ID NO: 32), DB03351 (SEQ ID NO: 33), DB03353 (SEQ ID NO: 34), DB03367 (SEQ ID NO: 35), and DB02475 (SEQ ID NO:4), showed clear separation from outgroup Halobacillus *halophilus*. Halobacillus is a genus closely related to *bacillus*. All "DB" strains tested also show differences in sharing clades from the 20 publicly available genomes used in the phylogenetic analysis. DB *B. subtilis* strains are different from commercially available ATCC strain by clades (FIG. 17).

Average Nucleotide Identity

Figure 18:
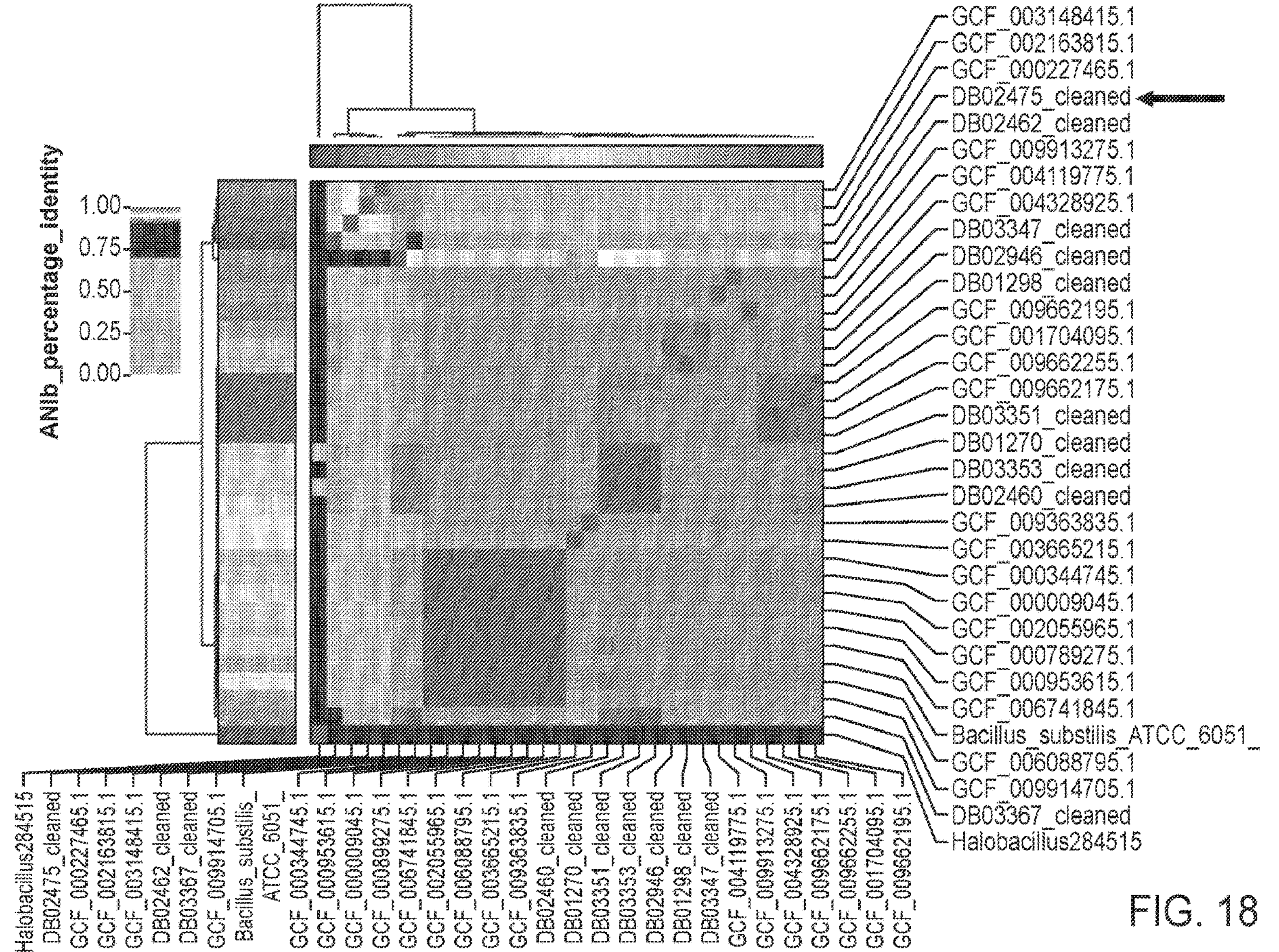
FIG. 18 shows results from an ANI analysis of whole genome sequences of *B. subtilis* DB02475 as compared to other DB *B. subtilis* strains and publicly-available *B. subtilis* reference strains.

Data represented in the heatmap shown in FIG. 18 show that 8 of 10 DB *B. subtilis* strains an identity range of around 95-99% similarity compared within that DB strain group and to the reference *B. subtilis* genomes, with the exception of DB02462 and DB02475. This confirms *B. subtilis* as the species of 8 of 10 genomes tested. None of the DB strains shares 100% identity within the DB group or when compared to any of the reference genomes, demonstrating clear strain level differences (FIG. 18). DB *B. subtilis* strains also show up to 99% identity to the genomes of commercially available ATCC strains, indicating strain level differences (FIG. 18).

Antismash

Antismash was used to produce lists of common compounds present in all DB *B. pumilus* strains (i.e., as provided in Table 25).

Common compounds present in all provided DB *B. subtilis* strains were Bacilysin, Subtilosin, Bacillibactin, Bacillaene and Fengycin. Interestingly, DB strain DB2475 does not contain overlapping genes for secondary metabolites except for Bacilysin.

TABLE 25

Conserved secondary metabolite profiles in *B. subtilis* DermBiont strains.

| | | | | | | |
|---|---|---|---|---|---|---|
| DB01270 | Bacilysin | Subtilosin | Bacillibactin | Bacillaene | Fengycin | — |
| DB01298 | Bacilysin | Subtilosin | Bacillibactin | Bacillaene | Fengycin | Surfactin |
| DB02460 | Bacilysin | Subtilosin | Bacillibactin | Bacillaene | Fengycin | — |
| DB02462 | — | Subtilosin | Bacillibactin | — | — | Paeninodin |
| DB02475 | Bacilysin | — | — | — | — | — |
| DB02946 | Bacilysin | Subtilosin | Bacillibactin | Bacillaene | Fengycin | — |
| DB03347 | Bacilysin | Subtilosin | Bacillibactin | Bacillaene | Fengycin | — |
| DB03351 | Bacilysin | Subtilosin | Bacillibactin | — | — | — |

TABLE 25-continued

| Conserved secondary metabolite profiles in *B. subtilis* DermBiont strains. | | | | | | |
|---|---|---|---|---|---|---|
| DB03353 | Bacilysin | Subtilosin | Bacillibactin | Bacillaene | — | — |
| DB03367 | — | — | — | — | — | — |

Example 13A: Pathway Analysis of *B. subtilis*

To further assess conserved pathways, all the bacterial genome assemblies for the conserved pathway comparison are annotated with the PROKKA annotation tool. The resultant .faa files, which contain the functional amino acid sequences, are used as input for blastkoala search. The file is uploaded on the blastkoala server and run using the genus level taxa KEGG orthology database. The tool assigns K numbers to the amino acid sequences based on orthology based on orthology based search. These K numbers represent molecular functions in terms of functional orthologs. Using this methods K numbers are generated to all genomes.

The common K numbers (functional amino acids) between genomes of comparison of taxa are isolated using custom R script. Resultant common K numbers from the genomes comparison are reconstructed into pathways using KEGG pathway reconstructed web server (hypertext transfer protocol secure on the world-wide web at kegg.jp/kegg/mapper/reconstruct.htmL). Once the common K numbers are uploaded, the pathways representing these K numbers are generated. From the common conserved pathways, those with antibiotic and antifungal properties based on literature review are further explored.

Based on analysis for conserved antimicrobial pathways in strains DB01270, DB01298, DB02460, DB02462, DB02946, DB03347, DB03351, DB03353, and DB02475, data are generated to show pathway conservation.

Example 14: Lyophilization of DB02473 *Janthinobacterium lividum* with Excipients Including Cryoprotectants Materials & Methods

*Janthinobacterium lividum* strain DB02473 was grown in a Bioflo-3000 fermentor at a 5 L scale. Fermentors were inoculated from 14-15 h old, 50 mL, shake flask cultures and the organism was grown for 15-16 h. In the fermentor, the pH was controlled at 7.0±0.1 by the addition of phosphoric acid/ammonium hydroxide. The dissolved oxygen was controlled at 30% by using continuous air purging and agitation. Depending on the oxygen requirements the agitation was varied to maintain dissolved oxygen content at 30%. At an absorbance of 4-5 AU at 600 nm, the fermentor was harvested and centrifuged at 8000 RPM for 30 minutes and the cell pellet was collected aseptically. The concentrated cell pellet was then resuspended in liquid vehicle at a concentration of about 10ˆ9-10ˆ10 CFU/mL.

Blending/Formulation

The *J. lividum* pellet was resuspended in a mixture comprising 2-20% disaccharide (cryoprotectant), PBS and ultra pure water.

Lyophilization

Lyophilization was conducted using Labconco Freezone-12 lyophilizer, and parameters optimized according to manufacturer's instructions.

The first lyophilized the composition at 2 mL volumes in 5 mL vials. The second lyophilized the composition at a volume of 24 mL in a tray and the third lyophilized 48 mL of the composition in a tray.

Stability Measurements and CFU Plating

Figure 19:
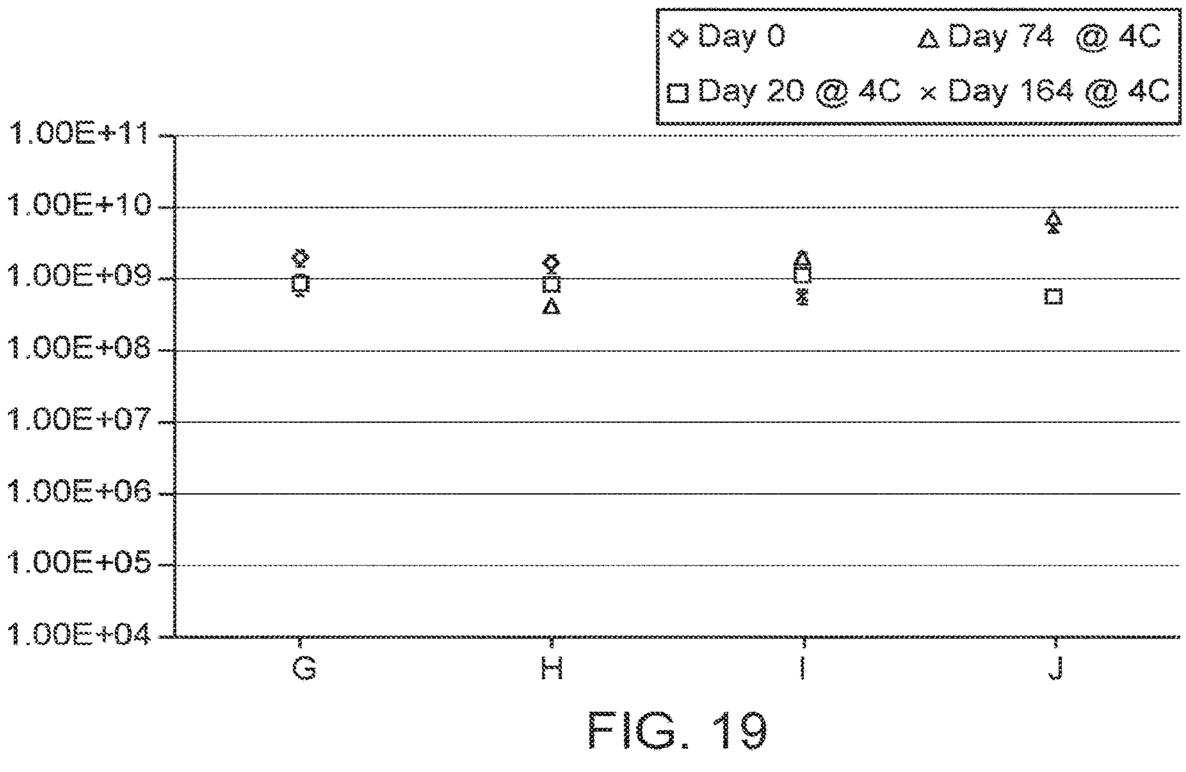
FIG. 19 shows data for experiments testing recovery of live colony forming units (CFU) of *J. lividum* strain DB02473 after lyophilization. Ordinate axis is CFU/mL of with 0.1 g of lyophilized material in 1 mL or 2 mL of solution. 5

Samples were either measured immediately after lyophilization (Day 0), or stored at 4° C. for number of days shown in FIG. 19. Samples were then reconstituted and measured for colony forming units (CFUs).

CFU/mL was evaluated by serial dilution and plating on agar for samples from each experimental method of lyophilization. To test the stability and recovery of the lyophilized material, 0.1 g of lyophilized sample was resuspended in 1 mL of solution. For each sample, 10× serial dilutions were performed seven times and the final 3 dilutions were plated for assessment. The full 0.1 mL of each dilution was spread onto LBS-50 plates and incubated at room temperature for 48 hrs. CFUs for each plate were counted and the stability and live bacterial recovery rates were calculated.

Results, Interpretations, and Conclusions

10ˆ9 CFU/mL were consistently recovered from 0.1 g of dry material after lyophilization reconstituted in 1 or 2 mL solution FIG. 19 depicts results of recovery of live CFUs of *J. lividum* DB02473 after lyophilization, over time. Viability over time was very stable and the concentration of live bacterial cells remained at 10ˆ9 CFU/mL from Day 0 to Day 164 after lyophilization. The powdered material from the lyophilization process was obtained with a water activity not exceeding 0.25 during storage. Results of stability are shown in FIG. 19. Thus, with the formulation and excipients provided herein, this lyophilized product retains its viability for at least up to 164 days at 4° C. Formulation G was lyophilized in a 5 mL vial, H was lyophilized in a tray, I was lyophilized in a tray with double the volume and J the same as I formulation, but stored in desiccated conditions.

Example 14A: Lyophilization of DB02473 *Janthinobacterium lividum* with Excipients Including Cryoprotectants Materials & Methods

*Janthinobacterium lividum* strain DB02473 was grown in a Bioflo-3000 fermentor at a 5 L scale. Fermentors were inoculated from 14-15 h old, 50 mL, shake flask cultures and the organism was grown for 15-16 h. In the fermentor, the pH was controlled at 7.0±0.1 by the addition of phosphoric acid/ammonium hydroxide. The dissolved oxygen was controlled at 30% by using continuous air purging and agitation. Depending on the oxygen requirements, agitation was varied to maintain dissolved oxygen content at 30%. At an absorbance of 4-5 AU at 600 nm, the fermentor was harvested and centrifuged at 8000 RPM for 30 minutes and the cell pellet was collected aseptically. The concentrated cell pellet was then resuspended in liquid vehicle at a concentration of about 10ˆ9-10ˆ10 CFU/mL.

Blending/Formulation

The *J. lividum* pellet was resuspended with a mixture composing of sterilized 0-20% disaccharide (cryoprotectant), 0-10% sugar alcohol, 0-1.0% amino acid, 0-1-1.0% simple alcohol, 0-3% thickener, and PBS and ultra pure water.

Lyophilization

Lyophilization was conducted using the composition at 2 mL volumes in 5 mL vials and Labconco Freezone-12 lyophilizer, and parameters optimized according to the manufacturer's instructions.

Stability Measurements and CFU plating

Samples were either measured immediately after lyophilization (Day 0), or stored at 4° C. for the number of days shown. Samples were then reconstituted and measured for colony forming units.

CFU/mL were evaluated by serial dilution and plating on agar for samples from each experimental method of lyophilization. To test the stability and recovery of the lyophilized material, 0.1 g of lyophilized sample was resuspended in 1 or 2 mL of solution. For each sample, 10× serial dilutions were performed 5 times and the final 3 dilutions were plated for assessment. 0.1 mL of each dilution was spread onto LBS-50 plates and incubated at room temperature for 48 hrs. CFUs for each plate were counted and the stability and live bacterial recovery rates were calculated.

Results, Interpretations, and Conclusions

Figure 20:
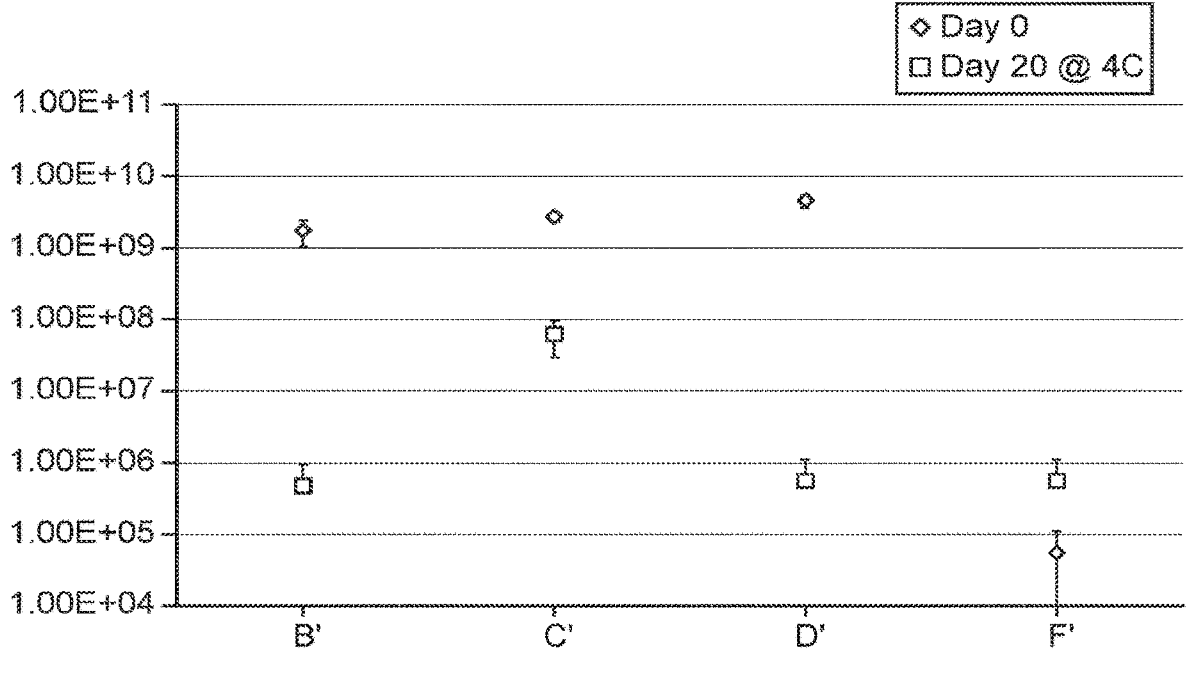
FIG. 20 shows data for experiments testing recovery of live colony forming units (CFU) of *J. lividum* strain DB02473 after lyophilization. Ordinate axis is CFU/mL of with 0.1 g of lyophilized material in 1 mL or 2 mL of solution.

CFU recovery and viability upon storage from 0.1 g of dry material after lyophilization reconstituted in 1 or 2 mL solution was low as shown in FIG. 20. The powdered material from the lyophilization process was obtained with a water activity not exceeding 0.35 during storage. Thus, the lyophilized product using formulations provided herein did not retain viability even for 20 days at 4° C. (FIG. 20, formulations B', C', D', and F'). Formulation B' is a complex formulation including cryoprotectant disaccharide, amino acid, simple alcohol and thickener. Formulation C' includes the cryoprotectant with simple alcohol. Formulation D' includes the cryoprotectant with amino acid, and Formulation F' comprises of sugar alcohol only.

Example 15: Lyophilization of *Alcaligenes Faecalis* with Excipients Including Cryoprotectants Materials & Methods

*Alcaligenes faecalis* strain DB05646 was grown in 5 L Bioflo 3000 fermentor with terrific broth as the nutrient medium. Fermentors were inoculated from 15-16 h old shake flask cultures. In the fermentor, the pH was controlled by the addition of phosphoric acid/ammonium hydroxide. Dissolved oxygen was maintained at 30% by using continuous air purging and agitation. Depending on the oxygen requirements, the agitation was varied to maintain the dissolved oxygen content at 30%. At an absorbance of 9-10 AU at 600 nm, the fermentor was harvested and centrifuged at 8000 RPM for 30 minutes and the cell pellet was collected aseptically. The concentrated cell pellet was then resuspended in liquid vehicle at a concentration of about 10^9-10^11 CFU/mL.

Blending/Formulation

The *A. faecalis* pellet was resuspended with a mixture composing of sterilized 0-10% disaccharide (cryoprotectant), 0-10% sugar alcohol, 0-1.0% amino acid, 0-1.0% simple alcohol, 0-3% thickener, and PBS and ultra pure water.

Lyophilization

Lyophilization was conducted using the composition at 2 mL volumes in 5 mL vials and Labconco Freezone-12 lyophilizer and parameters optimized according to the manufacturer's instructions.

Stability Measurements and CFU Plating

Figure 21:
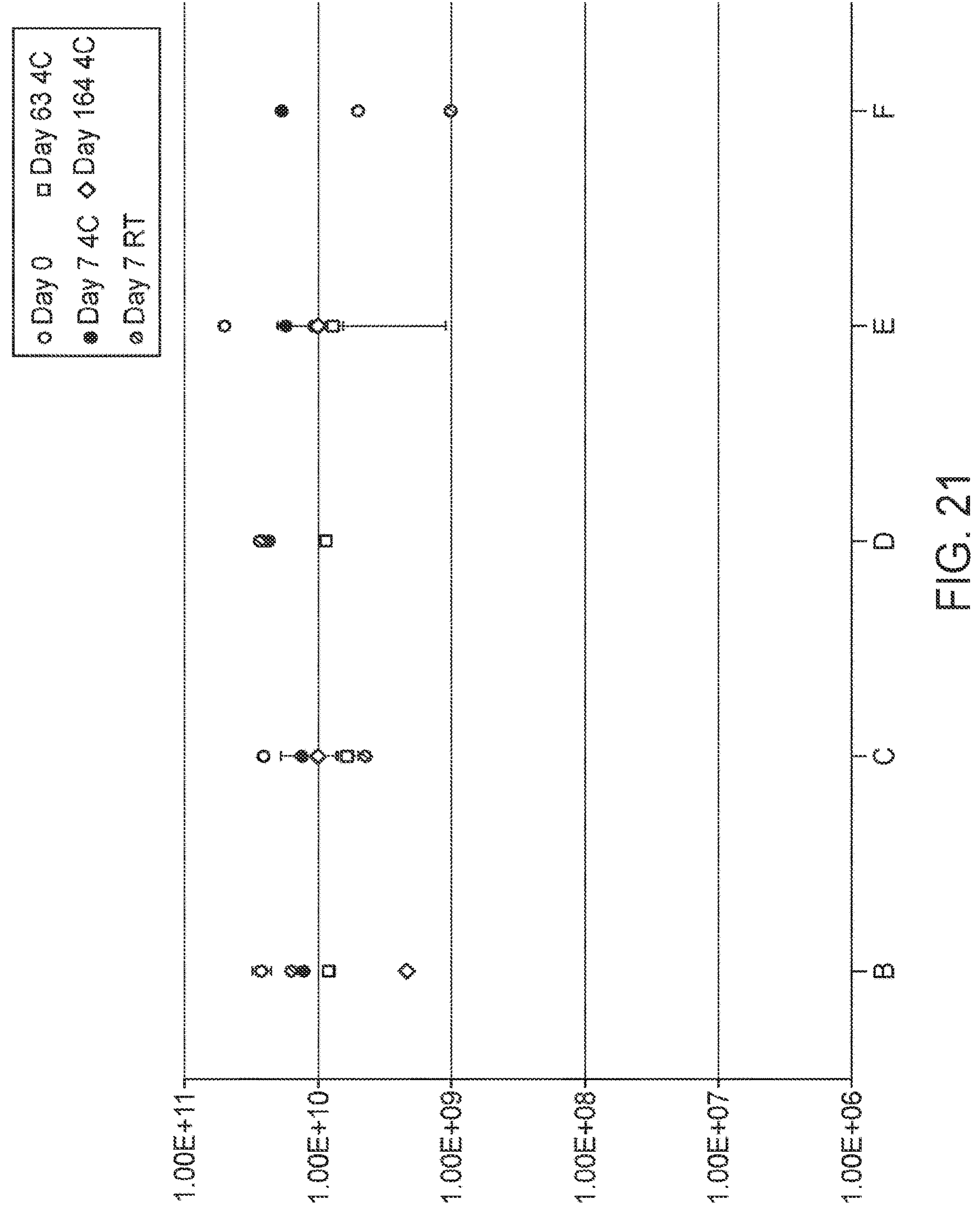
FIG. 21 shows data demonstrating recovery of live colony forming units (CFU) of *A. faecalis* strain DB05646 after lyophilization. Ordinate axis is CFU/mL of formulations with 0.1 g of lyophilized material in 1 mL or 2 mL of solution.

Samples were either measured immediately after lyophilization (Day 0), or stored at 4° C. for the number of days shown in FIG. 21. Samples were then reconstituted and measured for colony forming units (CFUs).

CFU/mL was evaluated by serial dilution and plating on agar for samples from each experimental approach to lyophilization (i.e., a sample from each formulation; one method of container, but different formulations). To test the stability and recovery of the lyophilized material, 0.1 g of lyophilized sample was resuspended in 1 mL of solution. For each sample, 10× serial dilutions were performed eight times and the final 3 dilutions were plated for assessment. 0.1 mL of each dilution was spread onto LBS plates and incubated at 37° C. for 48 hrs. CFUs for each plate were counted and the stability and live bacterial recovery rates were calculated.

Results, Interpretations, and Conclusions

Approximately 10^10 CFU/mL were consistently recovered from 0.1 g of dry material after lyophilization when reconstituted in 1 or 2 mL solution. Viability over time was very stable and the concentration of live bacterial cells remained at about 10^10 CFU/mL from Day 0 to Day 164 after lyophilization when stored at 4° C. (FIG. 21, formulations B, C, D, E, and F). Viability of 10^10 CFU/mL was also maintained at room temperature for a minimum of 7 days. Formulation F containing no disaccharide did not show the same viability retainment. The powdered material from the lyophilization process was obtained with a water activity not exceeding 0.25 during storage. Results of stability are shown in FIG. 20. Thus, this lyophilized product retains its viability for at least up to 164 days at 4° C. (FIG. 21). Formulation B is a complex formulation including cryoprotectant disaccharide, amino acid, simple alcohol and thickener. Formulation C includes the cryoprotectant with simple alcohol. Formulation D includes the cryoprotectant with amino acid, Formulation E is without additional excipients except the cryoprotectant, and Formulation F comprises of sugar alcohol only.

Example 16: Frozen Formulations of *J. lividum* with Excipients Including Cryoprotectants Materials & Methods

*Janthinobacterium lividum* strain DB02473 was grown in a Bioflo-3000 fermentor at a 5 L scale. Fermentors were inoculated from 14-15 h old, 50 mL, shake flask cultures and the organism was grown for 15-16 h. In the fermentor, the pH was controlled at 7.0±0.1 by the addition of phosphoric acid/ammonium hydroxide. The dissolved oxygen was controlled at 30% by using continuous air purging and agitation. Depending on the oxygen requirements agitation varied to maintain the dissolved oxygen content at 30%. At an absorbance of 4-5 AU at 600 nm, the fermentor was harvested and centrifuged at 8000 RPM for 30 minutes and the cell pellet was collected aseptically. The concentrated cell pellet was then resuspended in liquid vehicle at a concentration of about 10^9-10^10 CFU/mL.

Blending/Formulation

Excipients were dissolved and filter sterilized. Non-filterable additives were dispensed after filtering. A pellet of *J. lividum* was resuspended various formulations of excipients and cryoprotectants. After resuspension the samples were either flash frozen using liquid nitrogen or slow frozen in the −80° C. freezer. The formulations tested were primarily comprised of 2-20% disaccharides, 0.1-5.0% polysaccharide, 0-1.0% sugar alcohols, 0.1-2% simple alcohol, and 0.1-2.0% thickening agents, 0-0.1% amino acids.

1. Formulation K: 2-20% disaccharides, 0.1-2% simple alcohol, and 0.1-5.0% polysaccharides.
2. Formulation L: 2-20% disaccharides, 0.1-2% simple alcohol, 0-0.1% amino acids, and 0.1-5.0% polysaccharides.
3. Formulation M: 2-20% disaccharides, 0.1-2% sugar alcohol, 0.1-5.0% polysaccharides.
4. Formulation N: 2-20% disaccharides, 0.1-0-1.0% sugar alcohols, and 0.1-5.0% polysaccharides.
5. Formulation O: 2-20% disaccharides, 0.1-1.0% sugar alcohols, 0.1-5.0% polysaccharides, 0.1-2% simple alcohol, and 0-0.1% amino acids.
6. Formulation P: 2-20% disaccharides, 0.1-1.0% sugar alcohols, 0.1-5.0% polysaccharides, 0.1-2% simple alcohol, and 0-0.1% amino acids. Stability of the formulations stored at −80° C., −20° C., 4° C. were evaluated at scheduled intervals by measuring CFUs. The stability data are shown in FIGS. 22A-22F.

CFU/mL were evaluated by serial dilution and plating on agar for samples from each experimental method of spray drying. To test the stability and recovery of the frozen material, 1 mL of the sample was thawed. For each sample, 10× serial dilutions were performed 7 times and the final 3 dilutions were plated for assessment. 0.1 mL of each dilution was spread onto LBS-50 plates and incubated at room temperature for 48 hrs. CFUs for each plate were counted and the stability and live bacterial recovery rates were calculated.

Results, Interpretations, and Conclusions

Figure 22A:
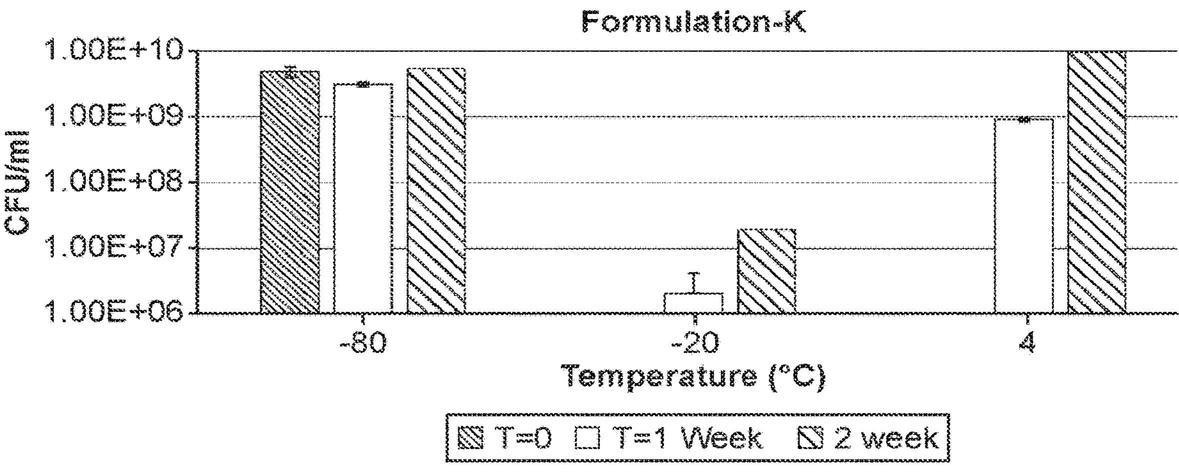
FIGS. 22A-22F show data demonstrating recovery of live colony forming units (CFU) of *J. lividum* strain DB02473. Stability of formulations were evaluated at −80° C., −20° C., 4° C. at scheduled intervals. (A) Formulation K, (B) Formulation L, (C) Formulation M, (D) Formulation N, (E) Formulation 0, and (F) Formulation P.
Figure 22B:
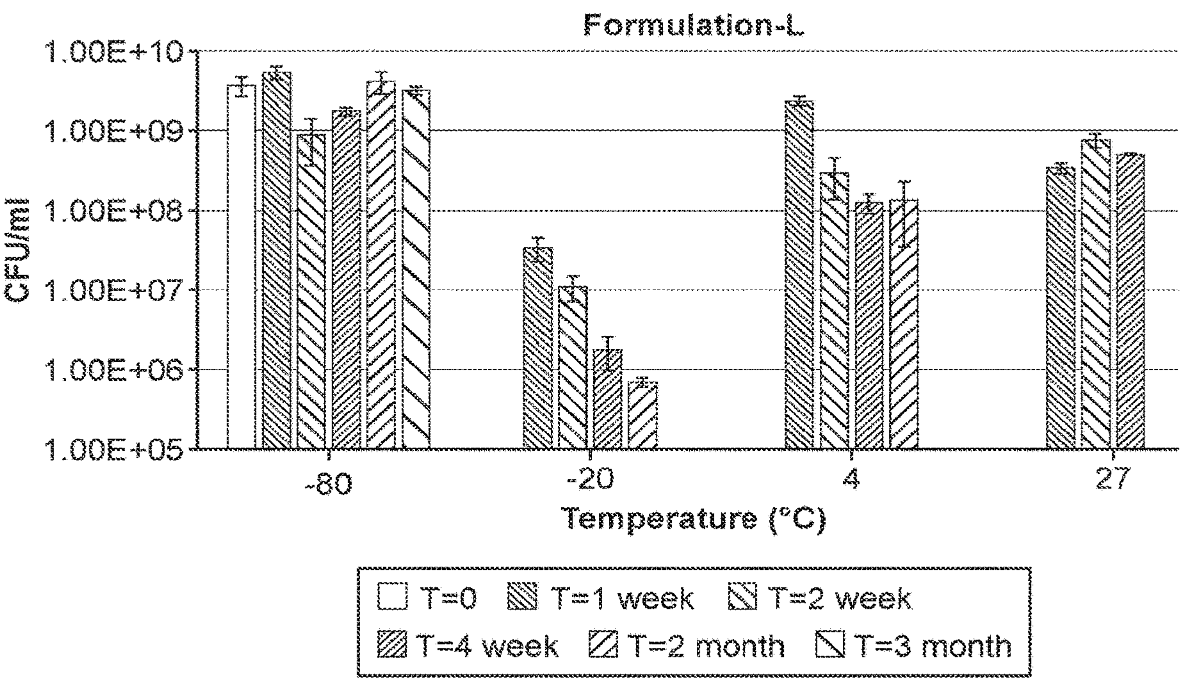
Figure 22C:
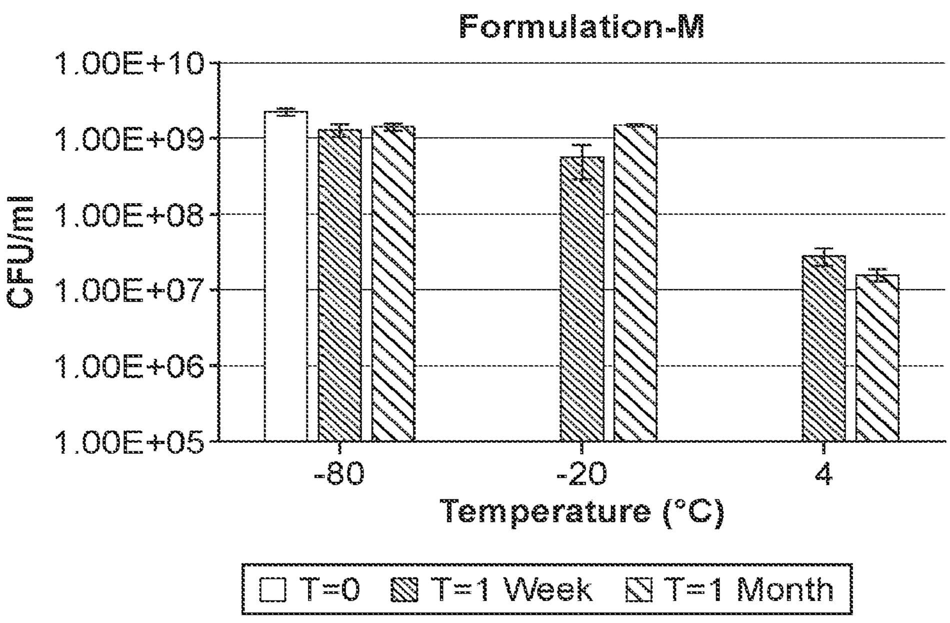
Figure 22D:
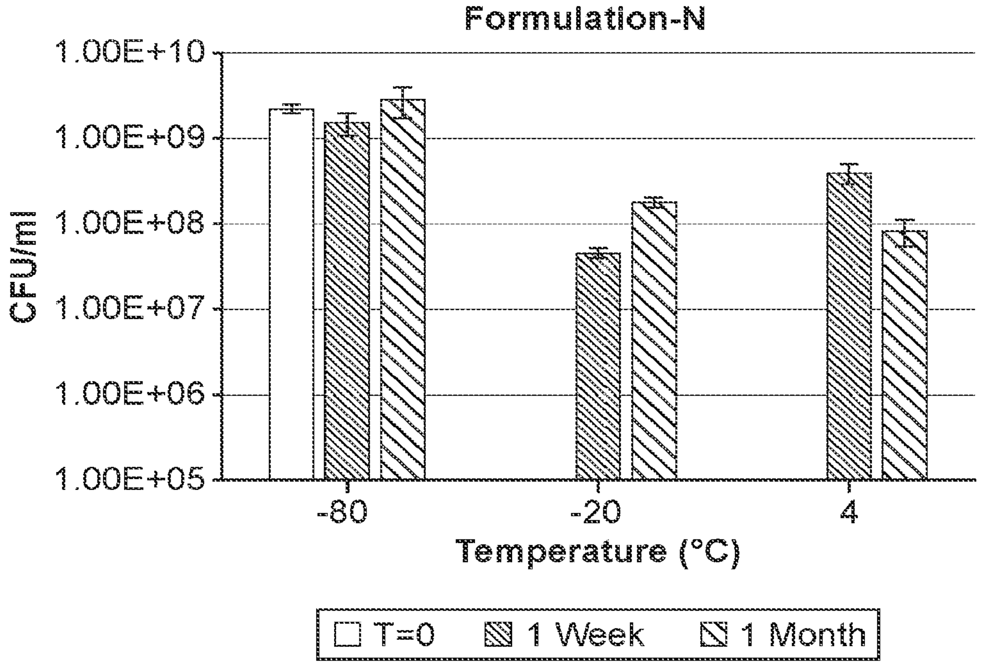
Figure 22E:
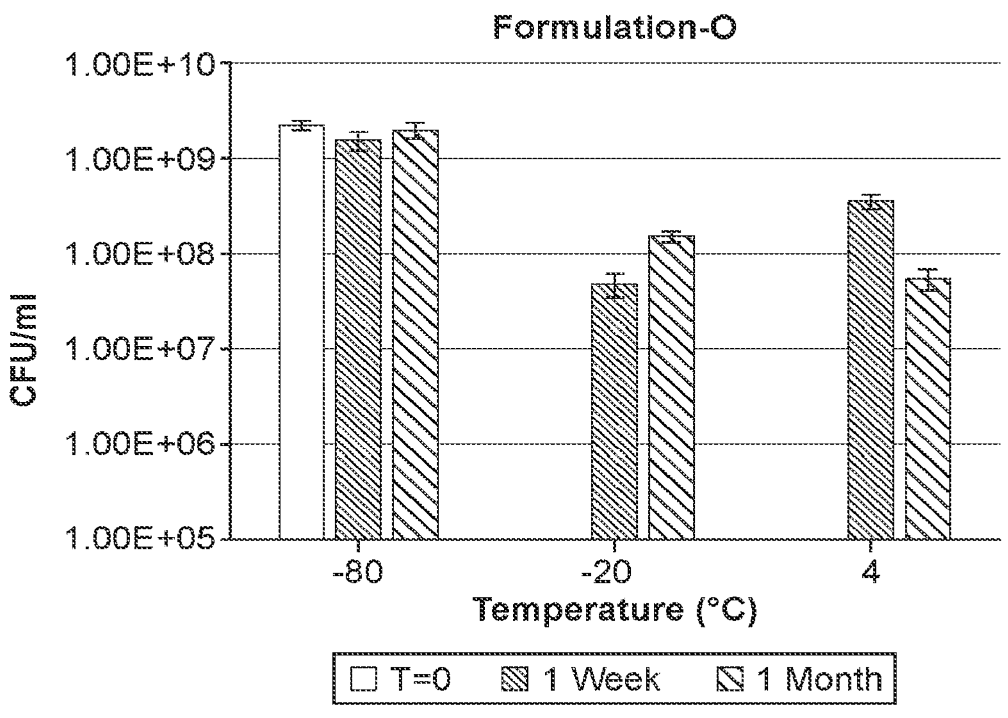
Figure 22F:
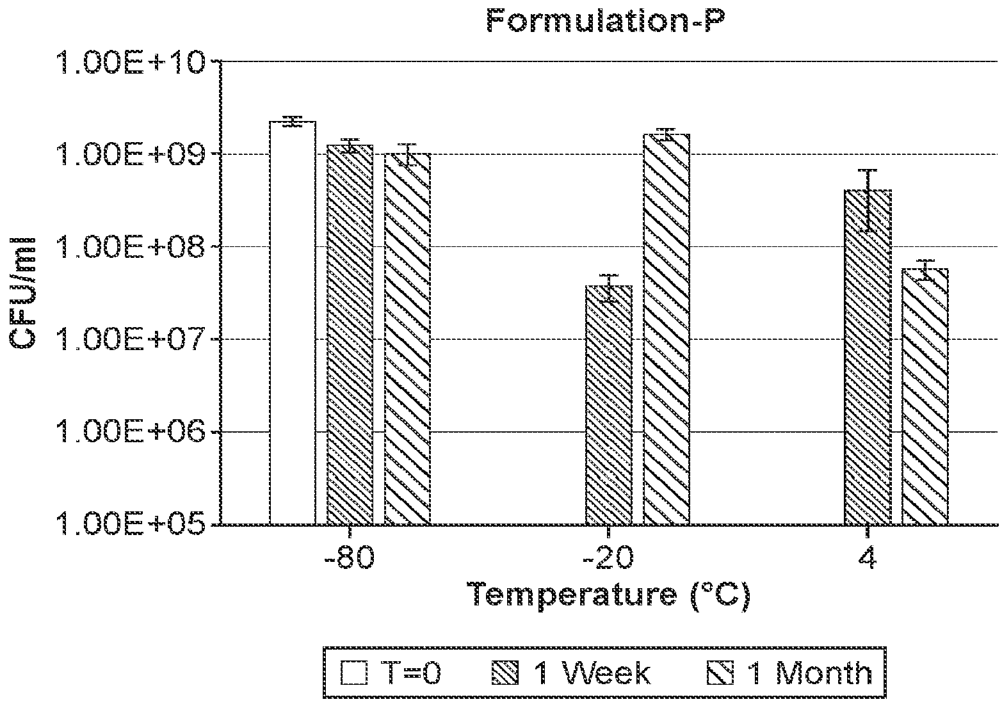

Between 10^9 and 10^10 CFU/mL were recovered from 1 mL of each composition maintained frozen at −80° C. Viability over time was very stable when stored at −80° C. and the concentration of live bacterial cells remained constant for at least one month and up to 4 months in some formulations (see FIGS. 22A-22F showing recovery of CFUs in DB02473 and stability at −80° C., −20° C., 4° C. at various time intervals including baseline, one week, two weeks, one, two, three, four, five, and/or six months). Formulation with *J. lividum* DB02473 in Formulation L was stable at −80° C. for the duration of testing (FIG. 22B). The stability declined at higher storage temperatures and became more variable in all formulations. In all formulations at temperatures of −20° C. and 4° C., there was almost a log loss or more of viability after 1 week of storage. There were some exceptions, such as Formulation K at 4° C. at 2 weeks, Formulation L at 4° C. at 1 week, Formulation M at −20° C. after one month, Formulation P−20° C. after one month, all maintained comparable viability to the initial viability of the composition at time 0 (FIGS. 22A-22C and 22F, respectively)

Example 18: Frozen Formulations of *A. faecalis* DB05646 with Excipients Including Cryoprotectants Materials & Methods

*Alcaligenes faecalis* strain DB05646 was grown in 5 L Bioflo 3000a fermentor with terrific broth as the nutrient medium. Fermentors were inoculated from 15-16 h old shake flask cultures. In the fermentor, the pH was controlled by the addition of phosphoric acid/ammonium hydroxide. The dissolved oxygen was controlled at 30% by using continuous air purging and agitation. Depending on the oxygen requirement, agitation was varied to maintain the dissolved oxygen content at 30%. At an absorbance of 9-10 AU at 600 nm, the fermentor was harvested and centrifuged for 30 minutes and the cell pellet was collected aseptically. The concentrated cell pellet was then resuspended in liquid vehicle at a concentration of about 10^10-10^11 CFU/mL.

Blending/Formulating

Excipients were dissolved and filter sterilized. Non-filterable additives were dispensed after filtering. The pellet of *A. faecalis* was resuspended various formulations of excipients and cryoprotectants. The formulations tested were a mixtures of 2-20% disaccharides, 0.2-5.0% polysaccharides, 0-1.0% sugar alcohols, 0.1-2% simple alcohol, and 0-0.1% amino acids.

1. Formulation Q: 2-20% disaccharide and 0.1-2.0% polysaccharides
2. Formulation R: of 2-20% disaccharides, 0.1-2% simple alcohol, and 0.1-5.0% polysaccharides.
3. Formulation S: 2-20% disaccharide, 0-1.0% sugar alcohol and 0.1-2.0% thickening agent.
4. Formulation T: 2-20% disaccharide, 0.2-5.0% polysaccharide, 0-1.0% sugar alcohol, 0.1-2% simple alcohol, and 0-0.1% amino acids.
5. Formulation U: of 2-20% disaccharide, 0-1.0% sugar alcohol, and 0.1-5.0% polysaccharide 0-0.1% amino acids.

Stability of the formulations stored at −80° C., −20° C., 4° C., 27° C., and 40° C. were evaluated at scheduled intervals by measuring CFUs. The stability data are shown in FIGS. 23A-23E.

CFU/mL were evaluated by serial dilution and plating on agar for samples from each experimental method of spray drying. To test the stability and recovery of the frozen material, 1 mL of the sample was thawed. For each sample, 10× serial dilutions were performed 8 times and the final 3 dilutions were plated for assessment. 0.1 mL of each dilution was spread onto LBS plates and incubated at 37° C. for 48 hrs. CFUs for each plate were counted and the stability and live bacterial recovery rates were calculated.

Results, Interpretations, and Conclusions

Figure 23A:
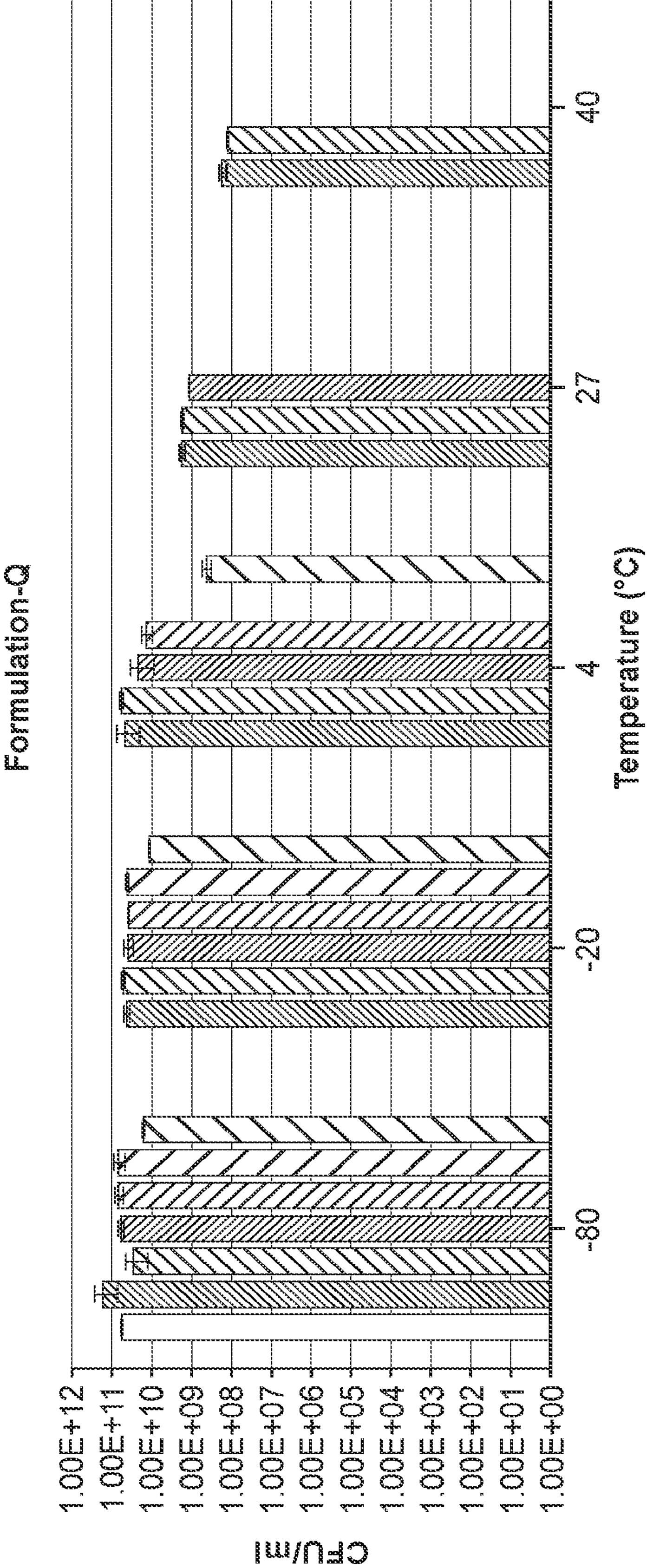
FIGS. 23A-23E shows data demonstrating recovery of live colony forming units (CFU) of *A. faecalis* strain DB05646. Stability of formulations were evaluated at −80° C., −20° C., and 4° C., along with 27° C., and 40° C. stability at scheduled intervals. (A) Formulation Q, (B) Formulation R, (C) Formulation S, (D) Formulation T, and (E) Formulation U.
Figure 23B:
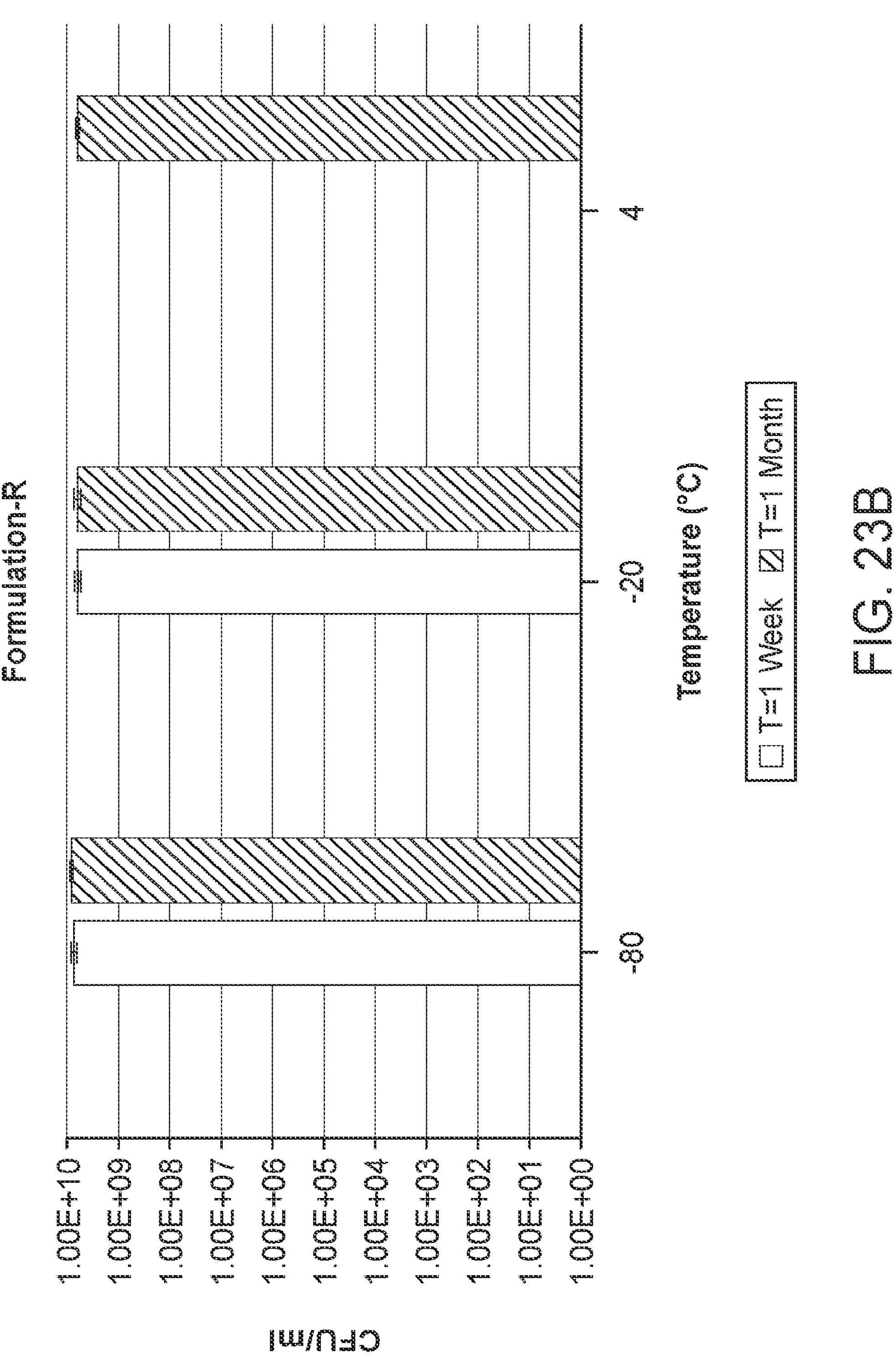
Figure 23C:
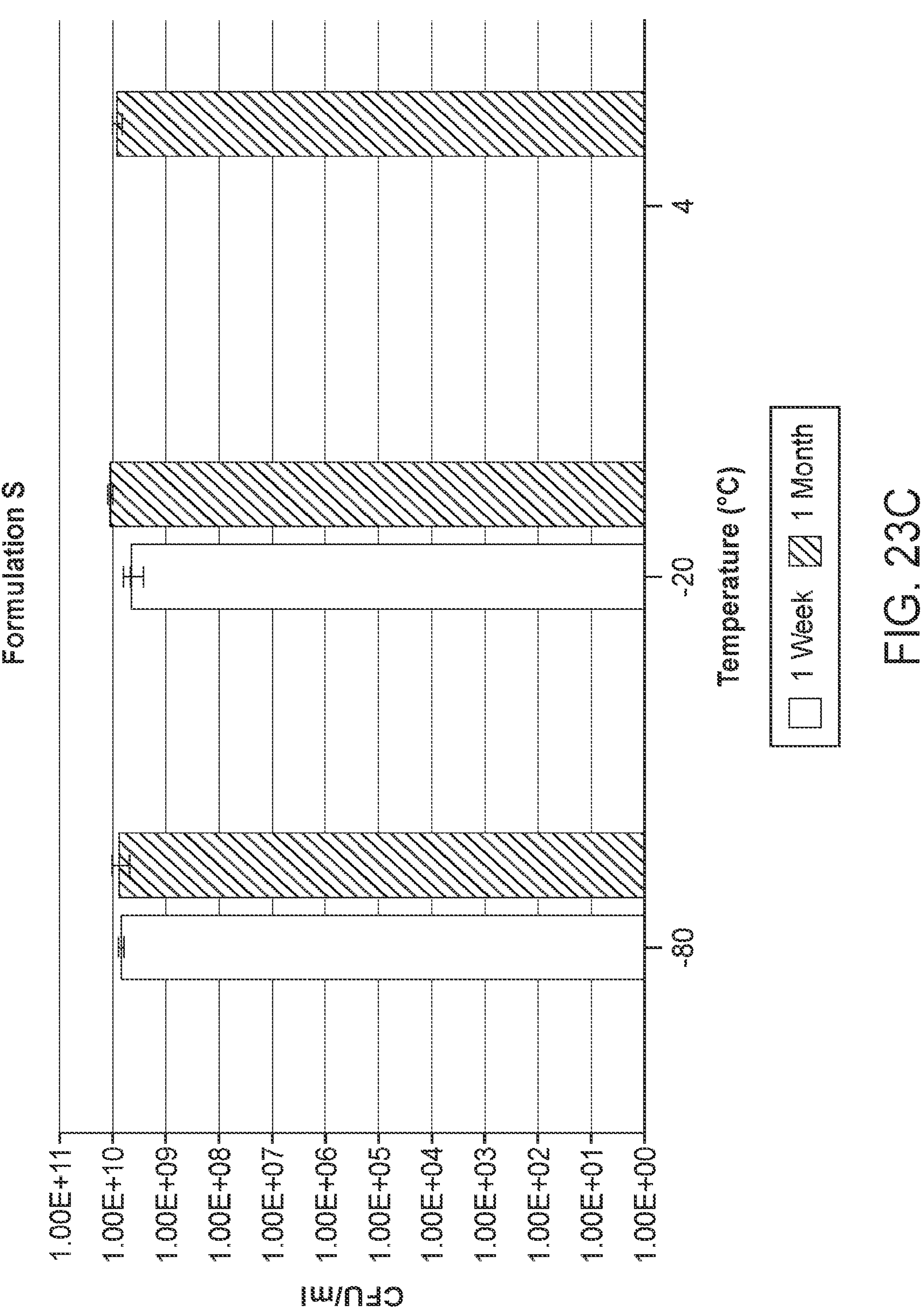
Figure 23D:
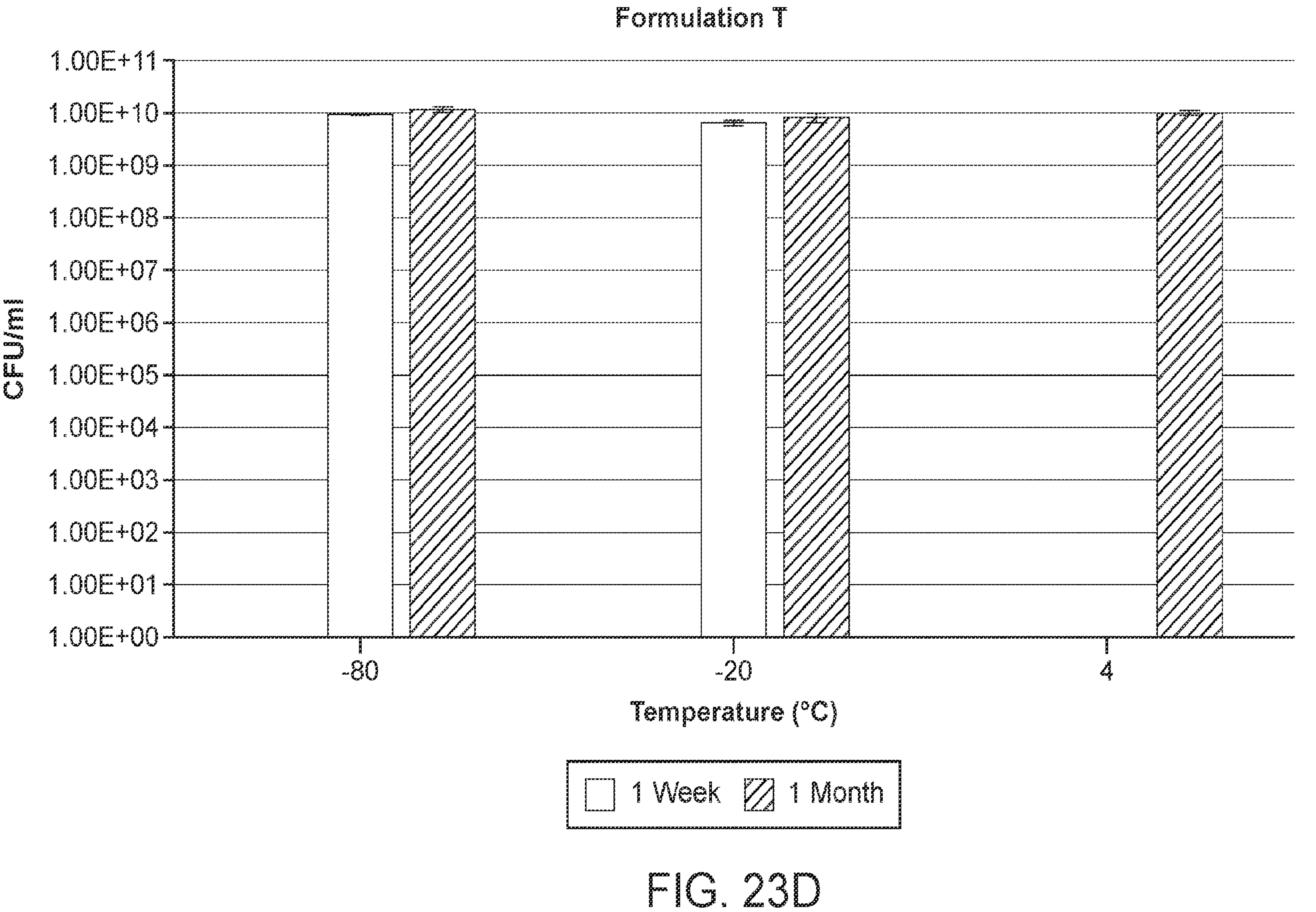
Figure 23E:
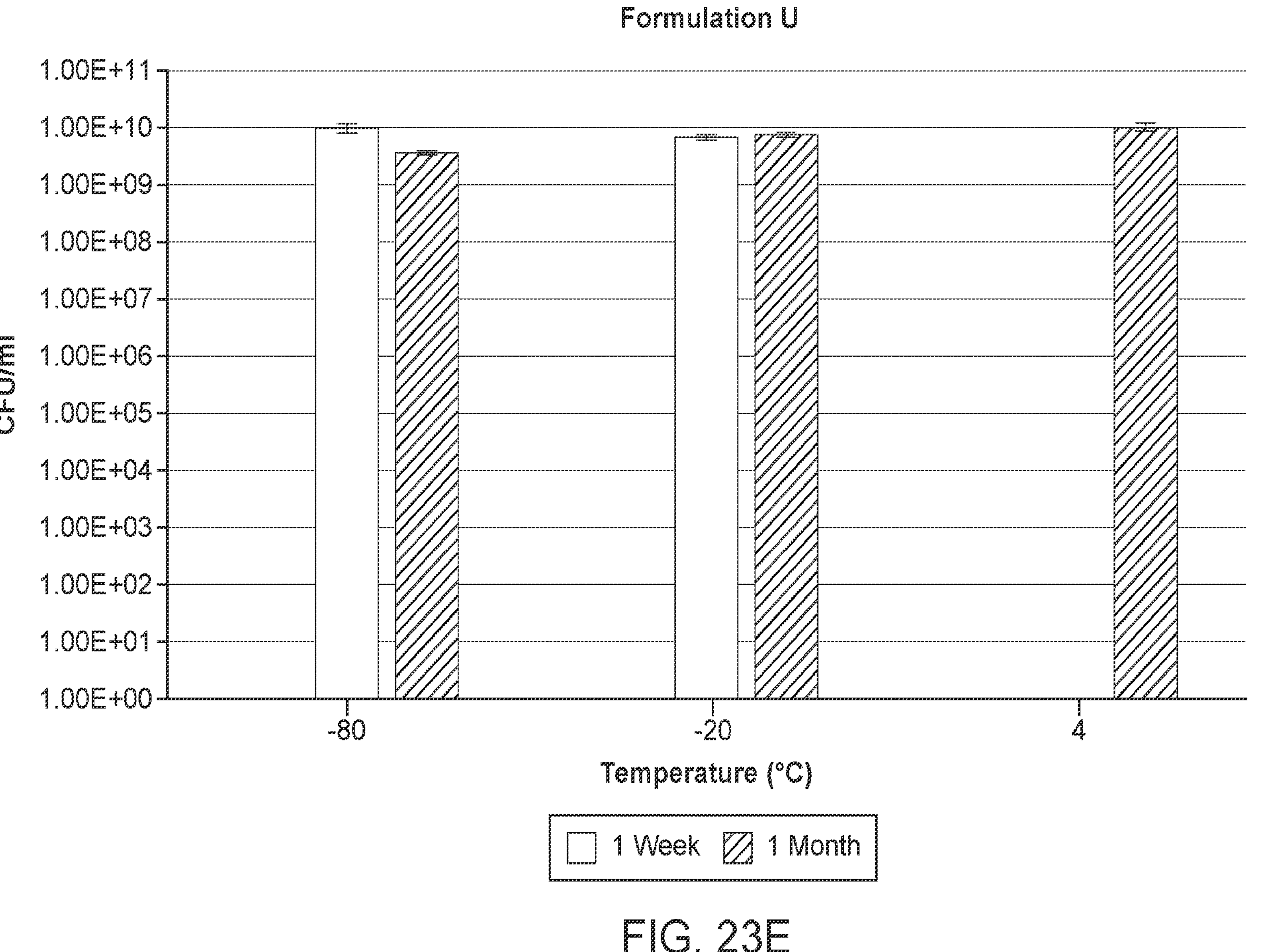

The stability data for DB05646 Formulation-Q shows that samples were stable at −80° C., −20° C., 4° C., 27° C., and 40° C. for up to at least 6 months (the longest timepoint from which data were collected) (see FIG. 23A). At higher temperatures a slight loss in viability was observed, which reduces the CFUs by about one log. Other formulations shown in Formulations R, S, T and U are similar in behavior with no loss of viability at −80° C., −20° C., 4° C. for over one month (see FIGS. 23B through 23E, respectively).

Between 10^10 and 10^11 CFU/mL were recovered from 1 mL of Formulation-Q maintained frozen at −80° C. (FIG. 23A). Viability over time was very stable when stored at −80° C., −20° C., and 4° C. for up to 4 months but some loss of viability appears begin around about 6 months. Stability of Formulation-Q also declined at 27° C. and 40° C. at all time periods tested (FIG. 23A). In all formulations the composition at temperatures of −80° C., −20° C. and 4° C., were stable and 10^10 CFU/mL were recoverable up to a month (FIGS. 23A through 23E).

Example 19: Engineered *A. faecalis* Compositions

The present Example provides engineered compositions comprising an *A. faecalis* probiotic. Reference strains as provided in Table 19 are obtained. Strains are engineered to encode a vegJ methyltransferase of SEQ ID NO: 6, or a variant thereof.

Methods

Genomic DNA from *Alcaligenes faecalis* strain DB05646 are used in a standard high-fidelity PCR using Primers, for example F-AGATCTTACCGATAGTTAAAAGTACTA (SEQ ID: 37) and R-CCTAGGT-TATCTGCCCCGCTTGCCTAAC(SEQ ID: 38). The PCR product is run on an agarose gel and the band of the right size corresponding to the size of the HDLJNHPI_02397 ycgJ putative methyltransferase (SEQ ID NO: 6) gene are excised and purified using standard techniques. The PCR product is digested using restriction enzymes XbaI and BamHI, or the appropriate restriction enzymes followed by purification before ligation into the selected vector. An appropriate vector (e.g. PSF-OXb13 medium expression *E. coli* vector from Sigma Aldrich) is linearized using XbaI and BamHI, or appropriate restriction enzymes, and purified using standard techniques. The PCR product is be ligated into the PSF-OXB13 medium expression *E. coli* vector, using manufacturer's specifications. Competent *E. coli* cells or cells of ATCC *A. faecalis* strain LRA 41 02 82 are transformed via electroporation with the PSF-OXB13 *E. coli* plasmid containing the HDLJNHPI_02397 ycgJ putative methyltransferase (SEQ ID NO: 6) gene. Kanamycin, or other appropriate antibiotic, is used as an antibiotic to select for transformed bacteria. Approximately twenty five single colonies, more if needed, are picked, cultured, stored, and confirmed to have the SEQ ID NO: 6 direct Sanger sequencing of the plasmid. The transformed strains are tested for inhibition activity against *T. rubrum, S. aureus*, and *Malassezia* species.

Targeted Mutagenesis for Loss of Function Experiments

A targeted mutagenesis kit (e.g., New England Biolabs Q5 kit) is used following manufacturer's instructions for the removal of the putative HDLJNHPI_02397 ycgJ putative methyltransferase (SEQ ID NO: 6) found in DB05646. Mutants are screened by PCR to confirm the removal of the targeted gene using primers such as F-AGATCTTACCGA-TAGTTAAAAGTACTA (SEQ ID: 39) and R-CCTAGGT-TATCTGCCCCGCTTGCCTAAC (SEQ ID: 40) and standard PCR thermocycler settings. The recovered strains missing the putative targeted gene are tested for their ability to inhibit *T. rubrum, S. aureus*, and *Malassezia* species. The inhibition assays described below are used to determine the ability of the mutant to inhibit pathogenic organisms as compared to strain DB05646 to determine the role of the HDLJNHPI_02397 ycgJ putative methyltransferase (SEQ ID NO: 6) gene in inhibition.

*Malassezia* Antibiosis Assay

In vitro assays are set up to test inhibition of *Malassezia* by transformed *E. coli* containing the ycgJ gene. Briefly, *Malassezia* is grown for 5-14 days on YPD-Mal agar plates then the fungal material from the plates are scraped into a cryotube containing 5 mm glass beads in 1 mL sterilized water. The tube is vortexed to homogenize the material. The OD 600 is measured and diluted to 0.3. 200 μl volumes of the scraped culture is spread using the beads onto Media 22 agar plates and allowed to dry to create a new cultured plate. One 5 μl spot of transformed *E. coli* with the HDLJNHPI_02397 ycgJ putative methyltransferase (SEQ ID NO: 6) gene is added to each plate and allowed to dry. Plates are incubated at 27° C. for 4 days. The widths of any zones of inhibition are measured.

Results are semi quantitative as zones of inhibition are measured. The widths of the zones are measured using ImageJ in pixels (straight line) and converted into mm based the pixel measurements of petri dishes.

*T. rubrum* Antibiosis Assay

In vitro assays are set up following a modified inhibition assay similar to the procedure reported by Ramsey et al. (2015) and optimized as described and provided herein. Briefly, *Alcaligenes faecalis* DB05646, *Bacillus* altitudinis DB10033, *Bacillus pumilus* DB03376, or *Bacillus subtilis* DB02475 cultures are grown for 24 hours in 50% LB-Lennox (LBS-50), to roughly $2\times10^9$ CFU/mL. Aliquots of cultures are applied onto 33% Tryptone agar plates in two straight perpendicular lines that run from the edge of one side of the plate to the other. Each line bisects the plate and the two lines cross in the center of the plate to make an even cross, and 4 sections are separated by lines of bacterial inoculum. The lines are struck out using a sterile cotton swab.

Conidia of *T. rubrum* are harvested from an approximately 2-week old culture grown on Sabouraud Dextrose Agar, counted using a hemocytometer under a standard light microscope, and applied at a concentration of $10^6$ spores/mL in four replicate spots with 5 μl per spot. The fungal inoculum is added to the four empty sections on the plate separated by the lines of bacterial inoculum. In this way the fungal colonies are surrounded by bacteria (or the edge of the petri dish) and do not grow into each other to make one larger colony, unless the bacteria are ineffective at inhibiting the fungal growth. The fungi have to grow over the bacteria to merge with a neighbor fungal colony. The positions of the transformed *E. coli* cross and spore spots are replicated on each plate using a template. Assay plates are incubated at ambient temperature or at 27° C. as indicated for 1 to 2 weeks. Images are taken at Day 7 and Day 14.

The inhibition of *T. rubrum* by the bacteria struck out on the plate in the cross formation are determined by the reduction of fungal colony size in mm compared to controls that have 4 *T. rubrum* dots of inoculum but no bacterial cross. Radii of *T. rubrum* colonies are first measured using ImageJ in pixels (straight line) and then converted into mm based the pixel measurements of petri dishes.

*S. aureus* Antibiosis Assay

In vitro assays are set up following standard experimental procedure. A research cell bank vial of *S. aureus* 25923 are thawed and diluted 100 fold in 50% LB-vegitone media (LB50). The final concentration of this suspension is $1\times10^6$ CFU/mL. 200 μl of this are added to LB50 agar plates, and a lawn of bacteria is dispersed over the agar using five to ten 5 mm sterile glass beads. The beads are removed and the plates allowed to dry. One or two 5 μl spots of transformed bacteria are added to each plate and allowed to dry. A mock control plate is left untouched. All plates are incubated for 24 hours at 27° C.

Results are semi quantitative as zones can be measured. The widths of the zones are first measured using ImageJ in pixels (straight line) and converted into mm based the pixel measurements of petri dishes.

| SEQUENCES |
|---|
| >DB05646_16s rRNA sequence |

(SEQ ID NO: 1)

GAACGGCAGCGCGAGAGAGCTTGCTCTCTTGGCGGCGAGTGGCGGACGGGTGAGTAATAT

ATCGGAACGTGCCCAGTAGCGGGGGATAACTACTCGAAAGAGTGGCTAATACCGCATACG

CCCTACGGGGGAAAGGGGGGGATCGCAAGACCTCTCACTATTGGAGCGGCCGATATCGGA

TTAGCTAGTTGGTGGGGTAAAGGCTCACCAAGGCAACGATCCGTAGCTGGTTTGAGAGGA

CGACCAGCCACACTGGGACTGAGACACGGCCCAGACTCCTACGGGAGGCAGCAGTGGGGA

ATTTTGGACAATGGGGGAAACCCTGATCCAGCCATCCCGCGTGTATGATGAAGGCCTTCG

GGTTGTAAAGTACTTTTGGCAGAGAAGAAAAGGTACCTCCTAATACGAGGTACTGCTGAC

GGTATCTGCAGAATAAGCACCGGCTAACTACGTGCCAGCAGCCGCGGTAATACGTAGGGT

GCAAGCGTTAATCGGAATTACTGGGCGTAAAGCGTGTGTAGGCGGTTCGGAAAGAAAGAT

GTGAAATCCCAGGGCTCAACCTTGGAACTGCATTTTTAACTGCCGAGCTAGAGTATGTCA

GAGGGGGGTAGAATTCCACGTGTAGCAGTGAAATGCGTAGATATGTGGAGGAATACCGAT

GGCGAAGGCAGCCCCCTGGGATAATACTGACGCTCAGACACGAAAGCGTGGGGAGCAAAC

AGGATTAGATACCCTGGTAGTCCACGCCCTAAACGATGTCAACTAGCTGTTGGGGCCGTT

AGGCCTTAGTAGCGCAGCTAACGCGTGAAGTTGACCGCCTGGGGAGTACGGTCGCAAGAT

TAAAACTCAAAGGAATTGACGGGGACCCGCACAAGCGGTGGATGATGTGGATTAATTCGA

TGCAACGCGAAAAACCTTACCTACCCTTGACATGTCTGGAAAGCCGAAGAGATTTGGCCG

TGCTCGCAAGAGAACCGGAACACAGGTGCTGCATGGCTGTCGTCAGCTCGTGTCGTGAGA

TGTTGGGTTAAGTCCCGCAACGAGCGCAACCCTTGTCATTAGTTGCTACGCAAGAGCACT

CTAATGAGACTGCCGGTGACAAACCGGAGGAAGGTGGGGATGACGTCAAGTCCTCATGGC

CCTTATGGGTAGGGCTTCACACGTCATACAATGGTCGGGACAGAGGGTCGCCAACCCGCG

AGGGGGAGCCAATCTCAGAAACCCGATCGTAGTCCGGATCGCAGTCTGCAACTCGACTGC

GTGAAGTCGGAATCGCTAGTAATCGCGGATCAGAATGTCGCGGTGAATACGTTCCCGGGT

CTTGTACACACCGCCCGTCACACCATGGGAGTGGGTTTCACCAGAAGTAGGTAGCCTAAC

CGTAAGGAGGGCGCTTACCACGGTGGGATTCAT

>DB10033_16S rRNA sequence (SEQ ID NO: 2)

GACTTCACCCCAATCATCTGCCCCACCTTCGGCGGCTGGCTCCATAAAGGTTACCTCACC

GACTTCGGGTGTTGCAAACTCTCGTGGTGTGACGGGCGGTGTGTACAAGGCCCGGGAACG

TATTCACCGCGGCATGCTGATCCGCGATTACTAGCGATTCCAGCTTCACGCAGTCGAGTT

GCAGACTGCGATCCGAACTGAGAACAGATTTGTGGGATTGGCTAAACCTTGCGGTCTCGC

AGCCCTTTGTTCTGTCCATTGTAGCACGTGTGTAGCCCAGGTCATAAGGGGCATGATGAT

TTGACGTCATCCCCACCTTCCTCCGGTTTGTCACCGGCAGTCACCTTAGAGTGCCCAACT

GAATGCTGGCAACTAAGATCAAGGGTTGCGCTCGTTGCGGGACTTAACCCAACATCTCAC

GACACGAGCTGACGACAACCATGCACCACCTGTCACTCTGTCCCCGAAGGGAAAGCCCTA

TCTCTAGGGTTGTCAGAGGATGTCAAGACCTGGTAAGGTTCTTCGCGTTGCTTCGAATTA

AACCACATGCTCCACCGCTTGTGCGGGCCCCCGTCAATTCCTTTGAGTTTCAGTCTTGCG

ACCGTACTCCCCAGGCGGAGTGCTTAATGCGTTAGCTGCAGCACTAAGGGGCGGAAACCC

CCTAACACTTAGCACTCATCGTTTACGGCGTGGACTACCAGGGTATCTAATCCTGTTCGC

TCCCCACGCTTTCGCTCCTCAGCGTCAGTTACAGACCAGAGAGTCGCCTTCGCCACTGGT

GTTCCTCCACATCTCTACGCATTTCACCGCTACACGTGGAATTCCACTCTCCTCTTCTGC

-continued

| SEQUENCES |
|---|

ACTCAAGTTTCCCAGTTTCCAATGACCCTCCCCGGTTGAGCCGGGGGCTTTCACATCAGA

CTTAAGAAACCGCCTGCGAGCCCTTTACGCCCAATAATTCCGGACAACGCTTGCCACCTA

CGTATTACCGCGGCTGCTGGCACGTAGTTAGCCGTGGCTTTCTGGTTAGGTACCGTCAAG

GTGCAAGCAGTTACTCTTGCACTTGTTCTTCCCTAACAACAGAGCTTTACGATCCGAAAA

CCTTCATCACTCACGCGGCGTTGCTCCGTCAGACTTTCGTCCATTGCGGAAGATTCCCTA

CTGCTGCCTCCCGTAGGAGTCTGGGCCGTGTCTCAGTCCCAGTGTGGCCGATCACCCTCT

CAGGTCGGCTACGCATCGTCGCCTTGGTGAGCCGTTACCTCACCAACTAGCTAATGCGCC

GCGGGTCCATCTGTAAGTGACAGCCGAAACCGTCTTTCATCCTTGAACCATGCGGTTCAA

GGAACTATCCGGTATTAGCTCCGGTTTCCCGGAGTTATCCCAGTCTTACAGGCAGGTTAC

CCACGTGTTACTCACCCGTCCGCCGCTAACATCCGGGAGCAAGCTCCCTTCTGTCCGCTC

GACTTGCATGTATTAGGCACGCCGCCAGCGTTCGTCCTGAGC

>DB03376_16s rRNA sequence (SEQ ID NO: 3)

TCATCTGTCCCACCTTCGGCGGCTGGCTCCATAAAGGTTACCTCACCGACTTCGGGTGTT

ACAAACTCTCGTGGTGTGACGGGCGGTGTGTACAAGGCCCGGGAACGTATTCACCGCGGC

ATGCTGATCCGCGATTACTAGCGATTCCAGCTTCACGCAGTCGAGTTGCAGACTGCGATC

CGAACTGAGAACAGATTTATGGGATTGGCTAAACCTTGCGGTCTCGCAGCCCTTTGTTCT

GTCCATTGTAGCACGTGTGTAGCCCAGGTCATAAGGGGCATGATGATTTGACGTCATCCC

CACCTTCCTCCGGTTTGTCACCGGCAGTCACCTTAGAGTGCCCAACTAAATGCTGGCAAC

TAAGATCAAGGGTTGCGCTCGTTGCGGGACTTAACCCAACATCTCACGACACGAGCTGAC

GACAACCATGCACCACCTGTCACTCTGTCCCCGAAGGGAAAGCCCTATCTCTAGGGTTGT

CAGAGGATGTCAAGACCTGGTAAGGTTCTTCGCGTTGCTTCGAATTAAACCACATGCTCC

ACCGCTTGTGCGGGCCCCCGTCAATTCCTTTGAGTTTCAGTCTTGCGACCGTACTCCCCA

GGCGGAGTGCTTAATGCGTTAGCTGCAGCACTAAGGGGCGGAAACCCCCTAACACTTAGC

ACTCATCGTTTACGGCGTGGACTACCAGGGTATCTAATCCTGTTCGCTCCCCACGCTTTC

GCTCCTCAGCGTCAGTTACAGACCAGAGAGTCGCCTTCGCCACTGGTGTTCCTCCACATC

TCTACGCATTTCACCGCTACACGTGGAATTCCACTCTCCTCTTCTGCACTCAAGTTTCCC

AGTTTCCAATGACCCTCCCCGGTTGAGCCGGGGGCTTTCACATCAGACTTAAGAAACCGC

CTGCGAGCCCTTTACGCCCAATAATTCCGGACAACGCTTGCCACCTACGTATTACCGCGG

CTGCTGGCACGTAGTTAGCCGTGGCTTTCTGGTTAGGTACCGTCAAGGTGCGAGCAGTTA

CTCTCGCACTTGTTCTTCCCTAACAACAGAGCTTTACGATCCGAAAACCTTCATCACTCA

CGCGGCGTTGCTCCGTCAGACTTTCGTCCATTGCGGAAGATTCCCTACTGCTGCCTCCCG

TAGGAGTCTGGGCCGTGTCTCAGTCCCAGTGTGGCCGATCACCCTCTCAGGTCGGCTACG

CATCGTCGCCTTGGTGAGCCATTACCCCACCAACTAGCTAATGCGCCGCGGGTCCATCTG

TAAGTGACAGCCGAAACCGTCTTTCATCCTTGAACCATGCGGTTCAAGGAACTATCCGGT

| SEQUENCES |
| --- |
| ATTAGCTCCGGTTTCCCGGAGTTATCCCAGTCTTACAGGCAGGTTACCCACGTGTTACTC |
| ACCCGTCCGCCGCTAACATCCGGGAGCAAGCTCCCTTCTGTCCGCTCGACTTGCA |
| >DB02475_16s rRNA sequence (SEQ ID NO: 4) |
| GCAGTCGAGCGGACAGATGGGAGCTTGCTCCCTGATGTTAGCGGCGGACGGGTGAGTAAC |
| ACGTGGGTAACCTGCCTGTAAGACTGGGATAACTCCGGGAAACCGGGGCTAATACCGGAT |
| GCTTGTTTGAACCGCATGGTTCAAACATAAAAGGTGGCTTCGGCTACCACTTACAGATGG |
| ACCCGCGGCGCATTAGCTAGTTGGTGAGGTAACGGCTCACCAAGGCAACGATGCGTAGCC |
| GACCTGAGAGGGTGATCGGCCACACTGGGACTGAGACACGGCCCAGACTCCTACGGGAGG |
| CAGCAGTAGGGAATCTTCCGCAATGGACGAAAGTCTGACGGAGCAACGCCGCGTGAGTGA |
| TGAAGGTTTTCGGATCGTAAAGCTCTGTTGTTAGGGAAGAACAAGTACCGTTCGAATAGG |
| GCGGTACCTTGACGGTACCTAACCAGAAAGCCACGGCTAACTACGTGCCAGCAGCCGCGG |
| TAATACGTAGGTGGCAAGCGTTGTCCGGAATTATTGGGCGTAAAGGGCTCGCAGGCGGTT |
| TCTTAAGTCTGATGTGAAAGCCCCCGGCTCAACCGGGGAGGGTCATTGGAAACTGGGGAA |
| CTTGAGTGCAGAAGAGGAGAGTGGAATTCCACGTGTAGCGGTGAAATGCGTAGAGATGTG |
| GAGGAACACCAGTGGCGAAGGCGACTCTCTGGTCTGTAACTGACGCTGAGGAGCGAAAGC |
| GTGGGGAGCGAACAGGATTAGATACCCTGGTAGTCCACGCCGTAAACGATGAGTGCTAAG |
| TGTTAGGGGTTTCCGCCCCTTAGTGCTGCAGCTAACGCATTAAGCACTCCGCCTGGGGAG |
| TACGGTCGCAAGACTGAAACTCAAAGGAATTGACGGGGGCCCGCACAAGCGGTGGAGCAT |
| GTGGTTTTTCGAAGCAACGCGAAGAACCTTACCAGTCTTGACATCCTCTGACTCCTAGAA |
| TAGGACGTCCCCTTCGGGGCAAGACGGCATATGGCGTCAGCTCGGTCTGAGTTGGGTAGT |
| CCGCACGACGGCGCACCGATCTCAGCATTCAGTTGGGCACTCTAAGGTGACTGCCGGTGA |
| CAAACCGGAGGAAGGTGGGGATGACGTCAAATCATCATGCCCCTTATGACCTGGGCTACA |
| CACGTGCTACAATGGACAGAACAAAGGGCAGCGAAACCGCGAGGTTAAGCCAATCCCACA |
| AATCTGTTCTCAGTTCGGATCGCAGTCTGCAACTCGACTGCGTGAAGCTGGAATCGCTAG |
| TAATCGCGGATCAGCATGCCGCGGTGAATACGTTCCCGGGCCTTGTACACACCGCCCGTC |
| ACACCACGAGAGTTTGTAACACCCGAAGTCGGTGAGGTAACTAACCA |
| >DB02473_16S rRNA sequence (SEQ ID NO: 5) |
| AAGGAGGTGATCCAGCCGCACCTTCCGATACGGCTACCTTGTTACGACTTCACCCCAGTC |
| ACGAATCCTACCGTGGTAAGCGCCCTCCTTACGGTTAAGCTACCTACTTCTGGTAAAACC |
| CGCTCCCATGGTGTGACGGGCGGTGTGTACAAGACCCGGGAACGTATTCACCGCGACATG |
| CTGATCCGCGATTACTAGCGATTCCAACTTCATGCAGTCGAGTTGCAGACTACAATCCGG |
| ACTACGATACACTTTCTGCGATTAGCTCCCCCTCGCGGGTTGGCGGCGCTCTGTATGTAC |
| CATTGTATGACGTGTGAAGCCCTACCCATAAGGGCCATGAGGACTTGACGTCATCCCCAC |
| CTTCCTCCGGTTTGTCACCGGCAGTCTCATTAGAGTGCCCTTTCGTAGCAACTAATGACA |
| AGGGTTGCGCTCGTTGCGGGACTTAACCCAACATCTCACGACACGAGCTGACGACAGCCA |
| TGCAGCACCTGTGTACTGGTTCTCTTTCGAGCACTCCCCAATCTCTCGAGGATTCCAGCC |
| ATGTCAAGGGTAGGTAAGGTTTTTCGCGTTGCATCGAATTAATCCACATCATCCACCGCT |
| TGTGCGGGTCCCCGTCAATTCCTTTGAGTTTTAATCTTGCGACCGTACTCCCCAGGCGGT |
| CTACTTCACGCGTTAGCTGCGTTACCAAGTCAATTAAGACCCGACAACTAGTAGACATCG |

-continued

SEQUENCES

TTTAGGGCGTGGACTACCAGGGTATCTAATCCTGTTTGCTCCCCACGCTTTCGTGCATGA

GCGTCAATCTTGACCCAGGGGGCTGCCTTCGCCATCGGTGTTCCTCCACATATCTACGCA

TTTCACTGCTACACGTGGAATTCTACCCCCCTCTGCCAGATTCTAGCCTTGCAGTCTCCA

ATGCAATTCCCAGGTTGAGCCCGGGGATTTCACATCAGACTTACAAAACCGCCTGCGCAC

GCTTTACGCCCAGTAATTCCGATTAACGCTTGCACCCTACGTATTACCGCGGCTGCTGGC

ACGTAGTTAGCCGGTGCTTATTCTTCAGGTACCGTCATTAGCAAGAGATATTAGCTCTCA

CCGTTTCTTCCCTGACAAAAGAGCTTTACAACCCGAAGGCCTTCTTCACTCACGCGGCAT

TGCTGGATCAGGCTTTCGCCCATTGTCCAAAATTCCCCACTGCTGCCTCCCGTAGGAGTC

TGGACCGTGTCTCAGTTCCAGTGTGGCTGGTCGTCCTCTCAGACCAGCTACTGATCGATG

CCTTGGTAGGCTTTTACCCTACCAACTAGCTAATCAGATATCGGCCGCTCCACGAGCATG

AGGTCTTGCGATCCCCCACTTTCATCCTTAGATCGTATGCGGTATTAGCGTAACTTTCGC

TACGTTATCCCCCACTCTAGGGTACGTTCCGATATATTACTCACCCGTTCGCCACTCGCC

ACCAGAGCAAGCTCCGTGCTGCCGTTCGACTTGCATGTGTAAGGCATGCCGCCAGCGTTC

AATCTGAGCCAGGATCAAACTCT

>HDLJNHPI_02397 ycgJ putative methyltransferase
(SEQ ID NO: 6)

ATGGCTATCAATTTTCATGATCAAAAGAATCGCAAAACCTACGCCACTCGTGAGGCGGAC

GGCTCCTGGGTGCAAGCTATCGAAACCCTGATCAACCTGTTCGGTTTGCGTGTGGCCGAT

ATAGGTTGCGGCGGCGGGATTTATTCCTCGGCCTTTCTGGATCAGGGCGCAAGCAGCGTG

GTGGGCGTGGATTTTTCTCAGGCCATGATTTCTGGCGCTCAAGAACGCAATGCGGGCCGG

GAGGGGATTGAGTTCCGTCAGGGGGACGCGACGGCGACCGGCTTGCCCTCTGAGAGTGTG

GACCTGGTTTTTCAGCGCGCCTTGATTCATCACCTGACAGACTATGAGGCCTGCTTTACC

GAAGCCAAGCGTTTGCTGGTTCCGGGTGGCGCTTTGCTGGTGCAGGACCGGACGGCGGTG

GATGTGCAGCAGCCTGCTTCAGCCTCTCATTTGCGGGGCTACTTCTTTGAATGTTTCCCC

CGCCTGTTGGAGGTGGAGCTGAAACGCCGCCCCGATACGTCCAAGGTACAGGCAGCACTG

CAGGCCGTCGGTTTTGTGGATCTGCAATCCAGCACCGTGTGGGAAGACCGGCGCTACTAC

AACAGCTTTGAGGACTATGCTCAGGAGCTGGTCCAGCGTACCGGGCGCTCTATCTTGCAT

GAGCTAAGTGACGCCGAGCTGCAAGAGCTGATCGACTATATTCGCGCCCGAGTTCCTGCG

AATCAGTCCTTTGTGGAGCGTGATTGCTGGACCTTGTGGTTAGGCAAGCGGGGCAGATAA

TABLE 31

Sequences of *Bacillus altidudinis* listed in Table 21.

| NAME | SEQUENCE | ID |
|---|---|---|
| DB02448 | GACTTCACCCCAATCATCTGCCCCACCTTCGGCGGCTGGCTCCATAAAGGTTACCTCACC<br>GACTTCGGGTGTTGCAAACTCTCGTGGTGTGACGGGCGGTGTGTACAAGGCCCGGGAACG<br>TATTCACCGCGGCATGCTGATCCGCGATTACTAGCGATTCCAGCTTCACGCAGTCGAGTT<br>GCAGACTGCGATCCGAACTGAGAACAGATTTGTGGGATTGGCTAAACCTTGCGGTCTCGC<br>AGCCCTTTGTTCTGTCCATTGTAGCACGTGTGTAGCCCAGGTCATAAGGGGCATGATGAT<br>TTGACGTCATCCCCACCTTCCTCCGGTTTGTCACCGGCAGTCACCTTAGAGTGCCCAACT<br>AAATGCTGGCAACTAAGATCAAGGGTTGCGCTCGTTGCGGGACTTAACCCAACATCTCAC<br>GACACGAGCTGACGACAACCATGCACCACCTGTCACTCTGTCCCCGAAGGGAAAGCCCTA<br>TCTCTAGGGTTGTCAGAGGATGTCAAGACCTGGTAAGGTTCTTCGCGTTGCTTCGAATTA<br>AACCACATGCTCCACCGCTTGTGCGGGCCCCCGTCAATTCCTTTGAGTTTCAGTCTTGCG<br>ACCGTACTCCCCAGGCGGAGTGCTTAATGCGTTAGCTGCAGCACTAAGGGGCGGAAACCC<br>CCTAACACTTAGCACTCATCGTTTACGGCGTGGACTACCAGGGTATCTAATCCTGTTCGC<br>TCCCCACGCTTTCGCTCCTCAGCGTCAGTTACAGACCAGAGAGTCGCCTTCGCCACTGGT | 7 |

TABLE 31-continued

Sequences of *Bacillus altidudinis* listed in Table 21.

| NAME | SEQUENCE | ID |
|---|---|---|
| | GTTCCTCCACATCTCTACGCATTTCACCGCTACACGTGGAATTCCACTCTCCTCTTCTGC<br>ACTCAAGTTTCCCAGTTTCCAATGACCCTCCCCGGTTGAGCCGGGGGCTTTCACATCAGA<br>CTTAAGAAACCGCCTGCGAGCCCTTTACGCCCAATAATTCCGGACAACGCTTGCCACCTA<br>CGTATTACCGCGGCTGCTGGCACGTAGTTAGCCGTGGCTTTCTGGTTAGGTACCGTCAAG<br>GTGCAAGCAGTTACTCTTGCACTTGTTCTTCCCTAACAACAGAGCTTTACGATCCGAAAA<br>CCTTCATCACTCACGCGGCGTTGCTCCGTCAGACTTTCGTCCATTGCGGAAGATTCCCTA<br>CTGCTGCCTCCCGTAGGAGTCTGGGCCGTGTCTCAGTCCCAGTGTGGCCGATCACCCTCT<br>CAGGTCGGCTACGCATCGTCGCCTTGGTGAGCCGTTACCTCACCAACTAGCTAATGCGCC<br>GCGGGTCCATCTGTAAGTGACAGCCGAAACCGTCTTTCATCCTTGAACCATGCGGTTCAA<br>GGAACTATCCGGTATTAGCTCCGGTTTCCCGGAGTTATCCCAGTCTTACAGGCAGGTTAC<br>CCACGTGTTACTCACCCGTCCGCCGCTAACATCCGGGAGCAAGCTCCCTTCTGTCCGCTC<br>GACTTGCATGTATTAGGCACGCCGCCAGCGTTCGTCCTGAGC | |
| DB02457 | GACTTCACCCCAATCATCTGCCCCACCTTCGGCGGCTGGCTCCATAAAGGTTACCTCACC<br>GACTTCGGGTGTTGCAAACTCTCGTGGTGTGACGGGCGGTGTGTACAAGGCCCGGGAACG<br>TATTCACCGCGGCATGCTGATCCGCGATTACTAGCGATTCCAGCTTCACGCAGTCGAGTT<br>GCAGACTGCGATCCGAACTGAGAACAGATTTGTGGGATTGGCTAAACCTTGCGGTCTCGC<br>AGCCCTTTGTTCTGTCCATTGTAGCACGTGTGTAGCCCAGGTCATAAGGGGCATGATGAT<br>TTGACGTCATCCCCACCTTCCTCCGGTTTGTCACCGGCAGTCACCTTAGAGTGCCCAACT<br>GAATGCTGGCAACTAAGATCAAGGGTTGCGCTCGTTGCGGGACTTAACCCAACATCTCAC<br>GACACGAGCTGACGACAACCATGCACCACCTGTCACTCTGTCCCCGAAGGGAAAGCCCTA<br>TCTCTAGGGTTGTCAGAGGATGTCAAGACCTGGTAAGGTTCTTCGCGTTGCTTCGAATTA<br>AACCACATGCTCCACCGCTTGTGCGGGCCCCCGTCAATTCCTTTGAGTTTCAGTCTTGCG<br>ACCGTACTCCCCAGGCGGAGTGCTTAATGCGTTAGCTGCAGCACTAAGGGGCGGAAACCC<br>CCTAACACTTAGCACTCATCGTTTACGGCGTGGACTACCAGGGTATCTAATCCTGTTCGC<br>TCCCCACGCTTTCGCTCCTCAGCGTCAGTTACAGACCAGAGAGTCGCCTTCGCCACTGGT<br>GTTCCTCCACATCTCTACGCATTTCACCGCTACACGTGGAATTCCACTCTCCTCTTCTGC<br>ACTCAAGTTTCCCAGTTTCCAATGACCCTCCCCGGTTGAGCCGGGGGCTTTCACATCAGA<br>CTTAAGAAACCGCCTGCGAGCCCTTTACGCCCAATAATTCCGGACAACGCTTGCCACCTA<br>CGTATTACCGCGGCTGCTGGCACGTAGTTAGCCGTGGCTTTCTGGTTAGGTACCGTCAAG<br>GTGCAAGCAGTTACTCTTGCACTTGTTCTTCCCTAACAACAGAGCTTTACGATCCGAAAA<br>CCTTCATCACTCACGCGGCGTTGCTCCGTCAGACTTTCGTCCATTGCGGAAGATTCCCTA<br>CTGCTGCCTCCCGTAGGAGTCTGGGCCGTGTCTCAGTCCCAGTGTGGCCGATCACCCTCT<br>CAGGTCGGCTACGCATCGTCGCCTTGGTGAGCCGTTACCTCACCAACTAGCTAATGCGCC<br>GCGGGTCCATCTGTAAGTGACAGCCGAAACCGTCTTTCATCCTTGAACCATGCGGTTCAA<br>GGAACTATCCGGTATTAGCTCCGGTTTCCCGGAGTTATCCCAGTCTTACAGGCAGGTTAC<br>CCACGTGTTACTCACCCGTCCGCCGCTAACATCCGGGAGCAAGCTCCCTTCTGTCCGCTC<br>GACTTGCATGTATTAGGCACGCCGCCAGCGTTCGTCCTGAGC | 8 |
| DB02461 | GACTTCACCCCAATCATCTGCCCCACCTTCGGCGGCTGGCTCCATAAAGGTTACCTCACC<br>GACTTCGGGTGTTGCAAACTCTCGTGGTGTGACGGGCGGTGTGTACAAGGCCCGGGAACG<br>TATTCACCGCGGCATGCTGATCCGCGATTACTAGCGATTCCAGCTTCACGCAGTCGAGTT<br>GCAGACTGCGATCCGAACTGAGAACAGATTTGTGGGATTGGCTAAACCTTGCGGTCTCGC<br>AGCCCTTTGTTCTGTCCATTGTAGCACGTGTGTAGCCCAGGTCATAAGGGGCATGATGAT<br>TTGACGTCATCCCCACCTTCCTCCGGTTTGTCACCGGCAGTCACCTTAGAGTGCCCAACT<br>GAATGCTGGCAACTAAGATCAAGGGTTGCGCTCGTTGCGGGACTTAACCCAACATCTCAC<br>GACACGAGCTGACGACAACCATGCACCACCTGTCACTCTGTCCCCGAAGGGAAAGCCCTA<br>TCTCTAGGGTTGTCAGAGGATGTCAAGACCTGGTAAGGTTCTTCGCGTTGCTTCGAATTA<br>AACCACATGCTCCACCGCTTGTGCGGGCCCCCGTCAATTCCTTTGAGTTTCAGTCTTGCG<br>ACCGTACTCCCCAGGCGGAGTGCTTAATGCGTTAGCTGCAGCACTAAGGGGCGGAAACCC<br>CCTAACACTTAGCACTCATCGTTTACGGCGTGGACTACCAGGGTATCTAATCCTGTTCGC<br>TCCCCACGCTTTCGCTCCTCAGCGTCAGTTACAGACCAGAGAGTCGCCTTCGCCACTGGT<br>GTTCCTCCACATCTCTACGCATTTCACCGCTACACGTGGAATTCCACTCTCCTCTTCTGC<br>ACTCAAGTTTCCCAGTTTCCAATGACCCTCCCCGGTTGAGCCGGGGGCTTTCACATCAGA<br>CTTAAGAAACCGCCTGCGAGCCCTTTACGCCCAATAATTCCGGACAACGCTTGCCACCTA<br>CGTATTACCGCGGCTGCTGGCACGTAGTTAGCCGTGGCTTTCTGGTTAGGTACCGTCAAG<br>GTGCAAGCAGTTACTCTTGCACTTGTTCTTCCCTAACAACAGAGCTTTACGATCCGAAAA<br>CCTTCATCACTCACGCGGCGTTGCTCCGTCAGACTTTCGTCCATTGCGGAAGATTCCCTA<br>CTGCTGCCTCCCGTAGGAGTCTGGGCCGTGTCTCAGTCCCAGTGTGGCCGATCACCCTCT<br>CAGGTCGGCTACGCATCGTCGCCTTGGTGAGCCGTTACCTCACCAACTAGCTAATGCGCC<br>GCGGGTCCATCTGTAAGTGACAGCCGAAACCGTCTTTCATCCTTGAACCATGCGGTTCAA<br>GGAACTATCCGGTATTAGCTCCGGTTTCCCGGAGTTATCCCAGTCTTACAGGCAGGTTAC<br>CCACGTGTTACTCACCCGTCCGCCGCTAACATCCGGGAGCAAGCTCCCTTCTGTCCGCTC<br>GACTTGCATGTATTAGGCACGCCGCCAGCGTTCGTCCTGAGC | 9 |
| DB02478 | GACTTCACCCCAATCATCTGCCCCACCTTCGGCGGCTGGCTCCATAAAGGTTACCTCACC<br>GACTTCGGGTGTTGCAAACTCTCGTGGTGTGACGGGCGGTGTGTACAAGGCCCGGGAACG<br>TATTCACCGCGGCATGCTGATCCGCGATTACTAGCGATTCCAGCTTCACGCAGTCGAGTT<br>GCAGACTGCGATCCGAACTGAGAACAGATTTGTGGGATTGGCTAAACCTTGCGGTCTCGC<br>AGCCCTTTGTTCTGTCCATTGTAGCACGTGTGTAGCCCAGGTCATAAGGGGCATGATGAT<br>TTGACGTCATCCCCACCTTCCTCCGGTTTGTCACCGGCAGTCACCTTAGAGTGCCCAACT<br>GAATGCTGGCAACTAAGATCAAGGGTTGCGCTCGTTGCGGGACTTAACCCAACATCTCAC<br>GACACGAGCTGACGACAACCATGCACCACCTGTCACTCTGTCCCCGAAGGGAAAGCCCTA<br>TCTCTAGGGTTGTCAGAGGATGTCAAGACCTGGTAAGGTTCTTCGCGTTGCTTCGAATTA<br>AACCACATGCTCCACCGCTTGTGCGGGCCCCCGTCAATTCCTTTGAGTTTCAGTCTTGCG<br>ACCGTACTCCCCAGGCGGAGTGCTTAATGCGTTAGCTGCAGCACTAAGGGGCGGAAACCC | 10 |

TABLE 31-continued

| Sequences of *Bacillus altidudinis* listed in Table 21. | | |
|---|---|---|
| NAME | SEQUENCE | ID |
| | CCTAACACTTAGCACTCATCGTTTACGGCGTGGACTACCAGGGTATCTAATCCTGTTCGC TCCCCACGCTTTCGCTCCTCAGCGTCAGTTACAGACCAGAGAGTCGCCTTCGCCACTGGT GTTCCTCCACATCTCTACGCATTTCACCGCTACACGTGGAATTCCACTCTCCTCTTCTGC ACTCAAGTTTCCCAGTTTCCAATGACCCTCCCCGGTTGAGCCGGGGGCTTTCACATCAGA CTTAAGAAACCGCCTGCGAGCCCTTTACGCCCAATAATTCCGGACAACGCTTGCCACCTA CGTATTACCGCGGCTGCTGGCACGTAGTTAGCCGTGGCTTTCTGGTTAGGTACCGTCAAG GTGCAAGCAGTTACTCTTGCACTTGTTCTTCCCTAACAACAGAGCTTTACGATCCGAAAA CCTTCATCACTCACGCGGCGTTGCTCCGTCAGACTTTCGTCCATTGCGGAAGATTCCCTA CTGCTGCCTCCCGTAGGAGTCTGGGCCGTGTCTCAGTCCCAGTGTGGCCGATCACCCTCT CAGGTCGGCTACGCATCGTCGCCTTGGTGAGCCGTTACCTCACCAACTAGCTAATGCGCC GCGGGTCCATCTGTAAGTGACAGCCGAAACCGTCTTTCATCCTTGAACCATGCGGTTCAA GGAACTATCCGGTATTAGCTCCGGTTTCCCGGAGTTATCCCAGTCTTACAGGCAGGTTAC CCACGTGTTACTCACCCGTCCGCCGCTAACATCCGGGAGCAAGCTCCCTTCTGTCCGCTC GACTTGCATGTATTAGGCACGCCGCCAGCGTTCGTCCTGAGC | |
| DB02549 | GCTCAGGACGAACGCTGGCGGCGTGCCTAATACATGCAAGTCGAGCGGACAGAAGGGAGC TTGCTCCCGGATGTTAGCGGCGGACGGGTGAGTAACACGTGGGTAACCTGCCTGTAAGAC TGGGATAACTCCGGGAAACCGGAGCTAATACCGGATAGTTCCTTGAACCGCATGGTTCAA GGATGAAAGACGGTTTCGGCTGTCACTTACAGATGGACCCGCGGCGCATTAGCTAGTTGG TGAGGTAACGGCTCACCAAGGCGACGATGCGTAGCCGACCTGAGAGGGTGATCGGCCACA CTGGGACTGAGACACGGCCCAGACTCCTACGGGAGGCAGCAGTAGGGAATCTTCCGCAAT GGACGAAAGTCTGACGGAGCAACGCCGCGTGAGTGATGAAGGTTTTCGGATCGTAAAGCT CTGTTGTTAGGGAAGAACAAGTGCAAGAGTAACTGCTTGCACCTTGACGGTACCTAACCA GAAAGCCACGGCTAACTACGTGCCAGCAGCCGCGGTAATACGTAGGTGGCAAGCGTTGTC CGGAATTATTGGGCGTAAAGGGCTCGCAGGCGGTTTCTTAAGTCTGATGTGAAAGCCCCC GGCTCAACCGGGGAGGGTCATTGGAAACTGGGAAACTTGAGTGCAGAAGAGGAGAGTGGA ATTCCACGTGTAGCGGTGAAATGCGTAGAGATGTGGAGGAACACCAGTGGCGAAGGCGAC TCTCTGGTCTGTAACTGACGCTGAGGAGCGAAAGCGTGGGGAGCGAACAGGATTAGATAC CCTGGTAGTCCACGCCGTAAACGATGAGTGCTAAGTGTTAGGGGGTTTCCGCCCCTTAGT GCTGCAGCTAACGCATTAAGCACTCCGCCTGGGGAGTACGGTCGCAAGACTGAAACTCAA AGGAATTGACGGGGGCCCGCACAAGCGGTGGAGCATGTGGTTTAATTCGAAGCAACGCGA AGAACCTTACCAGGTCTTGACATCCTCTGACAACCCTAGAGATAGGGCTTTCCCTTCGGG GACAGAGTGACAGGTGGTGCATGGTTGTCGTCAGCTCGTGTCGTGAGATGTTGGGTTAAG TCCCGCAACGAGCGCAACCCTTGATCTTAGTTGCCAGCATTTAGTTGGGCACTCTAAGGT GACTGCCGGTGACAAACCGGAGGAAGGTGGGGATGACGTCAAATCATCATGCCCCTTATG ACCTGGGCTACACACGTGCTACAATGGACAGAACAAAGGGCTGCGAGACCGCAAGGTTTA GCCAATCCCACAAATCTGTTCTCAGTTCGGATCGCAGTCTGCAACTCGACTGCGTGAAGC TGGAATCGCTAGTAATCGCGGATCAGCATGCCGCGGTGAATACGTTCCCGGGCCTTGTAC ACACCGCCCGTCACACCACGAGAGTTTGCAACACCCGAAGTCGGTGAGGTAACCTTTATG GAGCCAGCCGCCGAAGGTGGGGCAGATGATTGGGGTGAAGTC | 11 |
| DB02623 | GCTCAGGACGAACGCTGGCGGCGTGCCTAATACATGCAAGTCGAGCGGACAGAAGGGAGC TTGCTCCCGGATGTTAGCGGCGGACGGGTGAGTAACACGTGGGTAACCTGCCTGTAAGAC TGGGATAACTCCGGGAAACCGGAGCTAATACCGGATAGTTCCTTGAACCGCATGGTTCAA GGATGAAAGACGGTTTCGGCTGTCACTTACAGATGGACCCGCGGCGCATTAGCTAGTTGG TGAGGTAACGGCTCACCAAGGCGACGATGCGTAGCCGACCTGAGAGGGTGATCGGCCACA CTGGGACTGAGACACGGCCAAGACTCCTACGGGAGGCAGCAGTAGGGAATCTTCCGCAAT GGACGAAAGTCTGACGGAGCAACGCCGCGTGAGTGATGAAGGTTTTCGGATCGTAAAGCT CTGTTGTTAGGGAAGAACAAGTGCAAGAGTAACTGCTTGCACCTTGACGGTACCTAACCA GAAAGCCACGGCTAACTACGTGCCAGCAGCCGCGGTAATACGTAGGTGGCAAGCGTTGTC CGGAATTATTGGGCGTAAAGGGCTCGCAGGCGGTTTCTTAAGTCTGATGTGAAAGCCCCC GGCTCAACCGGGGAGGGTCATTGGAAACTGGGAAACTTGAGTGCAGAAGAGGAGAGTGGA ATTCCACGTGTAGCGGTGAAATGCGTAGAGATGTGGAGGAACACCAGTGGCGAAGGCGAC TCTCTGGTCTGTAACTGACGCTGAGGAGCGAAAGCGTGGGGAGCGAACAGGATTAGATAC CCTGGTAGTCCACGCCGTAAACGATGAGTGCTAAGTGTTAGGGGGTTTCCGCCCCTTAGT GCTGCAGCTAACGCATTAAGCACTCCGCCTGGGGAGTACGGTCGCAAGACTGAAACTCAA AGGAATTGACGGGGGCCCGCACAAGCGGTGGAGCATGTGGTTTAATTCGAAGCAACGCGA AGAACCTTACCAGGTCTTGACATCCTCTGACAACCCTAGAGATAGGGCTTTCCCTTCGGG GACAGAGTGACAGGTGGTGCATGGTTGTCGTCAGCTCGTGTCGTGAGATGTTGGGTTAAG TCCCGCAACGAGCGCAACCCTTGATCTTAGTTGCCAGCATTTAGTTGGGCACTCTAAGGT GACTGCCGGTGACAAACCGGAGGAAGGTGGGGATGACGTCAAATCATCATGCCCCTTATG ACCTGGGCTACACACGTGCTACAATGGACAGAACAAAGGGCTGCGAGACCGCAAGGTTTA GCCAATCCCACAAATCTGTTCTCAGTTCGGATCGCAGTCTGCAACTCGACTGCGTGAAGC TGGAATCGCTAGTAATCGCGGATCAGCATGCCGCGGTGAATACGTTCCCGGGCCTTGTAC ACACCGCCCGTCACACCACGAGAGTTTGCAACACCCGAAGTCGGTGAGGTAACCTTTATG GAGCCAGCCGCCGAAGGTGGGGCAGATGATTGGGGTGAAGTC | 12 |

TABLE 32

Sequences of *Bacillus pumilus* listed in Table 23.

| NAME | SEQUENCE | ID |
|---|---|---|
| DB01269 | TCATCTGTCCCACCTTCGGCGGCTGGCTCCATAAAGGTTACCTCACCGACTTCGGGTGTT<br>ACAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGT | 13 |
| DB02420 | TCATCTGCCCCACCTTCGGCGGCTGGCTCCATAAAGGTTACCTCACCGACTTCGGGTGTT<br>GCAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGTTCGCTCGACTTGCA | 14 |
| DB02429 | TCATCTGCCCCACCTTCGGCGGCTGGCTCCATAAAGGTTACCTCACCGACTTCGGGTGTT<br>GCAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTCCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGTTCGCTCGACTTGCA | 15 |

TABLE 32-continued

Sequences of *Bacillus pumilus* listed in Table 23.

| NAME | SEQUENCE | ID |
|---|---|---|
| DB02430 | TCATCTGTCCCACCTTCGGCGGCTGGCTCCATAAAGGTTACCTCACCGACTTCGGGTGTT<br>ACAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGTTCGCTCGACTTGCA | 16 |
| DB02485 | GCACTAAGGGGCGGAAACCCCCTAACACTTAGCACTCATCGTTTACGGCGTGGACTACCA<br>GGGTATCTAATCCTGTTCGCTCCCCACGCTTTCGCTCCTCAGCGTCAGTTACAGACCAGA<br>GAGTCGCCTTCGCCACTGGTGTTCCTCCACATCTCTACGCATTTCACCGCTACACGTGGA<br>ATTCCACTCTCCTCTTCTGCACTCAAGTTTCCCAGTTTCCAATGACCCTCCCCGGTTGAG<br>CCGGGGGCTTTCACATCAGACTTAAGAAACCGCCTGCGAGCCCTTTACGCCCAATAATTC<br>CGGACAACGCTTGCCACCTACGTATTACCGCGGCTGCTGGCACGTAGTTAGCCGTGGCTT<br>TCTGGTTAGGTACCGTCAAGGTGCGAGCAGTTACTCTCGCACTTGTTCTTCCCTAACAAC<br>AGAGCTTTACGATCCGAAAACCTTCATCACTCACGCGGCGTTGCTCCGTCAGACTTTCGT<br>CCATTGCGGAAGATTCCCTACTGCTGCCTCCCGTAGGAGTCTGGGCCGTGTCTCAGTCCC<br>AGTGTGGCCGATCACCCTCTCAGGTCGGCTACGCATCGTCGCCTTGGTGAGCCATTACCC<br>CACCAACTAGCTAATGCGCCGCGGGTCCATCTGTAAGTGACAGCCGAAACCGTCTTTCAT<br>CCTTGAACCATGCGGTTCAAGGAACTATCCGGTATTAGCTCCGGTTTCCCGGAGTTATCC<br>CAGTCTTACAGGCAGGTTACCCACGTGTTACTCACCCGTCCGCCGCTAACATCCGGGAGC<br>AAGCTCCCTTCTGTTCGCTCGACTTGCA | 17 |
| DB02492 | TCATCTGCCCCACCTTCGGCGGCTGGCTCCATAAAGGTTACCTCACCGACTTCGGGTGTT<br>GCAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGTTCGCTCGACTTGCA | 18 |
| DB02548 | TCGTGGTGTGACGGGCGGTGTGTACAAGGCCCGGGAACGTATTCACCGCGGCATGCTGAT<br>CCGCGATTACTAGCGATTCCAGCTTCACGCAGTCGAGTTGCAGACTGCGATCCGAACTGA<br>GAACAGATTTGTGGGATTGGCTAAACCTTGCGGTCTCGCAGCCCTTTGTTCTGTCCATTG<br>TAGCACGTGTGTAGCCCAGGTCATAAGGGGCATGATGATTTGACGTCATCCCCACCTTCC<br>TCCGGTTTGTCACCGGCAGTCACCTTAGAGTGCCCAACTGAATGCTGGCAACTAAGATCA<br>AGGGTTGCGCTCGTTGCGGGACTTAACCCAACATCTCACGACACGAGCTGACGACAACCA<br>TGCACCACCTGTCACTCTGTCCCCGAAGGGAAAGCCCTATCTCTAGGGTTGTCAGAGGAT<br>GTCAAGACCTGGTAAGGTTCTTCGCGTTGCTTCGAATTAAACCACATGCTCCACCGCTTG<br>TGCGGGCCCCCGTCAATTCCTTTGAGTTTCAGTCTTGCGACCGTACTCCCCAGGCGGAGT<br>GCTTAATGCGTTAGCTGCAGCACTAAGGGGCGGAAACCCCCTAACACTTAGCACTCATCG<br>TTTACGGCGTGGACTACCAGGGTATCTAATCCTGTTCGCTCCCCACGCTTTCGCTCCTCA | 19 |

TABLE 32-continued

Sequences of *Bacillus pumilus* listed in Table 23.

| NAME | SEQUENCE | ID |
|---|---|---|
| | GCGTCAGTTACAGACCAGAGAGTCGCCTTCGCCACTGGTGTTCCTCCACATCTCTACGCA<br>TTTCACCGCTACACGTGGAATTCCACTCTCCTCTTCTGCACTCAAGTTTCCCAGTTTCCA<br>ATGACCCTCCCCGGTTGAGCCGGGGGCTTTCACATCAGACTTAAGAAACCGCCTGCGAGC<br>CCTTTACGCCCAATAATTCCGGACAACGCTTGCCACCTACGTATTACCGCGGCTGCTGGC<br>ACGTAGTTAGCCGTGGCTTTCTGGTTAGGTACCGTCAAGGTGCAAGCAGTTACTCTTGCA<br>CTTGTTCTTCCCTAACAACAGAGCTTTACGATCCGAAAACCTTCATCACTCACGCGGCGT<br>TGCTCCGTCAGACTTTCGTCCATTGCGGAAGATTCCCTACTGCTGCCTCCCGTAGGAGTC<br>TGGGCCGTGTCTCAGTCCCAGTGTGGCCGATCACCCTCTCAGGTCGGCTACGCATCGTCG<br>CCTTGGTGAGCCGTTACCTCACCAACTAGCTAATGCGCCGCGGGTCCATCTGTAAGTGAC<br>AGCCGAAACCGTCTTTCATCCTTGAACCATGCGGTTCAAGGAACTATCCGGTATTAGCTC<br>CGGTTTCCCGGAGTTATCCCAGTCTTACAGGCAGGTTACCCACGTGTTACTCACCCGTCC<br>GCCGCTAACATCCGGGAGCAAGCTCCCTTCTGTCCGCTCGACTTGCA | |
| DB02622 | TCATCTGCCCCACCTTCGGCGGCTGGCTCCATAAAGGTTACCTCACCGACTTCGGGTGTT<br>GCAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGT | 20 |
| DB02626 | CACCGGCAGTCACCTTAGAGTGCCCAACTAAATGCTGGCAACTAAGATCAAGGGTTGCGC<br>TCGTTGCGGGACTTAACCCAACATCTCACGACACGAGCTGACGACAACCATGCACCACCT<br>GTCACTCTGTCCCCGAAGGGAAAGCCCTATCTCTAGGGTTGTCAGAGGATGTCAAGACCT<br>GGTAAGGTTCTTCGCGTTGCTTCGAATTAAACCACATGCTCCACCGCTTGTGCGGGCCCC<br>CGTCAATTCCTTTGAGTTTCAGTCTTGCGACCGTACTCCCCAGGCGGAGTGCTTAATGCG<br>TTAGCTGCAGCACTAAGGGGCGGAAACCCCCTAACACTTAGCACTCATCGTTTACGGCGT<br>GGACTACCAGGGTATCTAATCCTGTTCGCTCCCCACGCTTTCGCTCCTCAGCGTCAGTTA<br>CAGACCAGAGAGTCGCCTTCGCCACTGGTGTTCCTCCACATCTCTACGCATTTCACCGCT<br>ACACGTGGAATTCCACTCTCCTCTTCTGCACTCAAGTTTCCCAGTTTCCAATGACCCTCC<br>CCGGTTGAGCCGGGGGCTTTCACATCAGACTTAAGAAACCGCCTGCGAGCCCTTTACGCC<br>CAATAATTCCGGACAACGCTTGCCACCTACGTATTACCGCGGCTGCTGGCACGTAGTTAG<br>CCGTGGCTTTCTGGTTAGGTACCGTCAAGGTGCGAGCAGTTACTCTCGCACTTGTTCTTC<br>CCTAACAACAGAGCTTTACGATCCGAAAACCTTCATCACTCACGCGGCGTTGCTCCGTCA<br>GACTTTCGTCCATTGCGGAAGATTCCCTACTGCTGCCTCCCGTAGGAGTCTGGGCCGTGT<br>CTCAGTCCCAGTGTGGCCGATCACCCTCTCAGGTCGGCTACGCATCGTCGCCTTGGTGAG<br>CCATTACCCCACCAACTAGCTAATGCGCCGCGGGTCCATCTGTAAGTGACAGCCGAAACC<br>GTCTTTCATCCTTGAACCATGCGGTTCAAGGAACTATCCGGTATTAGCTCCGGTTTCCCG<br>GAGTTATCCCAGTCTTACAGGCAGGTTACCCACGTGTTACTCACCCGTCCGCCGCTAACA<br>TCCGGGAGCAAGCTCCCTTCTGTCCGCTCGACTTGCA | 21 |
| DB02680 | TCATCTGTCCCACCTTCGGCGGCTGGCTCCATAAAGGTTACCTCACCGACTTCGGGTGTT<br>ACAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA | 22 |

TABLE 32-continued

| Sequences of *Bacillus pumilus* listed in Table 23. | | |
|---|---|---|
| NAME | SEQUENCE | ID |
| | CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGTTCGCTCGACTTGCA | |
| DB02681 | TCATCTGTCCCACCTTCGGCGGCTGGCTCCATAAAGGTTACCTCACCGACTTCGGGTGTT<br>ACAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGTTCGCTCGACTTGCA | 23 |
| DB02708 | TCATCTGCCCCACCTTCGGCGGCTGGCTCCATAAAGGTTACCTCACCGACTTCGGGTGTT<br>GCAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG<br>TAGGAGTCTGGGCCGTGTCTCAGTCCCAGTGTGGCCGATCACCCTCTCAGGTCGGCTACG<br>CATCGTCGCCTTGGTGAGCCATTACCCCACCAACTAGCTAATGCGCCGCGGGTCCATCTG<br>TAAGTGACAGCCGAAACCGTCTTTCATCCTTGAACCATGCGGTTCAAGGAACTATCCGGT<br>ATTAGCTCCGGTTTCCCGGAGTTATCCCAGTCTTACAGGCAGGTTACCCACGTGTTACTC<br>ACCCGTCCGCCGCTAACATCCGGGAGCAAGCTCCCTTCTGTTCGCTCGACTTGCA | 24 |
| DB03355 | TCATCTGCCCCACCTTCGGCGGCTGGCTCCATAAAGGTTACCTCACCGACTTCGGGTGTT<br>GCAAACTCTCGTGGTGTGACGGGCGGTGTGTACAAGGCCCGGGAACGTATTCACCGCGGC<br>ATGCTGATCCGCGATTACTAGCGATTCCAGCTTCACGCAGTCGAGTTGCAGACTGCGATC<br>CGAACTGAGAACAGATTTATGGGATTGGCTAAACCTTGCGGTCTCGCAGCCCTTTGTTCT<br>GTCCATTGTAGCACGTGTGTAGCCCAGGTCATAAGGGGCATGATGATTTGACGTCATCCC<br>CACCTTCCTCCGGTTTGTCACCGGCAGTCACCTTAGAGTGCCCAACTAAATGCTGGCAAC<br>TAAGATCAAGGGTTGCGCTCGTTGCGGGACTTAACCCAACATCTCACGACACGAGCTGAC<br>GACAACCATGCACCACCTGTCACTCTGTCCCCGAAGGGAAAGCCCTATCTCTAGGGTTGT<br>CAGAGGATGTCAAGACCTGGTAAGGTTCTTCGCGTTGCTTCGAATTAAACCACATGCTCC<br>ACCGCTTGTGCGGGCCCCCGTCAATTCCTTTGAGTTTCAGTCTTGCGACCGTACTCCCCA<br>GGCGGAGTGCTTAATGCGTTAGCTGCAGCACTAAGGGGCGGAAACCCCCTAACACTTAGC<br>ACTCATCGTTTACGGCGTGGACTACCAGGGTATCTAATCCTGTTCGCTCCCCACGCTTTC<br>GCTCCTCAGCGTCAGTTACAGACCAGAGAGTCGCCTTCGCCACTGGTGTTCCTCCACATC<br>TCTACGCATTTCACCGCTACACGTGGAATTCCACTCTCCTCTTCTGCACTCAAGTTTCCC<br>AGTTTCCAATGACCCTCCCCGGTTGAGCCGGGGGCTTTCACATCAGACTTAAGAAACCGC<br>CTGCGAGCCCTTTACGCCCAATAATTCCGGACAACGCTTGCCACCTACGTATTACCGCGG<br>CTGCTGGCACGTAGTTAGCCGTGGCTTTCTGGTTAGGTACCGTCAAGGTGCGAGCAGTTA<br>CTCTCGCACTTGTTCTTCCCTAACAACAGAGCTTTACGATCCGAAAACCTTCATCACTCA<br>CGCGGCGTTGCTCCGTCAGACTTTCGTCCATTGCGGAAGATTCCCTACTGCTGCCTCCCG | 25 |

TABLE 32-continued

| Sequences of *Bacillus pumilus* listed in Table 23. | | |
|---|---|---|
| NAME | SEQUENCE | ID |
| | TAGGAGTCTGGGCCGTGTCTCAGTCCCAGTGTGGCCGATCACCCTCTCAGGTCGGCTACG CATCGTCGCCTTGGTGAGCCATTACCCCACCAACTAGCTAATGCGCCGCGGGTCCATCTG TAAGTGACAGCCGAAACCGTCTTTCATCCTTGAACCATGCGGTTCAAGGAACTATCCGGT ATTAGCTCCGGTTTCCCGGAGTTATCCCAGTCTTACAGGCAGGTTACCCACGTGTTACTC ACCCGTCCGCCGCTAACATCCGGGAGCAAGCTCCCTTCTGTTCGCTCGACTTGCA | |
| DB03366 | TCATCTGCCCCACCTTCGGCGGCTGGCTCCATAAAGGTTACCTCACCGACTTCGGGTGTT GCAAACTCTCGTGGTGTGACGGGCGGTGTGTACAAGGCCCGGGAACGTATTCACCGCGGC ATGCTGATCCGCGATTACTAGCGATTCCAGCTTCACGCAGTCGAGTTGCAGACTGCGATC CGAACTGAGAACAGATTTATGGGATTGGCTAAACCTTGCGGTCTCGCAGCCCTTTGTTCT GTCCATTGTAGCACGTGTGTAGCCCAGGTCATAAGGGGCATGATGATTTGACGTCATCCC CACCTTCCTCCGGTTTGTCACCGGCAGTCACCTTAGAGTGCCCAACTAAATGCTGGCAAC TAAGATCAAGGGTTGCGCTCGTTGCGGGACTTAACCCAACATCTCACGACACGAGCTGAC GACAACCATGCACCACCTGTCACTCTGTCCCCGAAGGGAAAGCCCTATCTCTAGGGTTGT CAGAGGATGTCAAGACCTGGTAAGGTTCTTCGCGTTGCTTCGAATTAAACCACATGCTCC ACCGCTTGTGCGGGCCCCCGTCAATTCCTTTGAGTTTCAGTCTTGCGACCGTACTCCCCA GGCGGAGTGCTTAATGCGTTAGCTGCAGCACTAAGGGGCGGAAACCCCCTAACACTTAGC ACTCATCGTTTACGGCGTGGACTACCAGGGTATCTAATCCTGTTCGCTCCCCACGCTTTC GCTCCTCAGCGTCAGTTACAGACCAGAGAGTCGCCTTCGCCACTGGTGTTCCTCCACATC TCTACGCATTTCACCGCTACACGTGGAATTCCACTCTCCTCTTCTGCACTCAAGTTTCCC AGTTTCCAATGACCCTCCCCGGTTGAGCCGGGGGCTTTCACATCAGACTTAAGAAACCGC CTGCGAGCCCTTTACGCCCAATAATTCCGGACAACGCTTGCCACCTACGTATTACCGCGG CTGCTGGCACGTAGTTAGCCGTGGCTTTCTGGTTAGGTACCGTCAAGGTGCGAGCAGTTA CTCTCGCACTTGTTCTTCCCTAACAACAGAGCTTTACGATCCGAAAACCTTCATCACTCA CGCGGCGTTGCTCCGTCAGACTTTCGTCCATTGCGGAAGATTCCCTACTGCTGCCTCCCG TAGGAGTCTGGGCCGTGTCTCAGTCCCAGTGTGGCCGATCACCCTCTCAGGTCGGCTACG CATCGTCGCCTTGGTGAGCCATTACCCCACCAACTAGCTAATGCGCCGCGGGTCCATCTG TAAGTGACAGCCGAAACCGTCTTTCATCCTTGAACCATGCGGTTCAAGGAACTATCCGGT ATTAGCTCCGGTTTCCCGGAGTTATCCCAGTCTTACAGGCAGGTTACCCACGTGTTACTC ACCCGTCCGCCGCTAACATCCGGGAGCAAGCTCCCTTCTGTTCGCTCGACTTGCA | 26 |

TABLE 33

| Sequences of *Bacillus subtilis* listed in Table 25. | | |
|---|---|---|
| NAME | SEQUENCE | ID |
| DB01270 | AGTCATCATGGGAATCCCTGCGTACGGCTATGACTGGGATGTAAAAGACGGAAGTACCAG CACAATAAGGGAATGGAATGAGCTCAAATCCCTCATCAAAAAACAAAAAGCAAAGCCGGC ATTCAACAAAAAATCAGGCTCGATGACATTTTCTTATGTTGACAAAAAGAAGCATAAACA TGTCGTGTGGTATGAAAACGAAAAAACCGTTCAAACGAAAAGCCATCTGGCAAAGCAATA TAAAATAGCAGGTGTTTCAGTTTACGCATTAGGAAACGAGTCAGAATCCTTTTGGAAAGC CATTCGAAAAGGGACAAAATAACAGTTTCTTTTTTCTCTGAAGTTATTGACAGTTAAAAG AGAAGCACGTATATTATGTTAATATATTCAGATCATAAAATTTGAGTTTTTCAGAAAACT AAAACACATAGATTGGGAGCAGTAAAAGAAAGTGATCAGAACAGAGAGCTGCGGGGTGGT GCGACGCAGCCTGATTCTTCTTTGAACTCGCCCGGGAGTGGTAAGACGGAACGGAATAGA TTGAATATTCCCTATGTTTTAACGGCTAACCTTCGTTACAGGTCAAAAGCAGGATTCTTC ATGAAGAATCAACAAGAGTGGTACCGCGGTCAGCCGAAGGCTCGTCGTCTCTTTATCTAT TAGATTAGGTAGGAGACGGCGGGCTTTTTTGTTTTTGAAAACGAGAATGAGAGGTAGAAG AGGATGAAAAACGACAATCAAACGTTAAAACGCACGATGACGTCCCGCCATATTATGATG ATGGCGCTGGGCGGAGCAATCGGCGCAGGTTTATTTAAGGGGGAGCAGCTCAGCGATCGAT GTGGCAGGGCCATCTGTCATTATCGCATACCTGCTCGGCGGGATTATTTTGCTGTTTATT ATGCAGGGGCTGGCGGAAATGGCTGTTCGAAACCGTAACGCCAGAACCTTCCGTGATCTT GTCCAGCAGGTATTGGGAAATTACGCTGCTTACTTTTTGGACTGGATCTACTGGAAAATG TGGGTGCTTAACATTGCGGCTGAAGCTGTTGTAGCTGCGATTTTCATTCAATATTGGCTG CCGGGCTGCCCGATCTGGGTGTTGGCATTAGGAATTTCTCTTATCGTCACGATTGTAAAC TTGCTTTCTGTTAAAATCTTCGCCGAAACTGAATATTGGCTGGCAATGATCAAGATTACC GTTATTATTATCTTTATTATTCTGGGATTGCTGCTCTTATTTGTATCATTCGGTGATCAT ACAGCATCCGGATTTTCCAACCTGACAGACCACGGCGGATTTTTCCCGCACGGCGGCACA GGGCTGATCACGGCGATGCTTGTCGTCATCTACTCTTACGGCGGTACAGAAATTATCGGT GTAACGCTTGCAGAGACAAAAAATCCGGAAAAGGTTGTCCCGAAAGCTGTCCGCAGCACA CTGACACGGATTGTCGCGTTTTACCTGCTGCCGTTTTTCATCATCGTCAGCCTGATTCCA TGGAACCAAGTCAATTCGGTTCCGGAAAGTCCTTTCGTGATGGTCTTTAAAATGGTAGGC ATTCCGGGCGCGGATCATATCATGAATGCAGTCATCCTGCTGGCGATCATTTCTTCTATG AATTCAGGTTTATACGGATCATCACGCATTTTGTATACACAGGCAAGTGACGGAAGGCTT CCAAAAATCTTCTCGAAGCTTTCATCGAAAAACGTACCGATGTTTGCGATTCTGATGTGC ACTTCTTCTCTCTATATTGGCGTATTGATTTCTCTGTTCGCAGGAAGCCAAACATTTAAT TATTTAATGGGATCATTGGGATATACCGTTTTATTCATTTGGCTGATCATCGGATTCGCT CATTTAAAATCGAGAAAACAGCAAACGGAAACACCGGCCTATTATGTAAAATGGTTCCCG TACACGACATGGTTTGCGATTGTGGCATTACTCGCCATTCTGATCGGGGTCATCATGACA ACATCAATTGTCATTACCGGCATTACTGC | 27 |

TABLE 33-continued

Sequences of *Bacillus subtilis* listed in Table 25.

| NAME | SEQUENCE | ID |
|---|---|---|
| DB01298 | GCAGTAATGCCGGTAATGACAATTGATGTTGTCATGATGACCCCGATCAGAATGGCGAGT<br>AATGCCACAATCGCAAACCATGTCGTGTACGGGAACCATTTTACATAATAGGCCGGTGTT<br>TCCGTTTGCTGTTTTCTCGATTTTAAATGAGCGAATCCGATGATCAGCCAAATGAATAAA<br>ACGGTATATCCCAATGATCCCATTAAATAATTAAATGTTTGGCTTCCTGCGAACAGAGAA<br>ATCAATACGCCAATATAGAGAGAAGAAGTGCACATCAGAATCGCAAACATCGGTACGTTT<br>TTCGATGAAAGCTTCGAGAAGACCTTTGGAAGCCTTCCGTCACTTGCCTGTGTATACAAA<br>ATGCGTGATGATCCGTATAAACCTGAATTCATAGAAGAAATGATCGCCAGCAGGATGACT<br>GCATTCATGATATGATCCGCGCCCGGAATGCCTACCATTTTAAAGACCATCACGAAAGGA<br>CTTTCCGGGACGGAATTGACTTGGTTCCATGGAATCAGGCTGACGATGATGAAAAACGGC<br>AGCAGGTAAAACGCGACAATCCGTGTCAGTGTGCTGCGGACAGCTTTCGGGACAACCTTT<br>TCCGGATTTTTTGTCTCTGCAAGCGTTACACCGATAATTTCTGTACCGCCGTAAGAGTAG<br>ATGACGACAAGCATCGCCGTGATCAGCCCTGTGCCGCCGTGCGGGAAAAATCCGCCGTGG<br>TCTGTCAGATTTGAAAATCCGGATGCTGTATGATCACCGAATGATACAAATAAGAGCAGC<br>AATCCCAGAATAATAAAGATAATAATAACGGTAATCTTGATCATTGCCAGCCAATATTCG<br>GTTTCGGCGAAGATTTTAACAGAAAGCAAGTTTACAATCGTGACGATAAGAGAAATTCCT<br>AATGCCAACACCCAGATCGGGCAGCCCGGCAGCCAATATTGAATGAAAATCGCAGCTACA<br>ACAGCTTCAGCCGCAATGTTAAGCACCCACATTTTCCAGTAGATCCAGTCCAAAAAGTAA<br>GCGGCGTAATTTCCCAATACCTGCTGGACAAGATCACGGAAGGTTCTGGCGTTACGGTTT<br>CGAACAGCCATTTCCGCCAGCCCCTGCATAATAAACAGCAAAATAATCCCGCCGAGCAGA<br>TATGCGAGAATTACAGATGGCCCTGCCACATCGATCGCTGAGCTGCTCCCCTTAAATAAA<br>CCTGCGCCGATTGCGCCGCCCAGCGCCATCATCATAATATGGCGGGACGTCATCGTGCGT<br>TTTAACGTTTGATTGTCGTTTTTCATCCTCTTCTACCTCTCCTTCTCGTTTTCAAAAACA<br>AAAAAGCCCGCCGTCTCCTACCTAATCTAATAGATAAAGAGACGACGAGCCTTCGGCTGA<br>CCGCGGTACCACTCTTGTTGATTCTTCATGAAGAATCCTGCTTTTGACCTGTAACGAAGG<br>TTAGCCGTTAAAACATAGGGAATATTCAATCTATTCCGTTCCGTCTTACCACTCCCGGGC<br>GAGTTCAAAGAAGAATCAGGCTGCGTCGCACCACCCCGCAGTTCTCTGTTCTGATCACTT<br>TCTTTTACTGCTCCCAATCTATGTGTTTTAGTTTTCTGAAAAACTCAAATTTTATGATCT<br>GAATATATTAACATAATATACGTGCTTCTCTTTTAACTGTCAATAACTTCAGAGAAAAAA<br>GAAACTGTTATTTTGTCCCTTTTCGAATGGCTTTCCAAAAGGATTCTGACTCGTTTCCTA<br>ATGCGTAAACTGAAACACCTGCTATTTTATATTGCTTTGCCAGATGGCTTTTCGTTTGAA<br>CGGTTTTTTCGTTTTCATACCACACGACATGTTTATGCTTCTTTTTGTCAACATAAGAAA<br>ACGTCATCGAGCCTGATTTTTTGTTGAATGCCGGCTTTGCTTTTTGTTTTTTGATGAGGG<br>ATTTGAGCTCATTCCATTCCCTTATTGTGCTGGTACTTCCGTCTTTTACATCCCAGTCAT<br>AGCCGTACGCAGGGATTCCCATGATGACT | 28 |
| DB02460 | GCAGTAATGCCGGTAATGACAATTGATGTTGTCATGATGACCCCGATCAGAATGGCGAGT<br>AATGCCACAATCGCAAACCATGTCGTGTACGGGAACCATTTTACATAATAGGCCGGTGTT<br>TCCGTTTGCTGTTTTCTCGATTTTAAATGAGCGAATCCGATGATCAGCCAAATGAATAAA<br>ACGGTATATCCCAATGATCCCATTAAATAATTAAATGTTTGGCTTCCTGCGAACAGAGAA<br>ATCAATACGCCAATATAGAGAGAAGAAGTGCACATCAGAATCGCAAACATCGGTACGTTT<br>TTCGATGAAAGCTTCGAGAAGATTTTTGGAAGCCTTCCGTCACTTGCCTGTGTATACAAA<br>ATGCGTGATGATCCGTATAAACCTGAATTCATAGAAGAAATGATCGCCAGCAGGATGACT<br>GCATTCATGATATGATCCGCGCCCGGAATGCCTACCATTTTAAAGACCATCACGAAAGGA<br>CTTTCCGGAACCGAATTGACTTGGTTCCATGGAATCAGGCTGACGATGATGAAAAACGGC<br>AGCAGGTAAAACGCGACAATCCGTGTCAGTGTGCTGCGGACAGCTTTCGGGACAACCTTT<br>TCCGGATTTTTTGTCTCTGCAAGCGTTACACCGATAATTTCTGTACCGCCGTAAGAGTAG<br>ATGACGACAAGCATCGCCGTGATCAGCCCTGTGCCGCCGTGCGGGAAAAATCCGCCGTGG<br>TCTGTCAGGTTGGAAAATCCGGATGCTGTATGATCACCGAATGATACAAATAAGAGCAGC<br>AATCCCAGAATAATAAAGATAATAATAACGGTAATCTTGATCATTGCCAGCCAATATTCA<br>GTTTCGGCGAAGATTTTAACAGAAAGCAAGTTTACAATCGTGACGATAAGAGAAATTCCT<br>AATGCCAACACCCAGATCGGGCAGCCCGGCAGCCAATATTGAATGAAAATCGCAGCTACA<br>ACAGCTTCAGCCGCAATGTTAAGCACCCACATTTTCCAGTAGATCCAGTCCAAAAAGTAA<br>GCAGCGTAATTTCCCAATACCTGCTGGACAAGATCACGGAAGGTTCTGGCGTTACGGTTT<br>CGAACAGCCATTTCCGCCAGCCCCTGCATAATAAACAGCAAAATAATCCCGCCGAGCAGG<br>TATGCGATAATGACAGATGGCCCTGCCACATCGATCGCTGAGCTGCTCCCCTTAAATAAA<br>CCTGCGCCGATTGCTCCGCCCAGCGCCATCATCATAATATGGCGGGACGTCATCGTGCGT<br>TTTAACGTTTGATTGTCGTTTTTCATCCTCTTCTACCTCTCATTCTCGTTTTCAAAAACA<br>AAAAAGCCCGCCGTCTCCTACCTAATCTAATAGATAAAGAGACGACGAGCCTTCGGCTGA<br>CCGCGGTACCACTCTTGTTGATTCTTCATGAAGAATCCTGCTTTTGACCTGTAACGAAGG<br>TTAGCCGTTAAAACATAGGGAATATTCAATCTATTCCGTTCCGTCTTACCACTCCCGGGC<br>GAGTTCAAAGAAGAATCAGGCTGCGTCGCACCACCCCGCAGCTCTCTGTTCTGATCACTT<br>TCTTTTACTGCTCCCAATCTATGTGTTTTAGTTTTCTGAAAAACTCAAATTTTATGATCT<br>GAATATATTAACATAATATACGTGCTTCTCTTTTAACTGTCAATAACTTCAGAGAAAAAA<br>GAAACTGTTATTTTGTCCCTTTTCGAATGGCTTTCCAAAAGGATTCTGACTCGTTTCCTA<br>ATGCGTAAACTGAAACACCTGCTATTTTATATTGCTTTGCCAGATGGCTTTTCGTTTGAA<br>CGGTTTTTTCGTTTTCATACCACACGACATGTTTATGCTTCTTTTTGTCAACATAAGAAA<br>ATGTCATCGAGCCTGATTTTTTGTTGAATGCCGGCTTTGCTTTTTGTTTTTTGATGAGGG<br>ATTTGAGCTCATTCCATTCCCTTATTGTGCTGGTACTTCCGTCTTTTACATCCCAGTCAT<br>AGCCGTACGCAGGGATTCCCATGATGACT | 29 |
| DB02462 | GCAGTAATGCCGGTAATGACAATTGATGTTGTCATGATGACCCCGATCAGAATGGCGAGT<br>AATGCCACAATCGCAAACCATGTCGTGTACGGGAACCATTTTACATAATAGGCCGGTGTT<br>TCCGTTTGCTGTTTTCTCGATTTTAAATGAGCGAATCCGATGATCAGCCAAATGAATAAA<br>ACGGTATATCCCAATGATCCCATTAAATAATTAAATGTTTGGCTTCCTGCGAACAGAGAA<br>ATCAATACGCCAATATAGAGAGAAGAAGTGCACATCAGAATCGCAAACATCGGTACGTTT<br>TTCGATGAAAGCTTCGAGAAGATTTTTGGAAGCCTTCCGTCACTTGCCTGTGTATACAAA | 30 |

TABLE 33-continued

Sequences of *Bacillus subtilis* listed in Table 25.

| NAME | SEQUENCE | ID |
|---|---|---|
| | ATGCGTGATGATCCGTATAAACCTGAATTCATAGAAGAAATGATCGCCAGCAGGATGACT GCATTCATGATATGATCCGCGCCCGGAATGCCTACCATTTTAAAGACCATCACGAAAGGA CTTTCCGGAACCGAATTGACTTGGTTCCATGGAATCAGGCTGACGATGATGAAAAACGGC AGCAGGTAAAACGCGACAATCCGTGTCAGTGTGCTGCGGACAGCTTTCGGGACAACCTTT TCCGGATTTTTTGTCTCTGCAAGCGTTACACCGATAATTTCTGTACCGCCGTAAGAGTAG ATGACGACAAGCATCGCCGTGATCAGCCCTGTGCCGCCGTGCGGGAAAAATCCGCCGTGG TCTGTCAGGTTGGAAAATCCGGATGCTGTATGATCACCGAATGATACAAATAAGAGCAGC AATCCCAGAATAATAAAGATAATAATAACGGTAATCTTGATCATTGCCAGCCAATATTCA GTTTCGGCGAAGATTTTAACAGAAAGCAAGTTTACAATCGTGACGATAAGAGAAATTCCT AATGCCAACACCCAGATCGGGCAGCCCGGCAGCCAATATTGAATGAAAATCGCAGCTACA ACAGCTTCAGCCGCAATGTTAAGCACCCACATTTTCCAGTAGATCCAGTCCAAAAAGTAA GCAGCGTAATTTCCCAATACCTGCTGGACAAGATCACGGAAGGTTCTGGCGTTACGGTTT CGAACAGCCATTTCCGCCAGCCCCTGCATAATAAACAGCAAAATAATCCCGCCGAGCAGG TATGCGATAATGACAGATGGCCCTGCCACATCGATCGCTGAGCTGCTCCCCTTAAATAAA CCTGCGCCGATTGCTCCGCCCAGCGCCATCATCATAATATGGCGGGACGTCATCGTGCGT TTTAACGTTTGATTGTCGTTTTTCATCCTCTTCTACCTCTCATTCTCGTTTTCAAAAACA AAAAAGCCCGCCGTCTCCTACCTAATCTAATAGATAAAGAGACGACGAGCCTTCGGCTGA CCGCGGTACCACTCTTGTTGATTCTTCATGAAGAATCCTGCTTTTGACCTGTAACGAAGG TTAGCCGTTAAAACATAGGGAATATTCAATCTATTCCGTTCCGTCTTACCACTCCCGGGC GAGTTCAAAGAAGAATCAGGCTGCGTCGCACCACCCCGCAGCTCTCTGTTCTGATCACTT TCTTTTACTGCTCCCAATCTATGTGTTTTAGTTTTCTGAAAAACTCAAATTTTATGATCT GAATATATTAACATAATATACGTGCTTCTCTTTTAACTGTCAATAACTTCAGAGAAAAAA GAAACTGTTATTTTGTCCCTTTTCGAATGGCTTTCCAAAAGGATTCTGACTCGTTTCCTA ATGCGTAAACTGAAACACCTGCTATTTTATATTGCTTTGCCAGATGGCTTTTCGTTTGAA CGGTTTTTTCGTTTTCATACCACACGACATGTTTATGCTTCTTTTTGTCAACATAAGAAA ATGTCATCGAGCCTGATTTTTTGTTGAATGCCGGCTTTGCTTTTTGTTTTTTGATGAGGG ATTTGAGCTCATTCCATTCCCTTATTGTGCTGGTACTTCCGTCTTTTACATCCCAGTCAT AGCCGTACGCAGGGATTCCCATGATGACT | |
| DB02946 | GCAGTAATGCCAGTAATGACAATTGATGTTGTCATGATGACCCCGATCAGAATGGCGAGT AATGCCACAATCGCAAACCATGTCGTGTACGGGAACCATTTTACATAATAAGCCGGTGTT TCCGTTTGCTGTTTTCTCGATTTTAAATGAGCGAATCCGATGATCAGCCAAATGAATAAA ACGGTATATCCCAATGATCCCATTAAATAATTAAATGTTTGGCTTCCTGCGAACAGAGAA ATCAATACGCCAATATAGAGAGAAGAAGTGCACATCAGAATCGCAAACATCGGTACGTTT TTCGATGAAAGCTTCGAGAAGACCTTTGGAAGCCTTCCGTCACTTGCCTGTGTATACAAA ATGCGTGATGATCCGTATAAACCTGAATTCATAGAAGAAATGATCGCCAGCAGGATGACT GCATTCATGATATGATCCGCGCCCGGAATGCCTACCATTTTAAAGACCATCACGAAAGGA CTTTCCGGAACGGAATTGACTTGGTTCCATGGAATCAGGCTGACGATGATGAAAAACGGC AGCAGGTAAAACGCGACAATCCGTGTCAGTGTGCTGCGGACAGCTTTCGGGACAACCTTT TCCGGATTTTTTGTCTCTGCAAGCGTTACACCGATAATTTCTGTACCGCCGTAAGAGTAG ATGACGACAAGCATCGCCGTGATCAGCCCTGTGCCGCCGTGCGGGAAAAATCCGCCGTGG TCTGTCAGATTTGAAAATCCGGATGCTGTATGATCACCGAATGATACAAATAAGAGCAGC AATCCCAGAATAATAAAGATAATAATAACGGTAATCTTGATCATTGCCAGCCAATATTCG GTTTCGGCGAAGATTTTAACAGAAAGCAAGTTTACAATCGTGACGATAAGAGAAATTCCT AATGCCAACACCCAGATCGGGCAGCCCGGCAGCCAATATTGAATGAAAATCGCAGCTACA ACAGCTTCAGCCGCAATGTTAAGCACCCACATTTTCCAGTAGATCCAGTCCAAAAAGTAA GCGGCGTAGTTTCCCAATACCTGCTGGACAAGATCACGGAAGGTTCTGGCGTTACGGTTT CGAACAGCCATTTCCGCCAGCCCCTGCATAATAAACAGCAAAATAATCCCGCCGAGCAGA TATGCGATAATGACAGATGGCCCTGCCACATCGATCGCTGAGCTGCTCCCCTTAAATAAA CCTGCGCCGATTGCTCCGCCCAGCGCCATCATCATAATATGGCGGGACGTCATCGTGCGT TTTAACGTTTGATTGTCGTTTTTCATCCTCTTCTACCTCTCCTTCTCGTTTTCAAAAACA AAAAAGCCCGCCGTCTCCTACCTAATCTAATAGATAAAGAGACGACGAGCCTTCGGCTGA CCGCGGTACCACTCTTGTTGATTCTTCATGAAGAATCCTGCTTTTGACCTGTAACGAAGG TTAGCCGTTAAAACATAGGGAATATTCAATCTATTCCGTTCCGTCTTACCACTCCCGGGC GAGTTCAAAGAAGAATCAGGCTGCGTCGCACCACCCCGCAGCTCTCTGTTCTGATCACTT TCTTTTACTGCTCCCAATCTATGTGTTTTAGTTTTCTGAAAAACTCAAATTTTATGATCT GAATATATTAACATAATATACGTGCTTCTCTTTTAACTGTCAATAACTTCAGAGAAAAAA GAAACTGTTATTTTGTCCCTTTTCGAATGGCTTTCCAAAAGGATTCTGACTCGTTTCCTA ATGCGTAAACTGAAACACCTGCTATTTTATATTGCTTTGCCAGATGGCTTTTCGTTTGAA CGGTTTTTTCGTTTTCATACCACACGACATGTTTATGCTTCTTTTTGTCAACATAAGAAA ACGTCATCGAGCCTGATTTTTTGTTGAATGCCGGCTTTGCTTTTTGTTTTTTGATGAGGG ATTTGAGCTCATTCCATTCCCTTATTGTGCTGGTACTTCCGTCTTTTACATCCCAGTCAT AGCCGTACGCAGGGATTCCCATGATGACT | 31 |
| DB03347 | GCAGTAATGCCGGTAATGACAATTGATGTTGTCATGATGACCCCGATCAGAATGGCGAGT AATGCCACAATCGCAAACCATGTCGTGTACGGGAACCATTTTACATAATAGGCCGGTGTT TCCGTTTGCTGTTTTCTCGATTTTAAATGAGCGAATCCGATAATCAGCCAAATGAATAAA ACGGTATATCCCAATGATCCCATTAAATAATTAAATGTTTGGCTTCCTGCGAACAGAGAA ATCAATACGCCAATATAGAGAGAAGAAGTGCACATCAGAATCGCAAACATCGGTACGTTT TTCGATGAAAGCTTAGAGAAGACCTTTGGAAGCCTTCCGTCACTTGCCTGTGTATACAAA ATGCGTGATGATCCGTATAAACCTGAATTCATAGAAGAAATGATCGCCAGCAGGATGACT GCATTCATGATATGATCCGCGCCCGGAATGCCTACCATTTTAAAGACCATTACGAAAGGA CTTTCCGGAACGGAATTGACTTGGTTCCATGGAATCAGGCTGACGATGATGAAAAACGGC AGCAGGTAAAACGCGACAATCCGTGTCAGTGTGCTGCGGACAGCTTTCGGGACAACCTTT TCCGGATTTTTTGTCTCTGCAAGCGTTACACCGATAATTTCTGTACCGCCGTAAGAGTAG ATGACGACAAGCATCGCCGTGATCAGCCCTGTGCCGCCGTGCGGGAAAAATCCGCCGTGG | 32 |

TABLE 33-continued

Sequences of *Bacillus subtilis* listed in Table 25.

| NAME | SEQUENCE | ID |
|---|---|---|
| | TCTGTCAGATTTGAAAATCCGGATGCTGTATGATCACCGAATGATACAAATAAGAGCAGC<br>AATCCCAGAATAATAAAGATAATAATAACGGTAATCTTGATCATTGCCAGCCAATATTCG<br>GTTTCGGCGAAGATTTTAACAGAAAGCAAGTTTACAATCGTGACGATAAGAGAAATTCCT<br>AATGCCAACACCCAGATCGGGCAGCCCGGCAGCCAATATTGAATGAAAATCGCAGCTACA<br>ACAGCTTCAGCCGCAATGTTAAGCACCCACATTTTCCAGTAGATCCAGTCCAAAAAGTAA<br>GCGGCGTAATTTCCCAATACCTGCTGGACAAGATCACGGAAGGTTCTGGCGTTACGGTTT<br>CGAACAGCCATTTCCGCCAGCCCCTGCATAATAAACAGCAAAATAATCCCGCCGAGCAGA<br>TATGCGAGAATGACAGATGGCCCTGCCACATCGATCGCTGAGCTGCTCCCCTTAAATAAA<br>CCTGCGCCGATTGCTCCGCCCAGCGCCATCATCATAATATGGCGGGACGTCATCGTGCGT<br>TTTAACGTTTGATTGTCGTTTTTCATCCTCTTCTACCTCTCCTTTTCGTTTTCAAAAACA<br>AAAAAGCCCGCCGTCTCCTACCTAATCTAATAGATAAAGAGACGACGAGCCTTCGGCTGA<br>CCGCGGTACCACTCTTGTTGATTCTTCATGAAGAATCCTGCTTTTGACCTGTAACGAAGG<br>TTAGCCGTTAAAACATAGGGAATATTTAATCTATTCCGTTCCGTCTTACCACTCCCGGGC<br>GAGTTCAAAGAAGAATCAGGCTGCGTCGCACCACCCCGCAGCTCTCTGTTCTGATCACTT<br>TCTTTTACTGCTCCCAATCTATGTGTTTTAGTTTTCTGAAAAACTCAAATTTTATGATCT<br>GAATATATTAACATAATATACGTGCTTCTCTTTTAACTGTCAATAACTTCAGAGAAAAAA<br>GAAACTGTTATTTTGTCCCTTTTCGAATGGCTTTCCAAAAGGATTCTGACTCGTTTCCTA<br>ATGCGTAAACTGAAACACCTGCTATTTTATATTGCTTTGCCAGATGGCTTTTCGTTTGAA<br>CGGTTTTTTCGTTTTCATACCACACGACATGTTTATGCTTCTTTTTGTCAACATAAGAAA<br>ACGTCATCGAACCTGATTTTTTGTTGAATGCCGGCTTTGCTTTTTGTTTTTGGATGAGGG<br>ATTTGAGCTCATTCCATTCCCTTATTGTGCTGGTACTTCCGTCTTTTACATCCCAGTCAT<br>AGCCGTACGCAGGGATTCCCATGATGACT | |
| DB03351 | GCAGTAATGCCGGTAATGACAATTGATGTTGTCATGATGACCCCGATCAGAATGGCGAGT<br>AATGCCACAATCGCAAACCATGTCGTGTACGGGAACCATTTTACATAATAGGCCGGTGTT<br>TCCGTTTGCTGTTTTCTCGATTTTAAATGAGCGAATCCGATGATCAGCCAAATGAATAAA<br>ACGGTATATCCCAATGATCCCATTAAATAATTAAATGTTTGGCTTCCTGCGAACAGAGAA<br>ATCAATACGCCAATATAGAGAGAAGAAGTGCACATCAGAATCGCAAACATCGGTACGTTT<br>TTCGATGAAAGCTTCGAGAAGATTTTTGGAAGCCTTCCGTCACTTGCCTGTGTATACAAA<br>ATGCGTGATGATCCGTATAAACCTGAATTCATAGAAGAAATGATCGCCAGCAGGATGACT<br>GCATTCATGATATGATCCGCGCCCGGAATGCCTACCATTTTAAAGACCATCACGAAAGGA<br>CTTTCCGGAACCGAATTGACTTGGTTCCATGGAATCAGGCTGACGATGATGAAAAACGGC<br>AGCAGGTAAAACGCGACAATCCGTGTCAGTGTGCTGCGGACAGCTTTCGGGACAACCTTT<br>TCCGGATTTTTTGTCTCTGCAAGCGTTACACCGATAATTTCTGTACCGCCGTAAGAGTAG<br>ATGACGACAAGCATCGCCGTGATCAGCCCTGTGCCGCCGTGCGGGAAAAATCCGCCGTGG<br>TCTGTCAGGTTGGAAAATCCGGATGCTGTATGATCACCGAATGATACAAATAAGAGCAGC<br>AATCCCAGAATAATAAAGATAATAATAACGGTAATCTTGATCATTGCCAGCCAATATTCA<br>GTTTCGGCGAAGATTTTAACAGAAAGCAAGTTTACAATCGTGACGATAAGAGAAATTCCT<br>AATGCCAACACCCAGATCGGGCAGCCCGGCAGCCAATATTGAATGAAAATCGCAGCTACA<br>ACAGCTTCAGCCGCAATGTTAAGCACCCACATTTTCCAGTAGATCCAGTCCAAAAAGTAA<br>GCAGCGTAATTTCCCAATACCTGCTGGACAAGATCACGGAAGGTTCTGGCGTTACGGTTT<br>CGAACAGCCATTTCCGCCAGCCCCTGCATAATAAACAGCAAAATAATCCCGCCGAGCAGG<br>TATGCGATAATGACAGATGGCCCTGCCACATCGATCGCTGAGCTGCTCCCCTTAAATAAA<br>CCTGCGCCGATTGCTCCGCCCAGCGCCATCATCATAATATGGCGGGACGTCATCGTGCGT<br>TTTAACGTTTGATTGTCGTTTTTCATCCTCTTCTACCTCTCATTCTCGTTTTCAAAAACA<br>AAAAAGCCCGCCGTCTCCTACCTAATCTAATAGATAAAGAGACGACGAGCCTTCGGCTGA<br>CCGCGGTACCACTCTTGTTGATTCTTCATGAAGAATCCTGCTTTTGACCTGTAACGAAGG<br>TTAGCCGTTAAAACATAGGGAATATTCAATCTATTCCGTTCCGTCTTACCACTCCCGGGC<br>GAGTTCAAAGAAGAATCAGGCTGCGTCGCACCACCCCGCAGCTCTCTGTTCTGATCACTT<br>TCTTTTACTGCTCCCAATCTATGTGTTTTAGTTTTCTGAAAAACTCAAATTTTATGATCT<br>GAATATATTAACATAATATACGTGCTTCTCTTTTAACTGTCAATAACTTCAGAGAAAAAA<br>GAAACTGTTATTTTGTCCCTTTTCGAATGGCTTTCCAAAAGGATTCTGACTCGTTTCCTA<br>ATGCGTAAACTGAAACACCTGCTATTTTATATTGCTTTGCCAGATGGCTTTTCGTTTGAA<br>CGGTTTTTTCGTTTTCATACCACACGACATGTTTATGCTTCTTTTTGTCAACATAAGAAA<br>ATGTCATCGAGCCTGATTTTTTGTTGAATGCCGGCTTTGCTTTTTGTTTTTTGATGAGGG<br>ATTTGAGCTCATTCCATTCCCTTATTGTGCTGGTACTTCCGTCTTTTACATCCCAGTCAT<br>AGCCGTACGCAGGGATTCCCATGATGACT | 33 |
| DB03353 | GCAGTAATGCCGGTAATGACAATTGATGTTGTCATGATGACCCCGATCAGAATGGCGAGT<br>AATGCCACAATCGCAAACCATGTCGTGTACGGGAACCATTTTACATAATAGGCCGGTGTT<br>TCCGTTTGCTGTTTTCTCGATTTTAAATGAGCGAATCCGATGATCAGCCAAATGAATAAA<br>ACGGTATATCCCAATGATCCCATTAAATAATTAAATGTTTGGCTTCCTGCGAACAGAGAA<br>ATCAATACGCCAATATAGAGAGAAGAAGTGCACATCAGAATCGCAAACATCGGTACGTTT<br>TTCGATGAAAGCTTCGAGAAGATTTTTGGAAGCCTTCCGTCACTTGCCTGTGTATACAAA<br>ATGCGTGATGATCCGTATAAACCTGAATTCATAGAAGAAATGATCGCCAGCAGGATGACT<br>GCATTCATGATATGATCCGCGCCCGGAATGCCTACCATTTTAAAGACCATCACGAAAGGA<br>CTTTCCGGAACCGAATTGACTTGGTTCCATGGAATCAGGCTGACGATGATGAAAAACGGC<br>AGCAGGTAAAACGCGACAATCCGTGTCAGTGTGCTGCGGACAGCTTTCGGGACAACCTTT<br>TCCGGATTTTTTGTCTCTGCAAGCGTTACACCGATAATTTCTGTACCGCCGTAAGAGTAG<br>ATGACGACAAGCATCGCCGTGATCAGCCCTGTGCCGCCGTGCGGGAAAAATCCGCCGTGG<br>TCTGTCAGGTTGGAAAATCCGGATGCTGTATGATCACCGAATGATACAAATAAGAGCAGC<br>AATCCCAGAATAATAAAGATAATAATAACGGTAATCTTGATCATTGCCAGCCAATATTCA<br>GTTTCGGCGAAGATTTTAACAGAAAGCAAGTTTACAATCGTGACGATAAGAGAAATTCCT<br>AATGCCAACACCCAGATCGGGCAGCCCGGCAGCCAATATTGAATGAAAATCGCAGCTACA<br>ACAGCTTCAGCCGCAATGTTAAGCACCCACATTTTCCAGTAGATCCAGTCCAAAAAGTAA<br>GCAGCGTAATTTCCCAATACCTGCTGGACAAGATCACGGAAGGTTCTGGCGTTACGGTTT | 34 |

TABLE 33-continued

Sequences of *Bacillus subtilis* listed in Table 25.

| NAME | SEQUENCE | ID |
|---|---|---|
| | CGAACAGCCATTTCCGCCAGCCCCTGCATAATAAACAGCAAAATAATCCCGCCGAGCAGG<br>TATGCGATAATGACAGATGGCCCTGCCACATCGATCGCTGAGCTGCTCCCCTTAAATAAA<br>CCTGCGCCGATTGCTCCGCCCAGCGCCATCATCATAATATGGCGGGACGTCATCGTGCGT<br>TTTAACGTTTGATTGTCGTTTTTCATCCTCTTCTACCTCTCATTCTCGTTTTCAAAAACA<br>AAAAAGCCCGCCGTCTCCTACCTAATCTAATAGATAAAGAGACGACGAGCCTTCGGCTGA<br>CCGCGGTACCACTCTTGTTGATTCTTCATGAAGAATCCTGCTTTTGACCTGTAACGAAGG<br>TTAGCCGTTAAAACATAGGGAATATTCAATCTATTCCGTTCCGTCTTACCACTCCCGGGC<br>GAGTTCAAAGAAGAATCAGGCTGCGTCGCACCACCCCGCAGCTCTCTGTTCTGATCACTT<br>TCTTTTACTGCTCCCAATCTATGTGTTTTAGTTTTCTGAAAAACTCAAATTTTATGATCT<br>GAATATATTAACATAATATACGTGCTTCTCTTTTAACTGTCAATAACTTCAGAGAAAAAA<br>GAAACTGTTATTTTGTCCCTTTTCGAATGGCTTTCCAAAAGGATTCTGACTCGTTTCCTA<br>ATGCGTAAACTGAAACACCTGCTATTTTATATTGCTTTGCCAGATGGCTTTTCGTTTGAA<br>CGGTTTTTTCGTTTTCATACCACACGACATGTTTATGCTTCTTTTTGTCAACATAAGAAA<br>ATGTCATCGAGCCTGATTTTTTGTTGAATGCCGGCTTTGCTTTTTGTTTTTTGATGAGGG<br>ATTTGAGCTCATTCCATTCCCTTATTGTGCTGGTACTTCCGTCTTTTACATCCCAGTCAT<br>AGCCGTACGCAGGGATTCCCATGATGACT | |
| DB03367 | GCAGTAATGCCGGTAATGACAATTGATGTTGTCATGATGACCCCGATCAGAATGGCGAGT<br>AATGCCACAATCGCAAACCATGTCGTGTACGGGAACCATTTTACATAATAGGCCGGTGTT<br>TCCGTTTGCTGTTTTCTCGATTTTAAATGAGCGAATCCGATGATCAGCCAAATGAATAAA<br>ACGGTATATCCCAATGATCCCATTAAATAATTAAATGTTTGGCTTCCTGCGAACAGAGAA<br>ATCAATACGCCAATATAGAGAGAAGAAGTGCACATCAGAATCGCAAACATCGGTACGTTT<br>TTCGATGAAAGCTTCGAGAAGATTTTTGGAAGCCTTCCGTCACTTGCCTGTGTATACAAA<br>ATGCGTGATGATCCGTATAAACCTGAATTCATAGAAGAAATGATCGCCAGCAGGATGACT<br>GCATTCATGATATGATCCGCGCCCGGAATGCCTACCATTTTAAAGACCATCACGAAAGGA<br>CTTTCCGGAACCGAATTGACTTGGTTCCATGGAATCAGGCTGACGATGATGAAAAACGGC<br>AGCAGGTAAAACGCGACAATCCGTGTCAGTGTGCTGCGGACAGCTTTCGGGACAACCTTT<br>TCCGGATTTTTTGTCTCTGCAAGCGTTACACCGATAATTTCTGTACCGCCGTAAGAGTAG<br>ATGACGACAAGCATCGCCGTGATCAGCCCTGTGCCGCCGTGCGGAAAAATCCGCCGTGG<br>TCTGTCAGGTTGGAAAATCCGGATGCTGTATGATCACCGAATGATACAAATAAGAGCAGC<br>AATCCCAGAATAATAAAGATAATAATAACGGTAATCTTGATCATTGCCAGCCAATATTCA<br>GTTTCGGCGAAGATTTTAACAGAAAGCAAGTTTACAATCGTGACGATAAGAGAAATTCCT<br>AATGCCAACACCCAGATCGGGCAGCCCGGCAGCCAATATTGAATGAAAATCGCAGCTACA<br>ACAGCTTCAGCCGCAATGTTAAGCACCCACATTTTCCAGTAGATCCAGTCCAAAAAGTAA<br>GCAGCGTAATTTCCCAATACCTGCTGGACAAGATCACGGAAGGTTCTGGCGTTACGGTTT<br>CGAACAGCCATTTCCGCCAGCCCCTGCATAATAAACAGCAAAATAATCCCGCCGAGCAGG<br>TATGCGATAATGACAGATGGCCCTGCCACATCGATCGCTGAGCTGCTCCCCTTAAATAAA<br>CCTGCGCCGATTGCTCCGCCCAGCGCCATCATCATAATATGGCGGGACGTCATCGTGCGT<br>TTTAACGTTTGATTGTCGTTTTTCATCCTCTTCTACCTCTCATTCTCGTTTTCAAAAACA<br>AAAAAGCCCGCCGTCTCCTACCTAATCTAATAGATAAAGAGACGACGAGCCTTCGGCTGA<br>CCGCGGTACCACTCTTGTTGATTCTTCATGAAGAATCCTGCTTTTGACCTGTAACGAAGG<br>TTAGCCGTTAAAACATAGGGAATATTCAATCTATTCCGTTCCGTCTTACCACTCCCGGGC<br>GAGTTCAAAGAAGAATCAGGCTGCGTCGCACCACCCCGCAGCTCTCTGTTCTGATCACTT<br>TCTTTTACTGCTCCCAATCTATGTGTTTTAGTTTTCTGAAAAACTCAAATTTTATGATCT<br>GAATATATTAACATAATATACGTGCTTCTCTTTTAACTGTCAATAACTTCAGAGAAAAAA<br>GAAACTGTTATTTTGTCCCTTTTCGAATGGCTTTCCAAAAGGATTCTGACTCGTTTCCTA<br>ATGCGTAAACTGAAACACCTGCTATTTTATATTGCTTTGCCAGATGGCTTTTCGTTTGAA<br>CGGTTTTTTCGTTTTCATACCACACGACATGTTTATGCTTCTTTTTGTCAACATAAGAAA<br>ATGTCATCGAGCCTGATTTTTTGTTGAATGCCGGCTTTGCTTTTTGTTTTTTGATGAGGG<br>ATTTGAGCTCATTCCATTCCCTTATTGTGCTGGTACTTCCGTCTTTTACATCCCAGTCAT<br>AGCCGTACGCAGGGATTCCCATGATGACT | 35 |

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

What is claimed is:

1. A composition comprising a probiotic, wherein the probiotic comprises human-isolated or synthetic *Alcaligenes faecalis* in an amount effective to treat a disease, disorder, or condition associated with a pathogenic microorganism, and a cryoprotectant, wherein the probiotic comprises a nucleic acid sequence at least 95% identical to that of SEQ ID NO: 6.

2. The composition of claim 1, formulated for topical application to a mammal for treating the disease, disorder, or condition, wherein the disease disorder, or condition is an infection.

3. The composition of claim 2, wherein the cryoprotectant results in greater efficacy, stability, and/or viability of the human-isolated or synthetic *Alcaligenes faecalis* as compared to a composition comprising the same human-isolated or synthetic *Alcaligenes faecalis* without the cryoprotectant.

4. The composition of claim 1, wherein the composition is frozen or lyophilized.

5. The composition of claim 1, wherein the cryoprotectant results in a greater percent recovery of the human-isolated or synthetic *Alcaligenes faecalis* after freezing or lyophilization as compared to a composition comprising the same human-isolated or synthetic *Alcaligenes faecalis* without the cryoprotectant.

6. The composition of claim 1, wherein the cryoprotectant comprises a disaccharide.

7. The composition of claim 6, wherein the disaccharide comprises trehalose.

8. The composition of claim 7, wherein the trehalose comprises D-trehalose, wherein the D-trehalose is about 2% to about 20% of the composition by weight.

9. The composition of claim 1, further comprising at least one additional isolated or synthetic microbe.

10. The composition of claim 9, wherein the additional isolated or synthetic microbe comprises a human-isolated or synthetic *Bacillus* altitudinis, *Bacillus pumilus, Bacillus subtilis*, or *Janthinobacterium lividum.*

11. The composition of claim 9, wherein the additional isolated or synthetic microbe comprises one or more microbes selected from *Lactobacillus, Lactococcus, Cutibacterium*, and *Propionibacterium.*

12. The composition of claim 1, further comprising a first additional isolated microbe and a second additional isolated microbe, wherein the first and second additional isolated microbes are independently selected from bacteria, virus, yeast, fungus, and any combination thereof.

13. The composition of claim 1, wherein:

a) the disease, disorder, or condition is associated with *Malassezia, Staphylococcus, Candida*, or *Trichophyton*; and/or b) the disease, disorder, or condition is *Tinea barbae, Tinea capitis, Tinea corporis, Tinea cruris, Tinea pedis, Tinea versicolor*, or onychomycosis or any combination thereof.

14. The composition of claim 1, further comprising a metabolite, cell lysate, or postbiotic from at least one species of human-isolated or synthetic bacteria selected from *Alcaligenes faecalis, Bacillus altitudinis, Bacillus pumilus*, and *Bacillus subtilis.*

15. A probiotic composition comprising *Alcaligenes faecalis* and at least one cryoprotectant for use as a medicament, wherein the probiotic comprises a nucleic acid sequence at least 95% identical to that of SEQ ID NO: 6.

16. The probiotic composition of claim 15, for use in the treatment of a disease, disorder, or condition associated with at least one pathogenic microorganism.

17. A kit comprising (i) at least one vial comprising the composition of claim 1, and (ii) instructions.

* * * * *